United States Patent
Cumming et al.

(10) Patent No.: US 10,597,380 B2
(45) Date of Patent: Mar. 24, 2020

(54) PYRIDAZINONE-BASED BROAD SPECTRUM ANTI-INFLUENZA INHIBITORS

(71) Applicant: Hoffmann-La Roche Inc., Little Falls, NJ (US)

(72) Inventors: John G. Cumming, Therwil (CH); Xianfeng Lin, Shanghai (CN); Haixia Liu, Shanghai (CN); Isabel Najera, Basel (CH); Zongxing Qiu, Shanghai (CN); Virginie Sandrin, Kembs (FR); Guozhi Tang, Shanghai (CN); Guolong Wu, Shanghai (CN)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 16/225,920

(22) Filed: Dec. 19, 2018

(65) Prior Publication Data

US 2019/0127349 A1    May 2, 2019

Related U.S. Application Data

(63) Continuation of application No. PCT/EP2017/065682, filed on Jun. 26, 2017.

(51) Int. Cl.

| | |
|---|---|
| C07D 401/12 | (2006.01) |
| C07D 401/14 | (2006.01) |
| C07D 403/12 | (2006.01) |
| C07D 403/14 | (2006.01) |
| A61P 31/16 | (2006.01) |
| C07D 491/04 | (2006.01) |
| C07D 471/04 | (2006.01) |
| C07D 491/052 | (2006.01) |
| C07D 405/12 | (2006.01) |
| C07D 405/14 | (2006.01) |
| C07D 413/14 | (2006.01) |

(52) U.S. Cl.
CPC ........... *C07D 401/12* (2013.01); *A61P 31/16* (2018.01); *C07D 401/14* (2013.01); *C07D 403/12* (2013.01); *C07D 405/12* (2013.01); *C07D 405/14* (2013.01); *C07D 413/14* (2013.01); *C07D 471/04* (2013.01); *C07D 491/04* (2013.01); *C07D 491/052* (2013.01)

(58) Field of Classification Search
CPC .. C07D 401/12; C07D 410/14; C07D 403/12; C07D 403/14
See application file for complete search history.

(56) References Cited

U.S. PATENT DOCUMENTS

| | | |
|---|---|---|
| 8,921,388 B2 | 12/2014 | Buschmann et al. |
| 9,434,745 B2 | 9/2016 | Wolkerstorfer et al. |
| 2014/0038990 A1 | 2/2014 | Buschmann et al. |
| 2016/0297763 A1 | 10/2016 | Classen-Houben et al. |
| 2016/0367557 A1 | 12/2016 | Wolkerstorfer et al. |
| 2016/0376286 A1 | 12/2016 | Classen-Houben et al. |

FOREIGN PATENT DOCUMENTS

| | | |
|---|---|---|
| WO | 2010/077947 A1 | 7/2010 |
| WO | 2011/000566 A2 | 1/2011 |

OTHER PUBLICATIONS

Healthline. Viral Diseases 101. (2019) Web <https://www.healthline.com/health/viral-diseases>.*
Burns et al., "Rethinking Prevention of HIV Type 1 Infection" Clinical Infectious Diseases 51(6):725-731 ( 2010).
Chan et al., "Determinants of Antiviral Effectiveness in Influenza Virus A Subtype H5N1" The Journal of Infectious Diseases 206:1359-1366 ( 2012).
Chang et al., "Combination of -glucosidase inhibitor and ribavirin for the treatment of dengue virus infection in vitro and in vivo" Antiviral Research 89:26-34 ( 2011).
Eriksson et al., "Inhibition of Influenza Virus Ribonucleic Acid Polymerase by Ribavirin Triphosphate" Antimicrobial Agents and Chemotherapy 11:946-951 ( 1977).
Furuta et al., "Mechanism of Action of T-705 against Influenza Virus" Antimicrobial Agents and Chemotherapy 49(3):981-986 (2005).
Hu et al., "Association between adverse clinical outcome in human disease caused by novel influenza A H7N9 virus and sustained viral shedding and emergence of antiviral resistance" The Lancet 381:2271-2279 ( 2013).

(Continued)

*Primary Examiner* — Emily A Bernhardt
*Assistant Examiner* — Laura M Daniel
(74) *Attorney, Agent, or Firm* — Zong-Qiang Bill Tian

(57) ABSTRACT

The present invention relates to compounds of formula (I):

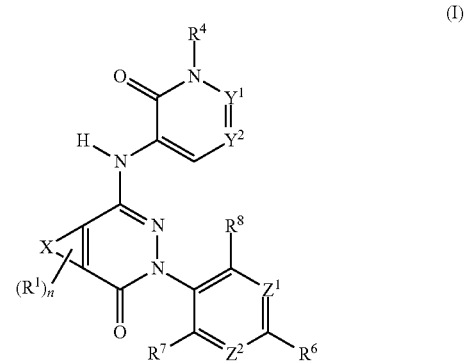

or pharmaceutically acceptable salts thereof, as well as processes for their manufacture, pharmaceutical compositions comprising them, and their use as medicaments.

42 Claims, No Drawings

(56) References Cited

OTHER PUBLICATIONS

International Preliminary Report of Patentability (IPRP) for PCT/EP2017/065682 dated Jan. 1, 2019.
International Search Report for PCT/EP2017/065682 dated Aug. 24, 2017.
Magden et al., "Inhibitors of virus replication: recent developments and prospects" Appl Microbiol Biotechnol 66:612-621 (2005).

* cited by examiner

PYRIDAZINONE-BASED BROAD SPECTRUM ANTI-INFLUENZA INHIBITORS

CROSS-REFERENCE TO RELATED APPLICATIONS

This application is a continuation of International Application No. PCT/EP2017/065682, filed on Jun. 26, 2017, which claims priority from International Application No. PCT/CN2016/087656, filed on Jun. 29, 2016, the contents of which are incorporated herein by reference in their entireties.

The present invention relates to a compound of formula (I):

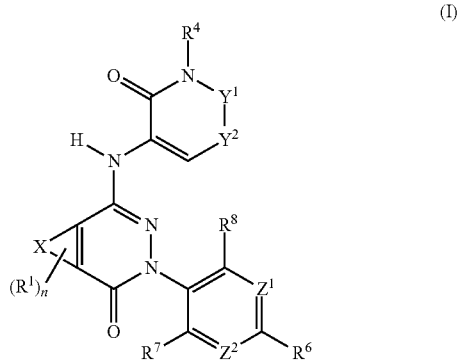

or a pharmaceutically acceptable salt thereof, wherein X, $Y^1, Y^2, Z^1, Z^2, n, R^1, R^4$ and $R^6$ to $R^8$ are as described herein, as well as processes for their manufacture, pharmaceutical compositions comprising them, and their use as medicaments.

BACKGROUND OF THE INVENTION

Influenza viruses infect humans and animals and have incurred great financial and societal cost for decades. The most common flu viruses infecting humans are the type A and type B viruses. Influenza A viruses are responsible for sporadic pandemics that usually cause higher mortality rates than seasonal influenza epidemics. The most severe pandemic ("the Spanish flu") occurred in 1918, with approximately 50 million deaths worldwide (1% of the world's population, 2.5% case:fatality rate). Most recently, the serious threat posed by influenza viruses to worldwide public health has been highlighted by, (i) firstly, the transmission to humans of the highly pathogenic avian influenza A viruses such as the recurrent H5N1 (53% mortality in infected humans; WHO/GIP data in HQ as of 9 May 2016, http://www.who.int/influenza/human_animal_interface/EN_GIP_220160509cumulativenumberH 5N1cases.pdf?ua=1), H7N9 (2 waves in China in 2013 and 2014 with high rates of severe illness and death) and H10N8 (first case reported in China in 2013), and (ii) secondly, the unexpected emergence in 2009 of a novel pandemic influenza virus strain, the swineA/H1N1, that has rapidly spread around the world (http://www.who.int/csr/disease/swineflu/en/). Fortunately, these strains were respectively highly pathogenic but poorly human-to-human transmissible, and highly transmissible but causing only mild illness. A catastrophic, yet plausible, scenario would be the generation by genetic mutation(s) of strains highly pathogenic and contagious and requires constant monitoring.

Besides pandemics, seasonal epidemics occur mainly during the winter months in temperate climates or throughout the year in tropical regions. WHO estimates that annual epidemics cause 3 to 5 million cases of severe illness and 250,000-500,000 deaths worldwide per year (http://www.who.int/mediacentre/factsheets/fs211/en/). Hospitalization and death occur mainly in high-risk populations, the very young, elderly, chronically ill, pregnant woman and immunocompromised patients. On the general population, flu epidemics can result in substantial absenteeism and productivity losses.

Convential prophylactic and therapeutic treatments are the seasonal vaccine and direct acting antivirals. The vaccine is, however, poorly effective in the elderly and children under the age of two, and some years poorly or totally ineffective due to failed prediction of the epidemic strains. Also, it should be noted that the delay in generating a vaccine (~6 months in the relatively favorable case of A/H1N1) and the lack of vaccinal coverage against highly pathogenic strains highlight the need for therapeutic options.

Two classes of licenced pathogen-targeting antivirals exist: the M2 ion channel blockers (amantadine and rimantadine) and the neuraminidase inhibitors (oseltamivir, zanamivir, peramivir, laninamivir). They respectively block the virus life cycle at the entry and release stages. The M2 blockers have not been extensively used due to their side effects and the rapid development of resistant virus mutants (Magden J et al., *Appl. Microbiol. Biotechnol.* (2005) 66:612-621). In addition, rather unspecific viral drugs, such as ribavirin, can be used to treat influenza and other virus infections (Eriksson, B. et al., *Antimicrob. Agents Chemother.* (1977) 11:946-951) but Ribavirin has been approved only in a few countries due to its severe side effects (Furuta et al., *Antimicrobial Agents and Chemotherapy* (2005) 49(3):981-986). The Standard of Care has been Oseltamivir for years, despite its significant limitations; 1) a rather limited treatment window as it has to be administred within 48 h of the onset of symptoms; 2) a partial efficacy in high-risk and hospitalized patients and the failure to prevent complications in some patients; 3) the existence of resistance by many influenza strains, as reported by IRIS (http://apps.who.int/iris/handle/10665/205523); and 4) a low potency against flu B and the fact that Oseltamivir monotherapy has not prevented death in patients with severe pandemic H1N1 (Nukiwa et al., *Clin Infect Dis* (2010) 51(6):725-731), H5N1 (Chan et al., *J Infect Dis* (2012) 206:1359-1366) or H7N9 (Hu et al., *Lancet* (2013) 381: 2271-2277). An obvious strategy to improve on the standard of care would be to combine drugs with different modes of action ("MOA") or develop drugs with new MOAs that could be used as stand-alone.

It is an object of the present invention to identify such new compounds with new MOA which are effective against viral diseases, particularly influenza, and which have improved pharmacological properties.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

"The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

Compounds of present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

The term "halo", "halogen", and "halide" are used interchangeably herein and denote fluoro, chloro, bromo, or iodo. Particular examples of halo are fluoro and chloro.

The term "hydrogen" and "hydro" are used interchangeably to denote a hydrogen radical (—H).

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl include methyl, ethyl, propyl, isopropyl, n-butyl, and tert-butyl.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl, and iso-butenyl. Particular example of alkenyl is ethenyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy include methoxy, ethoxy and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples of haloalkyl include trifluoromethyl and difluoromethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms. Particular examples of haloalkoxy include trifluoromethoxy and difluoromethoxy.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl. Particular example of hydroxyalkyl include hydroxymethyl, hydroxyethyl, hydroxypropyl, hydroxyisopropyl and hydroxyisobutyl.

The term "alkoxyalkyl" denotes an alkyl group wherein at least one of the hydrogen atoms of the alkyl group has been replaced by an alkoxy group. Exemplary alkoxyalkyl groups include 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular example of cycloalkyl is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl are azetidinyl, oxetanyl, pyrrolidinyl, piperazinyl, and morpholinyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl.

The term "aryloxy" denotes a group of the formula —O—R', wherein R' is aryl. An example of aryloxy is phenoxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular example of heteroaryl is imidazolyl.

The term "amino" denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "alkylamino" denotes a group —NR'R", wherein R' is hydrogen and R" is a alkyl. The term "dialkylamino" as used herein denotes a group —NR'R", wherein R' and R" are both alkyl. Examples of alkylamino groups include methylamino and ethylamino. Examples of alkylamino groups include dimethylamino, methylethylamino, diethylamino and di(1-methylethyl)amino.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "half maximal inhibitory concentration" (IC50) denotes the concentration of a particular compound or molecule required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

An "effective amount" of an agent, e.g., a pharmaceutical composition, refers to an amount effective, at dosages and for periods of time necessary, to achieve the desired therapeutic or prophylactic result.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

8-Fluoro-2H-phthalazin-1-one, i.e. a phthalazin-1-onyl with a fluoro-substituent in position 8, has the structure as follows:

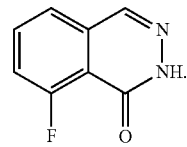 [SMILES: O=c1[nH]ncc2cccc(F)c12]

In detail, the present invention relates to a compound of formula (I)

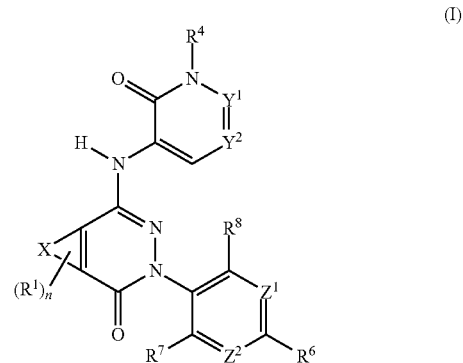

wherein

X is —$CH_2$—$CH_2$—$CH_2$—, —CH=CH—CH=CH—, —$CH_2$—$CH_2$—$CH_2$—$CH_2$—, —$CH_2$—O—$CH_2$—$CH_2$—, —$CH_2$—$CH_2$—O—$CH_2$—, —$CH_2$—$NR^2$—$CH_2$—$CH_2$—, or —$CH_2$—$CH_2$—$NR^2$—$CH_2$—;

n is 0, 1 or 2;

each $R^1$ is independently selected from halo, $C_{1-7}$ alkyl, $C_{2-7}$ alkenyl, hydroxy, $C_{1-7}$ alkoxy, $NR^{10}R^{11}$, and $CONR^{10}R^{11}$;

wherein $C_{1-7}$ alkyl and $C_{1-7}$ alkoxy are optionally substituted by one or more $C_{1-7}$ alkyl, hydroxy, $C_{1-7}$ alkoxy, $NR^{10}R^{11}$ or $COR^9$;

$R^2$ is H, $C_{1-7}$ alkyl, hydroxy-$C_{1-7}$ alkyl, $COR^9$, $CONR^{10}R^{11}$, or $SO_2$—$C_{1-7}$ alkyl;

$Y^1$ is N, CH or $CCH_3$, $Y^2$ is N or $CR^3$;

with the proviso that not both of $Y^1$ and $Y^2$ are N;

$R^3$ is H, halogen, $C_{1-7}$ alkyl, halo-$C_{1-7}$ alkyl, $CONR^{10}R^{11}$ or CO—$C_{1-7}$ alkoxy;

$R^4$ is H or $C_{1-7}$ alkyl, wherein $C_{1-7}$ alkyl is optionally substituted with one or more $R^5$;

each $R^5$ is independently selected from hydroxy, $C_{1-7}$ alkoxy, $NR^{12}R^{13}$, $COR^9$, $CONR^{10}R^{11}$, $SO_2$—$C_{1-7}$ alkyl, $SO_2$—$NR^{10}R^{11}$, heterocycloalkyl and heteroaryl;

wherein $C_{1-7}$ alkoxy is optionally substituted by $COR^9$ or $CONR^{10}R^{11}$;

wherein heterocycloalkyl and heteroaryl are optionally substituted with one or more substituents selected from halo, $C_{1-7}$ alkyl, halo-$C_{1-7}$ alkyl, hydroxy, $C_{1-7}$ alkoxy, oxo, $COR^9$, $C_{1-7}$ alkyl-$COR^9$ or $NR^{10}R^{11}$;

$Z^1$ is N, CH or CO—$CH_3$;

$Z^2$ is N or CH;

$R^6$ is $C_{1-7}$ alkyl, hydroxy-$C_{1-7}$ alkyl, halo-$C_{1-7}$ alkyl, $C_{1-7}$ alkoxy-$C_{1-7}$ alkyl, $C_{1-7}$ alkoxy, halo-$C_{1-7}$ alkoxy, $C_{1-7}$ alkoxy-$C_{1-7}$ alkoxy, S-halo-$C_{1-7}$ alkyl, $SF_5$, $C_{3-7}$ cycloalkyl, heterocycloalkyl or heterocycloalkyl substituted by $C_{1-7}$ alkyl;

$R^7$ is H, halogen or $C_{1-7}$ alkyl;

$R^8$ is H, halogen or $C_{1-7}$ alkyl;

$R^9$ is H, $C_{1-7}$ alkyl, hydroxy, or $C_{1-7}$ alkoxy;

$R^{10}$ is H or $C_{1-7}$ alkyl;

wherein $C_{1-7}$ alkyl is optionally substituted with one or more hydroxy, $C_{1-7}$ alkoxy, COOH, or CO—$C_{1-7}$ alkoxy;

$R^{11}$ is H, $C_{1-7}$ alkyl, CO—$C_{1-7}$ alkoxy or heterocycloalkyl, wherein $C_{1-7}$ alkyl is optionally substituted with one or more hydroxy, $C_{1-7}$ alkoxy, $NH_2$, $N(C_{1-7}$ alkyl$)_2$, COOH, or CO—$C_{1-7}$ alkoxy;

or $R^{10}$ and $R^{11}$ together with the interconnecting nitrogen form a heterocycloalkyl which is optionally substituted with one ore more halo, $C_{1-7}$ alkyl, halo-$C_{1-7}$ alkyl, hydroxy, $C_{1-7}$ alkoxy, oxo, COOH, CO—$C_{1-7}$ alkoxy or $NH_2$;

$R^{12}$ is H or $C_{1-7}$ alkyl;

wherein $C_{1-7}$ alkyl is optionally substituted with one or more hydroxy, $C_{1-7}$ alkoxy, COOH, or CO—$C_{1-7}$ alkoxy;

$R^{13}$ is H, $C_{1-7}$ alkyl, CO—$C_{1-7}$ alkoxy or heterocycloalkyl, wherein $C_{1-7}$ alkyl is optionally substituted with one or more hydroxy, $C_{1-7}$ alkoxy, $NH_2$, $N(C_{1-7}$ alkyl$)_2$, COOH, or CO—$C_{1-7}$ alkoxy;

or a pharmaceutically acceptable salt thereof.

Further, it is to be understood that every embodiment relating to a specific X, $Y^1$, $Y^2$, $Z^1$, $Z^2$, n, $R^1$, $R^2$, $R^3$, $R^4$, $R^5$, $R^6$, $R^7$, $R^8$, $R^9$, $R^{10}$, $R^{11}$, $R^{12}$, or $R^{13}$ as disclosed herein may be combined with any other embodiment relating to another X, $Y^1$, $Y^2$, $Z^1$, $Z^2$, n, $R^1$, $R^2$, $R^3$, $R^4$, $R^5$, $R^6$, $R^7$, $R^8$, $R^9$, $R^{10}$, $R^{11}$, $R^{12}$, or $R^{13}$ as disclosed herein.

In a particular embodiment, the present invention relates to a compound of formula (I)

(I)

wherein
X is —$CH_2$—$CH_2$—$CH_2$—, —CH═CH—CH═CH—, —$CH_2$—$CH_2$—$CH_2$—$CH_2$—, —$CH_2$—O—$CH_2$—$CH_2$—, —$CH_2$—$CH_2$—O—$CH_2$—, —$CH_2$—$NR^2$—$CH_2$—$CH_2$—, or —$CH_2$—$CH_2$—$NR^2$—$CH_2$—;

n is 0, 1 or 2;

each $R^1$ is independently selected from halo, $C_{1-7}$ alkyl, $C_{2-7}$ alkenyl, hydroxy, $C_{1-7}$ alkoxy, $NR^{10}R^{11}$, and $CONR^{10}R^{11}$;

wherein $C_{1-7}$ alkyl and $C_{1-7}$ alkoxy are optionally substituted by one or more $C_{1-7}$ alkyl, hydroxy, $C_{1-7}$ alkoxy, $NR^{10}R^{11}$ or $COR^9$;

with the proviso that if X is —CH═CH—CH═CH— then an optional R in position 8 of the phthalazin-1-onyl is fluoro;

$R^2$ is H, $C_{1-7}$ alkyl, hydroxy-$C_{1-7}$alkyl, $COR^9$, $CONR^{10}R^{11}$, or $SO_2$—$C_{1-7}$ alkyl;

$Y^1$ is N, CH or $CCH_3$, $Y^2$ is N or $CR^3$;

with the proviso that not both of $Y^1$ and $Y^2$ are N;

$R^3$ is H, halogen, $C_{1-7}$ alkyl, halo-$C_{1-7}$ alkyl, $CONR^{10}R^{11}$ or CO—$C_{1-7}$ alkoxy;

$R^4$ is H or $C_{1-7}$ alkyl, wherein $C_{1-7}$ alkyl is optionally substituted with one or more $R^5$;

each $R^5$ is independently selected from hydroxy, $C_{1-7}$ alkoxy, $NR^{12}R^{13}$, $COR^9$, $CONR^{10}R^{11}$, $SO_2$—$C_{1-7}$ alkyl, $SO_2$—$NR^{10}R^{11}$, heterocycloalkyl and heteroaryl;

wherein $C_{1-7}$ alkoxy is optionally substituted by $COR^9$ or $CONR^{10}R^{11}$;

wherein heterocycloalkyl and heteroaryl are optionally substituted with one or more substituents selected from halo, $C_{1-7}$ alkyl, halo-$C_{1-7}$ alkyl, hydroxy, $C_{1-7}$ alkoxy, oxo, $COR^9$, $C_{1-7}$ alkyl-$COR^9$ or $NR^{10}R^{11}$;

$Z^1$ is N, CH or CO—$CH_3$;

$Z^2$ is N or CH;

$R^6$ is $C_{1-7}$ alkyl, hydroxy-$C_{1-7}$ alkyl, halo-$C_{1-7}$ alkyl, $C_{1-7}$ alkoxy-$C_{1-7}$ alkyl, $C_{1-7}$ alkoxy, halo-$C_{1-7}$ alkoxy, $C_{1-7}$ alkoxy-$C_{1-7}$ alkoxy, S-halo-$C_{1-7}$ alkyl, $SF_5$, $C_{3-7}$ cycloalkyl, heterocycloalkyl or heterocycloalkyl substituted by $C_{1-7}$ alkyl;

$R^7$ is H, halogen or $C_{1-7}$ alkyl;

$R^8$ is H, halogen or $C_{1-7}$ alkyl;

$R^9$ is H, $C_{1-7}$ alkyl, hydroxy, or $C_{1-7}$ alkoxy;

$R^{10}$ is H or $C_{1-7}$ alkyl;

wherein $C_{1-7}$ alkyl is optionally substituted with one or more hydroxy, $C_{1-7}$ alkoxy, COOH, or CO—$C_{1-7}$ alkoxy;

$R^{11}$ is H, $C_{1-7}$ alkyl, CO—$C_{1-7}$ alkoxy or heterocycloalkyl;

wherein $C_{1-7}$ alkyl is optionally substituted with one or more hydroxy, $C_{1-7}$ alkoxy, $NH_2$, $N(C_{1-7}$ alkyl$)_2$, COOH, or CO—$C_{1-7}$ alkoxy;

or $R^{10}$ and $R^{11}$ together with the interconnecting nitrogen form a heterocycloalkyl which is optionally substituted with one ore more halo, $C_{1-7}$ alkyl, halo-$C_{1-7}$ alkyl, hydroxy, $C_{1-7}$ alkoxy, oxo, COOH, CO—$C_{1-7}$ alkoxy or $NH_2$;

$R^{12}$ is H or $C_{1-7}$ alkyl;

wherein $C_{1-7}$ alkyl is optionally substituted with one or more hydroxy, $C_{1-7}$ alkoxy, COOH, or CO—$C_{1-7}$ alkoxy;

$R^{13}$ is H, $C_{1-7}$ alkyl, CO—$C_{1-7}$ alkoxy or heterocycloalkyl, wherein $C_{1-7}$ alkyl is optionally substituted with one or more hydroxy, $C_{1-7}$ alkoxy, $NH_2$, $N(C_{1-7}$ alkyl$)_2$, COOH, or CO—$C_{1-7}$ alkoxy;

or a pharmaceutically acceptable salt thereof.

A particular embodiment of the invention relates to a compound of formula (IA)

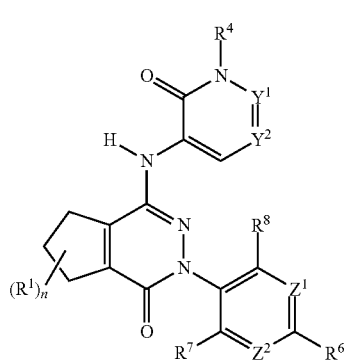

(IA)

wherein $Y^1$, $Y^2$, $Z^1$, $Z^2$, n, $R^1$, $R^4$ and $R^6$ to $R^8$ are as described herein, or a pharmaceutically acceptable salt thereof.

A particular embodiment of the invention relates to a compound of formula (IB)

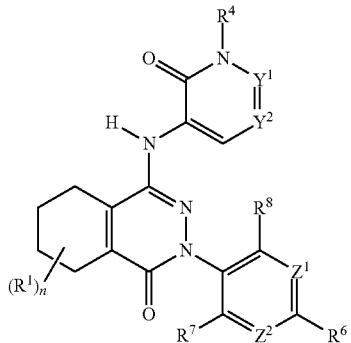

(IB)

wherein $Y^1$, $Y^2$, $Z^1$, $Z^2$, n, $R^1$, $R^4$ and $R^6$ to $R^8$ are as described herein, or a pharmaceutically acceptable salt thereof.

A particular embodiment of the invention relates to a compound of formula (IC)

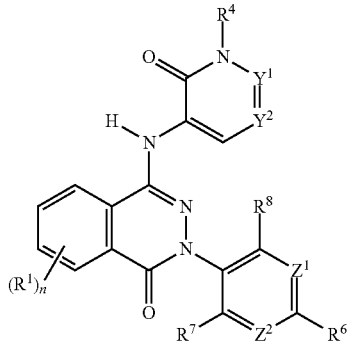

(IC)

wherein $Y^1$, $Y^2$, $Z^1$, $Z^2$, n, $R^1$, $R^4$ and $R^6$ to $R^8$ are as described herein, or a pharmaceutically acceptable salt thereof.

A particular embodiment of the invention relates to a compound of formula (ID)

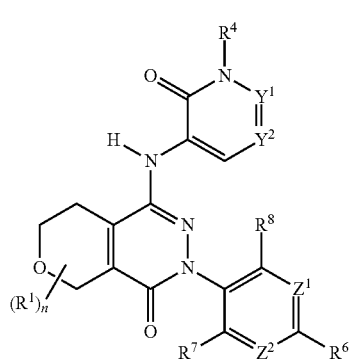

(ID)

wherein $Y^1$, $Y^2$, $Z^1$, $Z^2$, n, $R^1$, $R^4$ and $R^6$ to $R^8$ are as described herein, or a pharmaceutically acceptable salt thereof.

A particular embodiment of the invention relates to a compound of formula (IE)

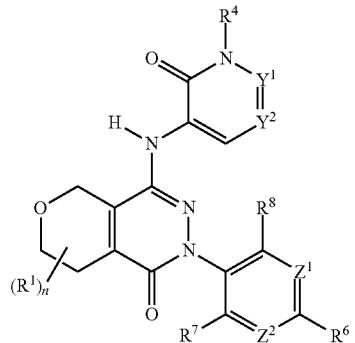

(IE)

wherein $Y^1$, $Y^2$, $Z^1$, $Z^2$, n, $R^1$, $R^4$ and $R^6$ to $R^8$ are as described herein, or a pharmaceutically acceptable salt thereof.

A particular embodiment of the invention relates to a compound of formula (IF)

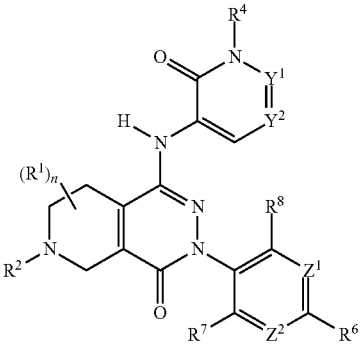

(IF)

wherein $Y^1$, $Y^2$, $Z^1$, $Z^2$, n, $R^1$, $R^2$, $R^4$ and $R^6$ to $R^8$ are as described herein, or a pharmaceutically acceptable salt thereof.

A particular embodiment of the invention relates to a compound of formula (IG)

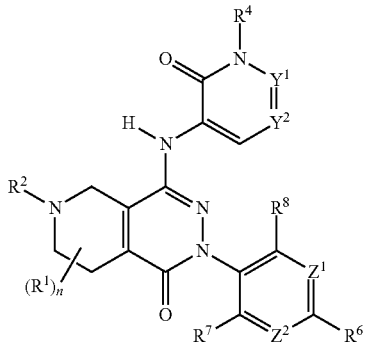

(IG)

wherein $Y^1$, $Y^2$, $Z^1$, $Z^2$, n, $R^1$, $R^2$, $R^4$ and $R^6$ to $R^8$ are as described herein, or a pharmaceutically acceptable salt thereof.

A particular embodiment of the present invention relates to compounds of formula (I), wherein X is —$CH_2$—$CH_2$—$CH_2$—, —CH=CH—CH=CH—, —$CH_2$—$CH_2$—$CH_2$—$CH_2$—, —$CH_2$—$NR^2$—$CH_2$—$CH_2$—, or —$CH_2$—$CH_2$—$NR^2$—$CH_2$—.

A particular embodiment of the present invention relates to compounds of formula (I), (IA), (IB), (IC), (ID), (IE), (IF) or (IG), wherein n is 0 or 1.

A particular embodiment of the present invention relates to compounds of formula (I), (IA), (IB), (IC), (ID), (IE), (IF) or (IG), wherein each $R^1$ is independently selected from $C_{1-7}$ alkyl, hydroxy, $C_{1-7}$ alkoxy, and $NR^{10}R^{11}$; wherein $C_{1-7}$ alkyl is optionally substituted by one hydroxy.

A particular embodiment of the present invention relates to compounds of formula (I), (IA), (IB), (IC), (ID), (IE), (IF) or (IG), wherein each $R^1$ is independently selected from $C_{1-7}$ alkyl and $C_{1-7}$ alkoxy; wherein $C_{1-7}$ alkyl is optionally substituted by one hydroxy.

A particular embodiment of the present invention relates to compounds of formula (I), (IA), (IB), (IC), (ID), (IE), (IF) or (IG), wherein each $R^1$ is independently selected from fluoro, methyl, ethyl, ethenyl, hydroxy, methoxy, ethoxy, $NH_2$ and $CONH_2$; wherein methyl, ethyl, methoxy, and ethoxy are optionally substituted by one methyl, hydroxy, methoxy, $NH_2$ or $N(CH_3)_2$.

A particular embodiment of the present invention relates to compounds of formula (I), (IA), (IB), (IC), (ID), (IE), (IF) or (IG), wherein each $R^1$ is independently selected from methyl, ethyl, hydroxy, methoxy, ethoxy, and $NH_2$; wherein methyl is optionally substituted by one hydroxy.

A particular embodiment of the present invention relates to compounds of formula (I), (IA), (IB), (IC), (ID), (IE), (IF) or (IG), wherein each $R^1$ is independently selected from methyl, ethyl, and methoxy; wherein methyl is optionally substituted by one hydroxy.

A particular embodiment of the present invention relates to compounds of formula (I), (IA), (IB), (IC), (ID), (IE), (IF) or (IG), wherein $R^2$ is $COR^9$.

A particular embodiment of the present invention relates to compounds of formula (I), (IA), (IB), (IC), (ID), (IE), (IF) or (IG), wherein $R^2$ is H, methyl, ethyl, isopropyl, propyl, isobutyl, hydroxy-methyl, hydroxy-ethyl, hydroxy-isopropyl, hydroxy-propyl, hydroxy-isobutyl, COH, $COCH_3$, $COOCH_3$, $CONHCH_3$, or $SO_2$—$CH_3$.

A particular embodiment of the present invention relates to compounds of formula (I), (IA), (IB), (IC), (ID), (IE), (IF) or (IG), wherein $R^2$ is $COCH_3$ or $COOCH_3$.

A particular embodiment of the present invention relates to compounds of formula (I), (IA), (IB), (IC), (ID), (IE), (IF) or (IG), wherein $R^2$ is $COCH_3$.

A particular embodiment of the present invention relates to compounds of formula (I), (IA), (IB), (IC), (ID), (IE), (IF) or (IG), wherein $Y^1$ is N or CH, with the proviso that not both of $Y^1$ and $Y^2$ are N.

A particular embodiment of the present invention relates to compounds of formula (I), (IA), (IB), (IC), (ID), (IE), (IF) or (IG), wherein $Y^1$ is CH.

A particular embodiment of the present invention relates to compounds of formula (I), (IA), (IB), (IC), (ID), (IE), (IF) or (IG), wherein $Y^2$ is N with the proviso that not both of $Y^1$ and $Y^2$ are N.

A particular embodiment of the present invention relates to compounds of formula (I), (IA), (IB), (IC), (ID), (IE), (IF) or (IG), wherein $Y^2$ is $CR^3$.

A particular embodiment of the present invention relates to compounds of formula (I), (IA), (IB), (IC), (ID), (IE), (IF) or (IG), wherein $R^3$ is H, halogen, or $C_{1-7}$ alkyl.

A particular embodiment of the present invention relates to compounds of formula (I), (IA), (IB), (IC), (ID), (IE), (IF) or (IG), wherein $R^3$ is H, fluoro, chloro, methyl, ethyl, isopropyl, trifluoromethyl, $CONHCH_3$ or $COOCH_3$.

A particular embodiment of the present invention relates to compounds of formula (I), (IA), (IB), (IC), (ID), (IE), (IF) or (IG), wherein $R^3$ is H, fluoro, chloro, or methyl.

A particular embodiment of the present invention relates to compounds of formula (I), (IA), (IB), (IC), (ID), (IE), (IF) or (IG), wherein $R^4$ is H or $C_{1-7}$ alkyl, wherein $C_{1-7}$ alkyl is optionally substituted with one $R^5$.

A particular embodiment of the present invention relates to compounds of formula (I), (IA), (IB), (IC), (ID), (IE), (IF) or (IG), wherein $R^4$ is $C_{1-7}$ alkyl optionally substituted with one or two $R^5$.

A particular embodiment of the present invention relates to compounds of formula (I), (IA), (IB), (IC), (ID), (IE), (IF) or (IG), wherein $R^4$ is $C_{1-7}$ alkyl optionally substituted with one $R^5$.

A particular embodiment of the present invention relates to compounds of formula (I), (IA), (IB), (IC), (ID), (IE), (IF) or (IG), wherein $R^4$ is H, methyl, ethyl, propyl or isobutyl, wherein methyl, ethyl, propyl and isobutyl are optionally substituted with one or two $R^5$.

A particular embodiment of the present invention relates to compounds of formula (I), (IA), (IB), (IC), (ID), (IE), (IF) or (IG), wherein $R^4$ is methyl, ethyl, propyl or isobutyl, each optionally substituted with one $R^5$.

A particular embodiment of the present invention relates to compounds of formula (I), (IA), (IB), (IC), (ID), (IE), (IF) or (IG), wherein $R^4$ is methyl, ethyl, or propyl, each optionally substituted with one $R^5$.

A particular embodiment of the present invention relates to compounds of formula (I), (IA), (IB), (IC), (ID), (IE), (IF) or (IG), wherein each $R^5$ is independently selected from hydroxy, $C_{1-7}$ alkoxy, $NR^{12}R^{13}$, $COR^9$, $CONR^{10}R^{11}$, $SO_2$—$C_{1-7}$ alkyl, $SO_2$—$NR^{10}R^{11}$, heterocycloalkyl and heteroaryl; wherein $C_{1-7}$ alkoxy is optionally substituted by $COR^9$ or $CONR^{10}R^{11}$;
wherein heterocycloalkyl and heteroaryl are optionally substituted with one or two substituents selected from halo, $C_{1-7}$ alkyl, halo-$C_{1-7}$ alkyl, hydroxy, $C_{1-7}$ alkoxy, oxo, $COR^9$, $C_{1-7}$ alkyl-$COR^9$ and $NR^{10}R^{11}$.

A particular embodiment of the present invention relates to compounds of formula (I), (IA), (IB), (IC), (ID), (IE), (IF) or (IG), wherein each $R^5$ is independently selected from hydroxy, $C_{1-7}$ alkoxy, $NR^{12}R^{13}$, $COR^9$, $CONR^{10}R^{11}$, $SO_2$—$C_{1-7}$ alkyl, $SO_2$—$NR^{10}R^{11}$, and heterocycloalkyl; wherein $C_{1-7}$ alkoxy is optionally substituted by $COR^9$ or $CONR^{10}R^{11}$;
wherein heterocycloalkyl is optionally substituted with one substituent selected from $C_{1-7}$ alkyl, hydroxy, $C_{1-7}$ alkoxy, and $COR^9$.

A particular embodiment of the present invention relates to compounds of formula (I), (IA), (IB), (IC), (ID), (IE), (IF) or (IG), wherein each $R^5$ is independently selected from hydroxy, $NR^{12}R^{13}$, $CONR^{10}R^{11}$, and heterocycloalkyl; wherein heterocycloalkyl is optionally substituted with one $C_{1-7}$ alkyl.

A particular embodiment of the present invention relates to compounds of formula (I), (IA), (IB), (IC), (ID), (IE), (IF) or (IG), wherein each $R^5$ is independently selected from hydroxy, methoxy, $NR^{12}R^{13}$, $COR^9$, $CONR^{10}R^{11}$, $SO_2$-methyl, $SO_2$—$NH_2$, azetidinyl, pyrrolidinyl, piperazinyl, morpholinyl and imidazolyl;
wherein methoxy is optionally substituted by $COR^9$ or $CONR^{10}R^{11}$;
wherein azetidinyl, pyrrolidinyl, piperazinyl, morpholinyl and imidazolyl are optionally substituted with one or two substituents selected from methyl, trifluoromethyl, hydroxy, methoxy, $COR^9$, and $NR^{10}R^{11}$.

A particular embodiment of the present invention relates to compounds of formula (I), (IA), (IB), (IC), (ID), (IE), (IF) or (IG), wherein each $R^5$ is independently selected from hydroxy, methoxy, $NH_2$, $NHCH_3$, $N(CH_3)$, $N(CH_2CH_3)_2$, $NH(CH_2COOH)$, $NH(COO$-tert-butyl$)$, $N(CH_3)(CH_2COOH)$, $N(CH_2COOH)(COO$-tert-butyl$)$, $NH($oxetanyl$)$, $COOH$, $COOCH_3$, $CONH_2$, $CONH(CH_3)$, $CONH(CH_2CH_2N(CH_3)_2)$, $CONH(CH_2CH_2OH)$, $CONH(CH_2CH_2CH_2OCH_3)$, $CONH(CH(CH_3)_2)$, $CON(CH_3)_2$, $SO_2$-methyl, $SO_2$—$NH_2$, azetidinyl, pyrrolidinyl, piperazinyl, morpholinyl and imidazolyl;
wherein methoxy is optionally substituted by $COOH$, $COOCH_2CH_3$, $CONH(CH_3)$, or $CON(CH_3)_2$;
wherein azetidinyl, pyrrolidinyl, piperazinyl, morpholinyl and imidazolyl are optionally substituted with one or two substituents selected from methyl, trifluoromethyl, hydroxy, methoxy, $COOH$, $COOCH_3$, and $COOCH_2CH_3$.

A particular embodiment of the present invention relates to compounds of formula (I), (IA), (IB), (IC), (ID), (IE), (IF) or (IG), wherein each $R^5$ is independently selected from hydroxy, methoxy, $NR^{12}R^{13}$, $COR^9$, $CONR^{10}R^{11}$, $SO_2$-methyl, $SO_2$—$NR^{10}R^{11}$, azetidinyl, pyrrolidinyl, piperazinyl, and morpholinyl;
wherein methoxy is optionally substituted by $COR^9$ or $CONR^{10}R^{11}$;
wherein azetidinyl, pyrrolidinyl, piperazinyl, and morpholinyl is optionally substituted with one substituent selected from methyl, hydroxy, methoxy, or $COR^9$.

A particular embodiment of the present invention relates to compounds of formula (I), (IA), (IB), (IC), (ID), (IE), (IF) or (IG), wherein each $R^5$ is independently selected from hydroxy, methoxy, $N(CH_3)$, $N(CH_2CH_3)_2$, $NH($oxetanyl$)$, $COOCH_3$, $CONH(CH_3)$, $CONH(CH_2CH_2CH_2OCH_3)$, $CON(CH_3)_2$, $SO_2$-methyl, $SO_2$—$NH_2$, azetidinyl, pyrrolidinyl, piperazinyl, and morpholinyl;
wherein methoxy is optionally substituted by $CONH(CH_3)$, or $CON(CH_3)_2$;
wherein azetidinyl, pyrrolidinyl, piperazinyl, and morpholinyl is optionally substituted with one substituent selected from methyl, hydroxy, methoxy, and $COOCH_3$.

A particular embodiment of the present invention relates to compounds of formula (I), (IA), (IB), (IC), (ID), (IE), (IF) or (IG), wherein each $R^5$ is independently selected from hydroxy, $N(CH_3)$, $CONH(CH_3)$, $CON(CH_3)_2$, piperazinyl, and piperazinyl substituted with one methyl.

A particular embodiment of the present invention relates to compounds of formula (I), (IA), (IB), (IC), (ID), (IE), (IF) or (IG), wherein $Z^1$ is N or CH.

A particular embodiment of the present invention relates to compounds of formula (I), (IA), (IB), (IC), (ID), (IE), (IF) or (IG), wherein $Z^1$ is N.

A particular embodiment of the present invention relates to compounds of formula (I), (IA), (IB), (IC), (ID), (IE), (IF) or (IG), wherein $Z^1$ is CH.

A particular embodiment of the present invention relates to compounds of formula (I), (IA), (IB), (IC), (ID), (IE), (IF) or (IG), wherein $Z^2$ is N.

A particular embodiment of the present invention relates to compounds of formula (I), (IA), (IB), (IC), (ID), (IE), (IF) or (IG), wherein $Z^2$ is CH.

A particular embodiment of the present invention relates to compounds of formula (I), (IA), (IB), (IC), (ID), (IE), (IF) or (IG), wherein $R^6$ is $C_{1-7}$ alkyl, halo-$C_{1-7}$ alkyl, or halo-$C_{1-7}$ alkoxy.

A particular embodiment of the present invention relates to compounds of formula (I), (IA), (IB), (IC), (ID), (IE), (IF) or (IG), wherein $R^6$ is tert-butyl, hydroxy-isopropyl, trifluoromethyl, methoxy, ethoxy, methoxy-ethoxy, difluoromethoxy, trifluoromethoxy, cyclopropyl, oxetanyl or methyl-oxetanyl.

A particular embodiment of the present invention relates to compounds of formula (I), (IA), (IB), (IC), (ID), (IE), (IF) or (IG), wherein $R^6$ is tert-butyl, trifluoromethyl, difluoromethoxy or trifluoromethoxy.

A particular embodiment of the present invention relates to compounds of formula (I), (IA), (IB), (IC), (ID), (IE), (IF) or (IG), wherein $R^6$ is tert-butyl, trifluoromethyl, or trifluoromethoxy.

A particular embodiment of the present invention relates to compounds of formula (I), (IA), (IB), (IC), (ID), (IE), (IF) or (IG), wherein $R^7$ is H.

A particular embodiment of the present invention relates to compounds of formula (I), (IA), (IB), (IC), (ID), (IE), (IF) or (IG), wherein $R^8$ is H, fluoro or methyl.

A particular embodiment of the present invention relates to compounds of formula (I), (IA), (IB), (IC), (ID), (IE), (IF) or (IG), wherein $R^8$ is H.

A particular embodiment of the present invention relates to compounds of formula (I), (IA), (IB), (IC), (ID), (IE), (IF) or (IG), wherein $R^9$ is H, $C_{1-7}$ alkyl or $C_{1-7}$ alkoxy.

A particular embodiment of the present invention relates to compounds of formula (I), (IA), (IB), (IC), (ID), (IE), (IF) or (IG), wherein $R^9$ is H, methyl, hydroxy, methoxy or ethoxy.

A particular embodiment of the present invention relates to compounds of formula (I), (IA), (IB), (IC), (ID), (IE), (IF) or (IG), wherein $R^9$ is methyl or methoxy.

A particular embodiment of the present invention relates to compounds of formula (I), (IA), (IB), (IC), (ID), (IE), (IF) or (IG), wherein $R^{10}$ is H, $C_{1-7}$ alkyl or $C_{1-7}$ alkyl substituted with one COOH.

A particular embodiment of the present invention relates to compounds of formula (I), (IA), (IB), (IC), (ID), (IE), (IF) or (IG), wherein $R^{10}$ is H, methyl, ethyl or $CH_2$—COOH.

A particular embodiment of the present invention relates to compounds of formula (I), (IA), (IB), (IC), (ID), (IE), (IF) or (IG), wherein $R^{10}$ is H, methyl or ethyl.

A particular embodiment of the present invention relates to compounds of formula (I), (IA), (IB), (IC), (ID), (IE), (IF) or (IG), wherein $R^{10}$ is H or methyl.

A particular embodiment of the present invention relates to compounds of formula (I), (IA), (IB), (IC), (ID), (IE), (IF) or (IG), wherein $R^{11}$ is is H, $C_{1-7}$ alkyl, $C_{1-7}$ alkyl substituted with one hydroxy, $C_{1-7}$ alkyl substituted with one $C_{1-7}$ alkoxy, $C_{1-7}$ alkyl substituted with one $N(CH_3)_2$, $C_{1-7}$ alkyl substituted with one COOH, CO—$C_{1-7}$ alkoxy or heterocycloalkyl.

A particular embodiment of the present invention relates to compounds of formula (I), (IA), (IB), (IC), (ID), (IE), (IF) or (IG), wherein $R^{11}$ is is H, $C_{1-7}$ alkyl, or $C_{1-7}$ alkyl substituted with one $C_{1-7}$ alkoxy.

A particular embodiment of the present invention relates to compounds of formula (I), (IA), (IB), (IC), (ID), (IE), (IF) or (IG), wherein $R^{11}$ is is H, methyl, ethyl, isopropyl, hydroxy-ethyl, methoxy-propyl, ethyl substituted with one $N(CH_3)_2$, $CH_2$—COOH, CO-tert-butoxy or oxetanyl.

A particular embodiment of the present invention relates to compounds of formula (I), (IA), (IB), (IC), (ID), (IE), (IF) or (IG), wherein $R^{11}$ is is H, methyl, ethyl, or methoxy-propyl.

A particular embodiment of the present invention relates to compounds of formula (I), (IA), (IB), (IC), (ID), (IE), (IF) or (IG), wherein $R^{11}$ is is methyl.

A particular embodiment of the present invention relates to compounds of formula (I), (IA), (IB), (IC), (ID), (IE), (IF) or (IG), wherein $R^{10}$ and $R^{11}$ together with the interconnecting nitrogen form a heterocycloalkyl which is optionally substituted with one ore more halo, $C_{1-7}$ alkyl, halo-$C_{1-7}$ alkyl, hydroxy, $C_{1-7}$ alkoxy, oxo, COOH, CO—$C_{1-7}$ alkoxy or $NH_2$.

A particular embodiment of the present invention relates to compounds of formula (I), (IA), (IB), (IC), (ID), (IE), (IF) or (IG), wherein $R^{10}$ and $R^{11}$ together with the interconnecting nitrogen form azetidinyl, piperazinyl, morpholinyl, imidazolyl or pyrrolidinyl, each optionally substituted with one ore two halo, $C_{1-7}$ alkyl, halo-$C_{1-7}$ alkyl, hydroxy, $C_{1-7}$ alkoxy, oxo, COOH, CO—$C_{1-7}$ alkoxy or $NH_2$.

A particular embodiment of the present invention relates to compounds of formula (I), (IA), (IB), (IC), (ID), (IE), (IF) or (IG), wherein $R^{10}$ and $R^{11}$ together with the interconnecting nitrogen form azetidinyl, piperazinyl, morpholinyl, imidazolyl or pyrrolidinyl, each optionally substituted with one ore two methyl, trifluoromethyl, hydroxy, methoxy, COOH, CO-methoxy or CO-ethoxy.

A particular embodiment of the present invention relates to compounds of formula (I), (IA), (IB), (IC), (ID), (IE), (IF) or (IG), wherein $R^{12}$ is H, $C_{1-7}$ alkyl or alkyl substituted by one COOH.

A particular embodiment of the present invention relates to compounds of formula (I), (IA), (IB), (IC), (ID), (IE), (IF) or (IG), wherein $R^{12}$ is H, methyl, ethyl or $CH_2$—COOH.

A particular embodiment of the present invention relates to compounds of formula (I), (IA), (IB), (IC), (ID), (IE), (IF) or (IG), wherein $R^{13}$ is H, $C_{1-7}$ alkyl, $C_{1-7}$ alkyl substituted with one COOH, CO—$C_{1-7}$ alkoxy or heterocycloalkyl.

A particular embodiment of the present invention relates to compounds of formula (I), (IA), (IB), (IC), (ID), (IE), (IF) or (IG), wherein $R^{13}$ is H, $C_{1-7}$ alkyl, $C_{1-7}$ alkyl substituted with one COOH, CO—$C_{1-7}$ alkoxy or oxetanyl.

A particular embodiment of the present invention relates to compounds of formula (I), (IA), (IB), (IC), (ID), (IE), (IF) or (IG), wherein $R^{13}$ is H, methyl, ethyl, $CH_2$—COOH, CO-tert butoxy or oxetanyl.

Particular compounds of formula (I) of the present invention are those selected from the group consisting of:

4-[(1-methyl-2-oxo-3-pyridyl)amino]-2-[4-(trifluoromethoxy)phenyl]phthalazin-1-one;

4-[(2-oxo-1H-pyridin-3-yl)amino]-2-[4-(trifluoromethoxy)phenyl]phthalazin-1-one;

methyl 2-[2-oxo-3-[[4-oxo-3-[4-(trifluoromethoxy)phenyl]phthalazin-1-yl]amino]-1-pyridyl]acetate;

methyl 2,2-dimethyl-3-[2-oxo-3-[[4-oxo-3-[4-(trifluoromethoxy)phenyl]phthalazin-1-yl]amino]-1-pyridyl]propanoate;

ethyl 2-[2-[2-oxo-3-[[4-oxo-3-[4-(trifluoromethoxy)phenyl]phthalazin-1-yl]amino]-1-pyridyl]ethoxy]acetate;

methyl (2R)-1-[2-[2-oxo-3-[[4-oxo-3-[4-(trifluoromethoxy)phenyl]phthalazin-1-yl]amino]-1-pyridyl]ethyl]pyrrolidine-2-carboxylate;

4-[(1-methyl-2-oxo-3-pyridyl)amino]-2-[2-methyl-4-(trifluoromethoxy)phenyl]phthalazin-1-one;

2-(6-tert-butyl-3-pyridyl)-4-[(1-methyl-2-oxo-3-pyridyl)amino]phthalazin-1-one;

2-(2-tert-butylpyrimidin-5-yl)-4-[(1-methyl-2-oxo-3-pyridyl)amino]phthalazin-1-one;

2-[4-(3-methyloxetan-3-yl)phenyl]-4-[(1-methyl-2-oxo-3-pyridyl)amino]phthalazin-1-one;

4-[(1-methyl-2-oxo-3-pyridyl)amino]-2-[4-(oxetan-3-yl)phenyl]phthalazin-1-one;

2-(4-cyclopropylphenyl)-4-[(1-methyl-2-oxo-3-pyridyl)amino]phthalazin-1-one;

2-[4-(2-methoxyethoxy)phenyl]-4-[(1-methyl-2-oxo-3-pyridyl)amino]phthalazin-1-one;

2-(4-tert-butylphenyl)-4-[(1-methyl-2-oxo-3-pyridyl)amino]phthalazin-1-one;

2-(4-tert-butylphenyl)-4-[(2-oxo-1H-pyridin-3-yl)amino]phthalazin-1-one;

7-methoxy-4-[(1-methyl-2-oxo-3-pyridyl)amino]-2-[4-(trifluoromethoxy)phenyl]phthalazin-1-one;

8-fluoro-4-[(1-methyl-2-oxo-3-pyridyl)amino]-2-[4-(trifluoromethoxy)phenyl]phthalazin-1-one;

5-fluoro-4-[(1-methyl-2-oxo-3-pyridyl)amino]-2-[4-(trifluoromethoxy)phenyl]phthalazin-1-one;

5-methoxy-4-[(1-methyl-2-oxo-3-pyridyl)amino]-2-[4-(trifluoromethoxy)phenyl]phthalazin-1-one;

2-(4-tert-butylphenyl)-7-ethyl-4-[(1-methyl-2-oxo-3-pyridyl)amino]phthalazin-1-one;

4-[(1-methyl-2-oxo-3-pyridyl)amino]-2-[4-(trifluoromethoxy)phenyl]-5,6,7,8-tetrahydrophthalazin-1-one;

4-[(1-methyl-6-oxo-pyrimidin-5-yl)amino]-2-[4-(trifluoromethoxy)phenyl]-5,6,7,8-tetrahydrophthalazin-1-one;

methyl 1-methyl-6-oxo-5-[[4-oxo-3-[4-(trifluoromethoxy)phenyl]-5,6,7,8-tetrahydrophthalazin-1-yl]amino]pyridine-3-carboxylate;

methyl 2-[2-oxo-3-[[4-oxo-3-[4-(trifluoromethoxy)phenyl]-5,6,7,8-tetrahydrophthalazin-1-yl]amino]-1-pyridyl]acetate;

4-[[1-[2-(dimethylamino)ethyl]-6-oxo-pyrimidin-5-yl]amino]-2-[4-(trifluoromethoxy)phenyl]-5,6,7,8-tetrahydrophthalazin-1-one;

2-(6-tert-butyl-3-pyridyl)-4-[(1-methyl-2-oxo-3-pyridyl)amino]-5,6,7,8-tetrahydrophthalazin-1-one;

2-[4-(difluoromethoxy)phenyl]-4-[(1-methyl-2-oxo-3-pyridyl)amino]-5,6,7,8-tetrahydrophthalazin-1-one;

1-[(1-methyl-2-oxo-3-pyridyl)amino]-3-[4-(trifluoromethoxy)phenyl]-6,7-dihydro-5H-cyclopenta[d]pyridazin-4-one;

1-[(2,6-dimethyl-3-oxo-pyridazin-4-yl)amino]-3-[4-(trifluoromethoxy)phenyl]-6,7-dihydro-5H-cyclopenta[d]pyridazin-4-one;

1-[(1-methyl-6-oxo-pyrimidin-5-yl)amino]-3-[4-(trifluoromethoxy)phenyl]-6,7-dihydro-5H-cyclopenta[d]pyridazin-4-one;

1-[(5-fluoro-1-methyl-2-oxo-3-pyridyl)amino]-3-[4-(trifluoromethoxy)phenyl]-6,7-dihydro-5H-cyclopenta[d]pyridazin-4-one;

1-[(1,5-dimethyl-2-oxo-3-pyridyl)amino]-3-[4-(trifluoromethoxy)phenyl]-6,7-dihydro-5H-cyclopenta[d]pyridazin-4-one;

1-[(5-chloro-1-methyl-2-oxo-3-pyridyl)amino]-3-[4-(trifluoromethoxy)phenyl]-6,7-dihydro-5H-cyclopenta[d]pyridazin-4-one;

1-[[1-methyl-2-oxo-5-(trifluoromethyl)-3-pyridyl]amino]-3-[4-(trifluoromethoxy)phenyl]-6,7-dihydro-5H-cyclopenta[d]pyridazin-4-one;

1-[(5-ethyl-1-methyl-2-oxo-3-pyridyl)amino]-3-[4-(trifluoromethoxy)phenyl]-6,7-dihydro-5H-cyclopenta[d]pyridazin-4-one;

1-[(5-isopropyl-1-methyl-2-oxo-3-pyridyl)amino]-3-[4-(trifluoromethoxy)phenyl]-6,7-dihydro-5H-cyclopenta[d]pyridazin-4-one;

methyl 4-[5-chloro-2-oxo-3-[[4-oxo-3-[4-(trifluoromethoxy)phenyl]-6,7-dihydro-5H-cyclopenta[d]pyridazin-1-yl]amino]-1-pyridyl]butanoate;

methyl 4-[2-oxo-3-[[4-oxo-3-[4-(trifluoromethoxy)phenyl]-6,7-dihydro-5H-cyclopenta[d]pyridazin-1-yl]amino]-1-pyridyl]butanoate;

ethyl 2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetate;

1-[[1-(2-imidazol-1-ylethyl)-2-oxo-3-pyridyl]amino]-3-[4-(trifluoromethoxy)phenyl]-6,7-dihydro-5H-cyclopenta[d]pyridazin-4-one;

ethyl 4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-2-carboxylate;

1-[[1-[2-(3-methoxypyrrolidin-1-yl)ethyl]-2-oxo-3-pyridyl]amino]-3-[4-(trifluoromethoxy)phenyl]-6,7-dihydro-5H-cyclopenta[d]pyridazin-4-one;

2-[tert-butoxycarbonyl-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]amino]acetic acid;

1-[[1-(3-morpholinopropyl)-2-oxo-3-pyridyl]amino]-3-[4-(trifluoromethoxy)phenyl]-6,7-dihydro-5H-cyclopenta[d]pyridazin-4-one;

tert-butyl N-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]carbamate;

1-[[1-[2-(3-hydroxyazetidin-1-yl)ethyl]-2-oxo-3-pyridyl]amino]-3-[4-(trifluoromethoxy)phenyl]-6,7-dihydro-5H-cyclopenta[d]pyridazin-4-one;

1-[[1-(2-hydroxyethyl)-6-oxo-pyrimidin-5-yl]amino]-3-[4-(trifluoromethoxy)phenyl]-6,7-dihydro-5H-cyclopenta[d]pyridazin-4-one;

1-[[1-[3-(4-methylpiperazin-1-yl)propyl]-2-oxo-3-pyridyl]amino]-3-[4-(trifluoromethoxy)phenyl]-6,7-dihydro-5H-cyclopenta[d]pyridazin-4-one;

1-[[1-(3-hydroxypropyl)-2-oxo-3-pyridyl]amino]-3-[4-(trifluoromethoxy)phenyl]-6,7-dihydro-5H-cyclopenta[d]pyridazin-4-one;

1-[[1-[2-(dimethylamino)ethyl]-6-oxo-pyrimidin-5-yl]amino]-3-[4-(trifluoromethoxy)phenyl]-6,7-dihydro-5H-cyclopenta[d]pyridazin-4-one;

1-[[1-[2-(diethylamino)ethyl]-6-oxo-pyrimidin-5-yl]amino]-3-[4-(trifluoromethoxy)phenyl]-6,7-dihydro-5H-cyclopenta[d]pyridazin-4-one;

1-[[6-oxo-1-(2-pyrrolidin-1-ylethyl)pyrimidin-5-yl]amino]-3-[4-(trifluoromethoxy)phenyl]-6,7-dihydro-5H-cyclopenta[d]pyridazin-4-one;

3-(4-tert-butyl-2-fluoro-phenyl)-1-[(1-methyl-2-oxo-3-pyridyl)amino]-6,7-dihydro-5H-cyclopenta[d]pyridazin-4-one;

3-[2-fluoro-4-(trifluoromethyl)phenyl]-1-[(1-methyl-2-oxo-3-pyridyl)amino]-6,7-dihydro-5H-cyclopenta[d]pyridazin-4-one;

3-(6-ethoxy-3-pyridyl)-1-[(1-methyl-2-oxo-3-pyridyl)amino]-6,7-dihydro-5H-cyclopenta[d]pyridazin-4-one;

3-(6-methoxy-3-pyridyl)-1-[(1-methyl-2-oxo-3-pyridyl)amino]-6,7-dihydro-5H-cyclopenta[d]pyridazin-4-one;

1-[(5-fluoro-1-methyl-2-oxo-3-pyridyl)amino]-3-(6-methoxy-3-pyridyl)-6,7-dihydro-5H-cyclopenta[d]pyridazin-4-one;

3-(6-tert-butyl-3-pyridyl)-1-[(1-methyl-2-oxo-3-pyridyl)amino]-6,7-dihydro-5H-cyclopenta[d]pyridazin-4-one;

3-[4-(difluoromethoxy)phenyl]-1-[(1-methyl-2-oxo-3-pyridyl)amino]-6,7-dihydro-5H-cyclopenta[d]pyridazin-4-one;

1-[(1-methyl-2-oxo-3-pyridyl)amino]-3-[4-(trifluoromethyl)phenyl]-6,7-dihydro-5H-cyclopenta[d]pyridazin-4-one;

6,6-dimethyl-1-[(1-methyl-2-oxo-3-pyridyl)amino]-3-[4-(trifluoromethoxy)phenyl]-5,7-dihydrocyclopenta[d]pyridazin-4-one;

1-[(1-methyl-2-oxo-3-pyridyl)amino]-3-[4-(trifluoromethoxy)phenyl]-7,8-dihydro-5H-pyrano[3,4-d]pyridazin-4-one;

4-[(1-methyl-2-oxo-3-pyridyl)amino]-2-[4-(trifluoromethoxy)phenyl]-7,8-dihydro-5H-pyrano[3,4-d]pyridazin-1-one;

4-[(1,6-dimethyl-2-oxo-3-pyridyl)amino]-2-[4-(trifluoromethoxy)phenyl]phthalazin-1-one;

4-[(2-methyl-6-oxo-1H-pyrimidin-5-yl)amino]-2-[4-(trifluoromethoxy)phenyl]phthalazin-1-one;

4-[(1-methyl-6-oxo-pyrimidin-5-yl)amino]-2-[4-(trifluoromethoxy)phenyl]phthalazin-1-one;

4-[(5-ethyl-1-methyl-2-oxo-3-pyridyl)amino]-2-[4-(trifluoromethoxy)phenyl]phthalazin-1-one;

4-[(6-methyl-2-oxo-1H-pyridin-3-yl)amino]-2-[4-(trifluoromethoxy)phenyl]phthalazin-1-one;

methyl 3-[2-oxo-3-[[4-oxo-3-[4-(trifluoromethoxy)phenyl]phthalazin-1-yl]amino]-1-pyridyl]propanoate;

4-[[1-[2-(dimethylamino)ethyl]-2-oxo-3-pyridyl]amino]-2-[4-(trifluoromethoxy)phenyl]phthalazin-1-one;

4-[[1-(2-methoxyethyl)-2-oxo-3-pyridyl]amino]-2-[4-(trifluoromethoxy)phenyl]phthalazin-1-one;

4-[[1-(2-methylsulfonylethyl)-2-oxo-3-pyridyl]amino]-2-[4-(trifluoromethoxy)phenyl]phthalazin-1-one;

methyl 4-[2-oxo-3-[[4-oxo-3-[4-(trifluoromethoxy)phenyl]phthalazin-1-yl]amino]-1-pyridyl]butanoate;

3-[2-oxo-3-[[4-oxo-3-[4-(trifluoromethoxy)phenyl]phthalazin-1-yl]amino]-1-pyridyl]propane-1-sulfonamide;

N,N-dimethyl-3-[2-oxo-3-[[4-oxo-3-[4-(trifluoromethoxy)phenyl]phthalazin-1-yl]amino]-1-pyridyl]propane-1-sulfonamide;

4-[[1-(2-morpholinoethyl)-2-oxo-3-pyridyl]amino]-2-[4-(trifluoromethoxy)phenyl]phthalazin-1-one;

4-[[1-[2-[3-hydroxy-3-(trifluoromethyl)azetidin-1-yl]
ethyl]-2-oxo-3-pyridyl]amino]-2-[4-(trifluoromethoxy)
phenyl]phthalazin-1-one;
4-[[1-[2-(3-hydroxypyrrolidin-1-yl)ethyl]-2-oxo-3-pyridyl]
amino]-2-[4-(trifluoromethoxy)phenyl]phthalazin-1-one;
methyl (2S)-1-[2-[2-oxo-3-[[4-oxo-3-[4-(trifluoromethoxy)
phenyl]phthalazin-1-yl]amino]-1-pyridyl]ethyl]pyrrolidine-2-carboxylate;
4-[[1-[2-(dimethylamino)ethyl]-6-oxo-pyrimidin-5-yl]
amino]-2-[4-(trifluoromethoxy)phenyl]phthalazin-1-one;
6-ethyl-4-[(1-methyl-2-oxo-3-pyridyl)amino]-2-[4-(trifluoromethoxy)phenyl]phthalazin-1-one;
7-ethyl-4-[(1-methyl-2-oxo-3-pyridyl)amino]-2-[4-(trifluoromethoxy)phenyl]phthalazin-1-one;
4-[(1-methyl-2-oxo-3-pyridyl)amino]-2-[4-(trifluoromethoxy)phenyl]-6-vinyl-phthalazin-1-one;
4-[(1-methyl-2-oxo-3-pyridyl)amino]-2-[4-(trifluoromethoxy)phenyl]-7-vinyl-phthalazin-1-one;
6-acetyl-1-[(1-ethyl-6-oxo-pyrimidin-5-yl)amino]-3-[4-(trifluoromethoxy)phenyl]-7,8-dihydro-5H-pyrido[3,4-d]pyridazin-4-one;
6-acetyl-1-[(6-oxo-1-propyl-pyrimidin-5-yl)amino]-3-[4-(trifluoromethoxy)phenyl]-7,8-dihydro-5H-pyrido[3,4-d]pyridazin-4-one;
6-acetyl-1-[(5-fluoro-1-methyl-2-oxo-3-pyridyl)amino]-3-[4-(trifluoromethoxy)phenyl]-7,8-dihydro-5H-pyrido[3,4-d]pyridazin-4-one;
4-[[1-(2-morpholino-2-oxo-ethyl)-2-oxo-3-pyridyl]amino]-2-[4-(trifluoromethoxy)phenyl]phthalazin-1-one;
N,N-dimethyl-2-[2-oxo-3-[[4-oxo-3-[4-(trifluoromethoxy)phenyl]phthalazin-1-yl]amino]-1-pyridyl]acetamide;
N-isopropyl-2-[2-oxo-3-[[4-oxo-3-[4-(trifluoromethoxy)phenyl]phthalazin-1-yl]amino]-1-pyridyl]acetamide;
N-methyl-2-[2-oxo-3-[[4-oxo-3-[4-(trifluoromethoxy)phenyl]phthalazin-1-yl]amino]-1-pyridyl]acetamide;
N-(2-hydroxyethyl)-2-[2-oxo-3-[[4-oxo-3-[4-(trifluoromethoxy)phenyl]phthalazin-1-yl]amino]-1-pyridyl]acetamide;
N-[2-(dimethylamino)ethyl]-2-[2-oxo-3-[[4-oxo-3-[4-(trifluoromethoxy)phenyl]phthalazin-1-yl]amino]-1-pyridyl]acetamide;
N-(3-methoxypropyl)-2-[2-oxo-3-[[4-oxo-3-[4-(trifluoromethoxy)phenyl]phthalazin-1-yl]amino]-1-pyridyl]acetamide;
N-methyl-3-[2-oxo-3-[[4-oxo-3-[4-(trifluoromethoxy)phenyl]phthalazin-1-yl]amino]-1-pyridyl]propanamide;
N,N-dimethyl-3-[2-oxo-3-[[4-oxo-3-[4-(trifluoromethoxy)phenyl]phthalazin-1-yl]amino]-1-pyridyl]propanamide;
N-methyl-4-[2-oxo-3-[[4-oxo-3-[4-(trifluoromethoxy)phenyl]phthalazin-1-yl]amino]-1-pyridyl]butanamide;
N,N-dimethyl-4-[2-oxo-3-[[4-oxo-3-[4-(trifluoromethoxy)phenyl]phthalazin-1-yl]amino]-1-pyridyl]butanamide;
N,2,2-trimethyl-3-[2-oxo-3-[[4-oxo-3-[4-(trifluoromethoxy)phenyl]phthalazin-1-yl]amino]-1-pyridyl]propanamide;
N,N,2,2-tetramethyl-3-[2-oxo-3-[[4-oxo-3-[4-(trifluoromethoxy)phenyl]phthalazin-1-yl]amino]-1-pyridyl]propanamide;
2,2-dimethyl-3-[2-oxo-3-[[4-oxo-3-[4-(trifluoromethoxy)phenyl]phthalazin-1-yl]amino]-1-pyridyl]propanamide;
N-methyl-2-[2-[2-oxo-3-[[4-oxo-3-[4-(trifluoromethoxy)phenyl]phthalazin-1-yl]amino]-1-pyridyl]ethoxy]acetamide;
N,N-dimethyl-2-[2-[2-oxo-3-[[4-oxo-3-[4-(trifluoromethoxy)phenyl]phthalazin-1-yl]amino]-1-pyridyl]ethoxy]acetamide;
N-methyl-2-[2-oxo-3-[[4-oxo-3-[4-(trifluoromethoxy)phenyl]-5,6,7,8-tetrahydrophthalazin-1-yl]amino]-1-pyridyl]acetamide;
N-methyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;
N,N-dimethyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;
N-methyl-2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide;
N,N-dimethyl-2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide;
3-[2-oxo-3-[[4-oxo-3-[4-(trifluoromethoxy)phenyl]phthalazin-1-yl]amino]-1-pyridyl]propanoic acid;
4-[2-oxo-3-[[4-oxo-3-[4-(trifluoromethoxy)phenyl]phthalazin-1-yl]amino]-1-pyridyl]butanoic acid;
2,2-dimethyl-3-[2-oxo-3-[[4-oxo-3-[4-(trifluoromethoxy)phenyl]phthalazin-1-yl]amino]-1-pyridyl]propanoic acid;
2-[2-[2-oxo-3-[[4-oxo-3-[4-(trifluoromethoxy)phenyl]phthalazin-1-yl]amino]-1-pyridyl]ethoxy]acetic acid;
2-[methyl-[2-[2-oxo-3-[[4-oxo-3-[4-(trifluoromethoxy)phenyl]phthalazin-1-yl]amino]-1-pyridyl]ethyl]amino]acetic acid;
1-[2-[2-oxo-3-[[4-oxo-3-[4-(trifluoromethoxy)phenyl]phthalazin-1-yl]amino]-1-pyridyl]ethyl]pyrrolidine-2-carboxylic acid;
(2S)-1-[2-[2-oxo-3-[[4-oxo-3-[4-(trifluoromethoxy)phenyl]phthalazin-1-yl]amino]-1-pyridyl]ethyl]pyrrolidine-2-carboxyli c acid;
(2R)-1-[2-[2-oxo-3-[[4-oxo-3-[4-(trifluoromethoxy)phenyl]phthalazin-1-yl]amino]-1-pyridyl]ethyl]pyrrolidine-2-carboxyli c acid;
4-[5-chloro-2-oxo-3-[[4-oxo-3-[4-(trifluoromethoxy)phenyl]-6,7-dihydro-5H-cyclopenta[d]pyridazin-1-yl]amino]-1-pyridyl]butanoic acid;
4-[2-oxo-3-[[4-oxo-3-[4-(trifluoromethoxy)phenyl]-6,7-dihydro-5H-cyclopenta[d]pyridazin-1-yl]amino]-1-pyridyl]butanoic acid;
2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetic acid;
1-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]pyrrolidine-3-carboxylic acid;
1-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]pyrrolidine-2-carboxylic acid;
4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-2-carboxylic acid;
4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-3-carboxylic acid;
4-[6-oxo-5-[[4-oxo-3-[4-(trifluoromethoxy)phenyl]-6,7-dihydro-5H-cyclopenta[d]pyridazin-1-yl]amino]pyrimidin-1-yl]butanoic acid;
7-hydroxy-4-[(1-methyl-2-oxo-3-pyridyl)amino]-2-[4-(trifluoromethoxy)phenyl]phthalazin-1-one;
6-hydroxy-4-[(1-methyl-2-oxo-3-pyridyl)amino]-2-[4-(trifluoromethoxy)phenyl]phthalazin-1-one;
1-[[1-(morpholin-3-ylmethyl)-6-oxo-pyrimidin-5-yl]amino]-3-[4-(trifluoromethoxy)phenyl]-6,7-dihydro-5H-cyclopenta[d]pyridazin-4-one;

1-[[1-[2-(methylamino)ethyl]-6-oxo-pyrimidin-5-yl]amino]-3-[4-(trifluoromethoxy)phenyl]-6,7-dihydro-5H-cyclopenta[d]pyridazin-4-one;

2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethylamino]acetic acid;

1-[[1-(2-aminoethyl)-2-oxo-3-pyridyl]amino]-3-[4-(trifluoromethoxy)phenyl]-6,7-dihydro-5H-cyclopenta[d]pyridazin-4-one;

1-[[2-oxo-1-(pyrrolidin-2-ylmethyl)-3-pyridyl]amino]-3-[4-(trifluoromethoxy)phenyl]-6,7-dihydro-5H-cyclopenta[d]pyridazin-4-one;

6-methyl-1-[(1-methyl-2-oxo-3-pyridyl)amino]-3-[4-(trifluoromethoxy)phenyl]-7,8-dihydro-5H-pyrido[3,4-d]pyridazin-4-one;

6-methyl-4-[(1-methyl-2-oxo-3-pyridyl)amino]-2-[4-(trifluoromethoxy)phenyl]-7,8-dihydro-5H-pyrido[3,4-d]pyridazin-1-one;

1-[(1-methyl-2-oxo-3-pyridyl)amino]-3-[4-(trifluoromethoxy)phenyl]-5,6,7,8-tetrahydropyrido[3,4-d]pyridazin-4-one;

1-[[1-[[(2S)-Morpholin-2-yl]methyl]-2-oxo-3-pyridyl]amino]-3-[4-(trifluoromethoxy)phenyl]-6,7-dihydro-5H-cyclopenta[d]pyridazin-4-one;

6-(2-methoxyethoxy)-4-[(1-methyl-2-oxo-3-pyridyl)amino]-2-[4-(trifluoromethoxy)phenyl]phthalazin-1-one;

7-(2-methoxyethoxy)-4-[(1-methyl-2-oxo-3-pyridyl)amino]-2-[4-(trifluoromethoxy)phenyl]phthalazin-1-one;

5-(2-methoxyethoxy)-4-[(1-methyl-2-oxo-3-pyridyl)amino]-2-[4-(trifluoromethoxy)phenyl]phthalazin-1-one;

1-[(1-methyl-2-oxo-3-pyridyl)amino]-4-oxo-3-[4-(trifluoromethoxy)phenyl]phthalazine-6-carboxamide;

7-(1-hydroxyethyl)-4-[(1-methyl-2-oxo-3-pyridyl)amino]-2-[4-(trifluoromethoxy)phenyl]phthalazin-1-one;

7-(hydroxymethyl)-4-[(1-methyl-2-oxo-3-pyridyl)amino]-2-[4-(trifluoromethoxy)phenyl]phthalazin-1-one;

7-amino-4-[(1-methyl-2-oxo-3-pyridyl)amino]-2-[4-(trifluoromethoxy)phenyl]phthalazin-1-one;

7-(aminomethyl)-4-[(1-methyl-2-oxo-3-pyridyl)amino]-2-[4-(trifluoromethoxy)phenyl]phthalazin-1-one;

7-[(dimethylamino)methyl]-4-[(1-methyl-2-oxo-3-pyridyl)amino]-2-[4-(trifluoromethoxy)phenyl]phthalazin-1-one;

6-(2-hydroxypropyl)-1-[(1-methyl-2-oxo-3-pyridyl)amino]-3-[4-(trifluoromethoxy)phenyl]-7,8-dihydro-5H-pyrido[3,4-d]pyridazin-4-one;

6-(2-hydroxy-2-methyl-propyl)-1-[(1-methyl-2-oxo-3-pyridyl)amino]-3-[4-(trifluoromethoxy)phenyl]-7,8-dihydro-5H-pyrido[3,4-d]pyridazin-4-one;

6-(2-hydroxyethyl)-1-[(1-methyl-2-oxo-3-pyridyl)amino]-3-[4-(trifluoromethoxy)phenyl]-7,8-dihydro-5H-pyrido[3,4-d]pyridazin-4-one;

6-acetyl-1-[(1-methyl-2-oxo-3-pyridyl)amino]-3-[4-(trifluoromethoxy)phenyl]-7,8-dihydro-5H-pyrido[3,4-d]pyridazin-4-one;

6-acetyl-4-[(1-methyl-2-oxo-3-pyridyl)amino]-2-[4-(trifluoromethoxy)phenyl]-7,8-dihydro-5H-pyrido[3,4-d]pyridazin-1-one;

6-acetyl-1-[(1-methyl-6-oxo-pyrimidin-5-yl)amino]-3-[4-(trifluoromethoxy)phenyl]-7,8-dihydro-5H-pyrido[3,4-d]pyridazin-4-one;

6-acetyl-4-[(1-methyl-6-oxo-pyrimidin-5-yl)amino]-2-[4-(trifluoromethoxy)phenyl]-7,8-dihydro-5H-pyrido[3,4-d]pyridazin-1-one;

methyl 4-[(1-methyl-2-oxo-3-pyridyl)amino]-1-oxo-2-[4-(trifluoromethoxy)phenyl]-7,8-dihydro-5H-pyrido[3,4-d]pyridazine-6-carboxylate;

methyl 1-[(1-methyl-2-oxo-3-pyridyl)amino]-4-oxo-3-[4-(trifluoromethoxy)phenyl]-7,8-dihydro-5H-pyrido[3,4-d]pyridazine-6-carboxylate;

4-[(1-methyl-2-oxo-3-pyridyl)amino]-1-oxo-2-[4-(trifluoromethoxy)phenyl]-7,8-dihydro-5H-pyrido[3,4-d]pyridazine-6-carbaldehyde;

1-[(1-methyl-2-oxo-3-pyridyl)amino]-4-oxo-3-[4-(trifluoromethoxy)phenyl]-7,8-dihydro-5H-pyrido[3,4-d]pyridazine-6-carbaldehyde;

1-[(1-methyl-2-oxo-3-pyridyl)amino]-6-methylsulfonyl-3-[4-(trifluoromethoxy)phenyl]-7,8-dihydro-5H-pyrido[3,4-d]pyridazin-4-one;

4-[(1-methyl-2-oxo-3-pyridyl)amino]-6-methylsulfonyl-2-[4-(trifluoromethoxy)phenyl]-7,8-dihydro-5H-pyrido[3,4-d]pyridazin-1-one;

6-ethyl-1-[(1-methyl-2-oxo-3-pyridyl)amino]-3-[4-(trifluoromethoxy)phenyl]-7,8-dihydro-5H-pyrido[3,4-d]pyridazin-4-one;

6-isopropyl-1-[(1-methyl-2-oxo-3-pyridyl)amino]-3-[4-(trifluoromethoxy)phenyl]-7,8-dihydro-5H-pyrido[3,4-d]pyridazin-4-one;

N-methyl-4-[(1-methyl-2-oxo-3-pyridyl)amino]-1-oxo-2-[4-(trifluoromethoxy)phenyl]-7,8-dihydro-5H-pyrido[3,4-d]pyridazine-6-carboxamide;

N-methyl-1-[(1-methyl-2-oxo-3-pyridyl)amino]-4-oxo-3-[4-(trifluoromethoxy)phenyl]-7,8-dihydro-5H-pyrido[3,4-d]pyridazine-6-carboxamide;

2-[4-(1-hydroxy-1-methyl-ethyl)phenyl]-4-[(1-methyl-2-oxo-3-pyridyl)amino]phthalazin-1-one;

4-[[1-(2-hydroxyethyl)-2-oxo-3-pyridyl]amino]-2-[4-(trifluoromethoxy)phenyl]phthalazin-1-one;

7-hydroxy-4-[(1-methyl-2-oxo-3-pyridyl)amino]-2-[4-(trifluoromethoxy)phenyl]-5,6,7,8-tetrahydrophthalazin-1-one;

6-hydroxy-4-[(1-methyl-2-oxo-3-pyridyl)amino]-2-[4-(trifluoromethoxy)phenyl]-5,6,7,8-tetrahydrophthalazin-1-one;

1-[[1-(3-amino-2-hydroxy-2-methyl-propyl)-2-oxo-3-pyridyl]amino]-3-[4-(trifluoromethoxy)phenyl]-6,7-dihydro-5H-cyclopenta[d]pyridazin-4-one;

1-[[2-Oxo-1-(2-oxo-2-piperazin-1-yl-ethyl)-3-pyridyl]amino]-3-[4-(trifluoromethoxy)phenyl]-6,7-dihydro-5H-cyclopenta[d]pyridazin-4-one;

1-[[1-[2-(Oxetan-3-ylamino)ethyl]-2-oxo-3-pyridyl]amino]-3-[4-(trifluoromethoxy)phenyl]-6,7-dihydro-5H-cyclopenta[d]pyridazin-4-one;

1-[[1-[2-(3-Hydroxyazetidin-1-yl)ethyl]-6-oxo-pyrimidin-5-yl]amino]-3-[4-(trifluoromethoxy)phenyl]-6,7-dihydro-5H-cyclopenta[d]pyridazin-4-one;

trans-1-[[1-[(5-Amino-1,3-dioxan-2-yl)methyl]-2-oxo-3-pyridyl]amino]-3-[4-(trifluoromethoxy)phenyl]-6,7-dihydro-5H-cyclopenta[d]pyridazin-4-one;

1-[(1-Methyl-2-oxo-3-pyridyl)amino]-3-[2-methyl-4-(trifluoromethoxy)phenyl]-6,7-dihydro-5H-cyclopenta[d]pyridazin-4-one;

3-(3,4-Dimethoxyphenyl)-1-[(1-methyl-2-oxo-3-pyridyl)amino]-6,7-dihydro-5H-cyclopenta[d]pyridazin-4-one;

3-[3-Methoxy-4-(trifluoromethyl)phenyl]-1-[(1-methyl-2-oxo-3-pyridyl)amino]-6,7-dihydro-5H-cyclopenta[d]pyridazin-4-one;

N,1-Dimethyl-6-oxo-5-[[4-oxo-3-[4-(trifluoromethoxy)phenyl]-5,6,7,8-tetrahydrophthalazin-1-yl]amino]pyridine-3-carboxamide;

N,1-Dimethyl-6-oxo-5-[[4-oxo-3-[4-(trifluoromethoxy)phenyl]phthalazin-1-yl]amino]pyridine-3-carboxamide;

4-[[1-methyl-2-oxo-5-(trifluoromethyl)-3-pyridyl]amino]-2-[4-(trifluoromethoxy)phenyl]phthalazin-1-one;

and pharmaceutically acceptable salts thereof.

Even more particular compounds of formula (I) of the present invention are those selected from the group consisting of:

4-[(1-methyl-2-oxo-3-pyridyl)amino]-2-[4-(trifluoromethoxy)phenyl]phthalazin-1-one;
methyl 2-[2-oxo-3-[[4-oxo-3-[4-(trifluoromethoxy)phenyl]phthalazin-1-yl]amino]-1-pyridyl]acetate;
methyl (2R)-1-[2-[2-oxo-3-[[4-oxo-3-[4-(trifluoromethoxy)phenyl]phthalazin-1-yl]amino]-1-pyridyl]ethyl]pyrrolidine-2-carboxylate;
7-methoxy-4-[(1-methyl-2-oxo-3-pyridyl)amino]-2-[4-(trifluoromethoxy)phenyl]phthalazin-1-one;
2-(4-tert-butylphenyl)-7-ethyl-4-[(1-methyl-2-oxo-3-pyridyl)amino]phthalazin-1-one;
4-[(1-methyl-2-oxo-3-pyridyl)amino]-2-[4-(trifluoromethoxy)phenyl]-5,6,7,8-tetrahydrophthalazin-1-one;
4-[(1-methyl-6-oxo-pyrimidin-5-yl)amino]-2-[4-(trifluoromethoxy)phenyl]-5,6,7,8-tetrahydrophthalazin-1-one;
methyl 2-[2-oxo-3-[[4-oxo-3-[4-(trifluoromethoxy)phenyl]-5,6,7,8-tetrahydrophthalazin-1-yl]amino]-1-pyridyl]acetate;
4-[[1-[2-(dimethylamino)ethyl]-6-oxo-pyrimidin-5-yl]amino]-2-[4-(trifluoromethoxy)phenyl]-5,6,7,8-tetrahydrophthalazin-1-one;
2-(6-tert-butyl-3-pyridyl)-4-[(1-methyl-2-oxo-3-pyridyl)amino]-5,6,7,8-tetrahydrophthalazin-1-one;
2-[4-(difluoromethoxy)phenyl]-4-[(1-methyl-2-oxo-3-pyridyl)amino]-5,6,7,8-tetrahydrophthalazin-1-one;
1-[(1-methyl-2-oxo-3-pyridyl)amino]-3-[4-(trifluoromethoxy)phenyl]-6,7-dihydro-5H-cyclopenta[d]pyridazin-4-one;
1-[(2,6-dimethyl-3-oxo-pyridazin-4-yl)amino]-3-[4-(trifluoromethoxy)phenyl]-6,7-dihydro-5H-cyclopenta[d]pyridazin-4-one;
1-[(1-methyl-6-oxo-pyrimidin-5-yl)amino]-3-[4-(trifluoromethoxy)phenyl]-6,7-dihydro-5H-cyclopenta[d]pyridazin-4-one;
1-[(5-fluoro-1-methyl-2-oxo-3-pyridyl)amino]-3-[4-(trifluoromethoxy)phenyl]-6,7-dihydro-5H-cyclopenta[d]pyridazin-4-one;
1-[(1,5-dimethyl-2-oxo-3-pyridyl)amino]-3-[4-(trifluoromethoxy)phenyl]-6,7-dihydro-5H-cyclopenta[d]pyridazin-4-one;
1-[(5-chloro-1-methyl-2-oxo-3-pyridyl)amino]-3-[4-(trifluoromethoxy)phenyl]-6,7-dihydro-5H-cyclopenta[d]pyridazin-4-one;
methyl 4-[5-chloro-2-oxo-3-[[4-oxo-3-[4-(trifluoromethoxy)phenyl]-6,7-dihydro-5H-cyclopenta[d]pyridazin-1-yl]amino]-1-pyridyl]butanoate;
methyl 4-[2-oxo-3-[[4-oxo-3-[4-(trifluoromethoxy)phenyl]-6,7-dihydro-5H-cyclopenta[d]pyridazin-1-yl]amino]-1-pyridyl]butanoate;
1-[[1-[2-(3-methoxypyrrolidin-1-yl)ethyl]-2-oxo-3-pyridyl]amino]-3-[4-(trifluoromethoxy)phenyl]-6,7-dihydro-5H-cyclopenta[d]pyridazin-4-one;
1-[[1-(3-morpholinopropyl)-2-oxo-3-pyridyl]amino]-3-[4-(trifluoromethoxy)phenyl]-6,7-dihydro-5H-cyclopenta[d]pyridazin-4-one;
1-[[1-[2-(3-hydroxyazetidin-1-yl)ethyl]-2-oxo-3-pyridyl]amino]-3-[4-(trifluoromethoxy)phenyl]-6,7-dihydro-5H-cyclopenta[d]pyridazin-4-one;
1-[[1-[3-(4-methylpiperazin-1-yl)propyl]-2-oxo-3-pyridyl]amino]-3-[4-(trifluoromethoxy)phenyl]-6,7-dihydro-5H-cyclopenta[d]pyridazin-4-one;
1-[[1-(3-hydroxypropyl)-2-oxo-3-pyridyl]amino]-3-[4-(trifluoromethoxy)phenyl]-6,7-dihydro-5H-cyclopenta[d]pyridazin-4-one;
1-[[1-[2-(dimethylamino)ethyl]-6-oxo-pyrimidin-5-yl]amino]-3-[4-(trifluoromethoxy)phenyl]-6,7-dihydro-5H-cyclopenta[d]pyridazin-4-one;
1-[[1-[2-(diethylamino)ethyl]-6-oxo-pyrimidin-5-yl]amino]-3-[4-(trifluoromethoxy)phenyl]-6,7-dihydro-5H-cyclopenta[d]pyridazin-4-one;
3-(4-tert-butyl-2-fluoro-phenyl)-1-[(1-methyl-2-oxo-3-pyridyl)amino]-6,7-dihydro-5H-cyclopenta[d]pyridazin-4-one;
3-(6-tert-butyl-3-pyridyl)-1-[(1-methyl-2-oxo-3-pyridyl)amino]-6,7-dihydro-5H-cyclopenta[d]pyridazin-4-one;
1-[(1-methyl-2-oxo-3-pyridyl)amino]-3-[4-(trifluoromethyl)phenyl]-6,7-dihydro-5H-cyclopenta[d]pyridazin-4-one;
4-[(1-methyl-2-oxo-3-pyridyl)amino]-2-[4-(trifluoromethoxy)phenyl]-7,8-dihydro-5H-pyrano[3,4-d]pyridazin-1-one;
4-[(1-methyl-6-oxo-pyrimidin-5-yl)amino]-2-[4-(trifluoromethoxy)phenyl]phthalazin-1-one;
4-[[1-[2-(dimethylamino)ethyl]-2-oxo-3-pyridyl]amino]-2-[4-(trifluoromethoxy)phenyl]phthalazin-1-one;
4-[[1-(2-methylsulfonylethyl)-2-oxo-3-pyridyl]amino]-2-[4-(trifluoromethoxy)phenyl]phthalazin-1-one;
methyl 4-[2-oxo-3-[[4-oxo-3-[4-(trifluoromethoxy)phenyl]phthalazin-1-yl]amino]-1-pyridyl]butanoate;
3-[2-oxo-3-[[4-oxo-3-[4-(trifluoromethoxy)phenyl]phthalazin-1-yl]amino]-1-pyridyl]propane-1-sulfonamide;
N,N-dimethyl-3-[2-oxo-3-[[4-oxo-3-[4-(trifluoromethoxy)phenyl]phthalazin-1-yl]amino]-1-pyridyl]propane-1-sulfonamide;
4-[[1-(2-morpholinoethyl)-2-oxo-3-pyridyl]amino]-2-[4-(trifluoromethoxy)phenyl]phthalazin-1-one;
4-[[1-[2-(3-hydroxypyrrolidin-1-yl)ethyl]-2-oxo-3-pyridyl]amino]-2-[4-(trifluoromethoxy)phenyl]phthalazin-1-one;
methyl (2S)-1-[2-[2-oxo-3-[[4-oxo-3-[4-(trifluoromethoxy)phenyl]phthalazin-1-yl]amino]-1-pyridyl]ethyl]pyrrolidine-2-carboxylate;
6-acetyl-1-[(6-oxo-1-propyl-pyrimidin-5-yl)amino]-3-[4-(trifluoromethoxy)phenyl]-7,8-dihydro-5H-pyrido[3,4-d]pyridazin-4-one;
6-acetyl-1-[(5-fluoro-1-methyl-2-oxo-3-pyridyl)amino]-3-[4-(trifluoromethoxy)phenyl]-7,8-dihydro-5H-pyrido[3,4-d]pyridazin-4-one;
4-[[1-(2-morpholino-2-oxo-ethyl)-2-oxo-3-pyridyl]amino]-2-[4-(trifluoromethoxy)phenyl]phthalazin-1-one;
N,N-dimethyl-2-[2-oxo-3-[[4-oxo-3-[4-(trifluoromethoxy)phenyl]phthalazin-1-yl]amino]-1-pyridyl]acetamide;
N-methyl-2-[2-oxo-3-[[4-oxo-3-[4-(trifluoromethoxy)phenyl]phthalazin-1-yl]amino]-1-pyridyl]acetamide;
N-(3-methoxypropyl)-2-[2-oxo-3-[[4-oxo-3-[4-(trifluoromethoxy)phenyl]phthalazin-1-yl]amino]-1-pyridyl]acetamide;
N,N-dimethyl-3-[2-oxo-3-[[4-oxo-3-[4-(trifluoromethoxy)phenyl]phthalazin-1-yl]amino]-1-pyridyl]propanamide;
N-methyl-4-[2-oxo-3-[[4-oxo-3-[4-(trifluoromethoxy)phenyl]phthalazin-1-yl]amino]-1-pyridyl]butanamide;
N,N-dimethyl-4-[2-oxo-3-[[4-oxo-3-[4-(trifluoromethoxy)phenyl]phthalazin-1-yl]amino]-1-pyridyl]butanamide;
N,N,2,2-tetramethyl-3-[2-oxo-3-[[4-oxo-3-[4-(trifluoromethoxy)phenyl]phthalazin-1-yl]amino]-1-pyridyl]propanamide;

N-methyl-2-[2-[2-oxo-3-[[4-oxo-3-[4-(trifluoromethoxy)phenyl]phthalazin-1-yl]amino]-1-pyridyl]ethoxy]acetamide;

N,N-dimethyl-2-[2-[2-oxo-3-[[4-oxo-3-[4-(trifluoromethoxy)phenyl]phthalazin-1-yl]amino]-1-pyridyl]ethoxy]acetamide;

N-methyl-2-[2-oxo-3-[[4-oxo-3-[4-(trifluoromethoxy)phenyl]-5,6,7,8-tetrahydrophthalazin-1-yl]amino]-1-pyridyl]acetamide;

N-methyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;

N,N-dimethyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;

N-methyl-2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide;

N,N-dimethyl-2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide;

1-[[1-(morpholin-3-ylmethyl)-6-oxo-pyrimidin-5-yl]amino]-3-[4-(trifluoromethoxy)phenyl]-6,7-dihydro-5H-cyclopenta[d]pyridazin-4-one;

1-[[2-oxo-1-(pyrrolidin-2-ylmethyl)-3-pyridyl]amino]-3-[4-(trifluoromethoxy)phenyl]-6,7-dihydro-5H-cyclopenta[d]pyridazin-4-one;

7-(1-hydroxyethyl)-4-[(1-methyl-2-oxo-3-pyridyl)amino]-2-[4-(trifluoromethoxy)phenyl]phthalazin-1-one;

7-(hydroxymethyl)-4-[(1-methyl-2-oxo-3-pyridyl)amino]-2-[4-(trifluoromethoxy)phenyl]phthalazin-1-one;

7-amino-4-[(1-methyl-2-oxo-3-pyridyl)amino]-2-[4-(trifluoromethoxy)phenyl]phthalazin-1-one;

6-acetyl-1-[(1-methyl-2-oxo-3-pyridyl)amino]-3-[4-(trifluoromethoxy)phenyl]-7,8-dihydro-5H-pyrido[3,4-d]pyridazin-4-one;

methyl 4-[(1-methyl-2-oxo-3-pyridyl)amino]-1-oxo-2-[4-(trifluoromethoxy)phenyl]-7,8-dihydro-5H-pyrido[3,4-d]pyridazine-6-carboxylate;

7-hydroxy-4-[(1-methyl-2-oxo-3-pyridyl)amino]-2-[4-(trifluoromethoxy)phenyl]-5,6,7,8;
tetrahydrophthalazin-1-one;

6-hydroxy-4-[(1-methyl-2-oxo-3-pyridyl)amino]-2-[4-(trifluoromethoxy)phenyl]-5,6,7,8-tetrahydrophthalazin-1-one;

1-[[1-[2-(Oxetan-3-ylamino)ethyl]-2-oxo-3-pyridyl]amino]-3-[4-(trifluoromethoxy)phenyl]-6,7-dihydro-5H-cyclopenta[d]pyridazin-4-one;

and pharmaceutically acceptable salts thereof.

Most particular compounds of formula (I) of the present invention are those selected from the group consisting of:

7-methoxy-4-[(1-methyl-2-oxo-3-pyridyl)amino]-2-[4-(trifluoromethoxy)phenyl]phthalazin-1-one;

2-(4-tert-butylphenyl)-7-ethyl-4-[(1-methyl-2-oxo-3-pyridyl)amino]phthalazin-1-one;

4-[(1-methyl-2-oxo-3-pyridyl)amino]-2-[4-(trifluoromethoxy)phenyl]-5,6,7,8-tetrahydrophthalazin-1-one;

4-[(1-methyl-6-oxo-pyrimidin-5-yl)amino]-2-[4-(trifluoromethoxy)phenyl]-5,6,7,8-tetrahydrophthalazin-1-one;

4-[[1-[2-(dimethylamino)ethyl]-6-oxo-pyrimidin-5-yl]amino]-2-[4-(trifluoromethoxy)phenyl]-5,6,7,8-tetrahydrophthalazin-1-one;

1-[(1-methyl-2-oxo-3-pyridyl)amino]-3-[4-(trifluoromethoxy)phenyl]-6,7-dihydro-5H-cyclopenta[d]pyridazin-4-one;

1-[(5-fluoro-1-methyl-2-oxo-3-pyridyl)amino]-3-[4-(trifluoromethoxy)phenyl]-6,7-dihydro-5H-cyclopenta[d]pyridazin-4-one;

1-[(1,5-dimethyl-2-oxo-3-pyridyl)amino]-3-[4-(trifluoromethoxy)phenyl]-6,7-dihydro-5H-cyclopenta[d]pyridazin-4-one;

1-[(5-chloro-1-methyl-2-oxo-3-pyridyl)amino]-3-[4-(trifluoromethoxy)phenyl]-6,7-dihydro-5H-cyclopenta[d]pyridazin-4-one;

1-[[1-[3-(4-methylpiperazin-1-yl)propyl]-2-oxo-3-pyridyl]amino]-3-[4-(trifluoromethoxy)phenyl]-6,7-dihydro-5H-cyclopenta[d]pyridazin-4-one;

1-[[1-(3-hydroxypropyl)-2-oxo-3-pyridyl]amino]-3-[4-(trifluoromethoxy)phenyl]-6,7-dihydro-5H-cyclopenta[d]pyridazin-4-one;

3-(6-tert-butyl-3-pyridyl)-1-[(1-methyl-2-oxo-3-pyridyl)amino]-6,7-dihydro-5H-cyclopenta[d]pyridazin-4-one;

1-[(1-methyl-2-oxo-3-pyridyl)amino]-3-[4-(trifluoromethyl)phenyl]-6,7-dihydro-5H-cyclopenta[d]pyridazin-4-one;

6-acetyl-1-[(5-fluoro-1-methyl-2-oxo-3-pyridyl)amino]-3-[4-(trifluoromethoxy)phenyl]-7,8-dihydro-5H-pyrido[3,4-d]pyridazin-4-one;

N-methyl-4-[2-oxo-3-[[4-oxo-3-[4-(trifluoromethoxy)phenyl]phthalazin-1-yl]amino]-1-pyridyl]butanamide;

N,N-dimethyl-4-[2-oxo-3-[[4-oxo-3-[4-(trifluoromethoxy)phenyl]phthalazin-1-yl]amino]-1-pyridyl]butanamide;

N-methyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;

N,N-dimethyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;

7-(hydroxymethyl)-4-[(1-methyl-2-oxo-3-pyridyl)amino]-2-[4-(trifluoromethoxy)phenyl]phthalazin-1-one;

and pharmaceutically acceptable salts thereof.

Manufacturing Process

General Procedure

Scheme 1.

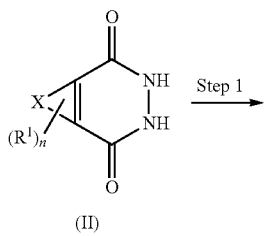

(II)

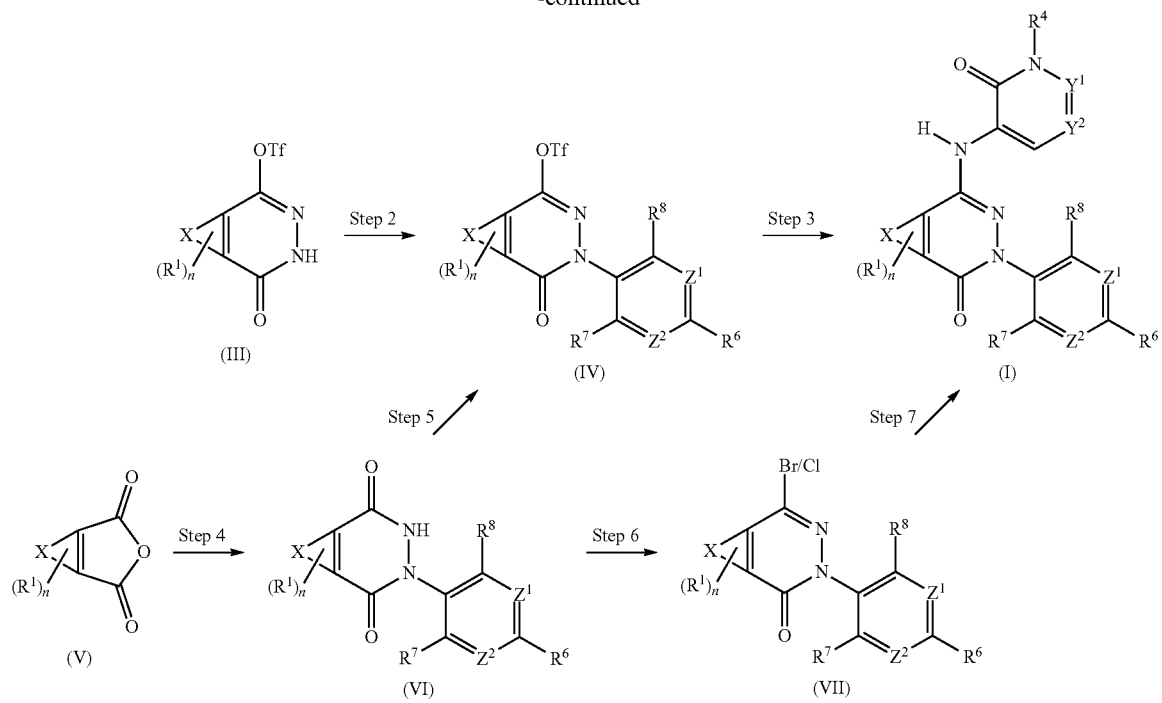

A method for the synthesis of compounds of formula (I) starts from the corresponding phthalazine or pyridazine diones of formula (II). In step 1 of the reaction sequence (scheme 1) the diones are converted into their corresponding monotriflates of formula (III) using methods well known to someone skilled in the art, e.g. reaction with triflic anhydride under basic conditions. Typically used bases are pyridine and triethylamine. The reaction is typically carried out in solvents such as acetonitrile or dichloromethane at temperatures between 0° C. and 100° C.

In step 2, the obtained compounds of formula (III) are converted with the appropriate aryl boronic acid into the compounds of formula (IV) using methods well known to someone skilled in the art, e.g. with copper (II) acetate under basic conditions. A typically used base is triethylamine and the reaction is carried out in a suitable aprotic solvent such as THF at temperatures between 0° C. and 100° C.

In step 3, the obtained compounds of formula (IV) are converted with the appropriate aryl amine into the compounds of formula (I) using methods well known to someone skilled in the art, e.g palladium-mediated amination of aryl triflates or aryl bromides or aryl chlorides. The reaction is typically carried out in solvents such as THF, dioxane, DME at temperatures between 40° C. and 110° C. Typically used bases are caesium carbonate, triethylamine, sodium tert-butoxide and appropriately ligated palladium (0) species can be generated using reagents such as palladium acetate, palladium dichloride, palladium tetrakis-triphenylphosphine, tris(dibenzylideneacetone)dipalladium, bis-triphenylphosphine palladium dichloride in conjunction with phosphine based ligands such as 4,5-bis(diphenylphosphino)-9,9-dimethylxanthene (Xantphos), 2,2'-bis(diphenylphosphino)-1,1'-binaphthyl (BINAP), and 2-(di-tert-butylphosphino)biphenyl.

An alternative method for the synthesis of compounds of formula (I) starts from the corresponding cyclic anhydride of formula (V). In step 4 of scheme 1, the anhydrides are converted with the appropriate hydrazine derivatives, into their corresponding phthalazine or pyridazine diones of formula (VI) using methods well known to someone skilled in the art. The reaction is typically carried out in aprotic solvents such as THF, DMF, NMP or protic solvents such as acetic acid, ethanol, and isopropanol and temperatures between 0° C. and 190° C. The hydrazine derivative may optionally be a salt, for example a hydrochloride salt. In certain cases the reaction produces a mixture of the corresponding compound of formula (VI) and the corresponding imide which can be converted to the compound of formula (VI) using methods well known to someone skilled in the art, e.g. reaction with a base in a protic solvent. The reaction is typically carried out with bases such as sodium ethoxide in solvents such as ethanol at temperatures between 0° C. and room temperature.

In step 5, the obtained compounds of formula (VI) are converted into the corresponding triflate of formula (IV) using methods well known to someone skilled in the art. Typical reaction conditions are the same as those used for step 2 described above.

An alternative method for the conversion of the diones of formula (VI) into the compounds of formula (I) proceeds via the corresponding bromides or chlorides of formula (VII). In step 6 of scheme 1 the diones are converted into the corresponding bromides or chlorides using methods well known to someone skilled in the art. The reaction is typically carried out with reagents such as phosphorus oxybromide or phosphorus oxychloride in solvents such as dichloromethane or dicholorethane at temperatures between 0° C. and 120° C.

In step 7, the obtained compounds of formula (VII) are converted into the corresponding compounds of formula (I) using methods well known to someone skilled in the art. Typical reaction conditions are the same as those used for step 3 as described above.

A particular embodiment of the invention relates to a process for the preparation of compounds of formula (I) and pharmaceutically acceptable salts thereof as defined herein, comprising a palladium-mediated amination reaction of a compound of formula (IV), wherein X, $Y^1$, $Y^2$, $Z^1$, $Z^2$, n, $R^1$, $R^4$ and $R^6$ to $R^8$ are as described herein and wherein TfO represents trifluoromethanesulfonate (triflate, $CF_3SO_3$).

Particularly, the palladium-mediated amination reaction of a compound of formula (IV) is carried out in solvents such as THF, dioxane, DME; at temperatures between 40° C. and 110° C.; in the presence of a base such as caesium carbonate, triethylamine, sodium tert-butoxide; and an appropriately ligated palladium (0) species; wherein the ligated palladium (0) species is generated using a palladium reagent such as palladium acetate, palladium dichloride, palladium tetrakis-triphenylphosphine, tris(dibenzylideneacetone)dipalladium, bis-triphenylphosphine palladium dichloride in conjunction with phosphine based ligands such as 4,5-bis(diphenylphosphino)-9,9-dimethylxanthene (Xantphos), 2,2'-bis(diphenylphosphino)-1,1'-binaphthyl (BINAP), and 2-(di-tert-butylphosphino)biphenyl.

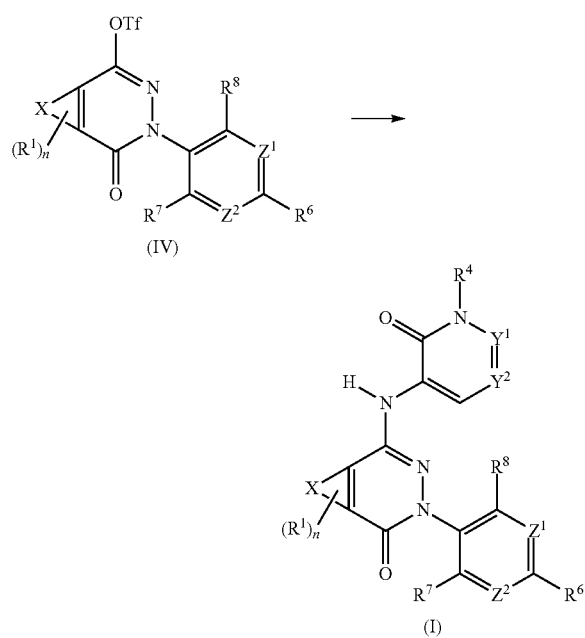

Another particular embodiment of the invention relates to a process for the preparation of compounds of formula (I) and pharmaceutically acceptable salts thereof as defined herein, comprising a palladium-mediated amination reaction of a compound of formula (VII), wherein X, $Y^1$, $Y^2$, $Z^1$, $Z^2$, n, $R^1$, $R^4$ and $R^6$ to $R^8$ are as described herein.

Particularly, the palladium-mediated amination reaction of a compound of formula (VII) is carried out in solvents such as THF, dioxane, DME; at temperatures between 40° C. and 110° C.; in the presence of a base such as caesium carbonate, triethylamine, sodium tert-butoxide; and an appropriately ligated palladium (0) species; wherein the ligated palladium (0) species is generated using a palladium reagent such as palladium acetate, palladium dichloride, palladium tetrakis-triphenylphosphine, tris(dibenzylideneacetone)dipalladium, bis-triphenylphosphine palladium dichloride in conjunction with phosphine based ligands such as 4,5-bis(diphenylphosphino)-9,9-dimethylxanthene (Xantphos), 2,2'-bis(diphenylphosphino)-1,1'-binaphthyl (BINAP), and 2-(di-tert-butylphosphino)biphenyl.

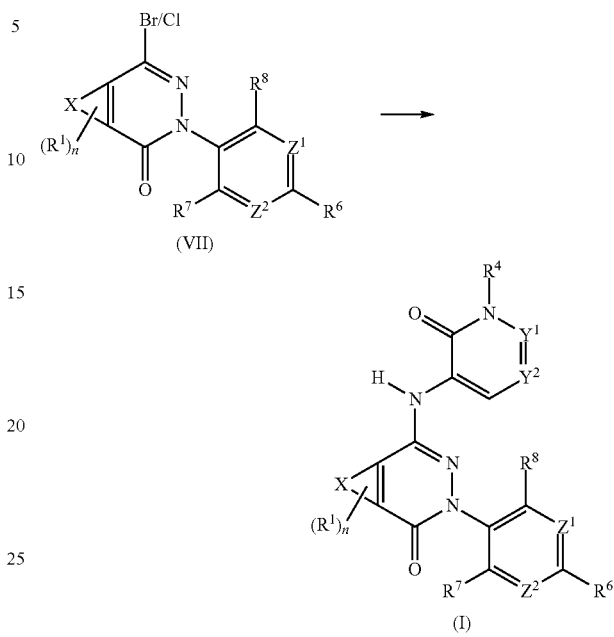

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C, Handbook of Pharmaceutical Excipients (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 m filter, to remove impurities and contaminants.

Therapeutic Uses

As described above, the compounds of formula (I) and their pharmaceutically acceptable salts possess valuable pharmacological properties and are particularly useful for treating, ameliorating, or preventing viral diseases.

The compounds of the present invention can be used, either alone or in combination with other drugs, for the treatment or prevention of viral diseases. Examples of possible viral diseases include, but are not limited to, viral diseases which are caused by Poxviridae, Herpesviridae, Adenoviridae, Papillomaviridae, Polyomaviridae, Parvoviridae, Hepadnaviridae, Reoviridae, Filoviridae, Paramyxoviridae, Rhabdoviridae, Orthomyxoviridae, Bunyaviridae, Arenaviridae, Coronaviridae, Picornaviridae, Hepeviridae, Caliciviridae, Astroviridae, Togaviridae, Flaviviridae, Deltavirus, Bornaviridae, and prions. Preferably viral diseases which are caused by Herpesviridae, Filoviridae, Paramyxoviridae, Rhabdoviridae, Orthomyxoviridae, Bunyaviridae, Arenaviridae, Coronaviridae, Picornaviridae, Togaviridae, and Flaviviridae.

Particularly, the compounds of the present invention can be used, either alone or in combination with other drugs, for the treatment or prevention of viral diseases which are caused by orthomyxoviridae.

Viruses to be treated include, but are not limited to, the viruses given in the Table 1:

TABLE 1

Viruses to be treated by the compounds of formula (I).

| Family | Viruses (particular examples) |
| --- | --- |
| Poxviridae | Smallpox virus |
|  | Molluscum contagiosum virus |
| Herpesviridae | Herpes simplex virus |
|  | Varicella zoster virus |
|  | Cytomegalovirus |
|  | Epstein Barr virus |
|  | Kaposi's sarcoma-associated herpesvirus |
| Adenoviridae | Human adenovirus A-F |
| Papillomaviridae | Papillomavirus |
| Polyomaviridae | BK-virus |
|  | JC-Virsu |
| Parvoviridae | B19 virus |
|  | Adeno associated virus 2/3/5 |
| Hepadnaviridae | Hepatitis B virus |
| Reoviridae | Reovirus 1/2/3 |
|  | Rotavirus A/B/C |
|  | Colorado tick fever virus |
| Filoviridae | Ebola virus |
|  | Marburg virus |
| Paramyxoviridae | Parainfluenza virus 1-4 |
|  | Mumps virus |
|  | Measles virus |
|  | Respiratory syncytial virus |
|  | Hendravirus |
| Rhabdoviridae | Vesicular stomatitis virus |
|  | Rabies virus |
|  | Mokola virus |
|  | European bat virus |
|  | Duvenhage virus |
| Orthomyxoviridae | Influenza virus types A-C |
| Bunyaviridae | California encephalitis virus |
|  | La Crosse virus |
|  | Hantaan virus |
|  | Puumala virus |
|  | Sin Nombre virus |
|  | Seoul virus |
|  | Crimean-Congo hemorrhagic fever virus |
|  | Sakhalin virus |
|  | Rift valley virus |
|  | Sandfly fever virus |
|  | Uukuniemi virus |
| Arenaviridae | Lassa virus |
|  | Lymphocytic choriomeningitis virus |
|  | Guanarito virus |
|  | Junin virus, |
|  | Machupo virus |
|  | Sabia virus |
| Coronaviridae | Human coronavirus |
| Picornaviridae | Human enterovirus types A-D (Poliovirus, Echovirus, Coxsackie virus A/B) |
|  | Rhinovirus types A/B/C |
|  | Hepatitis A virus |
|  | Parechovirus |
|  | Food and mouth disease virus |
| Hepeviridae | Hepatitis E virus |
| Caliciviridae | Norwalk virus |
|  | Sapporo virus |
| Astroviridae | Human astrovirus 1 |
| Togaviridae | Ross River virus |
|  | Chikungunya virus |
|  | O'nyong-nyong virus |
|  | Rubella virus |
| Flaviviridae | Tick-borne encephalitis virus |
|  | Dengue virus |
|  | Yellow Fever virus |
|  | Japanese encephalitis virus |
|  | Murray Valley virus |
|  | St. Louis encephalitis virus |
|  | West Nile virus |
|  | Hepatitis C virus |
|  | Hepatitis G virus |
|  | Hepatitis GB virus |
| Deltavirus | Hepatitis deltavirus |
| Bornaviridae | Bornavirus |
| Prions |  |

Preferably, the compounds of the present invention are employed to treat influenza. The present invention covers all virus genera belonging to the family of orthomyxoviridae, specifically influenza virus type A, B, and C, isavirus, and thogotovirus. Within the present invention, the term "influenza" includes influenza caused by any influenza virus such as influenza virus type A, B, and C including their various stains and isolates, and also covers influenza A virus strains commonly referred to as bird flu and swine flu. The subject to be treated is not particularly restricted and can be any vertebrate, such as birds and mammals (including humans).

Without wishing to be bound by theory it is assumed that the compounds of the present invention are capable of inhibiting pathogens using the cellular endocytic pathway at some point in their life cycle, particularly that of influenza virus. More specifically it is assumed that they directly interfere with the trafficking of the virus in the cellular endosomes, which is essential for influenza virus replication.

The compounds having the general formula (I) can be used in combination with one or more other medicaments. The type of the other medicaments is not particularly limited and will depend on the disorder to be treated. Preferably, the other medicament will be a further medicament which is useful in treating, ameliorating or preventing a viral disease, more preferably a further medicament which is useful in treating, ameliorating or preventing influenza that has been caused by influenza virus infection and conditions associated with this viral infection such as viral pneumonia or secondary bacterial pneumonia and medicaments to treat symptoms such as chills, fever, sore throat, muscle pains, severe headache, coughing, weakness and fatigue. Furthermore, the compounds having the general formula (I) can be used in combination with anti-inflammatories.

Widespread resistance to both classes of licensed influenza antivirals (M2 ion channel inhibitors (adamantanes) and neuraminidase inhibitors (e.g. oseltamivir)) occurs in both pandemic and seasonal emerging influenza strains, rendering these drugs to be of marginal utility in the treatment modality. For M2 ion channel inhibitors, the frequency of viral resistance has been increasing since 2003 and for seasonal influenza A/H3N2, adamantanes are now regarded as ineffective. Virtually all 2009 H1N1 and seasonal H3N2 strains are resistant to adamantanes (rimantadine and amantadine), and for oseltamivir, the most widely prescribed neuraminidase inhibitor (NAI), WHO reported on significant emergence of influenza A/H1N1 resistance starting in the influenza season 2007/2008; and for the second and third quarters of 2008 in the southern hemisphere. Even more serious numbers were published for the fourth quarter of 2008 (northern hemisphere) where 95% of all tested isolates revealed no oseltamivir-susceptibility.

Considering the fact that now most national governments have been stockpiling NAIs as part of their influenza pandemic preparedness plan, it is obvious that the demand for new, effective drugs is growing significantly. To address the need for more effective therapy, preliminary studies using double or even triple combinations of antiviral drugs with different mechanisms of action have been undertaken. Adamantanes and neuraminidase inhibitors in combination were analysed in vitro and in vivo and were found to act highly synergistically. However, it is known that for both types of antivirals resistant viruses emerge rather rapidly and this issue is not tackled by combining these established antiviral drugs.

In general, compounds targeting a host factor lead to less generation of viral resistance. Indeed, there is no pressure on cell to mutate its own factor hijacked by the virus and it is unlikely that the virus will mutate to alleviate its need to this required cellular factor. However, combination therapy may still be advantageous by decreasing the dose of each drug taken individually. Combining a drug that target the host (the present compound) and a drug with a different mechanism of action will increase the probability of synergism. The following medicaments may therefore be considered as potential options for combination therapy with the present compounds:

(i) The combination with direct acting antivirals such as endonuclease or with cap-binding inhibitors (targeting directly influenza). The endonuclease inhibitors are not particularly limited and can be any endonuclease inhibitor, particularly any viral endonuclease inhibitor. Preferred endonuclease inhibitors are those as defined in the US applications with the Ser. Nos. 61/550,045 (filed on Oct. 21, 2011), 61/650,713 (filed on May 23, 2012), 61/650,725 (filed on May 23, 2012) and 61/679,968 (filed on Aug. 6, 2012). The complete disclosure of these applications is incorporated herein by reference. In particular, all descriptions with respect to the general formula of the compounds according to these US applications, the preferred embodiments of the various substituents as well as the medical utility and advantages of the compounds are incorporated herein by reference.

The cap-binding inhibitors are not particularly limited either and can be any cap-binding inhibitor, particularly any viral cap-binding inhibitor. Preferred cap-binding inhibitors are those having the general formula (II) as defined in U.S. application 61/550,057 (filed on Oct. 21, 2011) and/or the compounds disclosed in WO2011/000566, the complete disclosure of which is incorporated by reference. In particular, all descriptions with respect to the general formula of the compounds according to U.S. 61/550,057 or WO2011/000566, the preferred embodiments of the various substituents as well as the medical utility and advantages of the compounds are incorporated herein by reference.

Both active sites are highly conserved among all influenza A strains (e.g., avian and human) and even influenza B viruses, and hence this high degree of sequence conservation underpins the perception that these targets are not likely to trigger rapid resistant virus generation. Thus, endonuclease and cap-binding inhibitors individually and in combination are ideal drug candidates to combat both seasonal and pandemic influenza, irrespectively of the virus strain.

(ii) Combination with compounds interfering with viral replication:
favipiravir and analogues, epigallocatechin gallate and analogues, as well as nucleoside analogs such as ribavirine.

(iii) The combination with neuraminidase inhibitors:
Based on the fact that the present compound acts on a cellular target and that NAI act on the virus, one can anticipate that their combination will lead to synergistial antiviral activity. This highly efficient drug combination would result in lower substance concentrations and hence improved dose-response-relationships and better side effect profiles.

The neuraminidase inhibitor (particularly influenza neuramidase inhibitor) is not specifically limited. Examples include zanamivir, oseltamivir, peramivir, KDN DANA, FANA, and cyclopentane derivatives.

(iv) The combination with M2 channel inhibitors:
Based on the fact that the present compound acts on a cellular target and that M2 ion channel blockers act on the virus, one can anticipate that their combination will lead to synergistial antiviral activity. This highly efficient drug combination would result in lower substance concentrations and hence improved dose-response-relationships and better side effect profiles. The M2 channel inhibitor (particularly influenza M2 channel inhibitor) is not specifically limited. Examples include amantadine and rimantadine.

(v) The combination with alpha glucosidase inhibitors:
This highly efficient drug combination would result in lower substance concentrations and hence improved dose-response-relationships and better side effect profiles.
The alpha glucosidase inhibitor is not specifically limited. Examples include the compounds described in Chang et al., Antiviral Research 2011, 89, 26-34.

(vi) The combination with ligands of other influenza targets
Based on the fact that the present compound acts on a cellular target and that other compounds act on the virus, one can anticipate that their combination will lead to synergistial antiviral activity.
Examples include compounds acting on the sialidase fusion protein (e.g., Fludase (DAS 181), siRNAs and phosphorothioate oligonucleotides).

(vii) The combination with a compound used as an adjuvant to minimize the symptoms of the disease (antibiotics, anti-inflammatory agents like COX inhibitors (e.g., COX-1/COX-2 inhibitors, selective COX-2 inhibitors), lipoxygenase inhibitors, EP ligands (particularly EP4 ligands), bradykinin ligands, and/or cannabinoid ligands (e.g., CB2 agonists)). This combination is expected to act synergistically because these different types of drugs exhibit completely different mechanisms of action requiring different pharmacokinetic properties which act advantageously and synergistically on the antiviral efficacy of the combination.

(viii) The combination with compounds modulating the cytokine storm triggered by the virus.
Viral diseases which are suitable to be treated or prevented by the compounds of present invention include, but are not limited, to the diseases given in the following Table 2:

TABLE 2

Viral diseases to be treated by the compounds of formula (I).

| Type | Family | Viral Disease |
|---|---|---|
| Adenovirus | Adenoviridae | gastroenteritis |
| | | keratoconjunctivitis |
| | | pharyngitis |
| | | croup |
| | | pharyngoconjunctival fever |
| | | pneumonia |
| | | cystitis |
| Coxsackievirus | Picornaviridae | Hand, foot and mouth disease |
| | | pleurodynia |
| | | aseptic meningitis |
| | | pericarditis |
| | | myocarditis |
| Epstein-Barr virus | Herpesviridae | infectious mononucleosis |
| | | Burkitt's lymphoma |
| | | Hodgkin's lymphoma |
| | | nasopharyngeal carcinoma |
| Hepatitis A virus | Picornaviridae | acute hepatitis |
| Hepatitis B virus | Hepadnaviridae | acute hepatitis |
| | | chronic hepatitis |
| | | hepatic cirrhosis |
| | | hepatocellular carcinoma |
| Hepatitis C virus | Flaviviridae | acute hepatitis |
| | | chronic hepatitis |
| | | hepatic cirrhosis |
| | | hepatocellular carcinoma |
| Herpes simplex virus, type 1 | Herpesviridae | herpes labialis, cold sores |
| | | gingivostomatitis in children |
| | | tonsillitis & pharyngitis in adults |
| | | keratoconjunctivitis |
| Herpes simplex virus, type 2 | Herpesviridae | Skin vesicles, mucosal ulcers |
| | | Aseptic meningitis |
| Cytomegalovirus | Herpesviridae | infectious mononucleosis |
| | | Cytomegalic inclusion disease |
| Human herpesvirus, type 8 | Herpesviridae | Kaposi sarcoma |
| | | multicentric Castleman disease |
| | | primary effusion lymphoma |
| HIV | Retroviridae | AIDS |
| Influenza virus | Orthomyxoviridae | influenza |
| | | Reye syndrome |
| Measles virus | Paramyxoviridae | measles |
| | | postinfectious encephalomyelitis |
| Mumps virus | Paramyxoviridae | mumps |
| Human papillomavirus | Papillomaviridae | hyperplastic epithelial lesions such as plantar and anogenital warts, laryngeal papillomas, andepidermodysplasia verruciformis |
| | | Malignancies such as cervical carcinoma and squamous cell carcinomas |
| Parainfluenza virus | Paramyxoviridae | croup |
| | | pneumonia |
| | | bronchiolitis |
| | | common cold |
| Poliovirus | Picornaviridae | poliomyelitis |
| Rabies virus | Rhabdoviridae | rabies (fatal encephalitis) |
| Respiratory syncytial virus | Paramyxoviridae | bronchiolitis |
| | | pneumonia |
| | | influenza-like syndrome |
| | | severe bronchiolitis with pneumonia |
| Rubella virus | Togaviridae | congenital rubella |
| | | German measles |
| Varicella-zoster virus | Herpesviridae | chickenpox |
| | | herpes zoster |
| | | Congenital varicella syndrome |

A particular embodiment of the invention also relates to a pharmaceutical composition comprising a compound of formula (I) as described herein and at least one pharmaceutically acceptable excipient.

A particular embodiment of the invention also relates to a compound of formula (I) as described herein for use as therapeutically active substances.

A particular embodiment of the invention also relates to a compound of formula (I) as described herein for use in the treatment or prevention of viral diseases, particularly for use in the treatment or prevention of the viral diseases as listed in Table 2, most particularly for use in the treatment or prevention of influenza.

In another embodiment, the invention relates to a method for the treatment or prevention of viral diseases, which method comprises administering a compound of formula (I) as described herein to a human being or animal.

In another embodiment, the invention relates to a method for the treatment or prevention of viral diseases as listed in Table 2, most particularly for treatment or prevention of influenza, which method comprises administering a compound of formula (I) as described herein to a human being or animal.

The invention also embraces the use of a compound of formula (I) as described herein for the treatment or prevention of viral diseases, particularly for the treatment or prevention of viral diseases as listed in Table 2, most particularly for treatment or prevention of influenza.

The invention also relates to the use of a compound of formula (I) as described herein for the preparation of medicaments useful for the treatment or prevention of viral diseases, particularly useful for the treatment or prevention of viral diseases as listed in Table 2, most particularly for treatment or prevention of influenza.

EXAMPLES

The following examples 1-177 are provided for illustration of the invention. They should not be considered as limiting the scope of the invention, but merely as being representative thereof.

Intermediate 1

[4-Oxo-3-[4-(trifluoromethoxy)phenyl]phthalazin-1-yl]trifluoromethanesulfonate

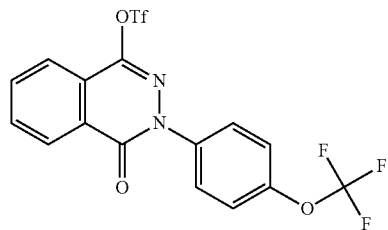 [SMILES: O=c1c2ccccc2c(OS(=O)(=O)C(F)(F)F)nn1-c1ccc(OC(F)(F)F)cc1]

A solution of (4-oxo-3H-phthalazin-1-yl) trifluoromethanesulfonate (CAS 1781216-89-4, 5.0 g, 17.0 mmol), [4-(trifluoromethoxy)phenyl]boronic acid (CAS 139301-27-2, 3.5 g, 17.0 mmol), Cu(AcO)$_2$ (6.1 g, 34.0 mmol) and Et$_3$N (5.1 g, 51.0 mmol) in THF was stirred at 15° C. for 40 h. The solvents were removed and the residue was purified by silica gel chromatography (petroleum ether:EtOAc=15:1/5:1) to give the title compound (3.0 g, 38.9%) as a white solid. MS (m/e): 455.0 (M+H)$^+$.

In analogy to Intermediate 1 compounds of the following table were prepared using different boronic acids as reactants:

| Intermediate No. | Structure | Systematic Name | Starting materials | mass found (M + H)$^+$ |
|---|---|---|---|---|
| 2 | OTf (structure) | [3-(6-Tert-butyl-3-pyridyl)-4-oxo-phthalazin-1-yl] trifluoromethanesulfonate | CAS 1781216-89-4 and CAS 1174312-53-8 | 428 |
| 3 | OTf (structure) | [3-(2-tert-butylpyrimidin-5-yl)-4-oxo-phthalazin-1-yl] trifluoromethanesulfonate | CAS 1781216-89-4 and CAS 1352570-51-4 | 429.0 |
| 4 | OTf (structure) | [3-[4-(3-methyloxetan-3-yl)phenyl]-4-oxo-phthalazin-1-yl] trifluoromethanesulfonate | 1781216-89-4 and CAS 1431616-42-0 | 441.1 |

-continued

| Intermediate No. | Structure | Systematic Name | Starting materials | mass found (M + H)+ |
|---|---|---|---|---|
| 5 | 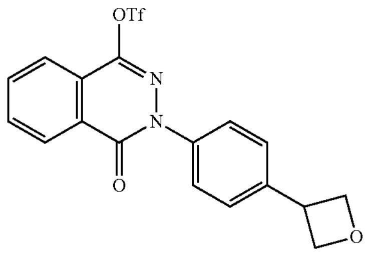 [SMILES: O=c1c2ccccc2c(OS(=O)(=O)C(F)(F)F)nn1-c1ccc(C2COC2)cc1] | [3-[4-(oxetan-3-yl)phenyl]-4-oxo-phthalazin-1-yl] trifluoromethanesulfonate | CAS 1781216-89-4 and CAS 1417887-72-9 | 427.0 |
| 6 | lp;3p | [3-(4-cyclopropylphenyl)-4-oxo-phthalazin-1-yl] trifluoromethanesulfonate | CAS 1781216-89-4 and CAS 302333-80-8 | 411.0 |
| 7 | 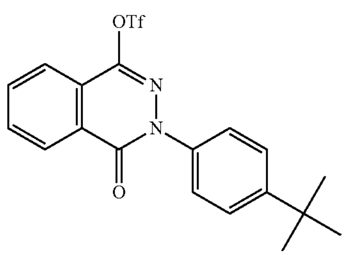 [SMILES: CC(C)(C)c1ccc(-n2nc(OS(=O)(=O)C(F)(F)F)c3ccccc3c2=O)cc1] | [3-(4-tert-butylphenyl)-4-oxo-phthalazin-1-yl] trifluoromethanesulfonate | CAS 1781216-89-4 and CAS 123324-71-0 | Only NMR |
| 8 | 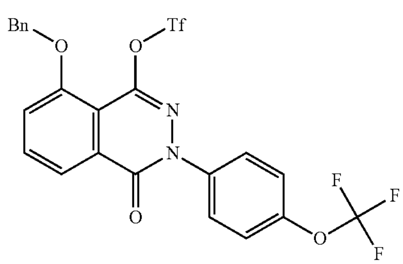 | [8-benzyloxy-4-oxo-3-[4-(trifluoromethoxy) phenyl]phthalazin-1-yl] trifluoromethanesulfonate | Intermediate 35 and CAS 139301-27-2 | Only NMR |

Intermediate 7

$^1$H NMR: (CDCl$_3$, 400 MHz) δ 8.52-8.45 (m, 1H), 7.95-7.82 (m, 3H), 7.52 (d, J=8.4 Hz, 1H), 7.43 (d, J=8.7 Hz, 1H), 1.29 (s, 9H).

Intermediate 8

$^1$H NMR: (CDCl$_3$, 400 MHz) δ 8.10 (d, J=7.8 Hz, 1 H), 7.79-7.70 (m, 3 H), 7.51-7.45 (m, 2 H), 7.44-7.30 (m, 6 H), 7.09 (d, J=8.5 Hz, 1 H), 6.82 (d, J=8.8 Hz, 1 H), 5.43 (s, 2 H).

Intermediate 9

[4-Oxo-3-[4-(trifluoromethoxy)phenyl]-6,7-dihydro-5H-cyclopenta[d]pyridazin-1-yl]trifluoromethanesulfonate

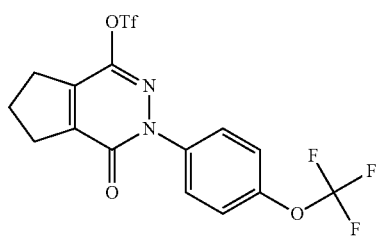 [SMILES: O=c1c2c(c(OS(=O)(=O)C(F)(F)F)nn1-c1ccc(OC(F)(F)F)cc1)CCC2]

Step 1: 3-[4-(trifluoromethoxy)phenyl]-2,5,6,7-tetrahydrocyclopenta[d]pyridazine-1,4-dione A mixture of 5,6-dihydro-4H-cyclopenta[c]furan-1,3-dione (CAS 3205-94-5; 276 mg, 2.0 mmol) and [4-(trifluoromethoxy)phenyl]hydrazine hydrochloride (CAS 133115-72-7; 456 mg, 2.0 mmol) was dissolved in NMP (5 mL). The mixture was heated to 180° C. and reacted for 20 min. The reaction was cooled to 30° C. and poured onto water (30 mL). The product was precipitated and then filtered. The solid was washed with $H_2O$ (10 mL×3). The solid was dissolved in DCM (50 mL) and dried over $Na_2SO_4$. The solvent was evaporated to give the title compound (500 mg, yield: 80%) as a off-white solid which was used in the next step without further purification.

Step 2: [4-oxo-3-[4-(trifluoromethoxy)phenyl]-6,7-dihydro-5H-cyclopenta[d]pyridazin-1-yl]trifluoromethanesulfonate To a solution of 3-[4-(trifluoromethoxy)phenyl]-2,5,6,7-tetrahydrocyclopenta[d]pyridazine-1,4-dione (500 mg, 1.6 mmol) and triethylamine (323 mg, 3.20 mmol) in DCM (10 mL) was added trifluoromethanesulfonic anhydride (542 mg, 1.92 mmol) at 0° C. After addition, the reaction was warmed to 30° C. and stirred for 1 h. The reaction was quenched with $H_2O$ (20 mL) and extracted with DCM (20 mL). The organic phase was evaporated and purified by column chromatography (petroleum ether:EtOAc=10:1) to give the title compound (480 mg, yield: 54%) as a white solid. $^1$H NMR: (DMSO, 400 MHz) δ 11.38 (br., s, 1H), 7.73-7.70 (d, J=5.2 Hz, 2H), 7.69-7.45 (d, J=3.6 Hz, 2H), 2.85-2.76 (t, J=15.2 Hz, 4H), 2.13-2.05 (td, J=15.2 Hz, 2H). MS (m/e): 444.1 (M+H)$^+$.

In analogy to Intermediate 9 compounds of the following table were prepared using different diones and hydrazine hydrochlorides as reactants:

| Intermediate No. | Structure | Systematic Name | Starting materials | mass found (M + H)$^+$ |
|---|---|---|---|---|
| 10 | 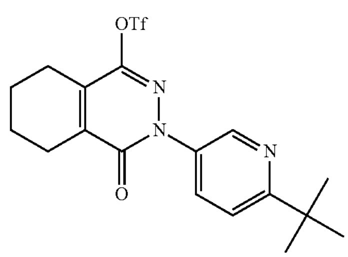 [SMILES: CC(C)(C)c1ccc(-n2nc(OS(=O)(=O)C(F)(F)F)c3c(c2=O)CCCC3)cn1] | [3-(6-tert-butyl-3-pyridyl)-4-oxo-5,6,7,8-tetrahydrophthalazin-1-yl]trifluoromethanesulfonate | CAS 2426-02-0 and CAS 848841-56-5 | 434.1 |
| 11 | 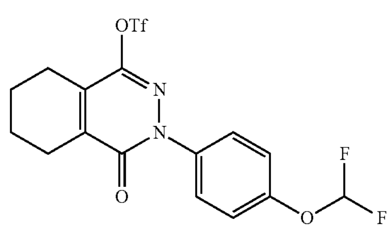 [SMILES: O=c1c2c(c(OS(=O)(=O)C(F)(F)F)nn1-c1ccc(OC(F)F)cc1)CCCC2] | [3-[4-(difluoromethoxy)phenyl]-4-oxo-5,6,7,8-tetrahydrophthalazin-1-yl]trifluoromethanesulfonate | CAS 2426-02-0 and CAS 1240527-90-5 | Only NMR |
| 12 | 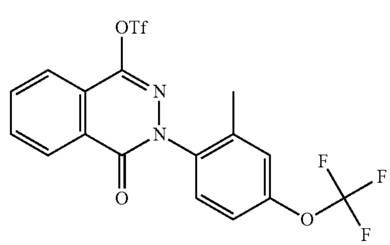 [SMILES: Cc1cc(OC(F)(F)F)ccc1-n1nc(OS(=O)(=O)C(F)(F)F)c2ccccc2c1=O] | [3-[2-methyl-4-(trifluoromethoxy)phenyl]-4-oxo-phthalazin-1-yl]trifluoromethanesulfonate | CAS 3205-94-5 and CAS 133115-72-7 | 469.0 |

-continued

| Intermediate No. | Structure | Systematic Name | Starting materials | mass found (M + H)+ |
|---|---|---|---|---|
| 13 | 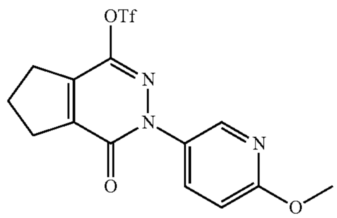 [SMILES: COc1ccc(-n2nc(OS(=O)(=O)C(F)(F)F)c3c(c2=O)CCC3)cn1] | [3-(6-methoxy-3-pyridyl)-4-oxo-6,7-dihydro-5H-cyclopenta[d]pyridazin-1-yl] trifluoromethanesulfonate | CAS 3205-94-5 and CAS 160664-95-9 | 392.0 |
| 14 | 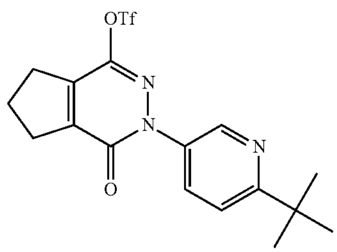 [SMILES: CC(C)(C)c1ccc(-n2nc(OS(=O)(=O)C(F)(F)F)c3c(c2=O)CCC3)cn1] | [3-(6-tert-butyl-3-pyridyl)-4-oxo-6,7-dihydro-5H-cyclopenta[d]pyridazin-1-yl] trifluoromethanesulfonate | CAS 3205-94-5 and CAS 848841-56-5 | 418.0 |
| 15 | 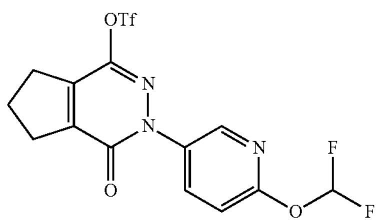 [SMILES: O=c1c2c(c(OS(=O)(=O)C(F)(F)F)nn1-c1ccc(OC(F)F)nc1)CCC2] | [3-[4-(difluoromethoxy)phenyl]-4-oxo-6,7-dihydro-5H-cyclopenta[d]pyridazin-1-yl] trifluoromethanesulfonate | CAS 3205-94-5 and CAS 1240527-90-5 | 427.0 |
| 16 | 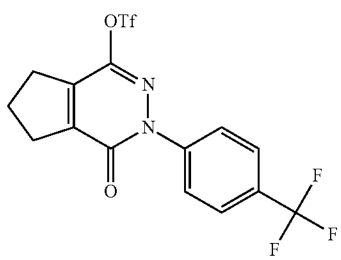 [SMILES: O=c1c2c(c(OS(=O)(=O)C(F)(F)F)nn1-c1ccc(C(F)(F)F)cc1)CCC2] | [4-oxo-3-[4-(trifluoromethyl)phenyl]-6,7-dihydro-5H-cyclopenta[d]pyridazin-1-yl] trifluoromethanesulfonate | CAS 3205-94-5 and CAS 2923-56-0 | Only NMR |
| 17 | 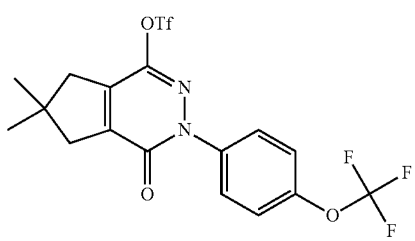 [SMILES: CC1(C)Cc2c(OS(=O)(=O)C(F)(F)F)nn(-c3ccc(OC(F)(F)F)cc3)c(=O)c2C1] | [6,6-dimethyl-4-oxo-3-[4-(trifluoromethoxy)phenyl]-5,7-dihydrocyclopenta[d]pyridazin-1-yl] trifluoromethanesulfonate | CAS 957755-07-6 and CAS 133115-72-7 | 473.0 |
| 18 | 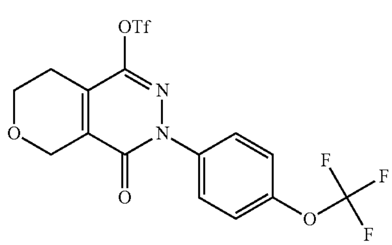 [SMILES: O=c1c2c(c(OS(=O)(=O)C(F)(F)F)nn1-c1ccc(OC(F)(F)F)cc1)CCOC2] | [4-oxo-3-[4-(trifluoromethoxy)phenyl]-7,8-dihydro-5H-pyrano[3,4-d]pyridazin-1-yl] trifluoromethanesulfonate | Intermediate 112 and CAS 133115-72-7 | 461.0 |

-continued

| Intermediate No. | Structure | Systematic Name | Starting materials | mass found (M + H)+ |
|---|---|---|---|---|
| 19 | 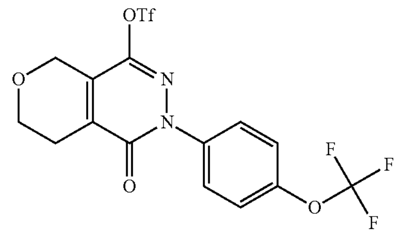 [SMILES: O=c1c2c(c(OS(=O)(=O)C(F)(F)F)nn1-c1ccc(OC(F)(F)F)cc1)COCC2] | [1-oxo-2-[4-(trifluoromethoxy)phenyl]-7,8-dihydro-5H-pyrano[3,4-d]pyridazin-4-yl] trifluoromethanesulfonate | Intermediate 112 and CAS 133115-72-7 | 461.0 |
| 20 | 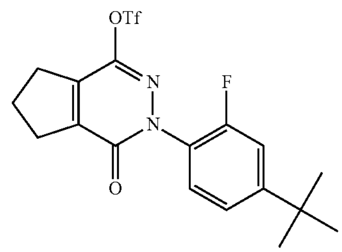 [SMILES: CC(C)(C)c1ccc(-n2nc(OS(=O)(=O)C(F)(F)F)c3c(c2=O)CCC3)c(F)c1] | [3-(4-tert-butyl-2-fluoro-phenyl)-4-oxo-6,7-dihydro-5H-cyclopenta[d]pyridazin-1-yl] trifluoromethanesulfonate | CAS 3205-94-5 and Intermediate 110 | 435.1 |
| 21 | 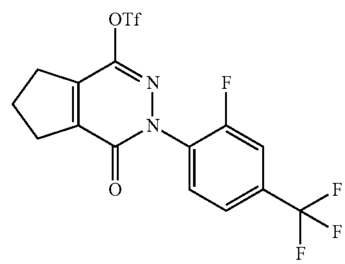 [SMILES: O=c1c2c(c(OS(=O)(=O)C(F)(F)F)nn1-c1ccc(C(F)(F)F)cc1F)CCC2] | [3-[2-fluoro-4-(trifluoromethyl)phenyl]-4-oxo-6,7-dihydro-5H-cyclopenta[d]pyridazin-1-yl] trifluoromethanesulfonate | CAS 3205-94-5 and CAS 1030313-53-1 | 447.0 |
| 22 | 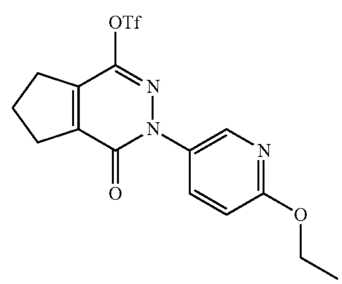 [SMILES: CCOc1ccc(-n2nc(OS(=O)(=O)C(F)(F)F)c3c(c2=O)CCC3)cn1] | [3-(6-ethoxy-3-pyridyl)-4-oxo-6,7-dihydro-5H-cyclopenta[d]pyridazin-1-yl] trifluoromethanesulfonate | CAS 3205-94-5 and Intermediate 111 | 406.0 |

Intermediate 11

$^1$H NMR: (CDCl$_3$, 400 MHz) δ 7.66 (m, J=9.0 Hz, 2H), 7.22 (d, J=9.0 Hz, 2H), 6.55 (t, J=76 Hz 1H), 2.74-2.58 (m, 4H), 1.91-1.81 (t, J=2.8 Hz, 4H).

Intermediate 16

$^1$H NMR: (CDCl$_3$, 400 MHz) δ 7.76-7.70 (m, 2H), 7.70-7.63 (m, 2H), 3.05-2.94 (m, 4H), 2.22 (q, J=7.7 Hz, 2H).

Intermediate 23

[4-Oxo-3-[4-(trifluoromethoxy)phenyl]-5,6,7,8-tetrahydrophthalazin-1-yl]trifluoromethanesulfonate

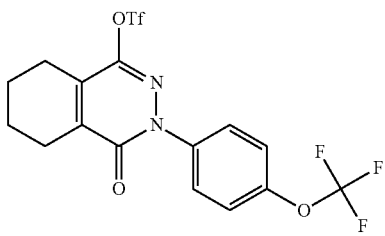 [SMILES: O=c1c2c(c(OS(=O)(=O)C(F)(F)F)nn1-c1ccc(OC(F)(F)F)cc1)CCCC2]

Step 1: 3-[4-(trifluoromethoxy)phenyl]-5,6,7,8-tetrahydro-2H-phthalazine-1,4-dione To a solution of 4,5,6,7-tetrahydroisobenzofuran-1,3-dione (CAS 2426-02-0, 3.04 g, 2.0 mmol) in AcOH (30 mL) was added [4-(trifluoromethoxy)phenyl]hydrazine hydrochloride (CAS 133115-72-7, 4.57 g, 2.0 mmol) at 15° C. After addition, the mixture was warmed to 120° C. and stirred for 20 h. The mixture was cooled to rt and poured into water (60 mL) and there was precipitate formed. The mixture was extracted with EtOAc (150 mL×2), the organic phase was washed with brine (100 mL), dried over Na₂SO₄. After filtration, the filtrate was concentrated in vacuo to get a crude product (6.0 g) as a off-white solid. To a solution of the crude product (6.0 g, 18.4 mmol) in EtOH (100 mL) was added EtONa (2.50 g, 36.8 mmol) at 15° C. After addition, the mixture was warmed to 20-25° C. and stirred for 20 h. The mixture was concentrated in vacuo and the residue was poured into water (100 mL). The mixture was acided with 1 N aq. HCl to pH=3, extracted with EtOAc (200 mL×2). The combined organic phase was washed with brine (100 mL), dried over Na₂SO₄. After filtration, the filtrate was concentrated in vacuo to get the title compound (6.0 g crude) as a light yellow solid which was used for the next step without purification.

Step 2: [4-oxo-3-[4-(trifluoromethoxy)phenyl]-5,6,7,8-tetrahydrophthalazin-1-yl]trifluoromethanesulfonate To a solution of 3-[4-(trifluoromethoxy)phenyl]-5,6,7,8-tetrahydro-2H-phthalazine-1,4-dione (6.0 g, 18.4 mmol) and Et₃N (7.43 g, 73.6 mmol) in DCM (100 mL) was added Tf₂O (10.4 g, 36.8 mmol) at 0° C. under N₂. Then the mixture was stirred at 15° C. for 20 h. Solvent was removed in vacuum to give a residue which was purified by column chromatography on silica gel (Petroleum ether/EtOAc from 150/1 to 100/1) to give the title compound (1.6 g, 19% yield) as yellow solid. ¹HNMR: (CDCl₃, 400 MHz) δ 7.72 (d, J=9.2 Hz, 2H), 7.33 (d, J=8.3 Hz, 2H), 2.74-2.61 (m, 4H), 1.92-1.82 (m, 4H).

In analogy to Intermediate 23 compounds of the following table were prepared using different 1,3-diones and hydrazines as reactants:

| Intermediate No. | Structure | Systematic Name | Starting materials | mass found (M + H)⁺ |
|---|---|---|---|---|
| 24 | | [6-methoxy-4-oxo-3-[4-(trifluoromethoxy)phenyl]phthalazin-1-yl]trifluoromethanesulfonate and [7-methoxy-4-oxo-3-[4-(trifluoromethoxy)phenyl]phthalazin-1-yl]trifluoromethanesulfonate | CAS 28281-76-7 and CAS 13957-54-5 | 485.0 |
| 25 | 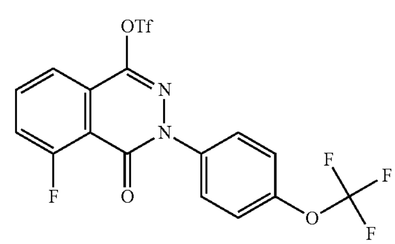 [SMILES: O=c1c2c(F)cccc2c(OS(=O)(=O)C(F)(F)F)nn1-c1ccc(OC(F)(F)F)cc1] | [5-fluoro-4-oxo-3-[4-(trifluoromethoxy)phenyl]phthalazin-1-yl]trifluoromethanesulfonate and [8-fluoro-4-oxo-3-[4-(trifluoromethoxy)phenyl]phthalazin-1-yl]trifluoromethanesulfonate | CAS 652-39-1 and CAS 133115-72-7 | 473.1 |

| Intermediate No. | Structure | Systematic Name | Starting materials | mass found (M + H)+ |
|---|---|---|---|---|
| | 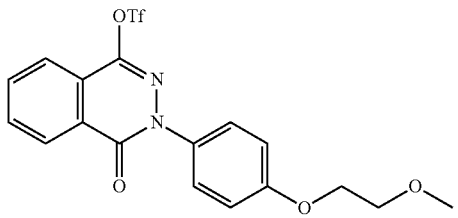 [SMILES: COCCOc1ccc(-n2nc(OS(=O)(=O)C(F)(F)F)c3ccccc3c2=O)cc1] | | | |

Intermediate 26

[3-[4-(2-Methoxyethoxy)phenyl]-4-oxo-phthalazin-1-yl]trifluoromethanesulfonate

Step 1: 2-(4-bromoanilino)isoindoline-1,3-dione

To a solution of isobenzofuran-1,3-dione (CAS 85-44-9, 5.0 g, 33.8 mmol) in AcOH (30 mL) was added (4-bromophenyl)hydrazine hydrochloride (CAS 622-88-8, 8.3 g, 37.1 mmol) in one portion. The mixture was stirred overnight at 120° C. After cooled to rt, the brown solution was poured into water (100 mL) and the mixture was filtered. The solid was washed with water and dried to give the title compound (8 g), which was used in the next step directly. MS (m/e): 317.1 & 319.1 (M+H)+.

Step 2: 3-(4-bromophenyl)-2H-phthalazine-1,4-dione

To a solution of 2-(4-bromoanilino)isoindoline-1,3-dione (8 g, 25.2 mmol) in EtOH (150 mL) was added sodium ethanolate (2.57 g, 37.8 mmol) at rt. The reaction mixture was stirred at rt for 30 min and then concentrated. The residue was poured into water (100 mL) and extracted with EtOAc (100 mL×2). The combined organic phase was washed with aq. HCl (1N) and brine, dried over Na2SO4 and concentrated. The residue was purified by flash column chromatography on silica gel with a gradient of 10%~50% EtOAc in DCM to afford the title compound (4.7 g) as white solid. MS (m/e): 317.1 & 319.1 (M+H)+.

Step 3: 3-[4-(2-methoxyethoxy)phenyl]-2H-phthalazine-1,4-dione

A mixture of 3-(4-bromophenyl)-2H-phthalazine-1,4-dione (1.0 g, 3.15 mmol), 2-methoxyethanol (4.8 g, 4.97 mL, 63.1 mmol), K2CO3 (1.31 g, 9.46 mmol) and cupric chloride (212 mg, 1.58 mmol) was stirred at 130° C. for 36 h. After cooled to rt, the mixture was diluted with EtOAc (100 mL) and washed with sat. aqueous NH4Cl and brine. The organic phase was dried over anhydrous Na2SO4 and concentrated. The residue was purified by column chromatography (eluting with 10%~50% EtOAc in DCM) to afford the title compound (0.65 g) as white powder. MS (m/e): 313.1 (M+H)+.

Step 4: [3-[4-(2-Methoxyethoxy)phenyl]-4-oxo-phthalazin-1-yl]trifluoromethanesulfonate To a mixture of 3-[4-(2-methoxyethoxy)phenyl]-2H-phthalazine-1,4-dione (650 mg, 2.08 mmol), and pyridine (1.68 mL, 20.8 mmol) in DCM (20 mL) was added Tf2O (410 μL, 2.5 mmol) dropwise at 0° C. The reaction mixture was stirred at rt for 2 h before quenched by sat. aqueous NH4Cl. The mixture was diluted with EtOAc (100 mL) and the organic phase was washed with aq. HCl and brine. The organic phase was dried over Na2SO4 and concentrated to give the title compound (600 mg, crude). MS (m/e): 445.1 (M+H)+.

Intermediate 27

[8-Methoxy-4-oxo-3-[4-(trifluoromethoxy)phenyl]phthalazin-1-yl]trifluoromethanesulfonate

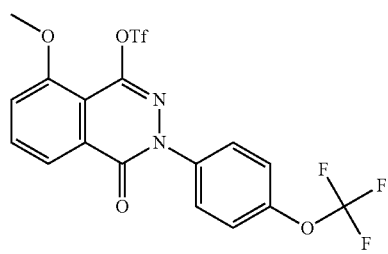 [SMILES: COc1cccc2c(=O)n(-c3ccc(OC(F)(F)F)cc3)nc(OS(=O)(=O)C(F)(F)F)c12]

Step 1: 4-hydroxy-2-[4-(trifluoromethoxy)anilino]isoindoline-1,3-dione

To a solution of 4-hydroxyisobenzofuran-1,3-dione (CAS 37418-88-5, 1.0 g, 6.09 mmol) in AcOH (10 mL) was added (4-(trifluoromethoxy)phenyl)hydrazine hydrochloride (CAS 133115-72-7, 1.53 g, 6.7 mmol). The reaction mixture was stirred overnight at 120° C. After cooling, the brown solution was poured into water (100 mL) and extracted with EtOAc (100 mL×2). The combined organic phase was washed with water and brine, dried over anhydrous Na$_2$SO$_4$ and concentrated. The residue was purified by column chromatography (eluting with 10%~40% EtOAc in petroleum ether) to afford the title compound (1.0 g) as a white solid. MS (m/e): 339.1 (M+H)$^+$.

Step 2: 8-hydroxy-3-[4-(trifluoromethoxy)phenyl]-2H-phthalazine-1,4-dione

To a solution of 4-hydroxy-2-[4-(trifluoromethoxy)anilino]isoindoline-1,3-dione (1 g, 2.96 mmol) in EtOH (100 mL) was added sodium ethanolate (302 mg, 4.43 mmol). The reaction mixture was stirred overnight at rt. After removal of the solvents, the residue was poured into water (100 mL). The mixture was acidified with concentrated HCl to pH 3 and extracted with EtOAc. The organic phase was washed with water and brine, dried over Na$_2$SO$_4$ and concentrated. The residue was purified by column chromatography (eluting with 10%~50% EtOAc in petroleum ether) to afford the title compound and the isomer 5-hydroxy-3-[4-(trifluoromethoxy)phenyl]-2H-phthalazine-1,4-dione (0.9 g in total) as a white solid. MS (m/e): 339.1 (M+H)$^+$.

Step 3: 8-methoxy-3-[4-(trifluoromethoxy)phenyl]-2H-phthalazine-1,4-dione

To a mixture of 8-hydroxy-3-[4-(trifluoromethoxy)phenyl]-2H-phthalazine-1,4-dione and 5-hydroxy-3-[4-(trifluoromethoxy)phenyl]-2H-phthalazine-1,4-dione (140 mg, 397 μmol) in Et$_2$O/MeOH (10 mL, v:v=4:1) was added (diazomethyl)trimethylsilane (1.42 mL, 2.84 mmol) at rt. After stirred at rt for 2 h, the reaction mixture was treated with water and the mixture was extracted with EtOAc. The combined organic extract was dried over Na$_2$SO$_4$ and concentrated. The residue was purified by column chromatography (eluting with 10%~50% EtOAc in petroleum ether) to afford a mixture of the title compound and its isomer 5-methoxy-3-[4-(trifluoromethoxy)phenyl]-2H-phthalazine-1,4-dione (300 mg in total) as a white solid. MS (m/e): 353.1 (M+H)$^+$.

Step 4: [8-methoxy-4-oxo-3-[4-(trifluoromethoxy)phenyl]phthalazin-1-yl]trifluoromethanesulfonate To a mixture of 8-methoxy-3-[4-(trifluoromethoxy)phenyl]-2H-phthalazine-1,4-dione and 5-methoxy-3-[4-(trifluoromethoxy)phenyl]-2H-phthalazine-1,4-dione (300 mg, 852 μmol), and pyridine (337 mg, 4.26 mmol) in DCM (20 mL) was added Tf$_2$O (168 μl, 1.02 mmol) dropwise at 0° C. The mixture was stirred at rt for 2 h. The reaction mixture was treated with saturated aqueous NH$_4$Cl and extracted with EtOAc (100 mL). The organic phase was washed with aq. HCl and brine, dried over Na$_2$SO$_4$ and concentrated to afford the title compound and its isomer [5-methoxy-4-oxo-3-[4-(trifluoromethoxy)phenyl]phthalazin-1-yl]trifluoromethanesulfonate (400 mg in total) as a solid. MS (m/e): 485.1 (M+H)$^+$.

Intermediate 28

[3-(4-Tert-butylphenyl)-6-ethyl-4-oxo-phthalazin-1-yl]trifluoromethanesulfonate

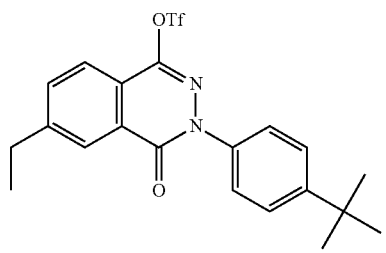 [SMILES: CCc1ccc2c(OS(=O)(=O)C(F)(F)F)nn(-c3ccc(C(C)(C)C)cc3)c(=O)c2c1]

Step 1: (6-bromo-4-oxo-3H-phthalazin-1-yl) trifluoromethanesulfonate and (7-bromo-4-oxo-3H-phthalazin-1-yl) trifluoromethanesulfonate To a solution of 6-bromo-2,3-dihydrophthalazine-1,4-dione (CAS 76240-49-8, 36.0 g, 150 mmol) and Et$_3$N (37.5 g, 375 mmol) in DCM (1.0 L) was added Tf$_2$O (42.3 g, 150 mol) dropwise over 1 h. The mixture was stirred at 0° C. for 2 h and then kept at 15° C. for 16 h. The mixture was filtered and the filtrate was concentrated. The residue was purified by flash column (petroleum ether:EtOAc from 5:1 to 3:1) to give a mixture of the title compounds (9.0 g, 16% yield) as a white solid.

Step 2: [6-bromo-3-(4-tert-butylphenyl)-4-oxo-phthalazin-1-yl]trifluoromethanesulfonate and [7-bromo-3-(4-tert-butylphenyl)-4-oxo-phthalazin-1-yl]trifluoromethanesulfonate A solution of (6-bromo-4-oxo-3H-phthalazin-1-yl) trifluoromethanesulfonate and (7-bromo-4-oxo-3H-phthalazin-1-yl) trifluoromethanesulfonate (9.0 g, 24.1 mmol), (4-tert-butylphenyl)boronic acid (CAS 123324-71-0, 4.2 g, 24.1 mmol), Cu(AcO)$_2$ (8.6 g, 48.2 mmol) and TEA (7.2 g, 72.3 mol) in THF (100 mL) was stirred at 15° C. for 16 h. The reaction mixture was filtered and the filtrate was concentrated. The residue was purified by column chromatography (petroleum ether:EtOAc from 20:1 to 10:1) to give [6-bromo-3-(4-tert-butylphenyl)-4-oxo-phthalazin-1-yl]trifluoromethanesulfonate (4.0 g, 33.0% yield) and [7-bromo-3-(4-tert-butylphenyl)-4-oxo-phthalazin-1-yl]trifluoromethanesulfonate (3.0 g, 25% yield) as white solids. MS (m/e): 505.1 and 507.1 (M+H)$^+$.

Step 3: 6-bromo-3-(4-tert-butylphenyl)-2H-phthalazine-1,4-dione

To a solution of [6-bromo-3-(4-tert-butylphenyl)-4-oxo-phthalazin-1-yl]trifluoromethanesulfonate (4.0 g, 7.93 mmol) in CH$_3$OH (40 mL) was added K$_2$CO$_3$ (5.4 g, 39.6 mmol) and the mixture was stirred at 60° C. for 16 h. The reaction mixture was filtered and the filtration was concentrated. The crude product was dissolved with EtOAc (100 mL) and washed with water (50 mL×2). The organic phase was dried (Na$_2$SO$_4$) and concentrated to yield the title compound (2.0 g, 67.7% yield). MS (m/e): 373.0 and 375.0 (M+H)$^+$.

Step 4: 3-(4-tert-butylphenyl)-6-vinyl-2H-phthalazine-1,4-dione

A mixture of 6-bromo-3-(4-tert-butylphenyl)-2H-phthalazine-1,4-dione (1.0 g, 2.5 mmol), potassium ethenyltrifluoroborate (CAS 13682-77-4, 0.56 g, 3.7 mmol), $K_2CO_3$ (0.86 g, 6.2 mmol), water (0.6 mL) and $Pd(dppf)Cl_2 \cdot DCM$ (0.1 g) in DME (15.0 mL) was stirred at 100° C. for 12 h. The mixture was concentrated and the residue was purified by flash chromatography (petroleum ether:EtOAc from 5:1 to 2:1) to afford the title compound (0.75 g, 94% yield) as a light yellow solid. MS (m/e): 321.1 $(M+H)^+$.

Step 5: 3-(4-tert-butylphenyl)-6-ethyl-2H-phthalazine-1,4-dione

A solution of 3-(4-tert-butylphenyl)-6-vinyl-2H-phthalazine-1,4-dione (0.75 g, 2.3 mmol) and Pd/C (0.3 g) in MeOH (20.0 mL) was purge with hydrogen by 3 times. Then the reaction mixture was stirred at rt under hydrogen (15 Psi) for 1 h. The reaction mixture was filtered, and the filtrate was concentrated to afford the title compound (0.6 g, 80.0% yield) as a white solid that was used in the next step without purification. MS (m/e): 323.2 $(M+H)^+$.

Step 6: [3-(4-tert-butylphenyl)-4-oxo-6-vinyl-phthalazin-1-yl]trifluoromethanesulfonate To a solution of 3-(4-tert-butylphenyl)-6-ethyl-2H-phthalazine-1,4-dione (0.7 g, 2.1 mol) and $Et_3N$ (0.52 g, 5.2 mol) in DCM (20.0 mL) was added $Tf_2O$ (0.61 g, 2.1 mol) dropwise at 0° C. The mixture was stirred at 0° C. for 1 h and kept at 15° C. for 16 h. The mixture was filtered. The filtrate was concentrated and the residue was purified by flash chromatography (petroleum ether:EtOAc from 20:1 to 10:1) to give the title compound (0.8 g, 84%) as a white solid. MS (m/e): 455.1 $(M+H)^+$.

Intermediate 29

4-Bromo-2-[4-(trifluoromethoxy)phenyl]phthalazin-1-one

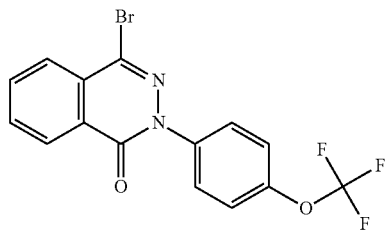 [SMILES: O=c1c2ccccc2c(Br)nn1-c1ccc(OC(F)(F)F)cc1]

Step 1: 3-[4-(trifluoromethoxy)phenyl]-2H-phthalazine-1,4-dione

To a solution of isobenzofuran-1,3-dione (CAS 85-44-9, 40 g, 270.0 mmol) in AcOH (400 mL) was added [4-(trifluoromethoxy)phenyl]hydrazine hydrochloride (CAS 133115-72-7, 61.77 g, 270 mmol) at 15° C. After addition, the mixture was warmed to 120° C. and stirred for 20 h. The mixture was cooled to rt and poured into water (700 mL), a white solid was formed. After about 15 min, the solid was filtered, the filter cake was washed with water (100 mL×2). The solid was dried under vacuo to get the a crude product (73 g, 84% yield) as an off-white solid. The solid (73.0 g, 226.5 mmol) was dissolved into EtOH (1000 mL) and to the mixture was added EtONa (31.0 g, 455.5 mmol) at 15° C. After addition, the mixture was warmed to 20-25° C. and stirred for 20 h. The mixture was concentrated in vacuo and the residue was poured into water (400 mL). The mixture was acidified with 1 N HCl to pH=3, a white precipitate formed. The solid was filtered and the solid was re-dissolved into EtOAc (1500 mL). The water was separated and the organic phase was dried over $Na_2SO_4$. The organic phase was concentrated in vacuo and residue was triturated with EtOAc (300 mL) to get the title crude product (53 g, 73% yield) as an off-white solid which was used for the next step without purification.

Step 2: 4-bromo-2-[4-(trifluoromethoxy)phenyl]phthalazin-1-one

To a solution of 3-[4-(trifluoromethoxy)phenyl]-2H-phthalazine-1,4-dione (40.0 g, 124.2 mmol) in DCE (40.0 mL) was added $POBr_3$ (178.6 g, 621.1 mmol) under $N_2$. Then the mixture was stirred at 80° C. for 16 h. The reaction mixture was poured into ice/water (1000 mL), extracted by EtOAc (1000 mL), dried and concentrated. The residue was purified by column (petroleum ether/EtOAc from 50/1 to 15/1) to give title compound as light yellow solid which was purified by trituration with petroleum ether/EtOAc (100 mL) to give the title compound (14 g, 29% yield) as an off white solid. MS (m/e): 385.0 and 387.0 $(M+H)^+$.

Intermediate 30

4-Bromo-6-ethyl-2-[4-(trifluoromethoxy)phenyl]phthalazin-1-one and 4-bromo-7-ethyl-2-[4-(trifluoromethoxy)phenyl]phthalazin-1-one

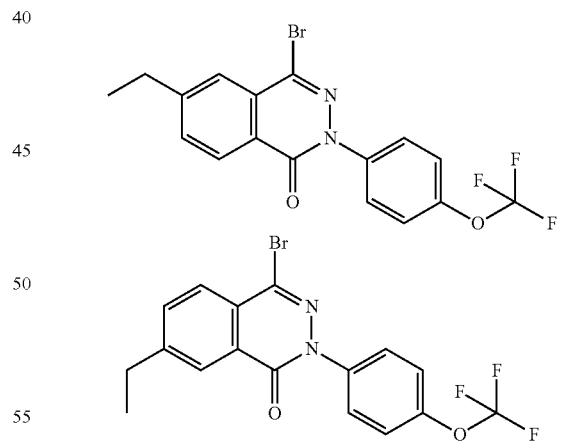

Step 1: 6-bromo-4-hydroxy-2-[4-(trifluoromethoxy)phenyl]phthalazin-1-one and 7-bromo-4-hydroxy-2-[4-(trifluoromethoxy)phenyl]phthalazin-1-one To a solution of 5-bromoisobenzofuran-1,3-dione (CAS 86-90-8, 2.27 g, 10.0 mmol) in AcOH (30 mL) was added (4-(trifluoromethoxy)phenyl)hydrazine hydrochloride (CAS 133115-72-7, 2.29 g, 10.0 mmol) and the reaction mixture was stirred at 80° C. for 2 h. When LC-MS indicated that the starting material was consumed, the mixture was concentrated to afford the crude product. To a solution of the product in EtOH (100 mL) was added sodium ethanolate (1.43 g, 20.9 mmol) at rt. The mixture was stirred at 80° C. for 2 h before concentrated to give the title compound mixture (4.80 g). MS (m/e): 401.0 and 403.0 (M+H)⁺.

Step 2: 4-hydroxy-2-[4-(trifluoromethoxy)phenyl]-6-vinyl-phthalazin-1-one and 4-hydroxy-2-[4-(trifluoromethoxy)phenyl]-7-vinyl-phthalazin-1-one A mixture of 6-bromo-4-hydroxy-2-(4-(trifluoromethoxy)phenyl)phthalazin-1 (2H)-one and 7-bromo-4-hydroxy-2-(4-(trifluoromethoxy)phenyl)phthalazin-1(2H)-one (490 mg, 1.22 mmol), potassium ethenyltrifluoroborate (CAS 13682-77-4, 245 mg, 1.83 mmol), K2CO3 (422 mg, 3.05 mmol), water (0.3 mL) and Pd(dppf)Cl₂.DCM (90 mg) in DME (7.0 mL) was stirred at 100° C. for 12 h. The mixture was filtered and the filtrate was concentrated. The residue was purified by flash chromatography to afford the title compound mixture (180 mg) as a light yellow solid. MS (m/e): 348.1 (M+H)⁺.

Step 3: 6-ethyl-4-hydroxy-2-[4-(trifluoromethoxy)phenyl]phthalazin-1-one and 7-ethyl-4-hydroxy-2-[4-(trifluoromethoxy)phenyl]phthalazin-1-one A solution of 4-hydroxy-2-[4-(trifluoromethoxy)phenyl]-6-vinyl-phthalazin-1-one and 4-hydroxy-2-[4-(trifluoromethoxy)phenyl]-7-vinyl-phthalazin-1-one (180 mg, 0.52 mmol), and Pd/C (11 mg) in MeOH (10 mL) was purge with hydrogen for 3 times. Then the reaction mixture was stirred under hydrogen (1 atm) at rt overnight. The reaction mixture was filtered, and the filtrate was concentrated to afford the title compound mixture (150 mg, 83% yield) as a white solid. MS (m/e): 350.1 (M+H)⁺.

Step 4: 4-bromo-6-ethyl-2-[4-(trifluoromethoxy)phenyl]phthalazin-1-one & 4-bromo-7-ethyl-2-[4-(trifluoromethoxy)phenyl]phthalazin-1-one To a stirred suspension of 6-ethyl-4-hydroxy-2-(4-(trifluoromethoxy)phenyl)phthalazin-1(2H)-one and 7-ethyl-4-hydroxy-2-(4-(trifluoromethoxy)phenyl)phthalazin-1 (2H)-one (380 mg, 1.08 mmol) in DCE (10 mL) was added phosphorus oxybromide (622 mg, 2.17 mmol). The mixture was stirred at 100° C. for 18 h before it was cooled to rt and poured into water. The aqueous phase was treated with aqueous Na₂CO₃ (1 M) to pH 8 and extracted with EtOAc. The organic phases were dried and concentrated in vacuo. The residue was purified by flash chromatography to give the title compound mixture as a solid (320 mg, in 71% yield). MS (m/e): 413.0 and 415.0 (M+H)⁺.

Intermediate 31

4-Bromo-2-[4-(trifluoromethoxy)phenyl]-6-vinyl-phthalazin-1-one and 4-bromo-2-[4-(trifluoromethoxy)phenyl]-7-vinyl-phthalazin-1-one

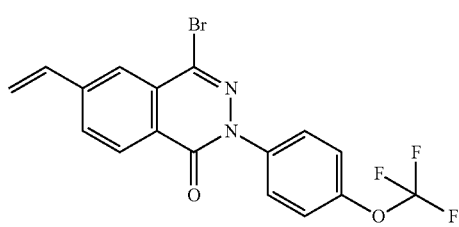

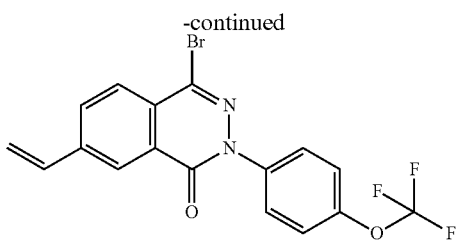

To a stirred suspension of 4-hydroxy-2-[4-(trifluoromethoxy)phenyl]-6-vinyl-phthalazin-1-one and 4-hydroxy-2-[4-(trifluoromethoxy)phenyl]-7-vinyl-phthalazin-1-one (Intermediate 30, step 2; 348 mg, 1.00 mmol) in DCE (10 mL) was added phosphorus oxybromide (573 mg, 2.00 mmol). The mixture was stirred at 100° C. for 18 h before it was cooled to rt and poured into water. The aqueous phase was treated with aqueous Na₂CO₃ (1M) to pH 8 and extracted with EtOAc. The organic phase were dried and concentrated in vacuo. The residue was purified by flash chromatography to give the title compound mixture as a solid (330 mg, in 80% yield). MS (m/e): 411.0 and 413.0 (M+H)⁺.

Intermediate 32

1-Bromo-6-methyl-3-[4-(trifluoromethoxy)phenyl]-7,8-dihydro-5H-pyrido[3,4-d]pyridazin-4-one and 4-bromo-6-methyl-2-[4-(trifluoromethoxy)phenyl]-7,8-dihydro-5H-pyrido[3,4-d]pyridazin-1-one

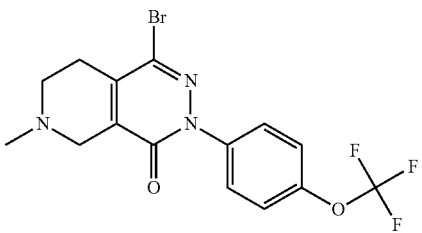

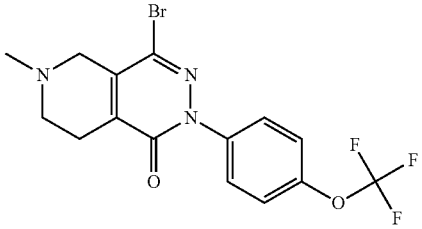

Step 1: 1-bromo-3H-pyrido[3,4-d]pyridazin-4-one and 4-bromo-2H-pyrido[3,4-d]pyridazin-1-one To a solution of 2,3-dihydropyrido[3,4-d]pyridazine-1,4-dione (CAS 31384-08-4, 8.0 g, 49.0 mmol) in DCE (4 mL) was added POBr₃ (84.2 g, 294.0 mmol) at 25° C., and then the mixture was stirred at 110° C. for 16 h. The mixture was poured into 30 mL ice-water, and then extracted with EtOAc (30 mL×3), combined the organic phase and dried over Na₂SO₄. The solid was filtered off and filtrate was concentrated to give the crude product, which was purified by chromatography on silica gel (petroleum ether:EtOAc=10:1) to give the title compound mixture (2.0 g, crude) as a yellow solid. MS (m/e): 226.1 and 228.1 (M+H)⁺.

Step 2: 1-bromo-3-[4-(trifluoromethoxy)phenyl] pyrido[3,4-d]pyridazin-4-one and 4-bromo-2-[4-(trifluoromethoxy)phenyl]pyrido[3,4-d]pyridazin-1-one To a solution of 4-bromo-2H-pyrido[3,4-d]pyridazin-1-one and 4-bromo-2H-pyrido[3,4-d]pyridazin-1-one (2.0 g, 8.85 mmol), [4-(trifluoromethoxy)phenyl]boronic acid (CAS 139301-27-2; 2.18 g, 10.6 mmol) and TEA (2.6 mL, 17.7 mmol) in THF (100 mL) was added Cu(OAc)$_2$ (3.2 g, 17.7 mmol), and then the mixture was stirred at 25° C. for 16 h. The solvent was removed by concentration to give the crude product, which was purified by chromatography on silica gel to give the title compound mixture (2 g, 58.8% yield) as a yellow solid. MS (m/e): 385.9 and 387.9 (M+H)$^+$.

Step 3: 1-bromo-6-methyl-3-[4-(trifluoromethoxy)phenyl]-7,8-dihydro-5H-pyrido[3,4-d]pyridazin-4-one and 4-bromo-6-methyl-2-[4-(trifluoromethoxy)phenyl]-7,8-dihydro-5H-pyrido[3,4-d]pyridazin-1-one To a solution of the mixture of 1-bromo-3-[4-(trifluoromethoxy)phenyl]pyrido[3,4-d]pyridazin-4-one and 4-bromo-2-[4-(trifluoromethoxy)phenyl]pyrido[3,4-d]pyridazin-1-one (600 mg, 1.6 mmol) in DMF (50 mL) was added MeI (0.68 g, 4.8 mmol), and then the solution was stirred at 60° C. for 16 h. The solvent was removed by concentration to give the crude product (0.9 g, crude) as red solid, which was used in the next step without any further purification. To a solution of the crude product (0.9 g, 1.6 mmol) and Ni(NO$_3$)$_2$(146.1 mg, 0.8 mmol) in MeOH (100 mL) was added NaBH$_3$CN (301.5 mg, 4.8 mmol), and then the mixture was stirred at 25° C. for 16 hr. The solvent was removed by concentration to give the crude product, which was purified by chromatography on silica gel to give the title compound mixture (250 mg, 38.6% yield) as a yellow solid. MS (m/e): 401.9 and 413.9 (M+H)$^+$.

Intermediate 33 and Intermediate 34

[6-Benzyloxy-4-oxo-3-[4-(trifluoromethoxy)phenyl]phthalazin-1-yl]trifluoromethanesulfonate and [7-benzyloxy-4-oxo-3-[4-(trifluoromethoxy)phenyl]phthalazin-1-yl]trifluoromethanesulfonate

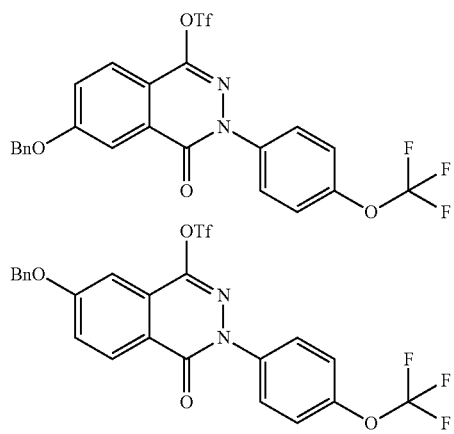

Step 1: 6-benzyloxy-3-[4-(trifluoromethoxy)phenyl]-2H-phthalazine-1,4-dione and 7-benzyloxy-3-[4-(trifluoromethoxy)phenyl]-2H-phthalazine-1,4-dione To a solution of 5-benzyloxyisobenzofuran-1,3-dione (CAS 5840-65-3; 8.5 g, 33.4 mmol) in AcOH (100 mL) was added [4-(trifluoromethoxy)phenyl]hydrazine (CAS 13957-54-5, 7.6 g, 33.4 mmol) at 20° C. Then the mixture was heated to 120° C. and stirred for 16 h. The mixture was poured into water (200 mL), the precipitate was collected by filtration and the solid was washed by water (100 mL), and dried in high vacuum to give a yellow solid. The solid was dissolved in EtOH (100 mL) and SOCl$_2$ (4.5 g, 37.4 mmol) was added at 20° C. Then the mixture was heated to 80° C. and stirred for 16 h. Solvent was removed in vacuum to dryness to give the title compound mixture (8.0 g, crude) as a yellow solid which was used in next step without further purification. MS (m/e): 429.1 (M+H)$^+$.

Step 2: [6-benzyloxy-4-oxo-3-[4-(trifluoromethoxy)phenyl]phthalazin-1-yl]trifluoromethanesulfonate and [7-benzyloxy-4-oxo-3-[4-(trifluoromethoxy)phenyl]phthalazin-1-yl]trifluoromethanesulfonate To a solution of 6-benzyloxy-3-[4-(trifluoromethoxy)phenyl]-2H-phthalazine-1,4-dione and 7-benzyloxy-3-[4-(trifluoromethoxy)phenyl]-2H-phthalazine-1,4-dione (8.0 g, 18.7 mmol) and TEA (7.6 g, 74.8 mmol) in DCM (100 mL) was added Tf$_2$O (10.5 g, 37.4 mmol) at 0° C. under N$_2$. Then the mixture was stirred at 20° C. for 2 h. Solvent was removed in vacuum to give a residue which was purified by column chromatography on silica gel (PE/EA from 200/1 to 100/1) to give [6-benzyloxy-4-oxo-3-[4-(trifluoromethoxy)phenyl]phthalazin-1-yl]trifluoromethanesulfonate (4.0 g, 38% yield; $^1$H NMR: (CDCl$_3$, 400 MHz) δ 7.92 (d, J=2.5 Hz, 1H), 7.77 (d, J=8.8 Hz, 1H), 7.68 (d, J=9.0 Hz, 2H), 7.50 (dd, J=2.5, 8.8 Hz, 1H), 7.43-7.38 (m, 2H), 7.38-7.34 (m, 2H), 7.33-7.29 (m, 1H), 7.26 (d, J=8.5 Hz, 2H), 5.21 (s, 2H) and [7-benzyloxy-4-oxo-3-[4-(trifluoromethoxy)phenyl]phthalazin-1-yl]trifluoromethanesulfonate (2.5 g, 23.8% yield; $^1$HNMR: (CDCl$_3$, 400 MHz) δ 8.38 (d, J=8.8 Hz, 1H), 7.67 (d, J=9.0 Hz, 2H), 7.46 (dd, J=2.3, 8.8 Hz, 1H), 7.44-7.29 (m, 6H), 7.26 (d, J=8.5 Hz, 2H), 5.20 (s, 2H)) as yellow solids.

Intermediate 35

(7-Benzyloxy-4-oxo-3H-phthalazin-1-yl)trifluoromethanesulfonate

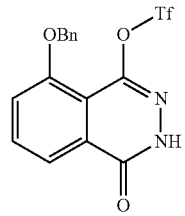

Step 1: 5-benzyloxy-2,3-dihydrophthalazine-1,4-dione

To a solution of 4-benzyloxyisobenzofuran-1,3-dione (CAS 63382-37-6; 7.2 g, 28.3 mmol) in EtOH (100 mL) was added AcOH (13.6 g, 141.5 mmol) at 20° C., and then N₂H₄.H₂O (11.5 g, 141.5 mmol) was added at 0° C. Then the mixture was heated to 80° C. and stirred for 16 h. The mixture was cooled to 25° C., solvent was removed and the residue poured into water (150 mL), filtered, washed with water (150 mL), the solid was collected to give the title compound (6.8 g, crude) as an off-white solid. MS (m/e): 269.1 (M+H)⁺.

Step 2: (7-benzyloxy-4-oxo-3H-phthalazin-1-yl) trifluoromethanesulfonate

To a solution of 5-benzyloxy-2,3-dihydrophthalazine-1, 4-dione (4.5 g, 16.8 mmol) in MeCN (80.0 mL) was added pyridine (40.0 mL) at 0° C. and then Tf₂O (5.7 g, 20.1 mmol) was added at 0° C. Then the mixture was stirred at 20° C. and stirred for 3 h. The reaction was quenched by 1N HCl (40.0 mL), extracted by DCM (50.0 mL), dried and concentrated in vacuum to give crude product which was purified by column chromatography on silica gel (PE/EA from 20/1 to 8/1 to 3/1) to give the title compound (2.5 g, 37.3% yield; ¹H NMR: (DMSO, 400 MHz) δ 12.52 (s, 1 H), 8.01 (t, J=8.2 Hz, 1 H), 7.66 (d, J=8.5 Hz, 1 H), 7.61 (d, J=7.3 Hz, 2 H), 7.39-7.45 (m, 2 H), 7.37-7.30 (m, 2 H), 5.37 (s, 2 H)) and (5-benzyloxy-4-oxo-3H-phthalazin-1-yl) trifluoromethanesulfonate (2.0 g, 29.8% yield; ¹H NMR: (DMSO, 400 MHz) δ 10.10 (br. s., 1 H), 8.06-7.98 (m, 1 H), 7.72 (t, J=8.2 Hz, 1 H), 7.50-7.44 (m, 2 H), 7.40 (t, J=7.2 Hz, 2 H), 7.38-7.31 (m, 2 H), 5.41 (s, 2 H)) as yellow solids.

Intermediate 36

6-Acetyl-1-bromo-3-[4-(trifluoromethoxy)phenyl]-7, 8-dihydro-5H-pyrido[3,4-d]pyridazin-4-one

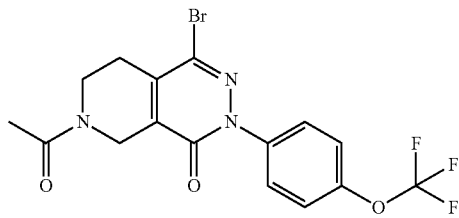 [SMILES: CC(=O)N1CCc2c(Br)nn(-c3ccc(OC(F)(F)F)cc3)c(=O)c2C1]

Step 1: 1-bromo-3-[4-(trifluoromethoxy)phenyl]-5, 6,7,8-tetrahydropyrido[3,4-d]pyridazin-4-one To a solution of 1-bromo-6-[(4-methoxyphenyl)methyl]-3-[4-(trifluoromethoxy)phenyl]-7,8-dihydro-5H-pyrido[3,4-d]pyridazin-4-one (Intermediate 55, step 1; 0.3 g, 0.59 mmol) and TEA (0.17 mL, 1.18 mmol) in DCM (20 mL) was added ClCOOCHClCH₃ (0.17 g, 1.18 mmol) at 25° C. for 16 h. The solvent was removed by concentration and the residue was dissolved in 10 mL MeOH, and then stirred at 80° C. for 2 h. The solvent was removed by concentration to give the crude title compound (0.3 g, crude) as a green solid, which was used in the next step without any further purification. MS (m/e): 391.8 (M+H)⁺.

Step 2: 6-acetyl-1-bromo-3-[4-(trifluoromethoxy) phenyl]-7,8-dihydro-5H-pyrido[3,4-d]pyridazin-4-one To a solution of 1-bromo-3-[4-(trifluoromethoxy)phenyl]-5,6,7,8-tetrahydropyrido[3,4-d]pyridazin-4-one (0.3 g, 0.59 mmol) and TEA (0.17 mL, 1.18 mmol) in DCM (20 mL) was added CH₃COCl (55.7 mg, 0.71 mmol) at 0° C. and the mixture was stirred for a further 3 h. The solvent was removed by concentration and the crude product was purified by chromatography on silica gel (PE:EA=3:1) to give the title compound (0.23 g, 90% yield) as a yellow solid. MS (m/e): 434.0 (M+H)⁺.

Intermediate 37

7-Benzyloxy-4-[(1-methyl-2-oxo-3-pyridyl)amino]-2-[4-(trifluoromethoxy)phenyl]phthalazin-1-one

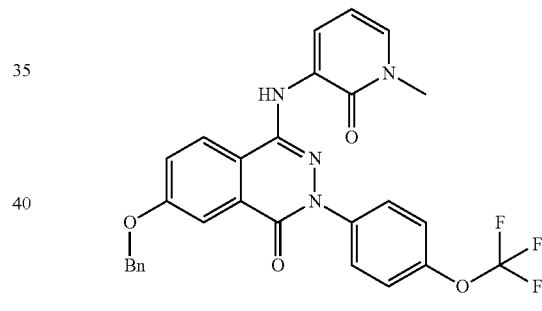

To a solution of [6-benzyloxy-4-oxo-3-[4-(trifluoromethoxy)phenyl]phthalazin-1-yl]trifluoromethanesulfonate (Intermediate 33; 500.0 mg, 0.89 mmol), 3-amino-1-methyl-pyridin-2-one (CAS 33631-01-5; 229.0 mg, 1.07 mmol), K₂CO₃ (357.3 mg, 2.67 mmol) and Xantphos (50.0 mg) in dioxane (100 mL) was added Pd₂(dba)₃ (80.0 mg) at 20° C. under N₂. Then the mixture was heated to 110° C. and stirred for 16 h. Solvent was removed in vacuum to dryness to give crude product. The crude product was purified by column chromatography on silica gel (petroleum ether/EtOAc from 10/1 to 1/1) to give the title compound (400 mg, crude) as off white solid which was used in next step without further purification.

In analogy to Intermediate 37 compounds of the following table were prepared using different trifluoromethanesulfonates or bromides and amines as reactants:

| Intermediate No. | Structure | Systematic Name | Starting materials | mass found (M + H)+ |
|---|---|---|---|---|
| 38 | 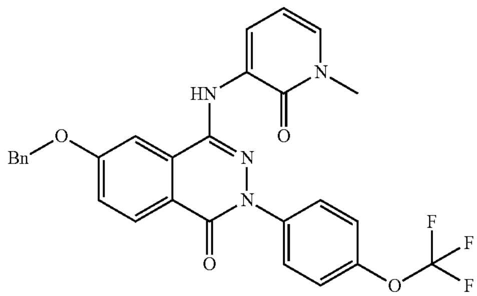 [SMILES: Cn1cccc(Nc2nn(-c3ccc(OC(F)(F)F)cc3)c(=O)c3ccc(OCc4ccccc4)cc23)c1=O] | 6-benzyloxy-4-[(1-methyl-2-oxo-3-pyridyl)amino]-2-[4-(trifluoromethoxy)phenyl]phthalazin-1-one | Intermediate 34 and CAS 33631-01-5 | 535.1 |
| 39 | 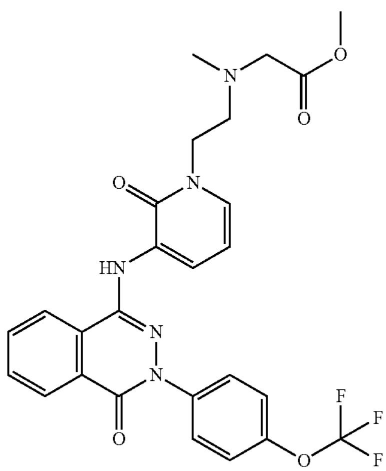 [SMILES: COC(=O)CN(C)CCn1cccc(Nc2nn(-c3ccc(OC(F)(F)F)cc3)c(=O)c3ccccc23)c1=O] | methyl 2-[methyl-[2-[2-oxo-3-[[4-oxo-3-[4-(trifluoromethoxy)phenyl]phthalazin-1-yl]amino]-1-pyridyl]ethyl]amino]acetate | Intermediate 29 and Intermediate 91 | 544.2 |
| 40 | 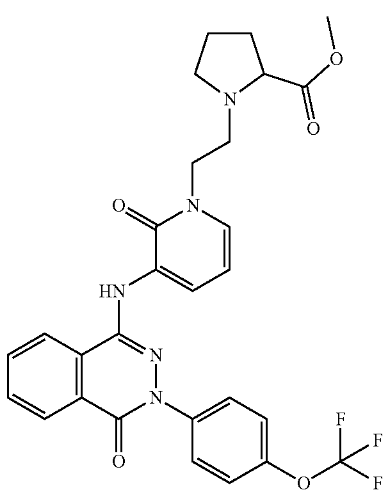 [SMILES: COC(=O)C1CCCN1CCn1cccc(Nc2nn(-c3ccc(OC(F)(F)F)cc3)c(=O)c3ccccc23)c1=O] | methyl 1-[2-[2-oxo-3-[[4-oxo-3-[4-(trifluoromethoxy)phenyl]phthalazin-1-yl]amino]-1-pyridyl]ethyl]pyrrolidine-2-carboxylate | Intermediate 29 and Intermediate 92 | 570.2 |

-continued

| Intermediate No. | Structure | Systematic Name | Starting materials | mass found (M + H)+ |
|---|---|---|---|---|
| 41 | 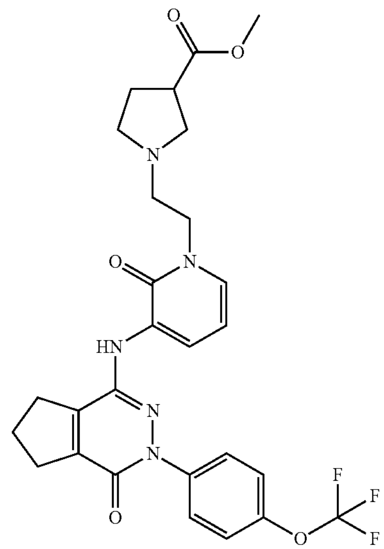 [SMILES: COC(=O)C1CCN(CCn2cccc(Nc3nn(-c4ccc(OC(F)(F)F)cc4)c(=O)c4c3CCC4)c2=O)C1] | methyl 1-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]pyrrolidine-3-carboxylate | Intermediate 9 and Intermediate 93 | 560.2 |
| 42 | 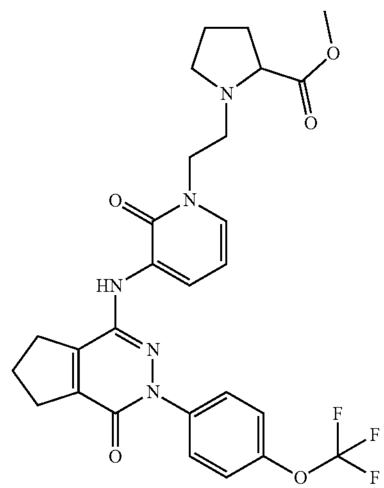 [SMILES: COC(=O)C1CCCN1CCn1cccc(Nc2nn(-c3ccc(OC(F)(F)F)cc3)c(=O)c3c2CCC3)c1=O] | methyl 1-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]pyrrolidine-2-carboxylate | Intermediate 9 and Intermediate 92 | 560.2 |
| 43 | 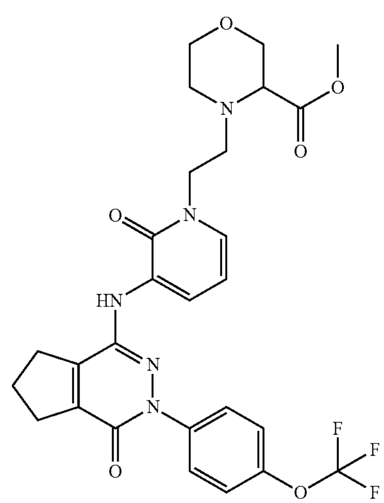 [SMILES: COC(=O)C1COCCN1CCn1cccc(Nc2nn(-c3ccc(OC(F)(F)F)cc3)c(=O)c3c2CCC3)c1=O] | methyl 4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-3-carboxylate | Intermediate 9 and Intermediate 94 | 576.2 |

-continued

| Intermediate No. | Structure | Systematic Name | Starting materials | mass found (M + H)+ |
|---|---|---|---|---|
| 44 | 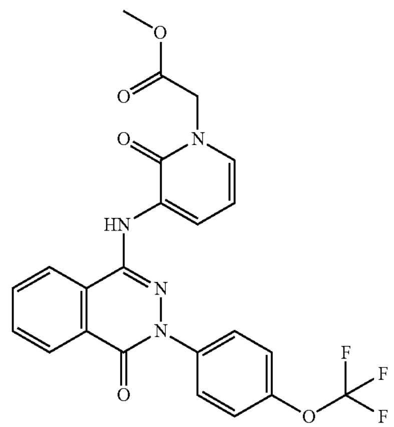 [SMILES: COC(=O)Cn1cccc(Nc2nn(-c3ccc(OC(F)(F)F)cc3)c(=O)c3ccccc23)c1=O] | methyl 2-[2-oxo-3-[[4-oxo-3-[4-(trifluoromethoxy)phenyl]phthalazin-1-yl]amino]-1-pyridyl]acetate | Intermediate 1 and Intermediate 70 | 487.2 |
| 45 | 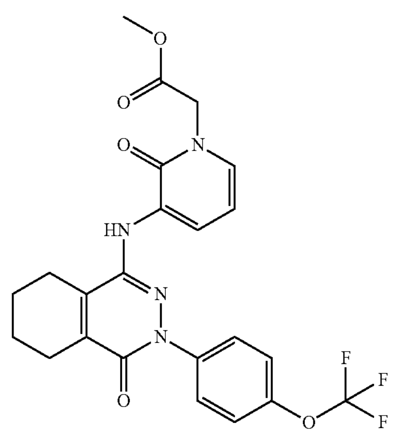 [SMILES: COC(=O)Cn1cccc(Nc2nn(-c3ccc(OC(F)(F)F)cc3)c(=O)c3c2CCCC3)c1=O] | 2-[2-oxo-3-[[4-oxo-3-[4-(trifluoromethoxy)phenyl]-5,6,7,8-tetrahydrophthalazin-1-yl]amino]-1-pyridyl]acetate | Intermediate 23 and Intermediate 70 | 491.0 |
| 46 | 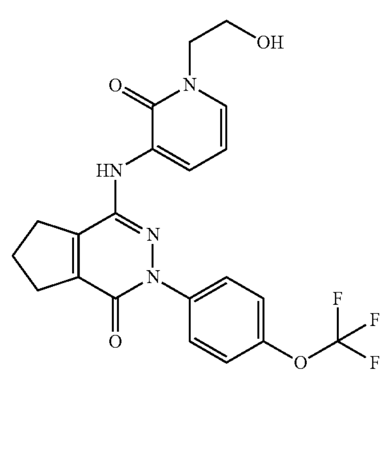 [SMILES: O=c1c(Nc2nn(-c3ccc(OC(F)(F)F)cc3)c(=O)c3c2CCC3)cccn1CCO] | 1-[[1-(2-hydroxyethyl)-2-oxo-3-pyridyl]amino]-3-[4-(trifluoromethoxy)phenyl]-6,7-dihydro-5H-cyclopenta[d]pyridazin-4-one | Intermediate 9 and CAS 1274075-70-5 | 449.1 |

| Intermediate No. | Structure | Systematic Name | Starting materials | mass found (M + H)+ |
|---|---|---|---|---|
| 47 | 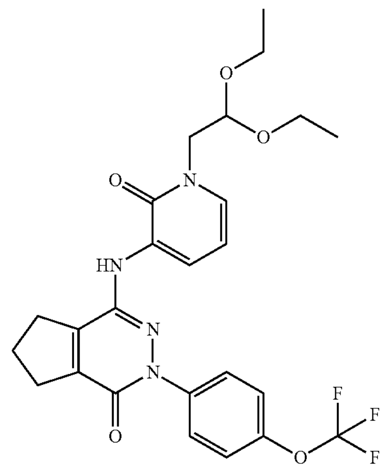 [SMILES: CCOC(Cn1cccc(Nc2nn(-c3ccc(OC(F)(F)F)cc3)c(=O)c3c2CCC3)c1=O)OCC] | 1-[[1-(2,2-diethoxyethyl)-2-oxo-3-pyridyl]amino]-3-[4-(trifluoromethoxy)phenyl]-6,7-dihydro-5H-cyclopenta[d]pyridazin-4-one | Intermediate 9 and Intermediate 80 | 521.2 |

Intermediate 48 tert-Butyl N-[7-(2-methoxyethoxy)-4-oxo-3-[4-(trifluoromethoxy)phenyl]phthalazin-1-yl]-N-(1-methyl-2-oxo-3-pyridyl)carbamate

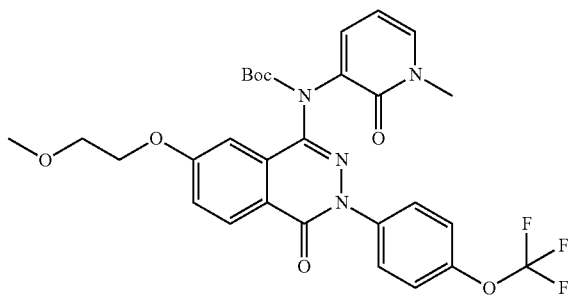 [SMILES: COCCOc1ccc2c(=O)n(-c3ccc(OC(F)(F)F)cc3)nc(N(C(=O)OC(C)(C)C)c3cccn(C)c3=O)c2c1]

Step 1: tert-butyl N-[7-benzyloxy-4-oxo-3-[4-(trifluoromethoxy)phenyl]phthalazin-1-yl]-N-(1-methyl-2-oxo-3-pyridyl)carbamate To a solution of 6-benzyloxy-4-[(1-methyl-2-oxo-3-pyridyl)amino]-2-[4-(trifluoromethoxy)phenyl]phthalazin-1-one (Intermediate 38; 300.0 mg, 0.56 mmol) and Boc$_2$O (146.1 mg, 0.67 mmol), DMAP (102.5 mg, 0.84 mmol) in DMF (20 mL) was stirred at 90° C. for 16 hr under N$_2$ atmosphere. The reaction was cooled to 20° C. and filtered, evaporation of solvent to give a residue, the residue was added EtOAc (100 mL) and water (100 mL), the water phase was washed with EtOAc (50 mL×2), the combined organic phase, dried (Na$_2$SO$_4$), filtered and evaporation of solvent to give a crude product. The crude was purified by column chromatography on silica gel to give the title compound (150.0 mg, yield: 42.24%) as a green solid. MS (m/e): 635.3 (M+H)+.

Step 2: tert-butyl N-[7-hydroxy-4-oxo-3-[4-(trifluoromethoxy)phenyl]phthalazin-1-yl]-N-(1-methyl-2-oxo-3-pyridyl)carbamate To a solution of tert-butyl N-[7-benzyloxy-4-oxo-3-[4-(trifluoromethoxy)phenyl]phthalazin-1-yl]-N-(1-methyl-2-oxo-3-pyridyl)carbamate (150 mg, 0.24 mmol) and Pd/C (100 mg), in THF (15 mL) was stirred at 25° C. for 2 hr under hydrogen atmosphere. The mixture was filtered and solvent was evaporated to give the title compound (110.0 mg, yield: 84.6%) as a green solid. MS (m/e): 545.1 (M+H)+.

Step 3: tert-butyl N-[7-(2-methoxyethoxy)-4-oxo-3-[4-(trifluoromethoxy)phenyl]phthalazin-1-yl]-N-(1-methyl-2-oxo-3-pyridyl)carbamate To a solution of tert-butyl N-[7-hydroxy-4-oxo-3-[4-(trifluoromethoxy)phenyl]phthalazin-1-yl]-N-(1-methyl-2-oxo-3-pyridyl)carbamate (110.0 mg, 0.20 mmol) and 1-bromo-2-methoxy-ethane (33.1 mg, 0.24 mmol) in MeCN (10 mL) was added K$_2$CO$_3$ (55.2 mg, 0.40 mmol). The reaction was heated to 80° C. for 4 hr under N$_2$ atmosphere. The mixture was filtered solvent was evaporated to give the title compound (91.0 mg, 75.7%) as a green solid. MS (m/e): 603.2 (M+H)+.

Intermediate 49 tert-Butyl N-[6-(2-methoxyethoxy)-4-oxo-3-[4-(trifluoromethoxy)phenyl]phthalazin-1-yl]-N-(1-methyl-2-oxo-3-pyridyl)carbamate

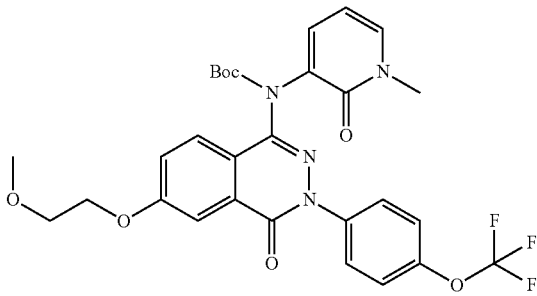 [SMILES: COCCOc1ccc2c(N(C(=O)OC(C)(C)C)c3cccn(C)c3=O)nn(-c3ccc(OC(F)(F)F)cc3)c(=O)c2c1]

The title compound was prepared from [6-benzyloxy-4-oxo-3-[4-(trifluoromethoxy)phenyl]phthalazin-1-yl]trifluoromethanesulfonate (Intermediate 33) using an analogous sequence to that used to prepare Intermediate 48 from [7-benzyloxy-4-oxo-3-[4-(trifluoromethoxy)phenyl]phthalazin-1-yl]trifluoromethanesulfonate. MS (m/e): 603.2 (M+H)$^+$.

Intermediate 50 tert-Butyl N-[8-(2-methoxyethoxy)-4-oxo-3-[4-(trifluoromethoxy)phenyl]phthalazin-1-yl]-N-(1-methyl-2-oxo-3-pyridyl)carbamate

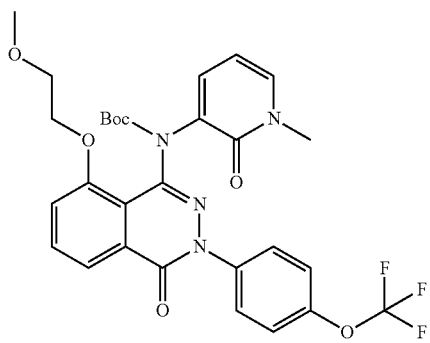 [SMILES: COCCOc1cccc2c(=O)n(-c3ccc(OC(F)(F)F)cc3)nc(N(C(=O)OC(C)(C)C)c3cccn(C)c3=O)c12]

The title compound was prepared from [8-benzyloxy-4-oxo-3-[4-(trifluoromethoxy)phenyl]phthalazin-1-yl]trifluoromethanesulfonate (Intermediate 8) using an analogous sequence to that used to prepare Intermediate 48 from [7-benzyloxy-4-oxo-3-[4-(trifluoromethoxy)phenyl]phthalazin-1-yl]trifluoromethanesulfonate. MS (m/e): 603.2 (M+H)$^+$.

Intermediate 51

Ethyl 1-[(1-methyl-2-oxo-3-pyridyl)amino]-4-oxo-3-[4-(trifluoromethoxy)phenyl]phthalazine-6-carboxylate

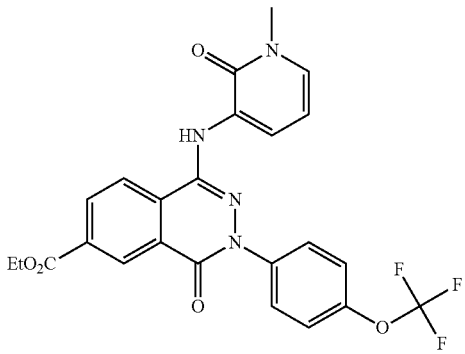 [SMILES: CCOC(=O)c1ccc2c(Nc3cccn(C)c3=O)nn(-c3ccc(OC(F)(F)F)cc3)c(=O)c2c1]

Step 1: 1,4-dioxo-3-[4-(trifluoromethoxy)phenyl]-2H-phthalazine-6-carboxylic acid and 1,4-dioxo-2-[4-(trifluoromethoxy)phenyl]-3H-phthalazine-6-carboxylic acid To a solution of 1,3-dioxoisobenzofuran-5-carboxylic acid (CAS 552-30-7; 30.0 g, 15.61 mmol) in AcOH (400 mL) was added [4-(trifluoromethoxy)phenyl]hydrazine hydrochloride (CAS 133115-72-7; 35.68 g, 15.61 mmol) at 20° C. After addition, the mixture was warmed to 120° C. and stirred for 18 h. The mixture was cooled to rt and poured into water (600 mL), there is a white solid was formed. After stirring about 15 min, the solid was filtered; the filter cake was washed with water (100 mL×2). The solid was dried under vacuo to get the crude title product mixture (42.0 g, 73.4% yield) as a gray solid. It was used for the next step without purification.

Step 2: ethyl 1,4-dioxo-3-[4-(trifluoromethoxy)phenyl]-2H-phthalazine-6-carboxylate and ethyl 1,4-dioxo-2-[4-(trifluoromethoxy)phenyl]-3H-phthalazine-6-carboxylate To a solution of 1,4-dioxo-3-[4-(trifluoromethoxy)phenyl]-2H-phthalazine-6-carboxylic acid and 1,4-dioxo-2-[4-(trifluoromethoxy)phenyl]-3H-phthalazine-6-carboxylic acid (37.0 g, 0.30 mmol) in EtOH (500 mL) was added SOCl$_2$ (36.0 g, 0.30 mmol) at 0° C. After addition, the mixture was heated to reflux (80-90° C.) and stirred for 6 h. The mixture was concentrated in dryness and the residue was triturated with petroleum/EtOAc (350 mL, v/v=5:1) to get the title compound mixture (35 g, 88% yield) as an off-white solid that was used for the next step without purification. MS (m/e): 395.1 (M+H)$^+$.

Step 3: ethyl 4-oxo-3-[4-(trifluoromethoxy)phenyl]-1-(trifluoromethylsulfonyloxy)phthalazine-6-carboxylate To a solution of ethyl 1,4-dioxo-3-[4-(trifluoromethoxy)phenyl]-2H-phthalazine-6-carboxylate and ethyl 1,4-dioxo-2-[4-(trifluoromethoxy)phenyl]-3H-phthalazine-6-carboxylate (35.0 g, 88.8 mmol) and Et$_3$N (35.6 g, 352 mmol) in DCM (500 mL) was added Tf$_2$O (5.01 g, 17.76 mmol) at −10° C. After addition, the mixture was warmed to 25° C. and stirred for 20 h. The reaction mixture was mixed with silica gel (150 g) and concentrated in vacuo. The residue was purified by column chromatography on silica gel (petroleum ether:EtOAc=30:1) to get the title compound (12.5 g, 27% yield) as an off-white solid. $^1$H NMR: (DMSO, 400 MHz) δ 9.17 (d, J=1.5 Hz, 1H), 8.62 (dd, J=1.5, 8.4 Hz, 1H), 7.99 (d, J=8.4 Hz, 1H), 7.77 (d, J=8.9 Hz, 2H), 7.37 (d, J=8.8 Hz, 2H), 4.51 (q, J=7.1 Hz, 2H), 1.47 (t, J=7.2 Hz, 3H).

Step 4: ethyl 1-[(1-methyl-2-oxo-3-pyridyl)amino]-4-oxo-3-[4-(trifluoromethoxy)phenyl]phthalazine-6-carboxylate A mixture of ethyl 4-oxo-3-[4-(trifluoromethoxy)phenyl]-1-(trifluoromethylsulfonyloxy)phthalazine-6-carboxylate (1.0 g, 1.89 mmol), 3-amino-1-methyl-pyridin-2-one (CAS 33631-01-5; 0.28 g, 2.26 mmol), Pd$_2$(dba)$_3$ (0.1 g), Xantphos (0.1 g) and K$_2$CO$_3$ (0.79 g, 5.67 mmol) in dioxane (100 mL) was stirred at 100° C. for 16 h. The reaction mixture was filtered and the filtrate was concentrated to give the crude product (1.1 g). The crude product was purified by recrystallized from CH$_3$OH (10 mL×2) to give the title compound (0.66 g, 70.2%) as a white solid. MS (m/e): 501.1 (M+H)$^+$.

Intermediate 52

1-[(1-Methyl-2-oxo-3-pyridyl)amino]-4-oxo-3-[4-(trifluoromethoxy)phenyl]phthalazine-6-carbaldehyde

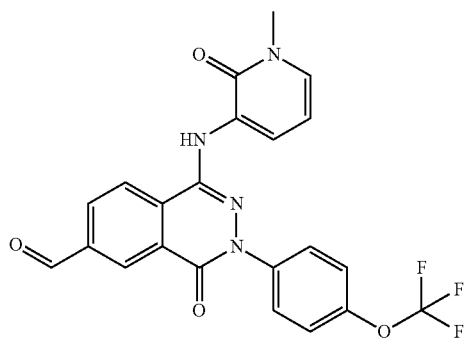 [SMILES: Cn1cccc(Nc2nn(-c3ccc(OC(F)(F)F)cc3)c(=O)c3cc(C=O)ccc23)c1=O]

A mixture of 7-(hydroxymethyl)-4-[(1-methyl-2-oxo-3-pyridyl)amino]-2-[4-(trifluoromethoxy)phenyl]phthalazin-1-one (example 141; 0.4 g, 0.88 mmol), MnO$_2$ (0.76 g, 8.8 mmol) in DCM (40 mL) was stirred at 25° C. for 16 h. The reaction mixture was filtered and the filtrate was concentrated to give the crude product (0.6 g). The crude product was purified by recrystallization from CH$_3$OH (20 mL×2) to give the title compound (0.3 g, 75.0%) as a white solid. MS (m/e): 457.0 (M+H)$^+$.

Intermediate 53

4-[(1-Methyl-2-oxo-3-pyridyl)amino]-7-nitro-2-[4-(trifluoromethoxy)phenyl]phthalazin-1-one

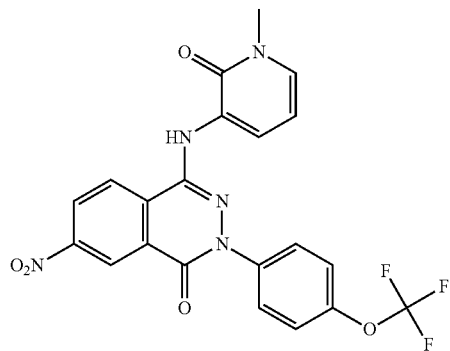 [SMILES: Cn1cccc(Nc2nn(-c3ccc(OC(F)(F)F)cc3)c(=O)c3cc([N+](=O)[O-])ccc23)c1=O]

The title compound was prepared from 5-nitroisobenzofuran-1,3-dione (CAS 5466-84-2), [4-(trifluoromethoxy)phenyl]hydrazine (CAS 13957-54-5) and 3-amino-1-methyl-pyridin-2-one (CAS 33631-01-5) using a sequence analogous to that used to prepare example 64. MS (m/e): 474.1 (M+H)$^+$.

Intermediate 54

1-[(1-Methyl-2-oxo-3-pyridyl)amino]-4-oxo-3-[4-(trifluoromethoxy)phenyl]phthalazine-6-carbaldehyde oxime

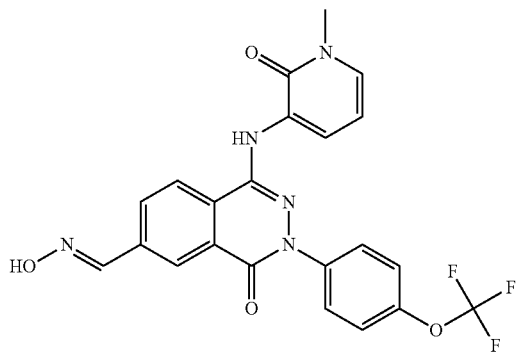 [SMILES: Cn1cccc(Nc2nn(-c3ccc(OC(F)(F)F)cc3)c(=O)c3cc(/C=N/O)ccc23)c1=O]

To a solution of 1-[(1-methyl-2-oxo-3-pyridyl)amino]-4-oxo-3-[4-(trifluoromethoxy)phenyl]phthalazine-6-carbaldehyde (Intermediate 52; 0.1 g, 0.22 mmol) in THF (2.0 mL) was added hydroxylamine hydrochloride (30.2 mg, 0.44 mmol) portion-wise over 1 min. After the addition was over, the mixture was stirred at 25° C. for 2 h. The sediment was filtered and dried under vacuum to give the title compound (80.0 mg, 80.0%) as a white solid. MS (m/e): 472.0 (M+H)$^+$.

Intermediate 55

4-[(1-Methyl-2-oxo-3-pyridyl)amino]-2-[4-(trifluoromethoxy)phenyl]-5,6,7,8-tetrahydropyrido[3,4-d]pyridazin-1-one

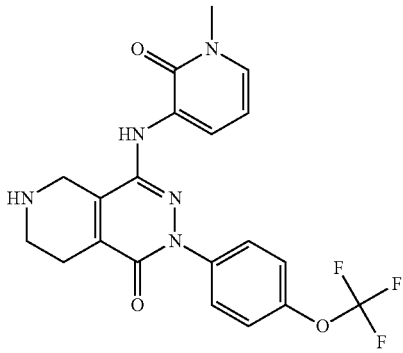 [SMILES: Cn1cccc(Nc2nn(-c3ccc(OC(F)(F)F)cc3)c(=O)c3c2CNCC3)c1=O]

Step 1: 4-bromo-6-[(4-methoxyphenyl)methyl]-2-[4-(trifluoromethoxy)phenyl]-7,8-dihydro-5H-pyrido[3,4-d]pyridazin-1-one and 1-bromo-6-[(4-methoxyphenyl)methyl]-3-[4-(trifluoromethoxy)phenyl]-7,8-dihydro-5H-pyrido[3,4-d]pyridazin-4-one To a solution of 1-bromo-3-[4-(trifluoromethoxy)phenyl]pyrido[3,4-d]pyridazin-4-one and 4-bromo-2-[4-(trifluoromethoxy)phenyl]pyrido[3,4-d]pyridazin-1-one (Intermediate 32, step 2; 0.2 g, 0.52 mmol) in MeCN (20 mL) was added 1-(chloromethyl)-4-methoxy-benzene (97 mg, 0.62 mmol) and NaI (93 mg, 0.62 mmol), and then the mixture was stirred at 60° C. for 16 h. The solvent was removed to give the crude product (0.4 g, crude), and to a solution of this mixture in MeOH (20 mL) was added NaBH$_3$CN (98 mg, 1.56 mmol) and Ni(NO$_3$)$_2$ at 25° C., and the solution was stirred for further 16 h. The solution was poured into 30 mL ice-water, and extracted with DCM (30 mL×3), the combined organic phase was dried over Na$_2$SO$_4$. The solid was filtered off and the filtrate was concentrated to give the crude product, which was purified by chromatography on silica gel (petroleum ether:EtOAc=10:1) to give the title 4-bromo-6-[(4-methoxyphenyl)methyl]-2-[4-(trifluoromethoxy)phenyl]-7,8-dihydro-5H-pyrido[3,4-d]pyridazin-1-one (0.1 g) as a yellow solid and 1-bromo-6-[(4-methoxyphenyl)methyl]-3-[4-(trifluoromethoxy)phenyl]-7,8-dihydro-5H-pyrido[3,4-d]pyridazin-4-one (0.1 g) as a yellow solid.

Step 2: 6-[(4-methoxyphenyl)methyl]-4-[(1-methyl-2-oxo-3-pyridyl)amino]-2-[4-(trifluoromethoxy)phenyl]-7,8-dihydro-5H-pyrido[3,4-d]pyridazin-1-one To a solution of 4-bromo-6-[(4-methoxyphenyl)methyl]-2-[4-(trifluoromethoxy)phenyl]-7,8-dihydro-5H-pyrido[3,4-d]pyridazin-1-one (110.0 mg, 0.22 mmol), K$_2$CO$_3$ (91 mg, 0.66 mmol) and 3-amino-1-methyl-pyridin-2-one hydrochloride (CAS 1523570-95-7; 43.4 mg, 0.27 mmol) in dioxane (10 mL) was added Xantphos (20 mg) and Pd$_2$(dba)$_3$ (10 mg) under N$_2$ atmosphere, and then the mixture was stirred at 110° C. for another 16 hr. The solvent was removed by concentration to give the crude product, which was purified by chromatography on silica gel (petroleum ether:EtOAc=1:1) to give the title compound (60 mg, 49.6% yield) as a yellow solid. $^1$H NMR: (CDCl$_3$, 400 MHz) δ 8.12 (dd, J=1.5, 7.5 Hz, 1H), 7.81 (d, J=9.0 Hz, 2H), 7.68 (s, 1H), 7.33 (dd, J=5.3, 8.3 Hz, 4H), 6.99-6.87 (m, 3H), 6.24 (t, J=7.2 Hz, 1H), 3.84 (s, 3H), 3.76 (s, 2H), 3.66 (s, 3H), 3.63 (s, 2H), 2.75 (d, J=3.8 Hz, 4H).

Step 3: 4-[(1-methyl-2-oxo-3-pyridyl)amino]-2-[4-(trifluoromethoxy)phenyl]-5,6,7,8-tetrahydropyrido[3,4-d]pyridazin-1-one To a solution of 6-[(4-methoxyphenyl)methyl]-4-[(1-methyl-2-oxo-3-pyridyl)amino]-2-[4-(trifluoromethoxy)phenyl]-7,8-dihydro-5H-pyrido[3,4-d]pyridazin-1-one (50 mg, 0.09 mmol) and TEA (0.04 mL) in DCM (10 mL) was added 1-chloroethyl carbonochloridate (CAS 50893-53-3; 38.6 mg, 0.27 mmol) at 25° C., and then stirred for further 2 h. The solvent was removed by concentration and the residue was dissolved in 10 mL MeOH, then the solution was heated to reflux for 2 h. The solvent was removed by concentration to give the crude title product (60 mg, crude), which was used in the next step without any further purification. MS (m/e): 434.1 (M+H)$^+$.

Intermediate 56

Ethyl 4-[6-oxo-5-[[4-oxo-3-[4-(trifluoromethoxy)phenyl]-6,7-dihydro-5H-cyclopenta[d]pyridazin-1-yl]amino]pyrimidin-1-yl]butanoate

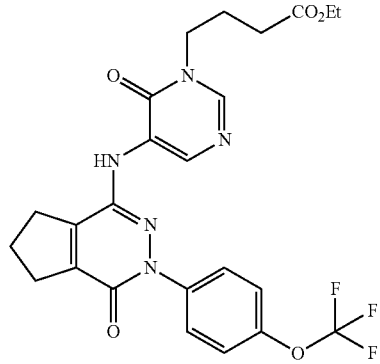 [SMILES: CCOC(=O)CCCn1cncc(Nc2nn(-c3ccc(OC(F)(F)F)cc3)c(=O)c3c2CCC3)c1=O]

The title compound was prepared from [4-oxo-3-[4-(trifluoromethoxy)phenyl]-6,7-dihydro-5H-cyclopenta[d]pyridazin-1-yl]trifluoromethanesulfonate (Intermediate 9), 5-bromo-1H-pyrimidin-6-one (CAS 19808-30-1) and ethyl 4-bromobutanoate (CAS 2969-81-5) using a sequence analogous to that used to prepare example 3. MS (m/e): 520.3 (M+H)$^+$.

Intermediate 57

1-[[1-[(4-Benzyl morpholin-3-yl)methyl]-2-oxo-3-pyridyl]amino]-3-[4-(trifluoromethoxy)phenyl]-6,7-dihydro-5H-cyclopenta[d]pyridazin-4-one

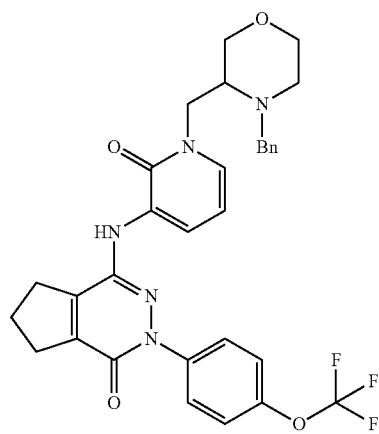 [SMILES: O=c1c(Nc2nn(-c3ccc(OC(F)(F)F)cc3)c(=O)c3c2CCC3)cccn1CC1COCCN1Cc1ccccc1]

Step 1: 1-[(4-benzylmorpholin-3-yl)methyl]-3-nitropyridin-2-one

A solution of (4-benzylmorpholin-3-yl)methyl methanesulfonate (CAS 1823508-49-1; 340.0 mg, 2.43 mmol), 3-nitro-1H-pyridin-2-one (CAS 6332-56-5; 692.5 mg, 2.43 mmol) and $K_2CO_3$ (670.8 mg, 4.85 mmol) in DMF (10 mL) was stirred at 70° C. for 12 hr. The reaction mixture was concentrated in vacuum to give the crude product. The crude product was purified by column chromatography ($SiO_2$, petroleum ether/EtOAc 10:1 to DCM/MeOH 10:1) to give the title compound (700 mg, yield 66.9%) as a yellow solid. MS (m/e): 352.1 $(M+Na)^+$.

Step 2: 3-amino-1-[(4-benzylmorpholin-3-yl)methyl]pyridin-2-one

A solution of 1-[(4-benzylmorpholin-3-yl)methyl]-3-nitro-pyridin-2-one (315.0 mg, 0.96 mmol), Zn (255.8 mg, 4.78 mmol) and $NH_4Cl$ (312.7 mg, 4.78 mmol) in THF (5 mL) and MeOH (5 mL) was stirred at 15° C. for 2 hr. The crude product was purified by prep-HPLC ($NH_4OH$) to give the title compound (120.0 mg, 41.91%) as a white oil. MS (m/e): 300.0 $(M+H)^+$.

Step 3: 1-[[1-[(4-benzylmorpholin-3-yl)methyl]-2-oxo-3-pyridyl]amino]-3-[4-(trifluoromethoxy)phenyl]-6,7-dihydro-5H-cyclopenta[d]pyridazin-4-one A mixture of [4-oxo-3-[4-(trifluoromethoxy)phenyl]-6,7-dihydro-5H-cyclopenta[d]pyridazin-1-yl]trifluoromethanesulfonate (Intermediate 9; 0.15 g, 0.34 mmol), 3-amino-1-[(4-benzylmorpholin-3-yl)methyl]pyridin-2-one (0.11 g, 0.34 mmol), $Pd_2(dba)_3$ (40 mg), Xantphos (40 mg) and $K_2CO_3$ (93.4 mg, 0.68 mmol) in dioxane (18.0 mL) was charged with $N_2$, and the mixture was stirred at 100° C. for 16 hr. The reaction mixture was cooled; solvent was removed in vacuum to dryness to give a residue which was purified by column chromatography on silica gel (petroleum ether/EtOAc from 10/1 to EtOAc) to give the title compound (0.2 g, crude) as a yellow solid. MS (m/e): 594.3 $(M+H)^+$.

Intermediate 58

1-[[1-[[(2S)-4-[(4-Methoxyphenyl)methyl]morpholin-2-yl]methyl]-2-oxo-3-pyridyl]amino]-3-[4-(trifluoromethoxy)phenyl]-6,7-dihydro-5H-cyclopenta[d]pyridazin-4-one

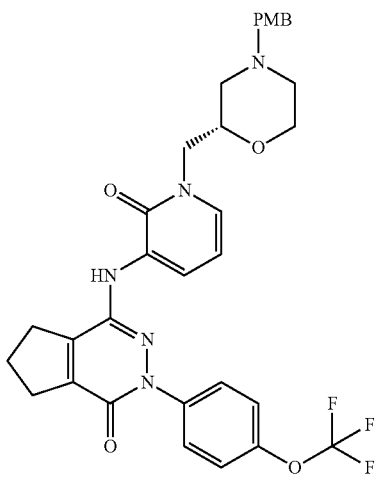

The title compound was prepared from [(2S)-4-[(4-methoxyphenyl)methyl]morpholin-2-yl]methyl methanesulfonate using a method analogous to that used to prepare Intermediate 57. MS (m/e): 624.1 $(M+H)^+$.

The [(2S)-4-[(4-methoxyphenyl)methyl]morpholin-2-yl]methyl methanesulfonate used as a starting material was prepared as follows:

Step 1: [(2S)-4-[(4-methoxyphenyl)methyl]morpholin-2-yl]methanol

A mixture of [(2S)-morpholin-2-yl]methanol (CAS 132073-83-7; 1.0 g, 6.5 mmol), p-methoxybenzyl chloride (1.24 g, 7.8 mmol) and $K_2CO_3$ (2.69 g, 19.5 mmol) in THF (20 mL) was stirred under nitrogen at 15° C. for 16 h. The reaction mixture was filtered and the filtration was concentrated under reduced pressure to remove solvent. The residue was diluted with water (10 mL) and extracted with EA (20 mL×3). The combined organic layers was washed with brine (20 mL×2), dried over $Na_2SO_4$, filtered and concentrated under reduced pressure to give a residue (2.1 g). The crude product was purified by column chromatography ($SiO_2$, PE/EA=1/1 to DCM: CH₃OH=10/1) to give the title compound (1.2 g, yield: 80.0%) as a white solid. MS (m/e): 238.1 (M+H)⁺.

Step 2: [(2S)-4-[(4-methoxyphenyl)methyl]morpholin-2-yl]methyl methanesulfonate

To a solution of [(2S)-4-[(4-methoxyphenyl)methyl]morpholin-2-yl]methanol (1.2 g, 5.0 mmol) in DCM (20 mL) was added Et₃N (0.76 g, 7.5 mmol) at 15° C. under N₂, then the mixture was treated with MsCl (0.63 g, 5.5 mmol). The reaction mixture was stirred at 15° C. for 3 h. The reaction was partitioned between DCM (30 mL) and H₂O (30 mL). The organic layer was dried over Na₂SO₄, concentrated under reduce pressure to get the crude title compound (1.4 g, crude). The crude product was used for next reaction directly with no further purification.

Intermediate 59

1-[[1-[2-[Benzyl(methyl)amino]ethyl]-6-oxo-pyrimidin-5-yl]amino]-3-[4-(trifluoromethoxy)phenyl]-6,7-dihydro-5H-cyclopenta[d]pyridazin-4-one

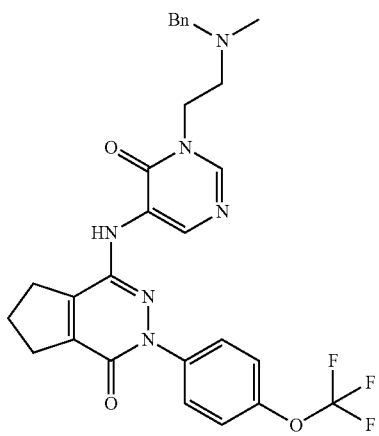 [SMILES: CN(CCn1cncc(Nc2nn(-c3ccc(OC(F)(F)F)cc3)c(=O)c3c2CCC3)c1=O)Cc1ccccc1]

Step 1: 5-amino-3-[2-[benzyl(methyl)amino]ethyl]pyrimidin-4-one

The title compound was prepared from 5-bromo-1H-pyrimidin-6-one (CAS 19808-30-1) and N-benzyl-2-chloro-N-methyl-ethanamine (CAS 17542-47-1) using a procedure analogous to that used to prepare Intermediate 95.

Step 2: 1-[[1-[2-[benzyl(methyl)amino]ethyl]-6-oxo-pyrimidin-5-yl]amino]-3-[4-(trifluoromethoxy)phenyl]-6,7-dihydro-5H-cyclopenta[d]pyridazin-4-one The title compound was prepared from 5-amino-3-[2-[benzyl(methyl)amino]ethyl]pyrimidin-4-one and [4-oxo-3-[4-(trifluoromethoxy)phenyl]-6,7-dihydro-5H-cyclopenta[d]pyridazin-1-yl]trifluoromethanesulfonate (Intermediate 12) using a procedure analogous to that used to prepare Intermediate 57 (step 3). MS (m/e): 553.1 (M+H)⁺.

Intermediate 60

1-[[1-[[1-[(4-Methoxyphenyl)methyl]pyrrolidin-2-yl]methyl]-2-oxo-3-pyridyl]amino]-3-[4-(trifluoromethoxy)phenyl]-6,7-dihydro-5H-cyclopenta[d]pyridazin-4-one

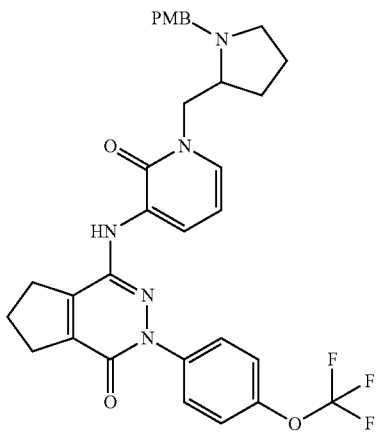

The title compound was prepared from [1-[(4-methoxyphenyl)methyl]pyrrolidin-2-yl]methyl methanesulfonate, 3-nitro-1H-pyridin-2-one (CAS 6332-56-5) and [4-oxo-3-[4-(trifluoromethoxy)phenyl]-6,7-dihydro-5H-cyclopenta[d]pyridazin-1-yl]trifluoromethanesulfonate (Intermediate 9) using a sequence analogous to that used to prepare Intermediate 57. MS (m/e): 608.2 (M+H)⁺.

The [1-[(4-methoxyphenyl)methyl]pyrrolidin-2-yl]methyl methanesulfonate used as a starting material was prepared as follows: To a solution of [1-[(4-methoxyphenyl)methyl]pyrrolidin-2-yl]methanol (CAS 1017413-27-2; 2.90 g, 13.10 mmol) and triethylamine (2.65 g, 26.21 mmol) in DCM (30 mL) was added methanesulfonyl chloride (3.50 g, 26.81 mmol) at 0° C. The mixture was stirred at 15° C. for 2 h. The reaction mixture was quenched by addition water 50 mL at 15° C. and extracted with DCM (50 mL×3). The combined organic phases were washed with brine (20 mL×2), dried over Na₂SO₄, filtered and concentrated under reduced pressure to give [1-[(4-methoxyphenyl)methyl]pyrrolidin-2-yl]methyl methanesulfonate (4 g, crude) which was used for the next step directly.

Intermediate 61

6-[(4-Methoxyphenyl)methyl]-1-[(1-methyl-2-oxo-3-pyridyl)amino]-3-[4-(trifluoromethoxy)phenyl]-7,8-dihydro-5H-pyrido[3,4-d]pyridazin-4-one

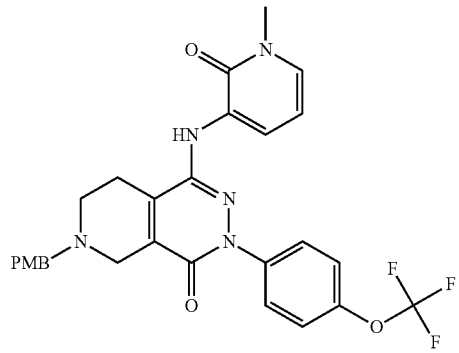

To a solution of 1-bromo-6-[(4-methoxyphenyl)methyl]-3-[4-(trifluoromethoxy)phenyl]-7,8-dihydro-5H-pyrido[3,4-d]pyridazin-4-one (Intermediate 55, step 1; 400 mg, 0.78 mmol), $K_2CO_3$ (162 mg, 1.17 mmol) and 3-amino-1-methyl-pyridin-2-one (CAS 33631-01-5; 116.7 mg, 0.94 mmol) in dioxane (40 mL) was added Xantphos (80 mg) and $Pd_2(dba)_3$ (40 mg) under $N_2$ atmosphere, and then the mixture was stirred at 110° C. for another 16 hr. The solvent was removed by concentration to give the crude product, which was purified by chromatography on silica gel (petroleum ether:EtOAc=1:1) to give the title compound (0.5 g, crude) as yellow solid. MS (m/e): 554.1 (M+H)$^+$.

Intermediate 62

1-[(1-Methyl-6-oxo-pyrimidin-5-yl)amino]-3-[4-(trifluoromethoxy)phenyl]-5,6,7,8-tetrahydropyrido[3,4-d]pyridazin-4-one

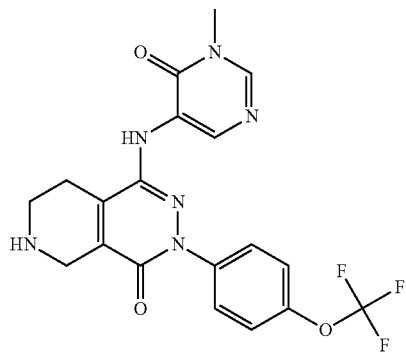 [SMILES: Cn1cncc(Nc2nn(-c3ccc(OC(F)(F)F)cc3)c(=O)c3c2CCNC3)c1=O]

Step 1: 6-[(4-methoxyphenyl)methyl]-1-[(1-methyl-6-oxo-pyrimidin-5-yl)amino]-3-[4-(trifluoromethoxy)phenyl]-7,8-dihydro-5H-pyrido[3,4-d]pyridazin-4-one The title compound was prepared from 1-bromo-6-[(4-methoxyphenyl)methyl]-3-[4-(trifluoromethoxy)phenyl]-7,8-dihydro-5H-pyrido[3,4-d]pyridazin-4-one (Intermediate 55, step 1) and 5-amino-3-methyl-pyrimidin-4-one (CAS 73922-41-5) using a procedure analogous to that used to prepare Intermediate 61. MS (m/e): 555.3 (M+H)$^+$.

Step 2: 1-[(1-methyl-6-oxo-pyrimidin-5-yl)amino]-3-[4-(trifluoromethoxy)phenyl]-5,6,7,8-tetrahydro-pyrido[3,4-d]pyridazin-4-one The title compound was prepared from 6-[(4-methoxyphenyl)methyl]-1-[(1-methyl-6-oxo-pyrimidin-5-yl)amino]-3-[4-(trifluoromethoxy)phenyl]-7,8-dihydro-5H-pyrido[3,4-d]pyridazin-4-one using a procedure analogous to that used to prepare example 131. MS (m/e): 435.1 (M+H)$^+$.

Intermediate 63

4-[(1-Methyl-6-oxo-pyrimidin-5-yl)amino]-2-[4-(trifluoromethoxy)phenyl]-5,6,7,8-tetrahydropyrido[3,4-d]pyridazin-1-one

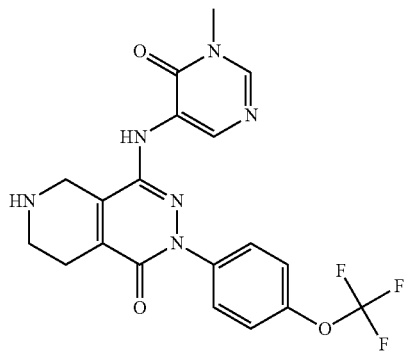 [SMILES: Cn1cncc(Nc2nn(-c3ccc(OC(F)(F)F)cc3)c(=O)c3c2CNCC3)c1=O]

Step 1: 6-[(4-methoxyphenyl)methyl]-4-[(1-methyl-6-oxo-pyrimidin-5-yl)amino]-2-[4-(trifluoromethoxy)phenyl]-7,8-dihydro-5H-pyrido[3,4-d]pyridazin-1-one The title compound was prepared from 4-bromo-6-[(4-methoxyphenyl)methyl]-2-[4-(trifluoromethoxy)phenyl]-7,8-dihydro-5H-pyrido[3,4-d]pyridazin-1-one (Intermediate 55, step 1) and 5-amino-3-methyl-pyrimidin-4-one (CAS 73922-41-5) using a procedure analogous to that used to prepare Intermediate 61. MS (m/e): 555.3 (M+H)$^+$.

Step 2: 4-[(1-methyl-6-oxo-pyrimidin-5-yl)amino]-2-[4-(trifluoromethoxy)phenyl]-5,6,7,8-tetrahydro-pyrido[3,4-d]pyridazin-1-one The title compound was prepared from 6-[(4-methoxyphenyl)methyl]-4-[(1-methyl-6-oxo-pyrimidin-5-yl)amino]-2-[4-(trifluoromethoxy)phenyl]-7,8-dihydro-5H-pyrido[3,4-d]pyridazin-1-one using a procedure analogous to that used to prepare example 131. MS (m/e): 435.1 (M+H)$^+$.

Intermediate 64 tert-Butyl 4-[2-[2-oxo-3-[[4-oxo-3-[4-(trifluoromethoxy)phenyl]-6,7-dihydro-5H-cyclopenta[d]pyridazin-1-yl]amino]-1-pyridyl]acetyl]piperazine-1-carboxylate

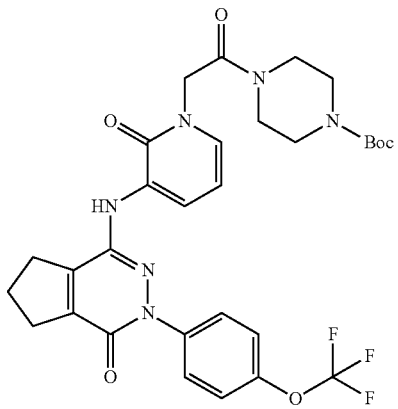 [SMILES: CC(C)(C)OC(=O)N1CCN(C(=O)Cn2cccc(Nc3nn(-c4ccc(OC(F)(F)F)cc4)c(=O)c4c3CCC4)c2=O)CC1]

The title compound was prepared from tert-butyl 4-(2-chloroacetyl)piperazine-1-carboxylate (CAS 190001-40-2), 3-nitro-1H-pyridin-2-one (CAS 6332-56-5) and [4-oxo-3-[4-(trifluoromethoxy)phenyl]-6,7-dihydro-5H-cyclopenta[d]pyridazin-1-yl]trifluoromethanesulfonate (Intermediate 9) using a sequence analagous to that used to prepare Intermediate 57. MS (m/e): 631.2 (M+H)$^+$.

Intermediate 65

Ethyl 4-[1-oxo-4-[(2-oxo-1H-pyridin-3-yl)amino]phthalazin-2-yl]benzoate

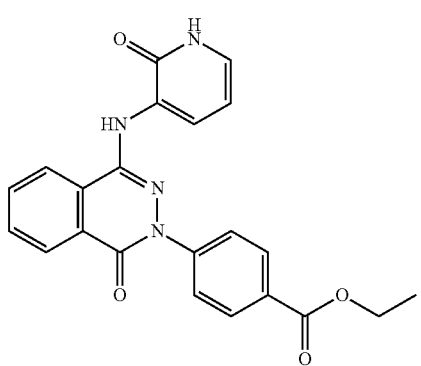 [SMILES: CCOC(=O)c1ccc(-n2nc(Nc3ccc[nH]c3=O)c3ccccc3c2=O)cc1]

Step 1: 4-[(1,3-dioxoisoindolin-2-yl)amino]benzoic acid

To a solution of isobenzofuran-1,3-dione (CAS 85-44-9, 5.0 g, 33.8 mmol) in AcOH (30 mL) was added 4-hydrazinylbenzoic acid hydrochloride (CAS 24589-77-3, 7.0 g, 37.1 mmol). The reaction mixture was stirred at 120° C. overnight. After cooled to rt, the brown solution was poured into water (100 mL) and the mixture was extracted with EtOAc (100 mL×2). The combined organic phase was washed with water and brine, dried over Na$_2$SO$_4$, and concentrated to give the title compound (8 g, crude) as a brown solid that was used in the next reaction directly. MS (m/e): 283.1 (M+H)$^+$.

Step 2: methyl 4-[(1,3-dioxoisoindolin-2-yl)amino]benzoate

To a mixture of 4-[(1,3-dioxoisoindolin-2-yl)amino]benzoic acid (3 g, 10.6 mmol) in MeOH (100 mL) was added SOCl$_2$ (13.1 g, 8 mL, 110 mmol) at 0° C. The mixture was stirred at 70° C. for 2 h. After removal of the solvents, the residue was dissolved in EtOAc (100 mL) and washed with aqueous NaHCO$_3$ and brine. The organic phase was dried over anhydrous Na$_2$SO$_4$ and concentrated. The residue was purified by column chromatography (eluting with 10%~50% EtOAc in DCM) to afford the title compound (3 g) as a brown solid. MS (m/e): 297.1 (M+H)$^+$.

Step 3: ethyl 4-(1,4-dioxo-3H-phthalazin-2-yl)benzoate

To a mixture of methyl 4-[(1,3-dioxoisoindolin-2-yl)amino]benzoate (1.0 g, 3.38 mmol) in EtOH (20 mL) was added sodium ethanolate (345 mg, 5.06 mmol) at 25° C. After stirred at rt for 10 h, the reaction mixture was concentrated in vacuo. The resulting mixture was poured into water and acidified with concentrated HCl to pH 3. The resulting solid was collected, washed with aq. HCl and dried to give the title compound (600 mg) as a light yellow solid that was used in the next step directly. MS (m/e): 311.1 (M+H)$^+$.

Step 4: ethyl 4-[1-oxo-4-(trifluoromethylsulfonyloxy)phthalazin-2-yl]benzoate To a mixture of ethyl 4-(1,4-dioxo-3H-phthalazin-2-yl)benzoate (600 mg, 1.93 mmol), and pyridine (1.64 mL, 20.3 mmol) in DCM (20 mL) was added Tf$_2$O (399 μl, 2.43 mmol) dropwise at 0° C. The mixture was stirred at rt for 2 h before quenched with sat. NH$_4$Cl. The mixture was extracted with EtOAc (80 mL), and the organic phase was washed with aq. HCl and brine, dried over Na$_2$SO$_4$ and concentrated to give the title compound (800 mg, crude). MS (m/e): 443.1 (M+H)$^+$.

Step 5: ethyl 4-[1-oxo-4-[(2-oxo-1H-pyridin-3-yl)amino]phthalazin-2-yl]benzoate A mixture of ethyl 4-[1-oxo-4-(trifluoromethylsulfonyloxy)phthalazin-2-yl]benzoate (300 mg, 678 μmol), 3-amino-1-methylpyridin-2(1H)-one (126.5 mg, 1.02 mmol), Pd$_2$(dba)$_3$ (124 mg, 136 μmol), Xantphos (157 mg, 271 μmol) and Cs$_2$CO$_3$ (442 mg, 1.36 mmol) in toluene (10 mL) was stirred at 100° C. for 2 h in a microwave reactor. After cooled to rt, the mixture was diluted with EtOAc (100 mL) and the organic phase was washed with water and brine. The organic phase was dried over anhydrous Na$_2$SO$_4$ and concentrated. The residue was purified by column chromatography (eluting with 10%~40% EtOAc in petroleum ether) to afford the title compound (50 mg) as a white solid. MS (m/e): 417.2 (M+H)$^+$.

Intermediate 66

4-[(1-Methyl-2-oxo-3-pyridyl)amino]-2-[4-(trifluoromethoxy)phenyl]-5,8-dihydrophthalazin-1-one

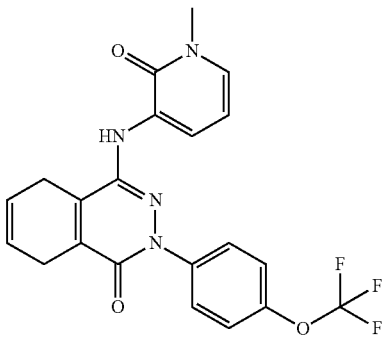 [SMILES: Cn1cccc(Nc2nn(-c3ccc(OC(F)(F)F)cc3)c(=O)c3c2CC=CC3)c1=O]

Step 1: dimethyl cyclohexa-1,4-diene-1,2-dicarboxylate

To a solution of 2,5-dihydrothiophene 1,1-dioxide (CAS 77-79-2, 19.3 g, 163 mmol) in xylene (150 mL) was added dimethyl but-2-ynedioate (CAS 762-42-5, 46.4 g, 32.1 mL, 327 mmol) at rt. After refluxed under argon for 2.5 h, the reaction mixture was concentrated in vacuo. The residue was purified by column chromatography (eluting with 10%~40% EtOAc in petroleum ether) to afford the title compound (28 g) as a light yellow oil. MS (m/e): 197.0 (M+H)$^+$.

Step 2: 4,7-dihydroisobenzofuran-1,3-dione

To a solution of dimethyl cyclohexa-1,4-diene-1,2-dicarboxylate (22 g, 112 mmol) in THF (100 mL) was added LiOH (2 M, 112 mL, 224 mmol) at 0° C. After stirred at rt for 56 h, the reaction mixture was neutralized with aq. HCl to pH 7. The resulting mixture was extracted with EtOAc (100 mL×3). The combined organic phase was washed with brine, dried over Na$_2$SO$_4$ and concentrated. The residue was treated with trifluoroacetic anhydride (78 mL, 561 mmol) and stirred at rt overnight. The mixture was concentrated under reduced pressure and the crude product was recrystallized from methanol to give the title compound (6.8 g). MS (m/e): 151.0 (M+H)$^+$.

Step 3: 3-[4-(trifluoromethoxy)phenyl]-5,8-dihydro-2H-phthalazine-1,4-dione

To a solution of 4,7-dihydroisobenzofuran-1,3-dione (3.4 g, 22.6 mmol) in AcOH (40 mL) was added (4-(trifluoromethoxy)phenyl)hydrazine hydrochloride (CAS 133115-72-7, 5.69 g, 24.9 mmol) in one portion. The reaction mixture was stirred at 120° C. overnight. After cooled to rt, the brown solution was poured into water and the mixture was extracted with EtOAc (100 mL×2). The combined organic phase was washed with water and brine, dried over anhydrous Na$_2$SO$_4$ and concentrated. The crude product was recrystallized from ethyl ether to afford the title compound (3 g). MS (m/e): 325.1 (M+H)$^+$.

Step 4: [4-oxo-3-[4-(trifluoromethoxy)phenyl]-5,8-dihydrophthalazin-1-yl]trifluoromethanesulfonate To a mixture of 3-[4-(trifluoromethoxy)phenyl]-5,8-dihydro-2H-phthalazine-1,4-dione (1.0 g, 3.08 mmol) and pyridine (2.5 mL, 30.8 mmol) in DCM (20 mL) was added Tf$_2$O (607 µl, 3.7 mmol) dropwise at 0° C. After stirred at rt for 2 h, the reaction mixture was treated with sat. NH$_4$Cl and diluted with EtOAc (100 mL). The organic phase was washed with aq. HCl and brine, dried over Na$_2$SO$_4$ and concentrated to give the title compound (1.4 g, crude). MS (m/e): 457.1 (M+H)$^+$.

Step 5: 4-[(1-methyl-2-oxo-3-pyridyl)amino]-2-[4-(trifluoromethoxy)phenyl]-5,8-dihydrophthalazin-1-one A mixture of [4-oxo-3-[4-(trifluoromethoxy)phenyl]-5,8-dihydrophthalazin-1-yl]trifluoromethanesulfonate (600 mg, 1.31 mmol), 3-amino-1-methylpyridin-2(1H)-one (CAS 33631-01-5, 245 mg, 1.97 mmol), Pd$_2$(dba)$_3$ (241 mg, 263 µmol), Xantphos (304 mg, 526 µmol) and Cs$_2$CO$_3$ (857 mg, 2.63 mmol) in toluene (10 mL) was stirred at 100° C. for 2 h in a microwave reactor. After cooled to rt, the mixture was diluted with EtOAc (100 mL) and the organic phase was washed with water and brine, dried over anhydrous Na$_2$SO$_4$ and concentrated. The crude product was recrystallized from methanol to afford the title compound (300 mg). MS (m/e): 431.1 (M+H)$^+$.

Intermediate 67

2-[2-Oxo-3-[[4-oxo-3-[4-(trifluoromethoxy)phenyl]phthalazin-1-yl]amino]-1-pyridyl]acetic acid

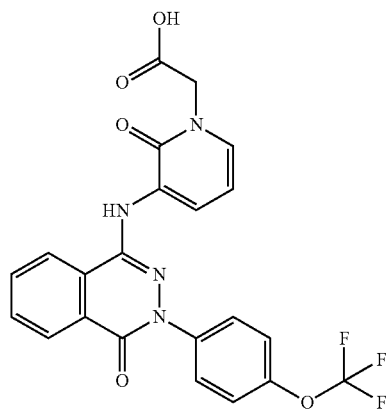 [SMILES: O=C(O)Cn1cccc(Nc2nn(-c3ccc(OC(F)(F)F)cc3)c(=O)c3ccccc23)c1=O]

This was prepared from methyl 2-[2-oxo-3-[[4-oxo-3-[4-(trifluoromethoxy)phenyl]phthalazin-1-yl]amino]-1-pyridyl]acetate (Intermediate 44) using a procedure analogous to that used to prepare example 109. MS (m/e): 473.2 (M+H)$^+$.

Intermediate 68

2-[2-Oxo-3-[[4-oxo-3-[4-(trifluoromethoxy)phenyl]-5,6,7,8-tetrahydrophthalazin-1-yl]amino]-1-pyridyl]acetic acid

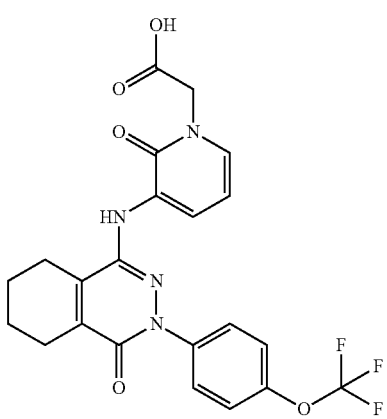 [SMILES: O=C(O)Cn1cccc(Nc2nn(-c3ccc(OC(F)(F)F)cc3)c(=O)c3c2CCCC3)c1=O]

The title compound was prepared from methyl 2-[2-oxo-3-[[4-oxo-3-[4-(trifluoromethoxy)phenyl]-5,6,7,8-tetrahydrophthalazin-1-yl]amino]-1-pyridyl]acetate (Intermediate 45) using a procedure analogous to that used to prepare example 109. MS (m/e): 477.0 (M+H)⁺.

Intermediate 69 trans-2-[2-[[2-Oxo-3-[[4-oxo-3-[4-(trifluoromethoxy)phenyl]-6,7-dihydro-5H-cyclopenta[d]pyridazin-1-yl]amino]-1-pyridyl]methyl]-1,3-dioxan-5-yl]isoindoline-1,3-dione

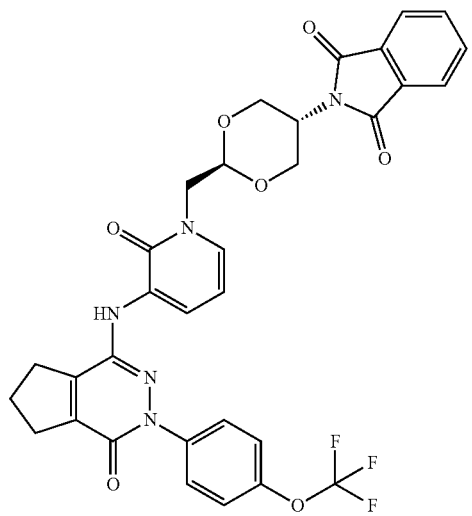 [SMILES: O=C1c2ccccc2C(=O)N1[C@H]1CO[C@H](Cn2cccc(Nc3nn(-c4ccc(OC(F)(F)F)cc4)c(=O)c4c3CCC4)c2=O)OC1]

To a solution of 1-[[1-(2,2-diethoxyethyl)-2-oxo-3-pyridyl]amino]-3-[4-(trifluoromethoxy)phenyl]-6,7-dihydro-5H-cyclopenta[d]pyridazin-4-one (Intermediate 47; 300 mg, 0.57 mmol) and 2-[2-hydroxy-1-(hydroxymethyl)ethyl]isoindoline-1,3-dione (127 mg, 0.57 mmol) in anhydrous toluene (10 mL) was added TsOH (20 mg, 0.11 mmol). The reaction was heated to 110° C. and stirred for 12 hr. The reaction was evaporated and the residue was dissolved in EtOAc (20 mL) and washed with aqueous NaHCO₃ (10 mL). The organic layer was evaporated and purified by column chromatography (PE:EA=3:1) to give the title product (200 mg, yield 54.0%) as a grey solid. MS (m/e): 649.9 (M+H)⁺.

Intermediate 70

Methyl 2-(3-amino-2-oxo-1-pyridyl)acetate hydrochloride salt

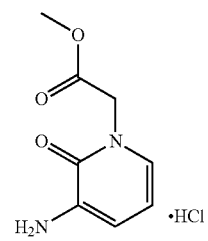

Step 1: methyl 2-(3-nitro-2-oxo-1-pyridyl)acetate

To a suspension of NaH (600 mg, 15 mmol) in DMF (30 mL) was added 3-nitropyridin-2(1H)-one (CAS 6332-56-5, 2.1 g, 15 mmol) portionwise and the mixture was stirred at 0° C. for 30 min and then at rt for 30 min. Methyl 2-bromoacetate (CAS 96-32-2, 2.29 g, 15 mmol) was added into the flask. The reaction mixture was stirred for 2 h before concentrated in vacuo. The residue was dissolved in EtOAc (100 mL) and washed with water (30 mL×2) and brine. The organic phase was dried over anhydrous Na2SO4 and concentrated. The residue was purified by flash chromatography (eluting with a gradient of petroleum ether:EtOAc) to afford the title compound as a yellow solid (2.2 g, 68% yield). MS (m/e): 213 (M+H)⁺.

Step 2: methyl 2-(3-amino-2-oxo-1-pyridyl)acetate; hydrochloride

To a solution of methyl 2-(3-nitro-2-oxopyridin-1(2H)-yl)acetate (2.1 g, 9.9 mmol) in MeOH (30 mL) and THF (10 mL) was added Pd/C (105 mg), and the mixture was charged with a hydrogen balloon and stirred at rt overnight. After filtration to remove the catalyst, the filtrate was treated with concentrated HCl (2 mL) and concentrated. The solid residue was washed with Et2O (10 mL×2) and dried under vacuum to give the title compound as a light grey product, which was used in the next step without purification (2.0 g, 92% yield). MS (m/e): 183.0 (M+H)⁺.

In analogy to Intermediate 70 compounds of the following table were prepared using 3-nitropyridin-2(1H)-one (CAS 6332-56-5) and different halides as reactants:

| Intermediate No. | Structure | Systematic Name | Starting materials | mass found (M + H)+ |
|---|---|---|---|---|
| 71 | (ethyl 2-[2-(3-amino-2-oxo-1-pyridyl)ethoxy]acetate structure) | ethyl 2-[2-(3-amino-2-oxo-1-pyridyl)ethoxy]acetate | CAS 867351-24-4 | 241.1 |
| 72 | (methyl 4-(3-amino-2-oxo-1-pyridyl)butanoate structure) | methyl 4-(3-amino-2-oxo-1-pyridyl)butanoate | CAS 4897-84-1 | 211.1 |
| 73 | (3-amino-1-(3-morpholinopropyl)pyridin-2-one structure) | 3-amino-1-(3-morpholinopropyl)pyridin-2-one | CAS 7357-67-7 | 238.2 |
| 74 | (3-amino-1-[3-(4-methylpiperazin-1-yl)propyl]pyridin-2-one structure) | 3-amino-1-[3-(4-methylpiperazin-1-yl)propyl]pyridin-2-one | CAS 6332-56-5 and CAS 104-16-5 | NMR only |
| 75 | (3-amino-1-(3-hydroxypropyl)pyridin-2-one structure) | 3-amino-1-(3-hydroxypropyl)pyridin-2-one | CAS 6332-56-5) and (CAS 627-18-9 | NMR only |

-continued

| Intermediate No. | Structure | Systematic Name | Starting materials | mass found (M + H)+ |
|---|---|---|---|---|
| 76 | 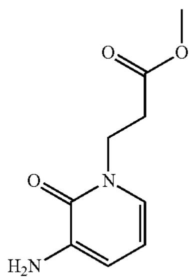 | methyl 3-(3-amino-2-oxo-1-pyridyl)propanoate | CAS 3395-91-3 | 197.1 |
| 77 | 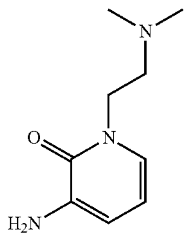 | 3-amino-1-[2-(dimethylamino)ethyl]pyridin-2-one | CAS 4584-46-7 | 182.1 |
| 78 | 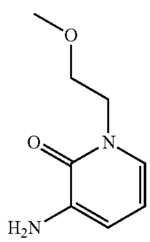 | 3-amino-1-(2-methoxyethyl)pyridin-2-one | CAS 627-42-9 | 169.0 |
| 79 | 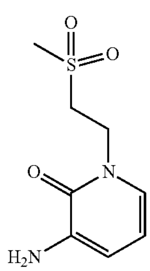 | 3-amino-1-(2-methylsulfonylethyl)pyridin-2-one | CAS 16523-02-7 | 217.1 |
| 80 | 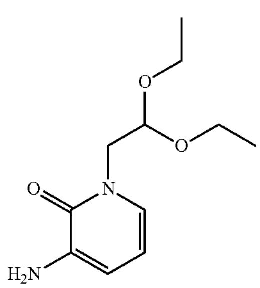 [SMILES: CCOC(Cn1cccc(N)c1=O)OCC] | 3-amino-1-(2,2-diethoxyethyl)pyridin-2-one | CAS 2032-35-1 | NMR only |

Intermediate 74

$^1$H NMR: (CDCl$_3$, 400 MHz) δ 6.85 (dd, J=1.8, 6.8 Hz, 1H), 6.41 (dd, J=1.8, 7.2 Hz, 1H), 6.01 (t, J=6.9 Hz, 1H), 5.06 (s, 2H), 3.87 (t, J=7.2 Hz, 2H), 2.40 (br. s., 3H), 2.26 (t, J=7.0 Hz, 2H), 2.21 (s, 3H), 1.77 (quin, J=7.1 Hz, 2H).

Intermediate 75

$^1$H NMR: (CDCl$_3$, 400 MHz) δ 6.82 (dd, J=1.8, 6.8 Hz, 1H), 6.39 (dd, J=1.8, 7.0 Hz, 1H), 6.00 (t, J=6.9 Hz, 1H), 5.04 (br. s., 2H), 4.55 (br. s., 1H), 3.88 (t, J=7.0 Hz, 2H), 3.40-3.32 (m, 2H), 1.73 (quin, J=6.6 Hz, 2H).

Intermediate 81

Methyl (2R)-1-[2-(3-amino-2-oxo-1-pyridyl)ethyl]pyrrolidine-2-carboxylate

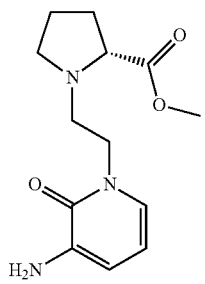 [SMILES: COC(=O)[C@H]1CCCN1CCn1cccc(N)c1=O]

Step 1: 1-(2-bromoethyl)-3-nitro-pyridin-2-one

To a suspension solution of NaH (400 mg, 9.99 mmol) in DMF (10 mL) was added 3-nitropyridin-2(1H)-one (CAS 6332-56-5, 1.4 g, 9.99 mmol) and the mixture was stirred at rt for 1 h. Then the mixture was added dropwise to a preheated solution of 1,2-dibromoethane (5.63 g, 30 mmol) in DMF (5 mL) at 80° C. The mixture was stirred at 80° C. for 1 h and cooled to rt. After removal of the solvent, the residue was dissolved in EtOAc (60 mL) and the organic phase was washed with water (20 mL), dried and concentrated. The residue was purified by silica gel chromatography (eluting with a gradient of petroleum ether:EtOAc) to afford 1-(2-bromoethyl)-3-nitro-pyridin-2-one as a light yellow oil (1.42 g, 58% yield). MS (m/e): 247.0 and 249.0 $(M+H)^+$.

Step 2: methyl (2R)-1-[2-(3-nitro-2-oxo-1-pyridyl)ethyl]pyrrolidine-2-carboxylate A mixture of 1-(2-bromoethyl)-3-nitropyridin-2(1H)-one (300 mg, 1.21 mmol), (R)-methyl pyrrolidine-2-carboxylate hydrochloride (CAS 65365-28-8, 201 mg, 1.21 mmol) and DIPEA (785 mg, 1.06 mL, 6.07 mmol) in DMF (5 mL) was stirred at 100° C. for 6 h. After removal of the solvent, the residue was purified by flash chromatography (eluting with a gradient of petroleum ether:EtOAc) to the title compound as a yellowish viscous oil (110 mg, 31% yield). MS (m/e): 296.1 $(M+H)^+$.

Step 3: methyl (2R)-1-[2-(3-amino-2-oxo-1-pyridyl)ethyl]pyrrolidine-2-carboxylate To a solution of (R)-methyl 1-(2-(3-nitro-2-oxopyridin-1(2H)-yl)ethyl)pyrrolidine-2-carboxylate (110 mg, 373 μmol) in MeOH (10 mL) was added Pd/C (7 mg, 65.8 μmol) and the mixture was charged with a hydrogen balloon and stirred at rt for 3 h. The mixture was filtered and the filtrate was concentrated under vacuum to afford the title compound as light brown viscous oil (87 mg, 88% yield). MS (m/e): 266.1 $(M+H)^+$.

In analogy to Intermediate 81 compounds of the following table were prepared using 1-(2-bromoethyl)-3-nitropyridin-2(1H)-one and different amines as reactants:

| Intermediate No. | Structure | Systematic Name | Starting materials | mass found $(M + H)^+$ |
|---|---|---|---|---|
| 82 | 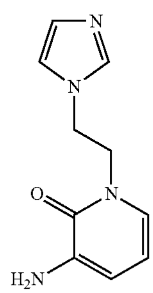 [SMILES: Nc1cccn(CCn2ccnc2)c1=O] | 3-amino-1-(2-imidazol-1-ylethyl)pyridin-2-one | CAS 288-32-4 | 215.1 |
| 83 | 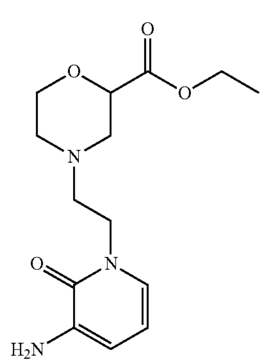 [SMILES: CCOC(=O)C1CN(CCn2cccc(N)c2=O)CCO1] | ethyl 4-[2-(3-amino-2-oxo-1-pyridyl)ethyl]morpholine-2-carboxylate | CAS 135072-31-0 | 296.1 |

-continued

| Intermediate No. | Structure | Systematic Name | Starting materials | mass found (M + H)+ |
|---|---|---|---|---|
| 84 | 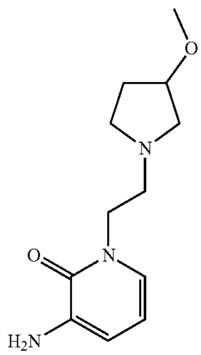 [SMILES: COC1CCN(CCn2cccc(N)c2=O)C1] | 3-amino-1-[2-(3-methoxypyrrolidin-1-yl)ethyl]pyridin-2-one | CAS 136725-50-3 | 238.1 |
| 85 | 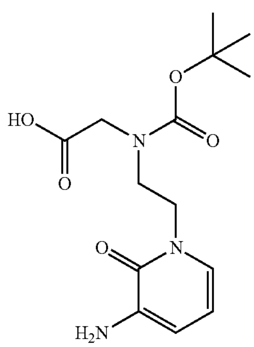 [SMILES: CC(C)(C)OC(=O)N(CCn1cccc(N)c1=O)CC(=O)O] | 2-[2-(3-amino-2-oxo-1-pyridyl)ethyl-tert-butoxycarbonyl-amino]acetic acid | CAS 31954-27-5 | 312.1 |
| 86 | 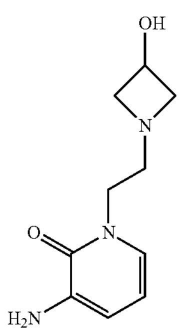 [SMILES: Nc1cccn(CCN2CC(O)C2)c1=O] | 3-amino-1-[2-(3-hydroxyazetidin-1-yl)ethyl]pyridin-2-one | CAS 1250507-61-9) and CAS 45347-82-8 | NMR only |
| 87 | 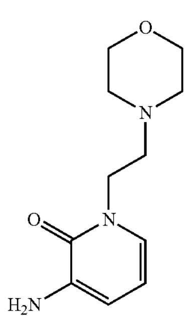 [SMILES: Nc1cccn(CCN2CCOCC2)c1=O] | 3-amino-1-(2-morpholinoethyl)pyridin-2-one | CAS 110-91-8 | 224.1 |

-continued

| Intermediate No. | Structure | Systematic Name | Starting materials | mass found (M + H)+ |
|---|---|---|---|---|
| 88 | 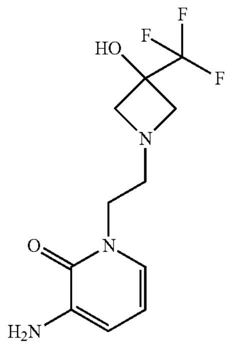 [SMILES: Nc1cccn(CCN2CC(O)(C(F)(F)F)C2)c1=O] | 3-amino-1-[2-[3-hydroxy-3-(trifluoromethyl)azetidin-1-yl]ethyl]pyridin-2-one | CAS 848192-96-1 | 278.1 |
| 89 | 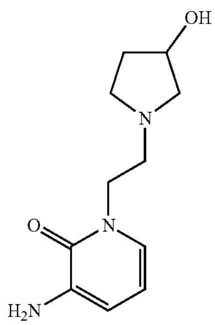 [SMILES: Nc1cccn(CCN2CCC(O)C2)c1=O] | 3-amino-1-[2-(3-hydroxypyrrolidin-1-yl)ethyl]pyridin-2-one | CAS 40499-83-0 | 224.1 |
| 90 | 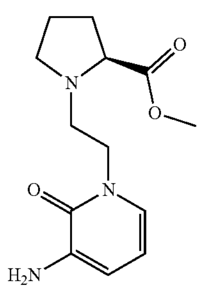 [SMILES: COC(=O)[C@@H]1CCCN1CCn1cccc(N)c1=O] | methyl (2S)-1-[2-[3-amino-2-oxo-1-pyridyl)ethyl]pyrrolidine-2-carboxylate | CAS 2133-40-6 | 266.1 |
| 91 | 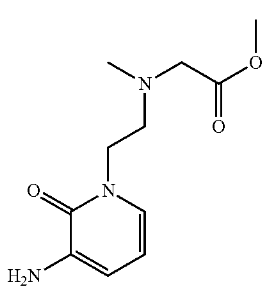 [SMILES: COC(=O)CN(C)CCn1cccc(N)c1=O] | methyl 2-[2-(3-amino-2-oxo-1-pyridyl)ethyl-methyl-amino]acetate | CAS 13515-93-0 | 240.1 |
| 92 | 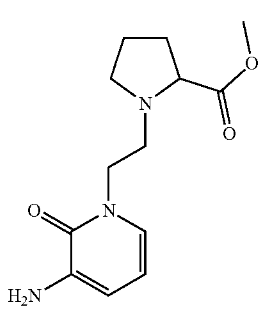 [SMILES: COC(=O)C1CCCN1CCn1cccc(N)c1=O] | methyl 1-[2-(3-amino-2-oxo-1-pyridyl)ethyl]pyrrolidine-2-carboxylate | CAS 79397-50-5 | 266.1 |

| Intermediate No. | Structure | Systematic Name | Starting materials | mass found (M + H)+ |
|---|---|---|---|---|
| 93 | 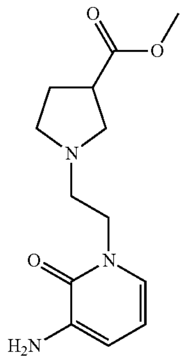 [SMILES: COC(=O)C1CCN(CCn2cccc(N)c2=O)C1] | methyl 1-[2-(3-amino-2-oxo-1-pyridyl)ethyl]pyrrolidine-3-carboxylate | CAS 72057-18-2 | 266.1 |
| 94 | 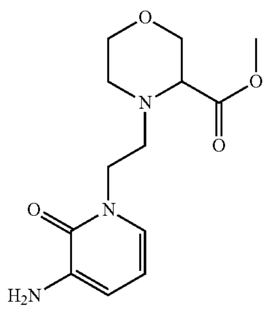 [SMILES: COC(=O)C1COCCN1CCn1cccc(N)c1=O] | methyl 4-[2-(3-amino-2-oxo-1-pyridyl)ethyl]morpholine-3-carboxylate | CAS 1214686-81-3 | 282.1 |

Intermediate 86

¹H NMR: (CDCl₃, 400 MHz) δ 6.81 (dd, J=1.7, 6.8 Hz, 1H), 6.41 (dd, J=1.7, 7.2 Hz, 1H), 5.99 (t, J=7.0 Hz, 1H), 5.26 (br. s., 1H), 5.04 (s, 2H), 4.11 (br. s., 1H), 3.79 (t, J=6.3 Hz, 2H), 3.53-3.42 (m, 2H), 2.76-2.57 (m, 4H).

Intermediate 95

5-Amino-3-[2-(dimethylamino)ethyl]pyrimidin-4-one hydrochloride

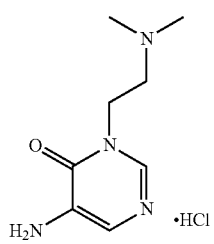

Step 1: 5-bromo-3-[2-(dimethylamino)ethyl]pyrimidin-4-one

To a solution of 5-bromo-1H-pyrimidin-6-one (CAS 19808-30-1; 3.0 g, 17.1 mmol) in DMF (50.0 mL) was added Cs₂CO₃ (8.4 g, 25.65 mmol) at 20° C. under N₂. Then 2-chloro-N,N-dimethyl-ethanamine hydrochloride (CAS 4584-46-7; 3.0 g, 20.6 mmol) was added. Then the reaction mixture was heated to 60° C. and stirred for 16 h. Solvent was removed in vacuo to dryness to give a residue which was diluted with EtOAc (100.0 mL), washed with water (50.0 mL), dried and concentrated to give crude product which was purified by column chromatography on silica gel (DCM/MeOH from 300:1 to 80:1) to give the title compound (1.6 g, 38.1% yield) as a yellow solid. ¹H NMR: (400 MHz, CDCl₃) δ 8.20 (s, 1H), 8.07 (s, 1H), 4.04-4.01 (t, J=5.6 Hz 2H), 2.64-2.61 (t, J=5.8 Hz, 2H), 2.26 (s, 6H).

Step 2: tert-butyl N-[1-[2-(dimethylamino)ethyl]-6-oxo-pyrimidin-5-yl]carbamate

A mixture of 5-bromo-3-[2-(dimethylamino)ethyl]pyrimidin-4-one (0.5 g, 2.03 mmol), NH₂Boc (0.35 g, 3.04 mmol), Pd₂(dba)₃ (100 mg), xantphos (100 mg) and K₂CO₃ (0.56 g, 4.06 mmol) in dioxane (8.0 mL) was charged with N₂ and the mixture was stirred at 100° C. for 16 hr. After cooling, solvent was removed in vacuum to dryness to give a residue which was purified by column chromatography on silica gel (from DCM to DCM/MeOH=80/1) to give the title compound (0.4 g, 71.2% yield) as a yellow solid. MS (m/e): 283.0 (M+H)+.

Step 3: 5-amino-3-[2-(dimethylamino)ethyl]pyrimidin-4-one hydrochloride

To the solution of tert-butyl N-[1-[2-(dimethylamino)ethyl]-6-oxo-pyrimidin-5-yl]carbamate (0.4 g, 1.42 mmol) in MeOH (4.0 mL) was added HCl/MeOH (4.0 mL) at 0° C. The reaction mixture was heated to 40° C. and stirred for 2 h. Solvent was removed in vacuum to dryness to give the title compound (0.3 g, crude) as yellow solid which was used in the next step without further purification. MS (m/e): 183.0 (M+H)+.

In analogy to Intermediate 95 compounds of the following table were prepared using 5-bromo-1H-pyrimidin-6-one (CAS 19808-30-1) and different halides as reactants:

| Intermediate No. | Structure | Systematic Name | Starting materials | mass found (M + H)+ |
|---|---|---|---|---|
| 96 | 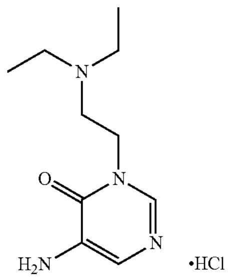 | 5-amino-3-[2-(diethylamino)ethyl]pyrimidin-4-one hydrochloride | CAS 869-24-9 | 211.0 |
| 97 | 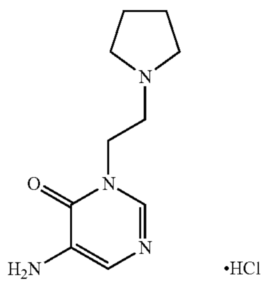 [SMILES: Nc1cncn(CCN2CCCC2)c1=O ; Cl] | 5-amino-3-(2-pyrrolidin-1-ylethyl)pyrimidin-4-one hydrochloride | CAS 7250-67-1 | 209.0 |
| 98 | 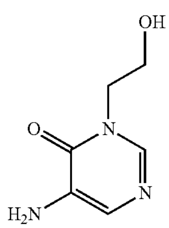 | 5-amino-3-(2-hydroxyethyl)pyrimidin-4-one hydrochloride | CAS 540-51-2 | NMR only |
| 99 | 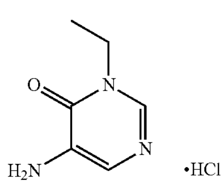 | 5-amino-3-ethyl-pyrimidin-4-one hydrochloride | CAS 75-03-6 | NMR only |
| 100 | 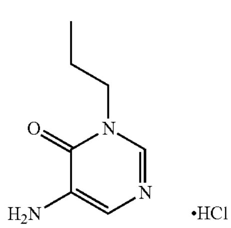 | 5-amino-3-propyl-pyrimidin-4-one hydrochloride | CAS 107-08-4 | NMR only |

Intermediate 101

Methyl 3-(3-amino-2-oxo-1-pyridyl)-2,2-dimethyl-propanoate

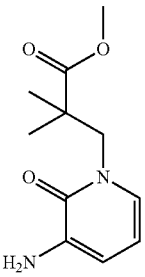

Step 1: methyl 3-bromo-2,2-dimethyl-propanoate

To a solution of 3-bromo-2,2-dimethylpropanoic acid (CAS 2843-17-6, 2.7 g, 14.9 mmol) in MeOH (30 mL) was added SOCl$_2$ (3.55 g, 2.18 mL, 29.8 mmol) dropwise. The mixture was stirred at refluxing conditions overnight. After cooled to rt, the mixture was concentrated and the residue was redisssolved in ether (50 mL). The organic phase was washed with aqueous NaHCO$_3$, dried over anhydrous Na$_2$SO$_4$ and concentrated under vacuum to afford a colorless oil that was used in the next step without further purification. (1.5 g, 52% yield).

Step 2: methyl 2,2-dimethyl-3-(3-nitro-2-oxo-1-pyridyl)propanoate

To a stirring mixture of 3-nitropyridin-2(1H)-one (CAS 6332-56-5, 420 mg, 3 mmol) and K$_2$CO$_3$ (621 mg, 4.5 mmol) in DMF (5 mL) was added methyl 3-bromo-2,2-dimethylpropanoate (643 mg, 3.3 mmol) and the mixture was stirred at 130° C. overnight in a sealed tube. After removal of DMF in vacuo, the residue was dissolved in EtOAc (50 mL) and filtered to remove solid particles. The fitrate was concentrated and the residue was purified by flash chromatography (eluting with a gradient of petroleum ether: EtOAc) to afford the title compound as a light yellow oil (300 mg, yield of 39%). MS (m/e): 255 (M+H)$^+$.

Step 3: methyl 3-(3-amino-2-oxo-1-pyridyl)-2,2-dimethyl-propanoate

A mixture of methyl 2,2-dimethyl-3-(3-nitro-2-oxopyridin-1(2H)-yl)propanoate (300 mg, 1.18 mmol) and Pd/C (12.6 mg, 118 μmol) in MeOH (20 mL) was charged with a hydrogen balloon, and the mixture was stirred at rt overnight. After filtration to remove the catalyst, the filtrate was concentrated under vacuum to afford the title compound as light yellow oil that was used in the next step without purification (263 mg, 99% yield). MS (m/e): 225.1 (M+H)$^+$.

Intermediate 102

Methyl 5-amino-1-methyl-6-oxo-pyridine-3-carboxylate

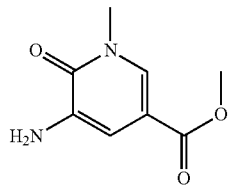

To a solution of methyl 1-methyl-5-nitro-6-oxo-1,6-dihydropyridine-3-carboxylate (CAS 153888-41-6, 0.95 g, 4.48 mmol) in MeOH (15 mL) and THF (10 mL) was added Pd/C (47.7 mg, 448 μmol), and the mixture was charged with a hydrogen balloon and stirred at rt for 4 h.

The mixture was filtered and the filtrate was concentrated under vacuum to give a light brown solid, which was washed with EtOAc (10 mL). The powder was collected and dried to give the title compound as a light grey solid (620 mg, 75% yield). MS (m/e): 183.0 (M+H)$^+$.

Intermediate 103

3-Amino-5-ethyl-1-methyl-pyridin-2-one

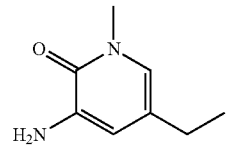

Step 1: 5-ethyl-3-nitro-1H-pyridin-2-one

To a solution of 5-ethyl-1H-pyridin-2-one (CAS 53428-03-8; 3.0 g, 24 mmol) in conc. H$_2$SO$_4$ (20 mL) was added conc. HNO$_3$ (6 mL) dropwise at 0-5° C. After addition, the reaction was warmed to 25° C. and stirred for 12 hr. The reaction was poured onto ice/water (100 g). The mixture was basified to pH at 7-8 and then extracted with DCM (50 mL×3). The organic phase was evaporated to give the crude product, the crude product was added to petroleum ether/EtOAc (20 mL/3 mL) and stirred for 2 hr. The mixture was then filtered to give the title compound (2.5 g) as a yellow solid. $^1$H NMR: (DMSO, 400 MHz) δ 8.37 (d, J=2.6 Hz, 1H), 7.74 (d, J=2.5 Hz, 1H), 2.45 (q, J=7.5 Hz, 2H), 1.12 (t, J=7.5 Hz, 3H).

Step 2: 5-ethyl-1-methyl-3-nitro-pyridin-2-one

To a solution of 5-ethyl-3-nitro-1H-pyridin-2-one (3.0 g, 17.8 mmol) and K$_2$CO$_3$ (4.9 g, 35.6 mmol) in DMF (20 mL) was added CH$_3$I (42.45 g, 300 mmol). The reaction was heated to 60-70° C. and stirred for 4 hr. The reaction was poured onto H$_2$O (100 mL) and the pH adjusted to 7-8. The mixture was extracted with EtOAc (150 mL). The organic phase was washed with brine (30 mL×3). The organic phase was evaporated to give the title compound (2.8 g, yield 85%) as a yellow solid. $^1$H NMR: (DMSO, 400 MHz) δ 8.35 (d, J=2.5 Hz, 1H), 8.12 (d, J=2.5 Hz, 1H), 3.55 (s, 3H), 2.46 (q, J=7.6 Hz, 2H), 1.14 (t, J=7.5 Hz, 3H).

Step 3: 3-amino-5-ethyl-1-methyl-pyridin-2-one

To a solution of 5-ethyl-1-methyl-3-nitro-pyridin-2-one (1.0 g, 5.5 mmol) in MeOH (14 mL) and EtOAc (6 mL) was added Pd/C (0.5 g). The mixture was degassed 3 times and then refilled with hydrogen (50 PSI). The reaction was stirred for 2 hr at 25° C. The reaction was filtered through celite and the filtrate was evaporated to give the title compound (0.66 g, yield 79%) as a black oil, which was used directly for the next step. ¹H NMR: (DMSO, 400 MHz) δ 6.71-6.66 (m, 1H), 6.36 (d, J=2.3 Hz, 1H), 5.04 (s, 2H), 3.39 (s, 3H), 2.26 (q, J=7.5 Hz, 2H), 1.07 (t, J=7.5 Hz, 3H).

Intermediate 104

3-Amino-5-isopropyl-1-methyl-pyridin-2-one

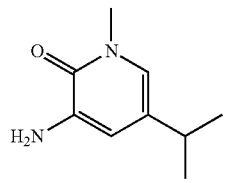

This was prepared from 5-isopropyl-1H-pyridin-2-one (CAS 137013-12-8) using an analogous procedure to that used to prepare Intermediate 103.

Intermediate 105

Methyl 4-(3-amino-5-chloro-2-oxo-1-pyridyl)butanoate

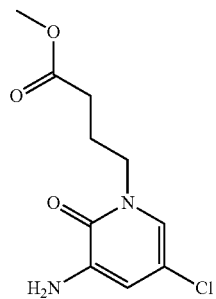 [SMILES: COC(=O)CCCn1cc(Cl)cc(N)c1=O]

Step 1: methyl 4-(5-chloro-3-nitro-2-oxo-1-pyridyl)butanoate

To a stirring mixture of 5-chloro-3-nitropyridin-2(1H)-one (CAS 21427-61-2, 698 mg, 4 mmol) and K₂CO₃ (829 mg, 6 mmol) in DMF (5 mL) preheated to 120° C. was added methyl 4-bromobutanoate (CAS 4897-84-1, 797 mg, 4.4 mmol) dropwise. The mixture was stirred at 120° C. for 2 h and concentrated in vacuo. The residue was dissolved in EtOAc (50 mL) and filtered to remove solid particles. The filtrate was concentrated and the residue was purified by flash chromatography (eluting with a gradient of petroleum ether:EtOAc) to afford the title compound as a light yellow oil (570 mg, yield of 52%). MS (m/e): 275 (M+H)⁺.

Step 2: methyl 4-(3-amino-5-chloro-2-oxo-1-pyridyl)butanoate

A mixture of methyl 4-(5-chloro-3-nitro-2-oxopyridin-1(2H)-yl)butanoate (200 mg, 728 mol, Eq: 1) and Pd/C (7.75 mg, 72.8 μmol, Eq: 0.1) in MeOH (10 mL) and CH₂Cl₂ (1 mL) was charged with a hydrogen balloon and stirred at rt for 40 min. After removal of the catalyst, the filtrate was concentrated under vacuum and the residue was purified by flash chromatography (eluting with a gradient of petroleum ether. EtOAc) to afford the title compound as light brown oil (40 mg, yield of 22%). MS (m/e): 245.0 (M+H)⁺.

Intermediate 106 tert-Butyl N-[2-(3-amino-2-oxo-1-pyridyl)ethyl]carbamate

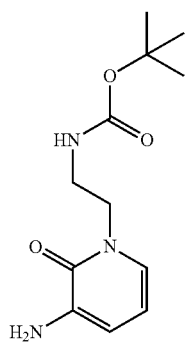

Step 1: tert-butyl N-[2-(3-nitro-2-oxo-1-pyridyl)ethyl]carbamate

To a mixture of 1-(2-bromoethyl)-3-nitropyridin-2(1H)-one (350 mg, 1.42 mmol) and tert-butyl carbamate (CAS 4248-19-5, 332 mg, 2.83 mmol) in DMF (5 mL) was added sodium tert-butoxide (136 mg, 1.42 mmol), and the mixture was stirred at rt overnight. After removal of the solvent under vacuum, the residue was dissolved in EtOAc (30 mL) and the organic phase was washed with water, dried and concentrated. The residue was purified by silica gel chromatography (eluting with a gradient of petroleum ether: EtOAc) to afford the title compound as a light yellow solid (120 mg, 30% yield). MS (m/e): 284 (M+H)⁺.

Step 2. tert-butyl N-[2-(3-amino-2-oxo-1-pyridyl)ethyl]carbamate

A mixture of tert-butyl (2-(3-nitro-2-oxopyridin-1 (2H)-yl)ethyl)carbamate (100 mg, 353 mol) and Pd/C (7 mg, 65.8 μmol) in MeOH (10 mL) was charged with a hydrogen balloon and stirred at rt for 3 h. After filtration, the filtrate was concentrated under vacuum to give the title compound as light brown viscous oil that was used in the next step directly (90 mg with 40% purity from LC-MS, yield of 40%). MS (m/e): 254 (M+H)⁺.

Intermediate 107

3-(3-Amino-2-oxo-1-pyridyl)propane-1-sulfonamide

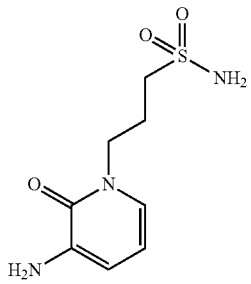 [SMILES: Nc1cccn(CCCS(N)(=O)=O)c1=O]

Step 1:
3-(3-nitro-2-oxo-1-pyridyl)propane-1-sulfonic acid

A solution of 3-nitropyridin-2(1H)-one (CAS 6332-56-5, 560 mg, 4 mmol), 1,2-oxathiolane 2,2-dioxide (CAS 1120-71-4, 635 mg, 5.2 mmol) and NaOH (208 mg, 5.2 mmol) in dry EtOH (30 mL) was stirred at 70° C. for 1 h. After the reaction was completed, the mixture was cooled to rt and filtered to afford the title compound (800 mg, 76% yield). MS (m/e): 263.0 (M+H)+.

Step 2:
3-(3-nitro-2-oxo-1-pyridyl)propane-1-sulfonyl chloride

To a solution of 3-(3-nitro-2-oxopyridin-1(2H)-yl)propane-1-sulfonic acid (1.05 g, 4 mmol) in dry THF (30 mL) was added SOCl$_2$ (4.76 g, 2.92 mL, 40 mmol) and the mixture was stirred at 70° C. for 1 h. The solvent was removed in vacuo to afford the title compound as a crude product (1.1 g). MS (m/e): 281.0 (M+H)+.

Step 3:
3-(3-nitro-2-oxo-1-pyridyl)propane-1-sulfonamide

To a solution of 3-(3-nitro-2-oxopyridin-1(2H)-yl)propane-1-sulfonyl chloride (200 mg, 713 μmol) in THF (10 mL) was added ammonia (14.3 mmol) at 0° C., and the mixture was stirred at rt overnight. The solvents were removed under reduced pressure to afford the title compound as a crude product (180 mg). MS (m/e): 262.0 (M+H)+.

Step 4:
3-(3-amino-2-oxo-1-pyridyl)propane-1-sulfonamide

A solution of 3-(3-nitro-2-oxopyridin-1(2H)-yl)propane-1-sulfonamide (180 mg, 689 mol) and Pd/C (14.7 mg, 138 μmol) in MeOH (10 mL) was charged with 1 atm of hydrogen and stirred at rt overnight. After filtration to remove the catalyst, the filtrate was concentrated under vacuum to give the title compound (84 mg, yield of 60%). MS (m/e): 232.0 (M+H)+.

Intermediate 108

3-(3-Amino-2-oxo-1-pyridyl)-N,N-dimethyl-propane-1-sulfonamide

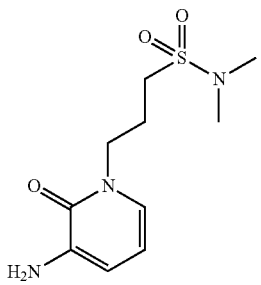 [SMILES: CN(C)S(=O)(=O)CCCn1cccc(N)c1=O]

The title compound was prepared from 3-(3-nitro-2-oxo-1-pyridyl)propane-1-sulfonyl chloride and dimethylamine hydrochloride using an analogous procedure to that used in the preparation of Intermediate 107.

Intermediate 109 tert-Butyl N-[2-hydroxy-2-methyl-3-[2-oxo-3-[[4-oxo-3-[4-(trifluoromethoxy)phenyl]-6,7-dihydro-5H-cyclopenta[d]pyridazin-1-yl]amino]-1-pyridyl]propyl]carbamate

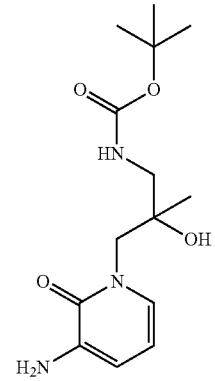 [SMILES: CC(O)(CNC(=O)OC(C)(C)C)Cn1cccc(N)c1=O]

Step 1: 1-azido-3-chloro-2-methyl-propan-2-ol

To a solution of 1-azido-3-chloro-2-methyl-propan-2-ol (CAS 1029615-90-4; 1.2 g, 8.7 mmol) in DMF (20.0 mL) was added Cs$_2$CO$_3$ (4.25 g, 13.0 mmol) at 20° C. under N$_2$. Then 3-nitro-1H-pyridin-2-one (CAS 6332-56-5; 1.3 g, 8.7 mmol) was added and the reaction mixture heated to 60° C. and stirred for 16 h. Solvent was removed in vacuum to dryness to give a residue which was diluted with EtOAc (50.0 mL), washed with water (50.0 mL), dried and concentrated to give a residue which was purified by column chromatography on silica gel (petroleum ether/EtOAc from 10/1 to 5/1) to give the title compound (0.7 g, 32% yield) as a colorless oil. $^1$H NMR: (CDCl$_3$, 400 MHz) δ 8.39-8.37 (m, 1 H), 7.82-7.79 (m, 1 H), 6.39-6.35 (t, J=7.2 Hz, 1 H), 4.27-4.12 (m, 2 H), 3.44-3.31 (m, 2 H), 1.31 (s, 3 H).

Step 2: tert-butyl N-[2-hydroxy-2-methyl-3-(3-nitro-2-oxo-1-pyridyl)propyl]carbamate To a solution of 1-azido-3-chloro-2-methyl-propan-2-ol (0.7 g, 2.37 mmol) in THF/H$_2$O (6/1.5 mL) was added PPh$_3$ (0.9 g, 3.56 mmol) at 5° C. under N$_2$. Then the reaction mixture was warmed to 20° C. and stirred for 16 h. To the reaction mixture was added Boc$_2$O (1.12 g, 4.74 mmol) and TEA (0.48 g, 4.74 mmol). The reaction was stirred at 20° C. for another 16 h. Solvent was removed in vacuum to dryness to give a residue which was purified by column chromatography in silica gel (petroleum ether/EtOAc from 10/1 to EtOAc) to give the title compound (0.27 g, 34.6% yield) as a yellow solid. MS (m/e): 350.1 (M+Na)$^+$.

Step 3: tert-butyl N-[3-(3-amino-2-oxo-1-pyridyl)-2-hydroxy-2-methyl-propyl]carbamate To a solution of tert-butyl N-[2-hydroxy-2-methyl-3-(3-nitro-2-oxo-1-pyridyl)propyl]carbamate (250.0 mg, 0.764 mmol) in MeOH (10.0 mL) was added Pd/C (200.0 mg) at 20° C. Then the reaction mixture was stirred at 20° C. under hydrogen (balloon) and stirred for 16 h. The mixture was filtered and concentrated to give the title compound (0.18 g, crude) as yellow solid which was used in next step without further purification. MS (m/e): 198.0 (M+H-Boc)$^{+.}$

Step 4: tert-butyl N-[2-hydroxy-2-methyl-3-[2-oxo-3-[[4-oxo-3-[4-(trifluoromethoxy)phenyl]-6,7-dihydro-5H-cyclopenta[d]pyridazin-1-yl]amino]-1-pyridyl]propyl]carbamate A mixture of tert-butyl N-[3-(3-amino-2-oxo-1-pyridyl)-2-hydroxy-2-methyl-propyl]carbamate (166.0 mg, 0.375 mmol), [4-oxo-3-[4-(trifluoromethoxy)phenyl]-6,7-dihydro-5H-cyclopenta[d]pyridazin-1-yl]trifluoromethanesulfonate (Intermediate 12; 150.0 mg, 0.375 mmol), Pd2(dba)3 (50 mg), Xantphos (50 mg) and K$_2$CO$_3$ (103.5 mg, 0.75 mmol) in dioxane (15.0 mL) was charged with N$_2$, and the mixture was stirred at 100° C. for 16 hr. The mixture was concentrated and the residue was purified by column chromatography on silica gel (petroleum ether/EtOAc from 10/1 to EtOAc) to give the title compound (0.15 g, crude) as yellow solid. MS (m/e): 492.2 (M+H-Boc)$^+$.

Intermediate 110

(4-tert-Butyl-2-fluoro-phenyl)hydrazine hydrochloride

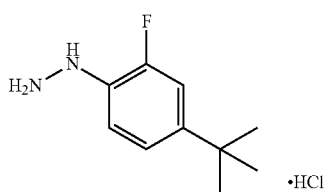

A solution of 4-tert-butyl-2-fluoro-aniline (CAS 129373-04-2; 1.2 g, 7.18 mmol) in 6N HCl (12 mL) was cooled to 0° C. NaNO$_2$ (0.59 g, 8.62 mmol) in water (5 mL) was added dropwise to a solution at 0° C. for 0.5 h. Then SnCl$_2$.2H$_2$O (4.1 g, 17.95 mmol) in 6N HCl (12 mL) was added dropwise to the solution at 0° C. for 3 hr, then the reaction was stirred and allowed to warm to 25° C. for 1 hr. The mixture was filtered to give the title compound (1.3 g, yield: 83.6%) as a white solid. $^1$HNMR: (DMSO, 400 MHz) δ 10.32 (br. s., 3H), 7.23-7.14 (m, 3H), 1.29-1.20 (m, 9H).

Intermediate 111

(6-Ethoxy-3-pyridyl)hydrazine hydrochloride

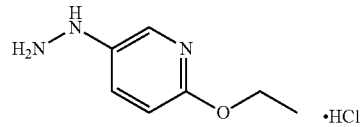

The title compound was prepared from 6-ethoxypyridin-3-amine (CAS 52025-34-0) using a procedure analogous to that used to prepare Intermediate 110.

Intermediate 112

6,7-Dihydro-4H-furo[3,4-c]pyran-1,3-dione

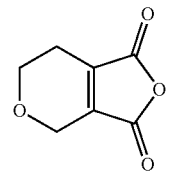 [SMILES: O=C1OC(=O)C2=C1CCOC2]

Step 1: 5-ethoxycarbonyl-3,6-dihydro-2H-pyran-4-carboxylic acid

A mixture of HCO$_2$Na (6.7 g, 98.6 mmol), Ac$_2$O (6.4 g, 63.6 mmol), and i-Pr$_2$NEt (8.0 g, 63.6 mmol) was stirred at 15° C. for 1 h. To this mixture were added ethyl 4-(trifluoromethyl sulfonyloxy)-3,6-dihydro-2H-pyran-5-carboxylate (CAS 1068523-55-6, 10.0 g, 32.8 mmol) in DMF (100 mL), Pd(OAc)$_2$ (0.37 g, 1.64 mmol), and LiCl (4.1 g, 98.6 mmol) sequentially, and the stirring was continued for another 1 h. The mixture was poured into a separatory funnel where it was partitioned between 2 N HCl and EtOAc. Then the organic extracts were combined, dried over Na$_2$SO$_4$, filtered, and concentrated to give the crude product (11.0 g, crude).

Step 2: 6,7-dihydro-4H-furo[3,4-c]pyran-1,3-dione

To a solution of 5-ethoxycarbonyl-3,6-dihydro-2H-pyran-4-carboxylic acid (10.0 g, 50.0 mmol) in CH$_3$OH (50.0 mL) and H$_2$O (50.0 mL) was added LiOH (6.7 g g, 150.0 mmol) at 15° C. under N$_2$. The reaction mixture was stirred at 15° C. for 3 h. The reaction mixture was concentrated, then added H$_2$O (100 mL) and adjust PH of the mixture to 3~5. The aqueous phase was extracted with EtOAc (100 mL×3). The combine organic phases were concentrated to give a white solid (11.0 g). The white solid (11.0 g, 63.9 mmol) in Ac₂O (110 mL) was stirred at 130° C. for 3 h. The mixture was concentrated to give the crude title product (5.0 g).

Intermediate 113

[3-[2-Methyl-4-(trifluoromethoxy)phenyl]-4-oxo-6,7-dihydro-5H-cyclopenta[d]pyridazin-1-yl]trifluoromethanesulfonate

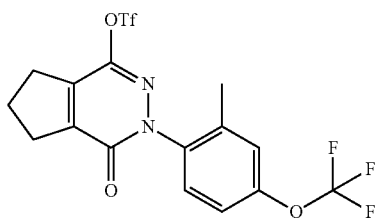 [SMILES: Cc1cc(OC(F)(F)F)ccc1-n1nc(OS(=O)(=O)C(F)(F)F)c2c(c1=O)CCC2]

The title compound was prepared from [2-methyl-4-(trifluoromethoxy)phenyl]hydrazine (CAS 1801321-38-9) and 5,6-dihydro-4H-cyclopenta[c]furan-1,3-dione (CAS 3205-94-5) using a procedure analogous to that used to prepare intermediate 9. MS (m/e): 459.0 (M+H)⁺.

Intermediate 114

[3-(3,4-Dimethoxyphenyl)-4-oxo-6,7-dihydro-5H-cyclopenta[d]pyridazin-1-yl]trifluoromethanesulfonate

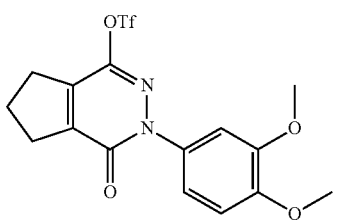 [SMILES: COc1ccc(-n2nc(OS(=O)(=O)C(F)(F)F)c3c(c2=O)CCC3)cc1OC]

The title compound was prepared from (3,4-dimethoxyphenyl)hydrazine (CAS 63756-98-9) and 5,6-dihydro-4H-cyclopenta[c]furan-1,3-dione (CAS 3205-94-5) using a procedure analogous to that used to prepare intermediate 9. MS (m/e): 421.0 (M+H)⁺.

Intermediate 115

[3-[3-Methoxy-4-(trifluoromethyl)phenyl]-4-oxo-6,7-dihydro-5H-cyclopenta[d]pyridazin-1-yl]trifluoromethanesulfonate

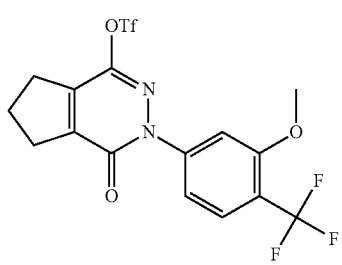 [SMILES: COc1cc(-n2nc(OS(=O)(=O)C(F)(F)F)c3c(c2=O)CCC3)ccc1C(F)(F)F]

The title compound was prepared from [3-methoxy-4-(trifluoromethyl)phenyl]hydrazine (CAS 1388058-17-0) and 5,6-dihydro-4H-cyclopenta[c]furan-1,3-dione (CAS 3205-94-5) using a procedure analogous to that used to prepare intermediate 9. MS (m/e): 459.0 (M+H)⁺.

Intermediate 116

1-Methyl-6-oxo-5-[[4-oxo-3-[4-(trifluoromethoxy)phenyl]-5,6,7,8-tetrahydrophthalazin-1-yl]amino]pyridine-3-carboxylic acid

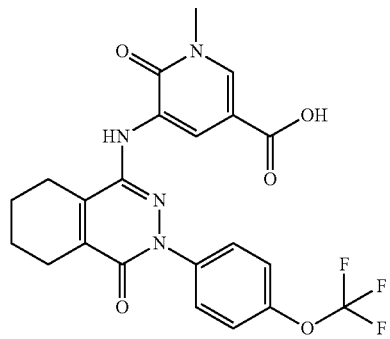 [SMILES: Cn1cc(C(=O)O)cc(Nc2nn(-c3ccc(OC(F)(F)F)cc3)c(=O)c3c2CCCC3)c1=O]

To a solution of methyl 1-methyl-6-oxo-5-[[4-oxo-3-[4-(trifluoromethoxy)phenyl]-5,6,7,8-tetrahydrophthalazin-1-yl]amino]pyridine-3-carboxylate (Example 23; 70 mg, 143 µmol) in water (5 mL) and THF (5 mL) was added lithium hydroxide monohydrate (59.9 mg, 1.43 mmol), and the mixture was heated to reflux for 4 hr. The mixture was evaporated, the remaining aqueous solution was acidified by HCl to pH~2 to precipitate a solid. The mixture was filtered, and the solid residue was washed with water. The solid was collected and dried to give the title compound (67 mg, 97.5%). MS (m/e): 477.2 (M+H)⁺.

Intermediate 117

1-Methyl-6-oxo-5-[[4-oxo-3-[4-(trifluoromethoxy)phenyl]phthalazin-1-yl]amino]pyridine-3-carboxylic acid

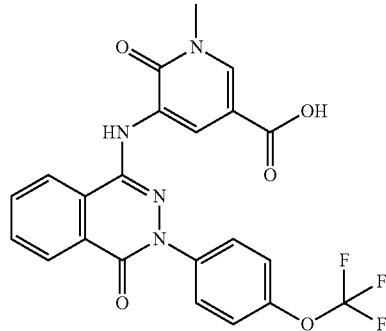 [SMILES: Cn1cc(C(=O)O)cc(Nc2nn(-c3ccc(OC(F)(F)F)cc3)c(=O)c3ccccc23)c1=O]

The title compound was prepared from methyl 1-methyl-6-oxo-5-[[4-oxo-3-[4-(trifluoromethoxy)phenyl]phthalazin-1-yl]amino]pyridine-3-carboxylate (Intermediate 118) using a procedure analogous to that used to prepare intermediate 116. MS (m/e): 473.1 (M+H)+.

Intermediate 118

Methyl 1-methyl-6-oxo-5-[[4-oxo-3-[4-(trifluoromethoxy)phenyl]phthalazin-1-yl]amino]pyridine-3-carboxylate

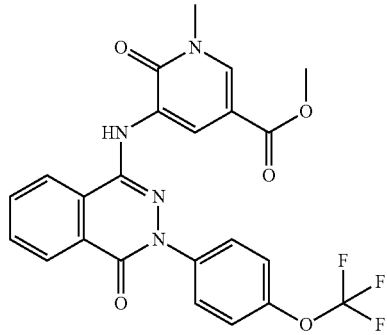 [SMILES: COC(=O)c1cc(Nc2nn(-c3ccc(OC(F)(F)F)cc3)c(=O)c3ccccc23)c(=O)n(C)c1]

The title compound was prepared from [4-oxo-3-[4-(trifluoromethoxy)phenyl]phthalazin-1-yl]trifluoromethanesulfonate (Intermediate 1) and methyl 5-amino-1-methyl-6-oxo-pyridine-3-carboxylate (Intermediate 103) using a method analogous to that used to prepare Example 23. MS (m/e): 487.3 (M+H)+.

Example 1

4-[(1-methyl-2-oxo-3-pyridyl)amino]-2-[4-(trifluoromethoxy)phenyl]phthalazin-1-one

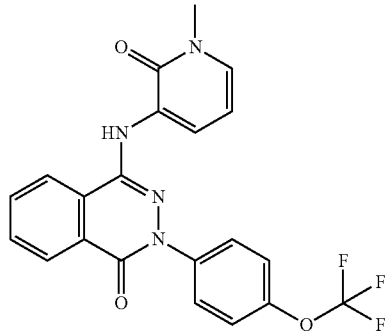 [SMILES: Cn1cccc(Nc2nn(-c3ccc(OC(F)(F)F)cc3)c(=O)c3ccccc23)c1=O]

A mixture of [4-oxo-3-[4-(trifluoromethoxy)phenyl]phthalazin-1-yl]trifluoromethanesulfonate (Intermediate 1; 0.3 g, 0.66 mmol), 3-amino-1-methyl-pyridin-2-one (CAS 33631-01-5; 0.16 g, 1.32 mmol), Pd$_2$(dba)$_3$ (0.11 g, 0.13 mmol), Xantphos (70.0 mg, 0.13 mmol) and K$_2$CO$_3$ (0.27 g, 1.98 mmol) in dioxane (30 mL) was stirred at 100° C. for 16 h. The reaction mixture was filtered and the filtrate was concentrated to give the crude product (0.5 g). The crude product was purified by silica gel (PE:EA=3:1/1:1) and recrystallized from CH$_3$OH (10 mL) to give the title compound (96.0 mg, 34.2%) as a white solid. MS (m/e): 429.1 (M+H)+.

In analogy to Example 1 compounds of the following table were prepared using different amines and trifluoromethanesulfonates or bromides as reactants:

| Example No. | Structure | Systematic Name | Starting materials | mass found (M + H)+ |
|---|---|---|---|---|
| 2 | 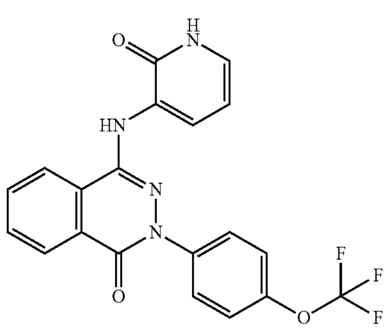 [SMILES: O=c1[nH]cccc1Nc1nn(-c2ccc(OC(F)(F)F)cc2)c(=O)c2ccccc12] | 4-[(2-oxo-1H-pyridin-3-yl)amino]-2-[4-(trifluoromethoxy)phenyl]phthalazin-1-one | Intermediate 1 and CAS 33630-99-8 | 415.1 |

-continued

| Example No. | Structure | Systematic Name | Starting materials | mass found (M + H)+ |
|---|---|---|---|---|
| 3 | 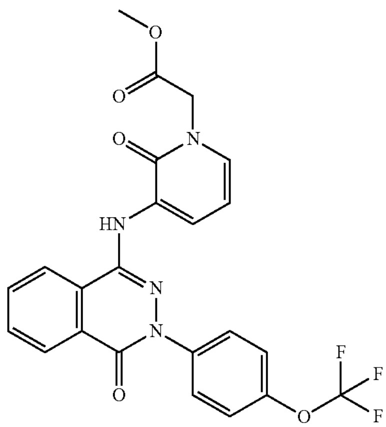 [SMILES: COC(=O)Cn1cccc(Nc2nn(-c3ccc(OC(F)(F)F)cc3)c(=O)c3ccccc23)c1=O] | methyl 2-[2-oxo-3-[[4-oxo-3-[4-(trifluoromethoxy)phenyl]phthalazin-1-yl]amino]-1-pyridyl]acetate | Intermediate 1 and Intermediate 70 | 487.2 |
| 4 | 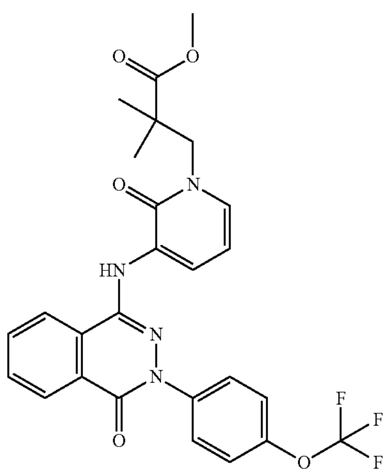 [SMILES: COC(=O)C(C)(C)Cn1cccc(Nc2nn(-c3ccc(OC(F)(F)F)cc3)c(=O)c3ccccc23)c1=O] | methyl 2,2-dimethyl-3-[2-oxo-3-[[4-oxo-3-[4-(trifluoromethoxy)phenyl]phthalazin-1-yl]amino]-1-pyridyl]propanoate | Intermediate 1 and Intermediate 101 | 529.2 |
| 5 | 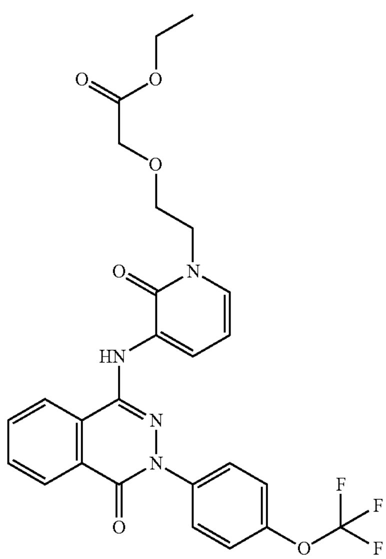 [SMILES: CCOC(=O)COCCn1cccc(Nc2nn(-c3ccc(OC(F)(F)F)cc3)c(=O)c3ccccc23)c1=O] | ethyl 2-[2-[2-oxo-3-[[4-oxo-3-[4-(trifluoromethoxy)phenyl]phthalazin-1-yl]amino]-1-pyridyl]ethoxy]acetate | Intermediate 1 and Intermediate 71 | 545.3 |

| Example No. | Structure | Systematic Name | Starting materials | mass found (M + H)+ |
|---|---|---|---|---|
| 6 | 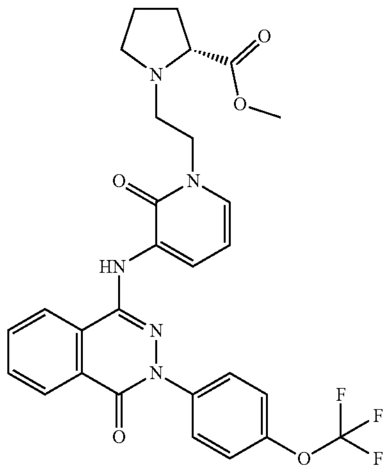 [SMILES: COC(=O)[C@H]1CCCN1CCn1cccc(Nc2nn(-c3ccc(OC(F)(F)F)cc3)c(=O)c3ccccc23)c1=O] | methyl (2R)-1-[2-[2-oxo-3-[[4-oxo-3-[4-(trifluoromethoxy)phenyl]phthalazin-1-yl]amino]-1-pyridyl]ethyl]pyrrolidine-2-carboxylate | Intermediate 1 and Intermediate 81 | 570.2 |
| 7 | 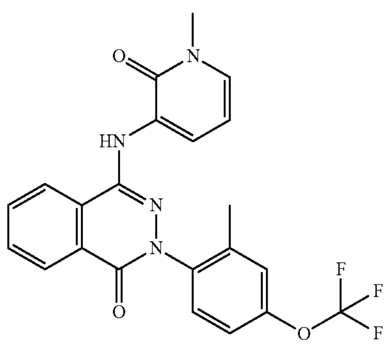 [SMILES: Cc1cc(OC(F)(F)F)ccc1-n1nc(Nc2cccn(C)c2=O)c2ccccc2c1=O] | 4-[(1-methyl-2-oxo-3-pyridyl)amino]-2-[2-methyl-4-(trifluoromethoxy)phenyl]phthalazin-1-one | Intermediate 12 and CAS 33631-01-5 | 443.1 |
| 8 | 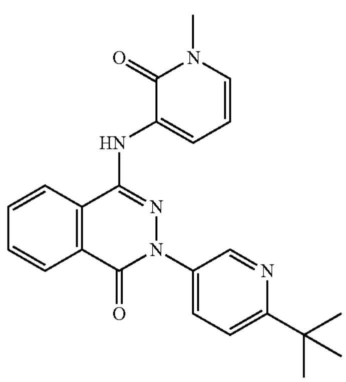 [SMILES: Cn1cccc(Nc2nn(-c3ccc(C(C)(C)C)nc3)c(=O)c3ccccc23)c1=O] | 2-(6-tert-butyl-3-pyridyl)-4-[(1-methyl-2-oxo-3-pyridyl)amino]phthalazin-1-one | Intermediate 2 and CAS 33631-01-5 | 402.3 |
| 9 | 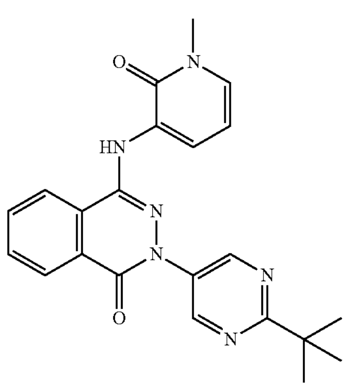 [SMILES: Cn1cccc(Nc2nn(-c3cnc(C(C)(C)C)nc3)c(=O)c3ccccc23)c1=O] | 2-(2-tert-butylpyrimidin-5-yl)-4-[(1-methyl-2-oxo-3-pyridyl)amino]phthalazin-1-one | Intermediate 3 and CAS 1523570-95-7 | 403.2 |

-continued

| Example No. | Structure | Systematic Name | Starting materials | mass found (M + H)+ |
|---|---|---|---|---|
| 10 | 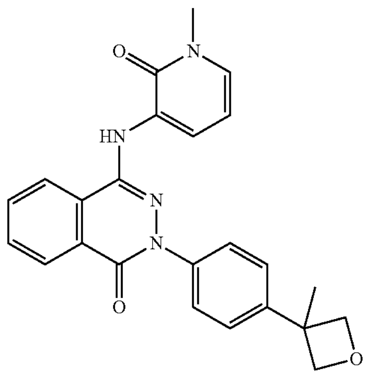 [SMILES: Cn1cccc(Nc2nn(-c3ccc(C4(C)COC4)cc3)c(=O)c3ccccc23)c1=O] | 2-[4-(3-methyloxetan-3-yl)phenyl]-4-[(1-methyl-2-oxo-3-pyridyl)amino]phthalazin-1-one | Intermediate 4 and CAS 1523570-95-7 | 415.1 |
| 11 | 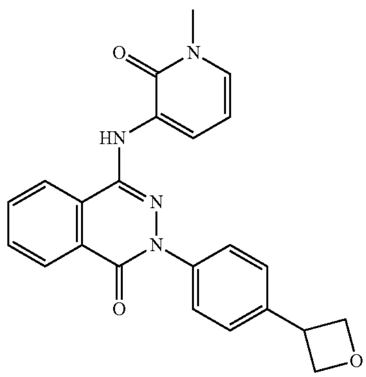 [SMILES: Cn1cccc(Nc2nn(-c3ccc(C4COC4)cc3)c(=O)c3ccccc23)c1=O] | 4-[(1-methyl-2-oxo-3-pyridyl)amino]-2-[4-(oxetan-3-yl)phenyl]phthalazin-1-one | Intermediate 5 and CAS 1523570-95-7 | 401.1 |
| 12 | 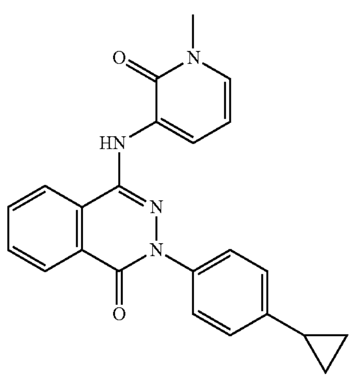 [SMILES: Cn1cccc(Nc2nn(-c3ccc(C4CC4)cc3)c(=O)c3ccccc23)c1=O] | 2-(4-cyclopropylphenyl)-4-[(1-methyl-2-oxo-3-pyridyl)amino]phthalazin-1-one | Intermediate 6 and CAS 1523570-95-7 | 385.2 |
| 13 | 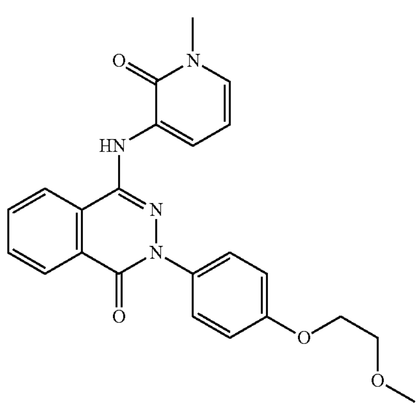 [SMILES: COCCOc1ccc(-n2nc(Nc3cccn(C)c3=O)c3ccccc3c2=O)cc1] | 2-[4-(2-methoxyethoxy)phenyl]-4-[(1-methyl-2-oxo-3-pyridyl)amino]phthalazin-1-one | Intermediate 26 and CAS 33631-01-5 | 419.1 |

-continued

| Example No. | Structure | Systematic Name | Starting materials | mass found (M + H)+ |
|---|---|---|---|---|
| 14 | 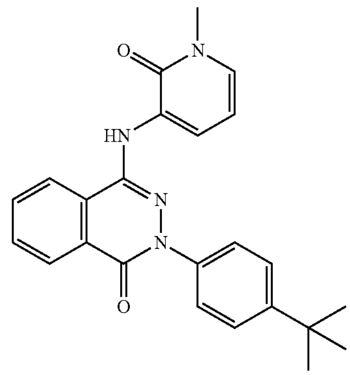 [SMILES: Cn1cccc(Nc2nn(-c3ccc(C(C)(C)C)cc3)c(=O)c3ccccc23)c1=O] | 2-(4-tert-butylphenyl)-4-[(1-methyl-2-oxo-3-pyridyl)amino]phthalazin-1-one | Intermediate 7 and CAS 33631-01-5 | 401.2 |
| 15 | 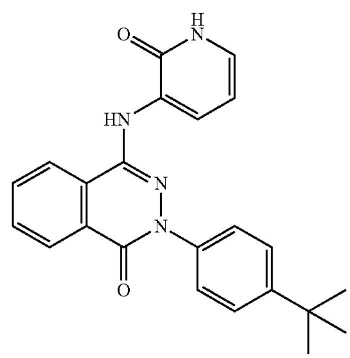 [SMILES: CC(C)(C)c1ccc(-n2nc(Nc3ccc[nH]c3=O)c3ccccc3c2=O)cc1] | 2-(4-tert-butylphenyl)-4-[(2-oxo-1H-pyridin-3-yl)amino]phthalazin-1-one | Intermediate 7 and CAS 33630-99-8 | 387.1 |
| 16 | 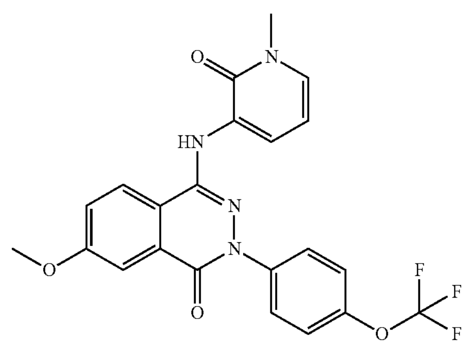 [SMILES: COc1ccc2c(Nc3cccn(C)c3=O)nn(-c3ccc(OC(F)(F)F)cc3)c(=O)c2c1] | 7-methoxy-4-[(1-methyl-2-oxo-3-pyridyl)amino]-2-[4-(trifluoromethoxy)phenyl]phthalazin-1-one | Intermediate 24 and CAS 33631-01-5 | 459.1 |
| 17 | 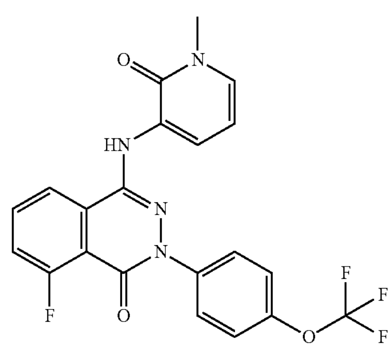 [SMILES: Cn1cccc(Nc2nn(-c3ccc(OC(F)(F)F)cc3)c(=O)c3c(F)cccc23)c1=O] | 8-fluoro-4-[(1-methyl-2-oxo-3-pyridyl)amino]-2-[4-(trifluoromethoxy)phenyl]phthalazin-1-one | Intermediate 25 and CAS 33631-01-5 | 447.2 |

-continued

| Example No. | Structure | Systematic Name | Starting materials | mass found (M + H)+ |
|---|---|---|---|---|
| 18 | 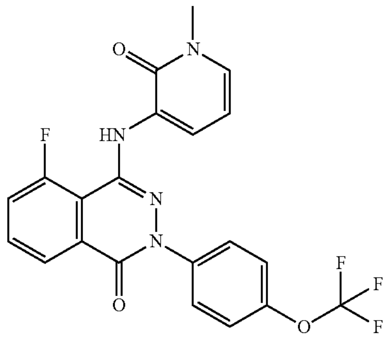 [SMILES: Cn1cccc(Nc2nn(-c3ccc(OC(F)(F)F)cc3)c(=O)c3cccc(F)c23)c1=O] | 5-fluoro-4-[(1-methyl-2-oxo-3-pyridyl)amino]-2-[4-(trifluoromethoxy)phenyl]phthalazin-1-one | Intermediate 25 and CAS 33631-01-5 | 447.2 |
| 19 | 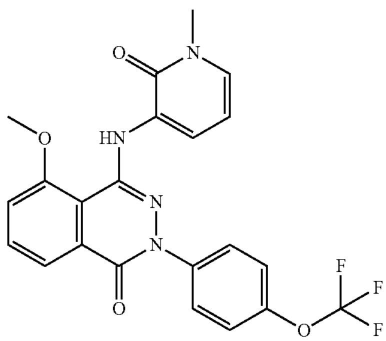 [SMILES: COc1cccc2c(=O)n(-c3ccc(OC(F)(F)F)cc3)nc(Nc3cccn(C)c3=O)c12] | 5-methoxy-4-[(1-methyl-2-oxo-3-pyridyl)amino]-2-[4-(trifluoromethoxy)phenyl]phthalazin-1-one | Intermediate 27 and CAS 33631-01-5 | 459.2 |
| 20 | 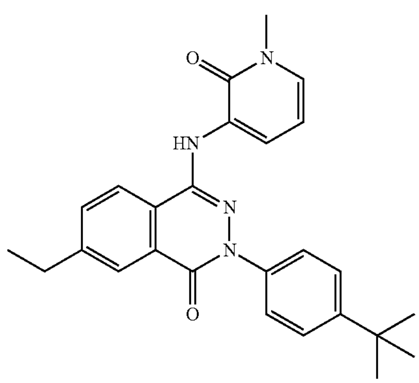 [SMILES: CCc1ccc2c(Nc3cccn(C)c3=O)nn(-c3ccc(C(C)(C)C)cc3)c(=O)c2c1] | 2-(4-tert-butylphenyl)-7-ethyl-4-[(1-methyl-2-oxo-3-pyridyl)amino]phthalazin-1-one | Intermediate 28 and CAS 33631-01-5 | 429.2 |
| 21 | 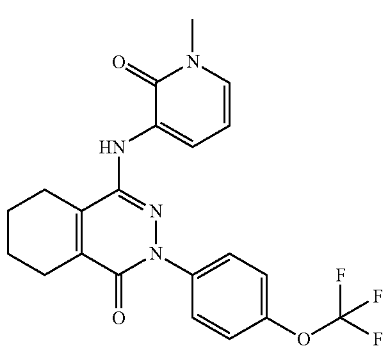 [SMILES: Cn1cccc(Nc2nn(-c3ccc(OC(F)(F)F)cc3)c(=O)c3c2CCCC3)c1=O] | 4-[(1-methyl-2-oxo-3-pyridyl)amino]-2-[4-(trifluoromethoxy)phenyl]-5,6,7,8-tetrahydrophthalazin-1-one | Intermediate 23 and CAS 33631-01-5 | 433.1 |

-continued

| Example No. | Structure | Systematic Name | Starting materials | mass found (M + H)+ |
|---|---|---|---|---|
| 22 | 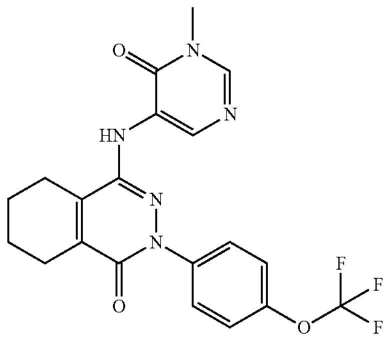 [SMILES: Cn1cncc(Nc2nn(-c3ccc(OC(F)(F)F)cc3)c(=O)c3c2CCCC3)c1=O] | 4-[(1-methyl-6-oxo-pyrimidin-5-yl)amino]-2-[4-(trifluoromethoxy)phenyl]-5,6,7,8-tetrahydrophthalazin-1-one | Intermediate 23 and CAS 73922-41-5 | 434.1 |
| 23 | 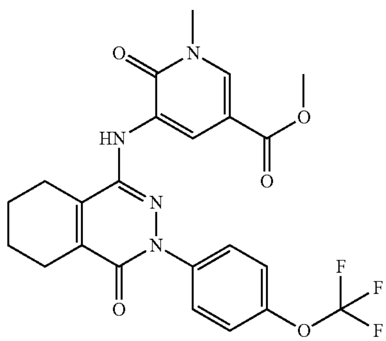 [SMILES: COC(=O)c1cc(Nc2nn(-c3ccc(OC(F)(F)F)cc3)c(=O)c3c2CCCC3)c(=O)n(C)c1] | methyl 1-methyl-6-oxo-5-[[4-oxo-3-[4-(trifluoromethoxy)phenyl]-5,6,7,8-tetrahydrophthalazin-1-yl]amino]pyridine-3-carboxylate | Intermediate 23 and Intermediate 102 | 491.2 |
| 24 | 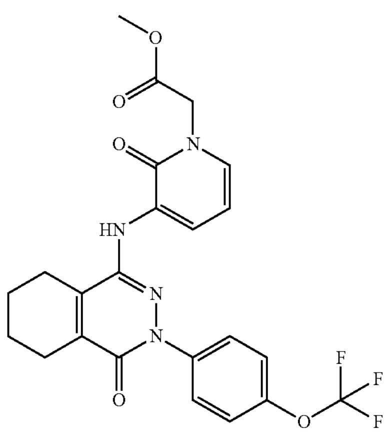 [SMILES: COC(=O)Cn1cccc(Nc2nn(-c3ccc(OC(F)(F)F)cc3)c(=O)c3c2CCCC3)c1=O] | methyl 2-[2-oxo-3-[[4-oxo-3-[4-(trifluoromethoxy)phenyl]-5,6,7,8-tetrahydrophthalazin-1-yl]amino]-1-pyridyl]acetate | Intermediate 23 and Intermediate 70 | 491.2 |
| 25 | 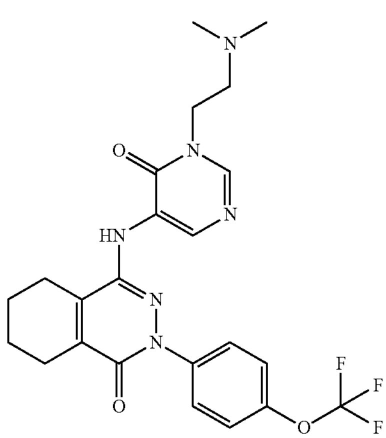 [SMILES: CN(C)CCn1cncc(Nc2nn(-c3ccc(OC(F)(F)F)cc3)c(=O)c3c2CCCC3)c1=O] | 4-[[1-[2-(dimethylamino)ethyl]-6-oxo-pyrimidin-5-yl]amino]-2-[4-(trifluoromethoxy)phenyl]-5,6,7,8-tetrahydrophthalazin-1-one | Intermediate 23 and Intermediate 95 | 491.2 |

-continued

| Example No. | Structure | Systematic Name | Starting materials | mass found (M + H)+ |
|---|---|---|---|---|
| 26 | 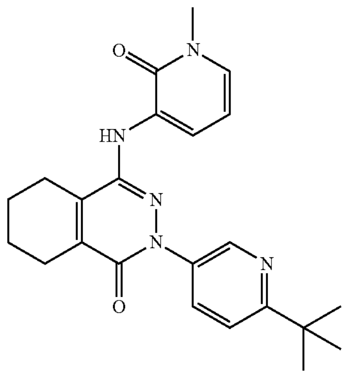 [SMILES: Cn1cccc(Nc2nn(-c3ccc(C(C)(C)C)nc3)c(=O)c3c2CCCC3)c1=O] | 2-(6-tert-butyl-3-pyridyl)-4-[(1-methyl-2-oxo-3-pyridyl)amino]-5,6,7,8-tetrahydrophthalazin-1-one | Intermediate 10 and CAS 33631-01-5 | 406.1 |
| 27 | 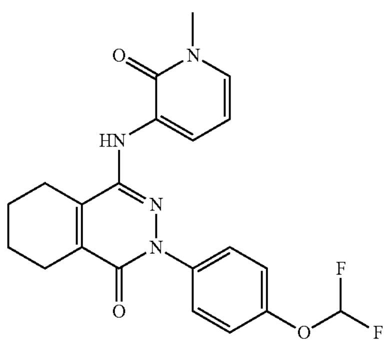 [SMILES: Cn1cccc(Nc2nn(-c3ccc(OC(F)F)cc3)c(=O)c3c2CCCC3)c1=O] | 2-[4-(difluoromethoxy)phenyl]-4-[(1-methyl-2-oxo-3-pyridyl)amino]-5,6,7,8-tetrahydrophthalazin-1-one | Intermediate 11 and CAS 33631-01-5 | 415.1 |
| 28 | 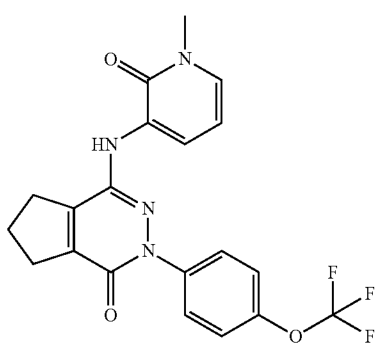 [SMILES: Cn1cccc(Nc2nn(-c3ccc(OC(F)(F)F)cc3)c(=O)c3c2CCC3)c1=O] | 1-[(1-methyl-2-oxo-3-pyridyl)amino]-3-[4-(trifluoromethoxy)phenyl]-6,7-dihydro-5H-cyclopenta[d]pyridazin-4-one | Intermediate 9 and CAS 33631-01-5 | 419.1 |
| 29 | 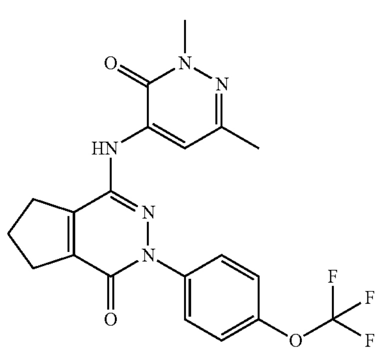 [SMILES: Cc1cc(Nc2nn(-c3ccc(OC(F)(F)F)cc3)c(=O)c3c2CCC3)c(=O)n(C)n1] | 1-[(2,6-dimethyl-3-oxo-pyridazin-4-yl)amino]-3-[4-(trifluoromethoxy)phenyl]-6,7-dihydro-5H-cyclopenta[d]pyridazin-4-one | Intermediate 9 and CAS 2256-43-1 | 434.1 |

| Example No. | Structure | Systematic Name | Starting materials | mass found (M + H)+ |
|---|---|---|---|---|
| 30 | 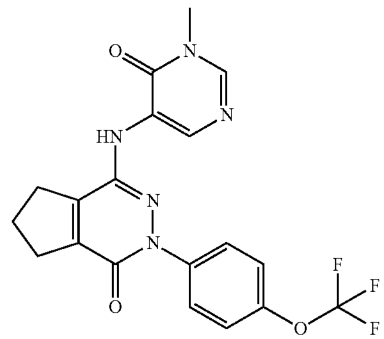 [SMILES: Cn1cncc(Nc2nn(-c3ccc(OC(F)(F)F)cc3)c(=O)c3c2CCC3)c1=O] | 1-[(1-methyl-6-oxo-pyrimidin-5-yl)amino]-3-[4-(trifluoromethoxy)phenyl]-6,7-dihydro-5H-cyclopenta[d]pyridazin-4-one | Intermediate 9 and CAS 73922-41-5 | 420.1 |
| 31 | 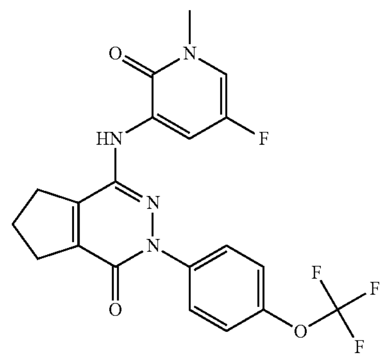 [SMILES: Cn1cc(F)cc(Nc2nn(-c3ccc(OC(F)(F)F)cc3)c(=O)c3c2CCC3)c1=O] | 1-[(5-fluoro-1-methyl-2-oxo-3-pyridyl)amino]-3-[4-(trifluoromethoxy)phenyl]-6,7-dihydro-5H-cyclopenta[d]pyridazin-4-one | Intermediate 9 and CAS 1781125-38-9 | 437.2 |
| 32 | 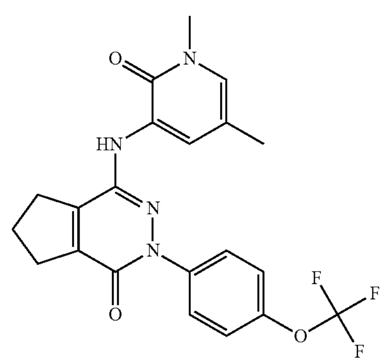 [SMILES: Cc1cc(Nc2nn(-c3ccc(OC(F)(F)F)cc3)c(=O)c3c2CCC3)c(=O)n(C)c1] | 1-[(1,5-dimethyl-2-oxo-3-pyridyl)amino]-3-[4-(trifluoromethoxy)phenyl]-6,7-dihydro-5H-cyclopenta[d]pyridazin-4-one | Intermediate 9 and CAS 1394734-82-7 | 433.3 |
| 33 | 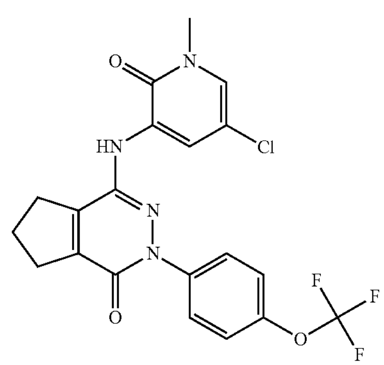 [SMILES: Cn1cc(Cl)cc(Nc2nn(-c3ccc(OC(F)(F)F)cc3)c(=O)c3c2CCC3)c1=O] | 1-[(5-chloro-1-methyl-2-oxo-3-pyridyl)amino]-3-[4-(trifluoromethoxy)phenyl]-6,7-dihydro-5H-cyclopenta[d]pyridazin-4-one | Intermediate 9 and CAS 1441769-24-9 | 453.1 |

-continued

| Example No. | Structure | Systematic Name | Starting materials | mass found (M + H)+ |
|---|---|---|---|---|
| 34 | 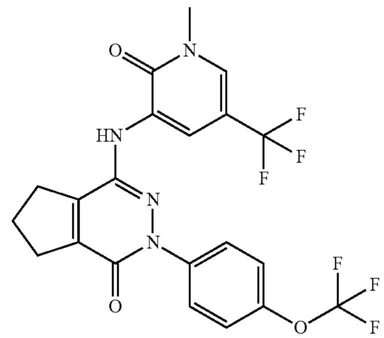 [SMILES: Cn1cc(C(F)(F)F)cc(Nc2nn(-c3ccc(OC(F)(F)F)cc3)c(=O)c3c2CCC3)c1=O] | 1-[[1-methyl-2-oxo-5-(trifluoromethyl)-3-pyridyl]amino]-3-[4-(trifluoromethoxy)phenyl]-6,7-dihydro-5H-cyclopenta[d]pyridazin-4-one | Intermediate 9 and CAS 1553950-73-4 | 487.1 |
| 35 | 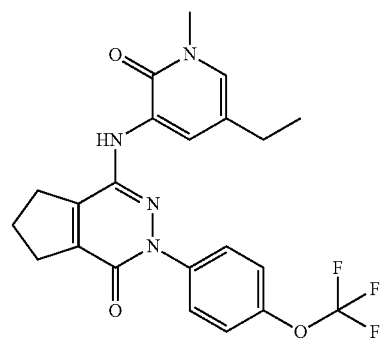 [SMILES: CCc1cc(Nc2nn(-c3ccc(OC(F)(F)F)cc3)c(=O)c3c2CCC3)c(=O)n(C)c1] | 1-[(5-ethyl-1-methyl-2-oxo-3-pyridyl)amino]-3-[4-(trifluoromethoxy)phenyl]-6,7-dihydro-5H-cyclopenta[d]pyridazin-4-one | Intermediate 9 and Intermediate 103 | 447.1 |
| 36 | 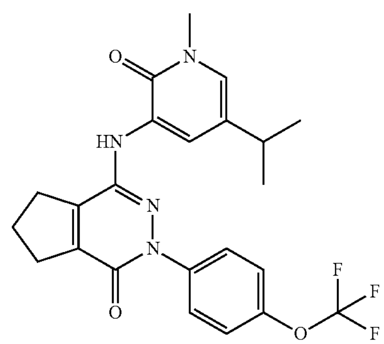 [SMILES: CC(C)c1cc(Nc2nn(-c3ccc(OC(F)(F)F)cc3)c(=O)c3c2CCC3)c(=O)n(C)c1] | 1-[(5-isopropyl-1-methyl-2-oxo-3-pyridyl)amino]-3-[4-(trifluoromethoxy)phenyl]-6,7-dihydro-5H-cyclopenta[d]pyridazin-4-one | Intermediate 9 and Intermediate 104 | 461.2 |
| 37 | 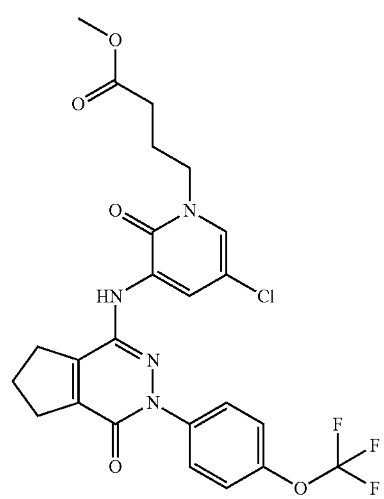 [SMILES: COC(=O)CCCn1cc(Cl)cc(Nc2nn(-c3ccc(OC(F)(F)F)cc3)c(=O)c3c2CCC3)c1=O] | methyl 4-[5-chloro-2-oxo-3-[[4-oxo-3-[4-(trifluoromethoxy)phenyl]-6,7-dihydro-5H-cyclopenta[d]pyridazin-1-yl]amino]-1-pyridyl]butanoate | Intermediate 9 and Intermediate 105 | 539.2 |

-continued

| Example No. | Structure | Systematic Name | Starting materials | mass found (M + H)+ |
|---|---|---|---|---|
| 38 | 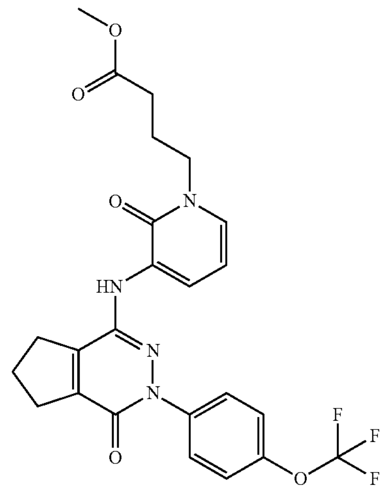 [SMILES: COC(=O)CCCn1cccc(Nc2nn(-c3ccc(OC(F)(F)F)cc3)c(=O)c3c2CCC3)c1=O] | methyl 4-[2-oxo-3-[[4-oxo-3-[4-(trifluoromethoxy)phenyl]-6,7-dihydro-5H-cyclopenta[d]pyridazin-1-yl]amino]-1-pyridyl]butanoate | Intermediate 9 and Intermediate 72 | 505.2 |
| 39 | 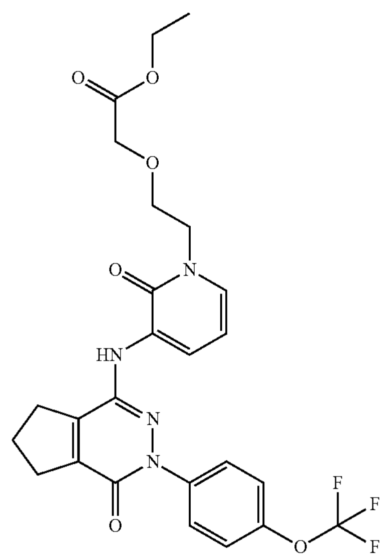 [SMILES: CCOC(=O)COCCn1cccc(Nc2nn(-c3ccc(OC(F)(F)F)cc3)c(=O)c3c2CCC3)c1=O] | ethyl 2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetate | Intermediate 9 and Intermediate 71 | 535.2 |
| 40 | 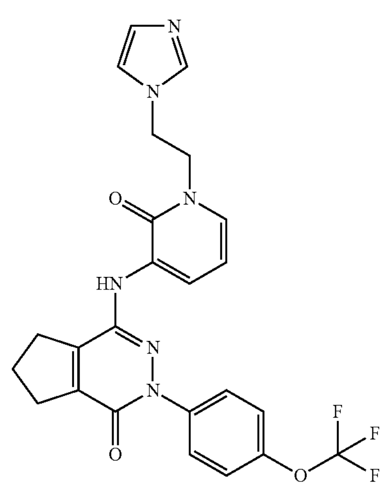 [SMILES: O=c1c(Nc2nn(-c3ccc(OC(F)(F)F)cc3)c(=O)c3c2CCC3)cccn1CCn1ccnc1] | 1-[[1-(2-imidazol-1-ylethyl)-2-oxo-3-pyridyl]amino]-3-[4-(trifluoromethoxy)phenyl]-6,7-dihydro-5H-cyclopenta[d]pyridazin-4-one | Intermediate 9 and Intermediate 82 | 499.2 |

| Example No. | Structure | Systematic Name | Starting materials | mass found (M + H)+ |
|---|---|---|---|---|
| 41 | 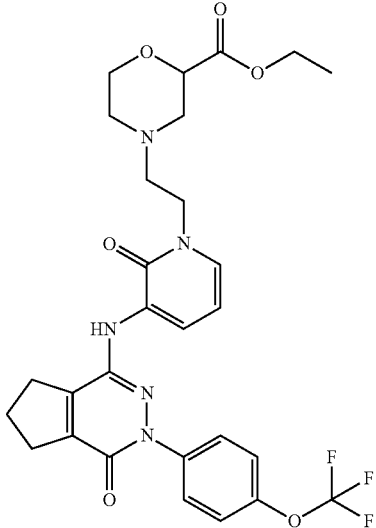 [SMILES: CCOC(=O)C1CN(CCn2cccc(Nc3nn(-c4ccc(OC(F)(F)F)cc4)c(=O)c4c3CCC4)c2=O)CCO1] | ethyl 4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-2-carboxylate | Intermediate 9 and Intermediate 83 | 590.3 |
| 42 | 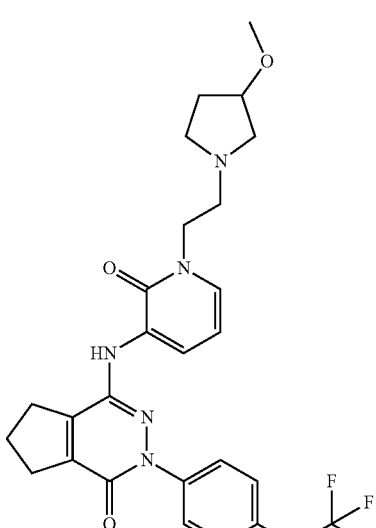 | 1-[[1-[2-(3-methoxypyrrolidin-1-yl)ethyl]-2-oxo-3-pyridyl]amino]-3-[4-(trifluoromethoxy)phenyl]-6,7-dihydro-5H-cyclopenta[d]pyridazin-4-one | Intermediate 9 and Intermediate 84 lp;10p | 532.2 |

| Example No. | Structure | Systematic Name | Starting materials | mass found (M + H)+ |
|---|---|---|---|---|
| 43 | 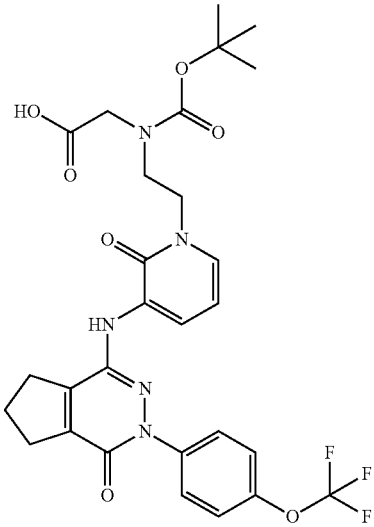 [SMILES: CC(C)(C)OC(=O)N(CCn1cccc(Nc2nn(-c3ccc(OC(F)(F)F)cc3)c(=O)c3c2CCC3)c1=O)CC(=O)O] | 2-[tert-butoxycarbonyl-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]amino]acetic acid | Intermediate 9 and Intermediate 85 | 606.2 |
| 44 | 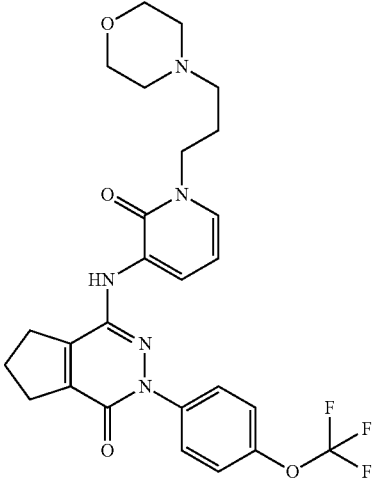 [SMILES: O=c1c(Nc2nn(-c3ccc(OC(F)(F)F)cc3)c(=O)c3c2CCC3)cccn1CCCN1CCOCC1] | 1-[[1-(3-morpholinopropyl)-2-oxo-3-pyridyl]amino]-3-[4-(trifluoromethoxy)phenyl]-6,7-dihydro-5H-cyclopenta[d]pyridazin-4-one | Intermediate 9 and Intermediate 73 | |
| 45 | 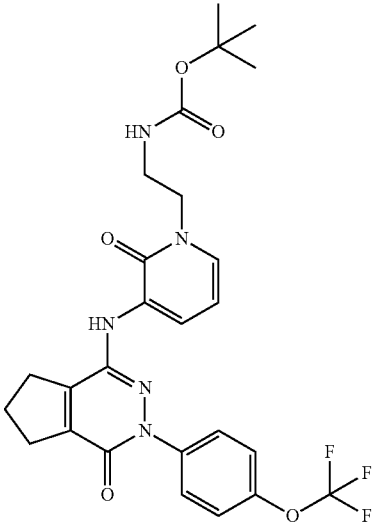 [SMILES: CC(C)(C)OC(=O)NCCn1cccc(Nc2nn(-c3ccc(OC(F)(F)F)cc3)c(=O)c3c2CCC3)c1=O] | tert-butyl N-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]carbamate | Intermediate 9 and Intermediate 106 | 548.2 |

| Example No. | Structure | Systematic Name | Starting materials | mass found (M + H)+ |
|---|---|---|---|---|
| 46 | 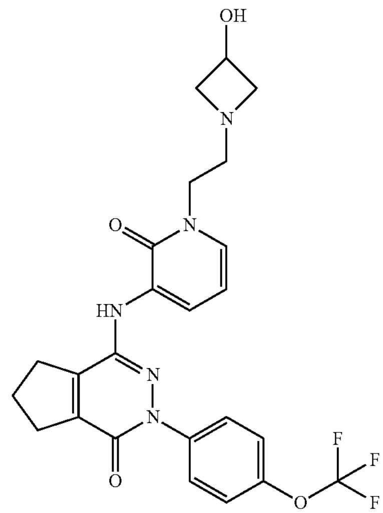 [SMILES: O=c1c(Nc2nn(-c3ccc(OC(F)(F)F)cc3)c(=O)c3c2CCC3)cccn1CCN1CC(O)C1] | 1-[[1-[2-(3-hydroxyazetidin-1-yl)ethyl]-2-oxo-3-pyridyl]amino]-3-[4-(trifluoromethoxy)phenyl]-6,7-dihydro-5H-cyclopenta[d]pyridazin-4-one | Intermediate 9 and Intermediate 86 | 504.3 |
| 47 | 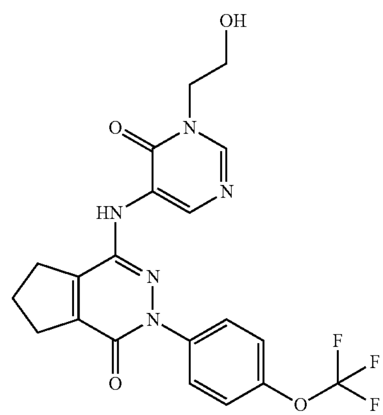 [SMILES: O=c1c(Nc2nn(-c3ccc(OC(F)(F)F)cc3)c(=O)c3c2CCC3)cncn1CCO] | 1-[[1-(2-hydroxyethyl)-6-oxo-pyrimidin-5-yl]amino]-3-[4-(trifluoromethoxy)phenyl]-6,7-dihydro-5H-cyclopenta[d]pyridazin-4-one | Intermediate 9 and Intermediate 98 | 450.2 |
| 48 | 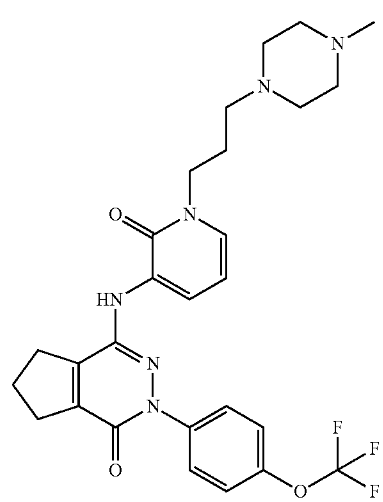 [SMILES: CN1CCN(CCCn2cccc(Nc3nn(-c4ccc(OC(F)(F)F)cc4)c(=O)c4c3CCC4)c2=O)CC1] | 1-[[1-[3-(4-methylpiperazin-1-yl)propyl]-2-oxo-3-pyridyl]amino]-3-[4-(trifluoromethoxy)phenyl]-6,7-dihydro-5H-cyclopenta[d]pyridazin-4-one | Intermediate 9 and Intermediate 74 | 545.3 |

-continued

| Example No. | Structure | Systematic Name | Starting materials | mass found (M + H)+ |
|---|---|---|---|---|
| 49 | 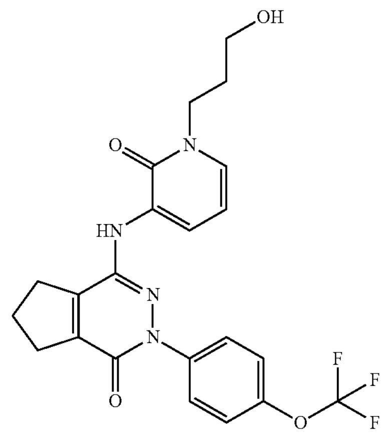 [SMILES: O=c1c(Nc2nn(-c3ccc(OC(F)(F)F)cc3)c(=O)c3c2CCC3)cccn1CCCO] | 1-[[1-(3-hydroxypropyl)-2-oxo-3-pyridyl]amino]-3-[4-(trifluoromethoxy)phenyl]-6,7-dihydro-5H-cyclopenta[d]pyridazin-4-one | Intermediate 9 and Intermediate 75 | 463.0 |
| 50 | 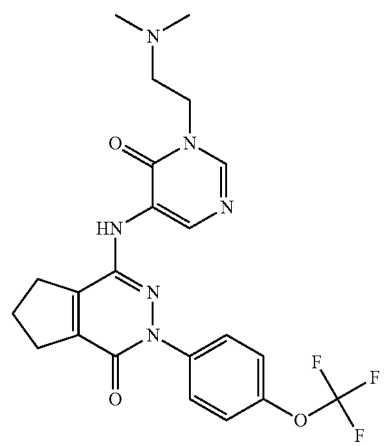 [SMILES: CN(C)CCn1cncc(Nc2nn(-c3ccc(OC(F)(F)F)cc3)c(=O)c3c2CCC3)c1=O] | 1-[[1-[2-(dimethylamino)ethyl]-6-oxo-pyrimidin-5-yl]amino]-3-[4-(trifluoromethoxy)phenyl]-6,7-dihydro-5H-cyclopenta[d]pyridazin-4-one | Intermediate 9 and Intermediate 95 | 477.0 |
| 51 | 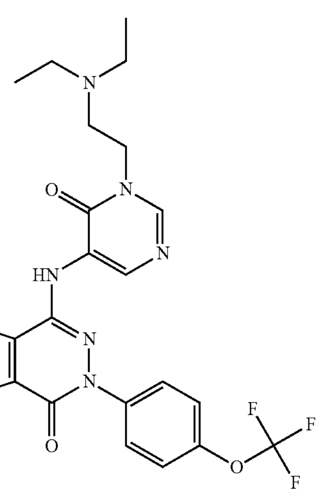 | 1-[[1-[2-(diethylamino)ethyl]-6-oxo-pyrimidin-5-yl]amino]-3-[4-(trifluoromethoxy)phenyl]-6,7-dihydro-5H-cyclopenta[d]pyridazin-4-one | Intermediate 9 and Intermediate 96 | 505.1 |

-continued

| Example No. | Structure | Systematic Name | Starting materials | mass found (M + H)+ |
|---|---|---|---|---|
| 52 | 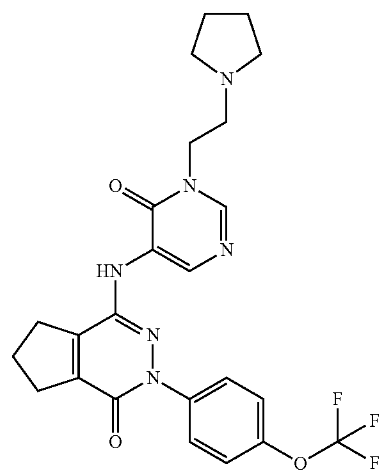 [SMILES: O=c1c(Nc2nn(-c3ccc(OC(F)(F)F)cc3)c(=O)c3c2CCC3)cncn1CCN1CCCC1] | 1-[[6-oxo-1-(2-pyrrolidin-1-ylethyl)pyrimidin-5-yl]amino]-3-[4-(trifluoromethoxy)phenyl]-6,7-dihydro-5H-cyclopenta[d]pyridazin-4-one | Intermediate 9 and Intermediate 97 | 503.1 |
| 53 | 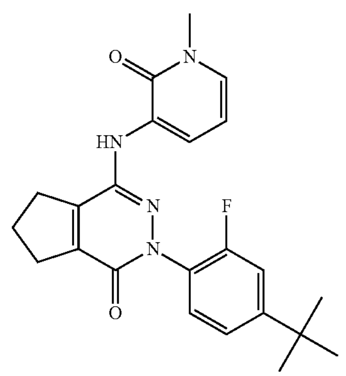 [SMILES: Cn1cccc(Nc2nn(-c3ccc(C(C)(C)C)cc3F)c(=O)c3c2CCC3)c1=O] | 3-(4-tert-butyl-2-fluorophenyl)-1-[(1-methyl-2-oxo-3-pyridyl)amino]-6,7-dihydro-5H-cyclopenta[d]pyridazin-4-one | Intermediate 20 and CAS 33631-01-5 | 409.3 |
| 54 | 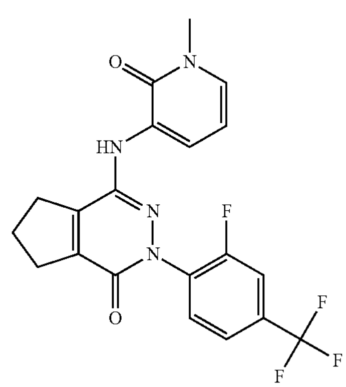 [SMILES: Cn1cccc(Nc2nn(-c3ccc(C(F)(F)F)cc3F)c(=O)c3c2CCC3)c1=O] | 3-[2-fluoro-4-(trifluoromethyl)phenyl]-1-[(1-methyl-2-oxo-3-pyridyl)amino]-6,7-dihydro-5H-cyclopenta[d]pyridazin-4-one | Intermediate 21 and CAS 33631-01-5 | 421.1 |

-continued

| Example No. | Structure | Systematic Name | Starting materials | mass found (M + H)+ |
|---|---|---|---|---|
| 55 | 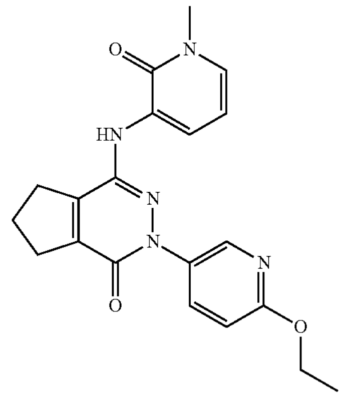 [SMILES: CCOc1ccc(-n2nc(Nc3cccn(C)c3=O)c3c(c2=O)CCC3)cn1] | 3-(6-ethoxy-3-pyridyl)-1-[(1-methyl-2-oxo-3-pyridyl)amino]-6,7-dihydro-5H-cyclopenta[d]pyridazin-4-one | Intermediate 22 and CAS 33631-01-5 | 380.2 |
| 56 | 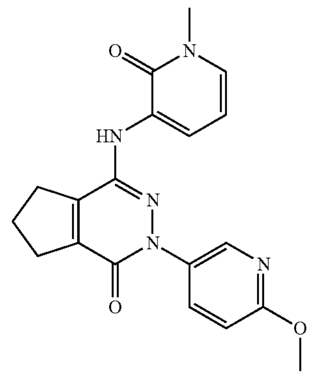 [SMILES: COc1ccc(-n2nc(Nc3cccn(C)c3=O)c3c(c2=O)CCC3)cn1] | 3-(6-methoxy-3-pyridyl)-1-[(1-methyl-2-oxo-3-pyridyl)amino]-6,7-dihydro-5H-cyclopenta[d]pyridazin-4-one | Intermediate 13 and CAS 33631-01-5 | 366.1 |
| 57 | 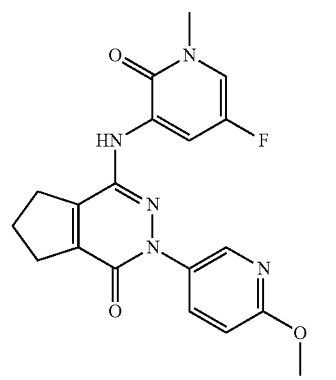 [SMILES: COc1ccc(-n2nc(Nc3cc(F)cn(C)c3=O)c3c(c2=O)CCC3)cn1] | 1-[(5-fluoro-1-methyl-2-oxo-3-pyridyl)amino]-3-(6-methoxy-3-pyridyl)-6,7-dihydro-5H-cyclopenta[d]pyridazin-4-one | Intermediate 13 and CAS 1781125-38-9 | 384.1 |
| 58 | 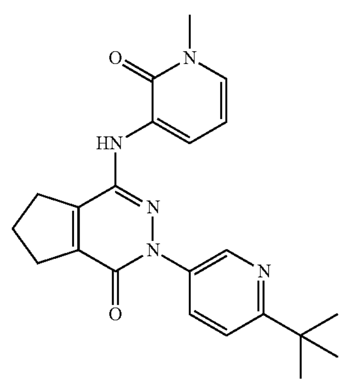 [SMILES: Cn1cccc(Nc2nn(-c3ccc(C(C)(C)C)nc3)c(=O)c3c2CCC3)c1=O] | 3-(6-tert-butyl-3-pyridyl)-1-[(1-methyl-2-oxo-3-pyridyl)amino]-6,7-dihydro-5H-cyclopenta[d]pyridazin-4-one | Intermediate 14 and CAS 33631-01-5 | 392.2 |

| Example No. | Structure | Systematic Name | Starting materials | mass found (M + H)+ |
|---|---|---|---|---|
| 59 | 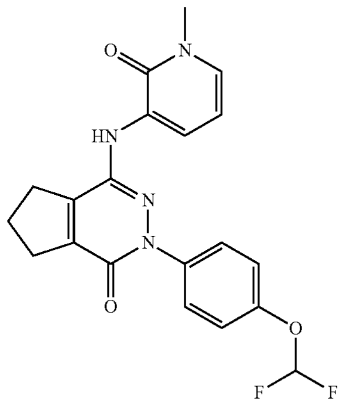 [SMILES: Cn1cccc(Nc2nn(-c3ccc(OC(F)F)cc3)c(=O)c3c2CCC3)c1=O] | 3-[4-(difluoromethoxy)phenyl]-1-[(1-methyl-2-oxo-3-pyridyl)amino]-6,7-dihydro-5H-cyclopenta[d]pyridazin-4-one | Intermediate 15 and CAS 33631-01-5 | 401.2 |
| 60 | 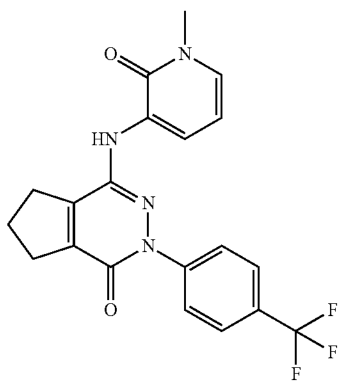 [SMILES: Cn1cccc(Nc2nn(-c3ccc(C(F)(F)F)cc3)c(=O)c3c2CCC3)c1=O] | 1-[(1-methyl-2-oxo-3-pyridyl)amino]-3-[4-(trifluoromethyl)phenyl]-6,7-dihydro-5H-cyclopenta[d]pyridazin-4-one | Intermediate 16 and CAS 33631-01-5 | 403.2 |
| 61 | 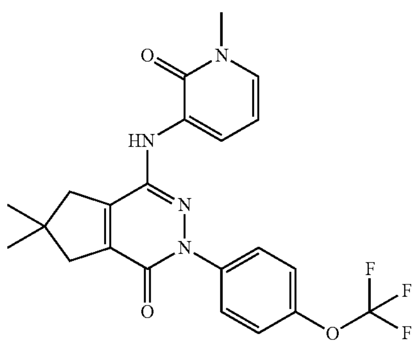 [SMILES: Cn1cccc(Nc2nn(-c3ccc(OC(F)(F)F)cc3)c(=O)c3c2CC(C)(C)C3)c1=O] | 6,6-dimethyl-1-[(1-methyl-2-oxo-3-pyridyl)amino]-3-[4-(trifluoromethoxy)phenyl]-5,7-dihydrocyclopenta[d]pyridazin-4-one | Intermediate 17 and CAS 33631-01-5 | 447.2 |
| 62 | 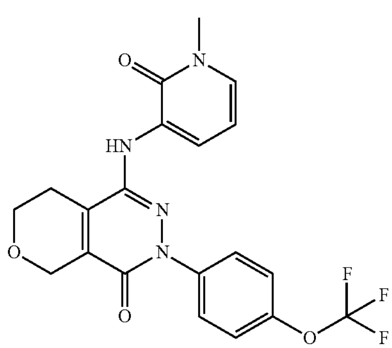 [SMILES: Cn1cccc(Nc2nn(-c3ccc(OC(F)(F)F)cc3)c(=O)c3c2CCOC3)c1=O] | 1-[(1-methyl-2-oxo-3-pyridyl)amino]-3-[4-(trifluoromethoxy)phenyl]-7,8-dihydro-5H-pyrano[3,4-d]pyridazin-4-one | Intermediate 18 and CAS 33631-01-5 | 435.1 |

-continued

| Example No. | Structure | Systematic Name | Starting materials | mass found (M + H)+ |
|---|---|---|---|---|
| 63 | 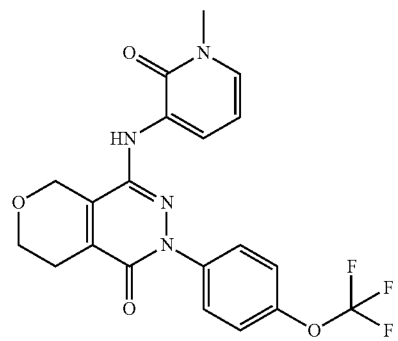 [SMILES: Cn1cccc(Nc2nn(-c3ccc(OC(F)(F)F)cc3)c(=O)c3c2COCC3)c1=O] | 4-[(1-methyl-2-oxo-3-pyridyl)amino]-2-[4-(trifluoromethoxy)phenyl]-7,8-dihydro-5H-pyrano[3,4-d]pyridazin-1-one | Intermediate 19 and CAS 33631-01-5 | 435.1 |
| 64 | 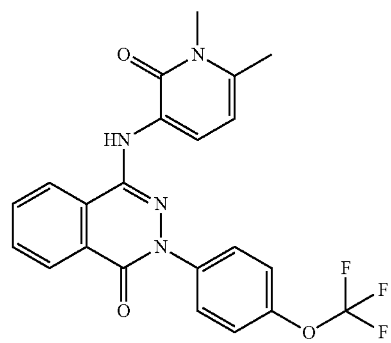 [SMILES: Cc1ccc(Nc2nn(-c3ccc(OC(F)(F)F)cc3)c(=O)c3ccccc23)c(=O)n1C] | 4-[(1,6-dimethyl-2-oxo-3-pyridyl)amino]-2-[4-(trifluoromethoxy)phenyl]phthalazin-1-one | Intermediate 29 and CAS 1423034-54-1 | 443.2 |
| 65 | 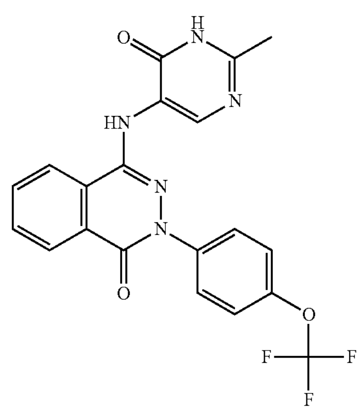 [SMILES: Cc1ncc(Nc2nn(-c3ccc(OC(F)(F)F)cc3)c(=O)c3ccccc23)c(=O)[nH]1] | 4-[(2-methyl-6-oxo-1H-pyrimidin-5-yl)amino]-2-[4-(trifluoromethoxy)phenyl]phthalazin-1-one | Intermediate 29 and CAS 53135-22-1 | 430.2 |
| 66 | 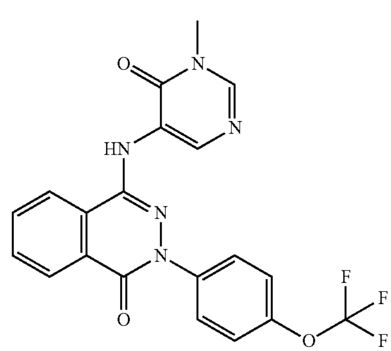 [SMILES: Cn1cncc(Nc2nn(-c3ccc(OC(F)(F)F)cc3)c(=O)c3ccccc23)c1=O] | 4-[(1-methyl-6-oxo-pyrimidin-5-yl)amino]-2-[4-(trifluoromethoxy)phenyl]phthalazin-1-one | Intermediate 29 and CAS 73922-41-5 | 430.1 |

-continued

| Example No. | Structure | Systematic Name | Starting materials | mass found (M + H)+ |
|---|---|---|---|---|
| 67 | 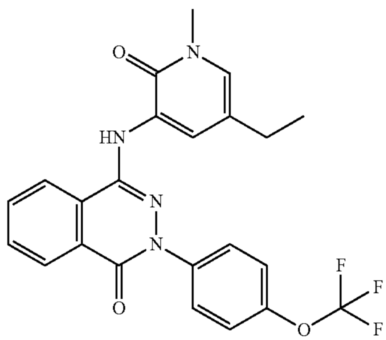 [SMILES: CCc1cc(Nc2nn(-c3ccc(OC(F)(F)F)cc3)c(=O)c3ccccc23)c(=O)n(C)c1] | 4-[(5-ethyl-1-methyl-2-oxo-3-pyridyl)amino]-2-[4-(trifluoromethoxy)phenyl]phthalazin-1-one | Intermediate 29 and Intermediate 103 | 457.1 |
| 68 | 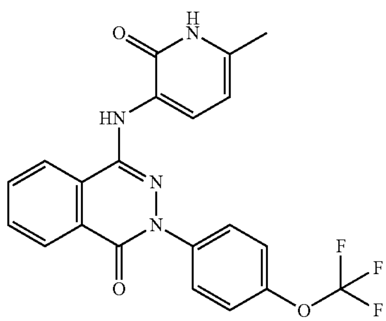 [SMILES: Cc1ccc(Nc2nn(-c3ccc(OC(F)(F)F)cc3)c(=O)c3ccccc23)c(=O)[nH]1] | 4-[(6-methyl-2-oxo-1H-pyridin-3-yl)amino]-2-[4-(trifluoromethoxy)phenyl]phthalazin-1-one | Intermediate 29 and CAS 52334-79-9 | 429.2 |
| 69 | 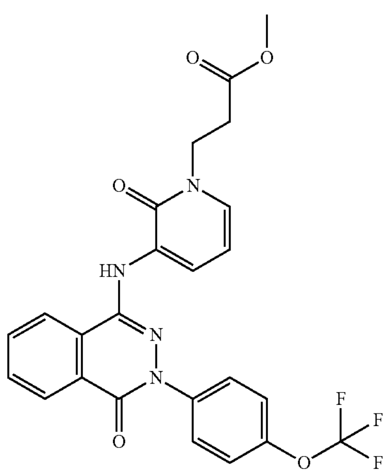 [SMILES: COC(=O)CCn1cccc(Nc2nn(-c3ccc(OC(F)(F)F)cc3)c(=O)c3ccccc23)c1=O] | methyl 3-[2-oxo-3-[[4-oxo-3-[4-(trifluoromethoxy)phenyl]phthalazin-1-yl]amino]-1-pyridyl]propanoate | Intermediate 29 and Intermediate 76 | 501.1 |
| 70 | 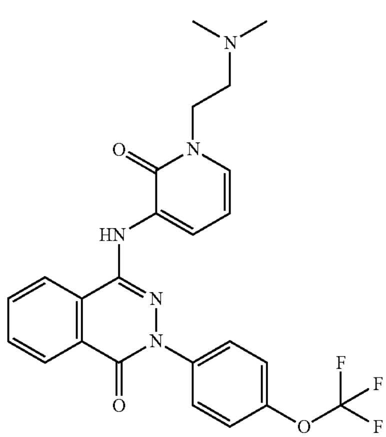 [SMILES: CN(C)CCn1cccc(Nc2nn(-c3ccc(OC(F)(F)F)cc3)c(=O)c3ccccc23)c1=O] | 4-[[1-[2-(dimethylamino)ethyl]-2-oxo-3-pyridyl]amino]-2-[4-(trifluoromethoxy)phenyl]phthalazin-1-one | Intermediate 29 and Intermediate 77 | 486.2 |

-continued

| Example No. | Structure | Systematic Name | Starting materials | mass found (M + H)+ |
|---|---|---|---|---|
| 71 | 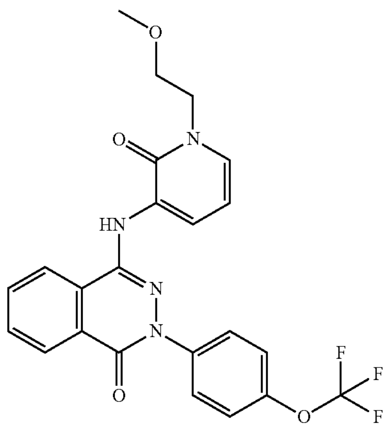 [SMILES: COCCn1cccc(Nc2nn(-c3ccc(OC(F)(F)F)cc3)c(=O)c3ccccc23)c1=O] | 4-[[1-(2-methoxyethyl)-2-oxo-3-pyridyl]amino]-2-[4-(trifluoromethoxy)phenyl]phthalazin-1-one | Intermediate 29 and Intermediate 78 | 473.2 |
| 72 | 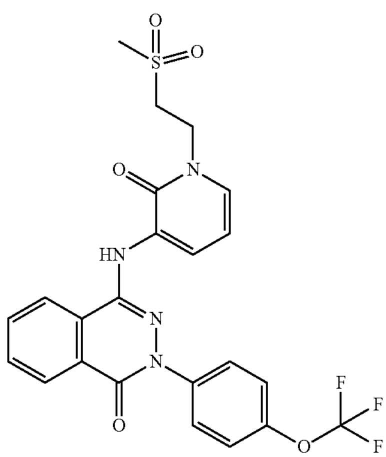 [SMILES: CS(=O)(=O)CCn1cccc(Nc2nn(-c3ccc(OC(F)(F)F)cc3)c(=O)c3ccccc23)c1=O] | 4-[[1-(2-methylsulfonylethyl)-2-oxo-3-pyridyl]amino]-2-[4-(trifluoromethoxy)phenyl]phthalazin-1-one | Intermediate 29 and Intermediate 79 | 521.2 |
| 73 | 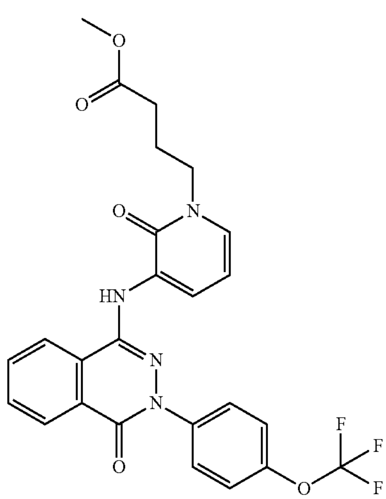 [SMILES: COC(=O)CCCn1cccc(Nc2nn(-c3ccc(OC(F)(F)F)cc3)c(=O)c3ccccc23)c1=O] | methyl 4-[2-oxo-3-[[4-oxo-3-[4-(trifluoromethoxy)phenyl]phthalazin-1-yl]amino]-1-pyridyl]butanoate | Intermediate 29 and Intermediate 72 | 515.2 |

| Example No. | Structure | Systematic Name | Starting materials | mass found (M + H)+ |
|---|---|---|---|---|
| 74 | 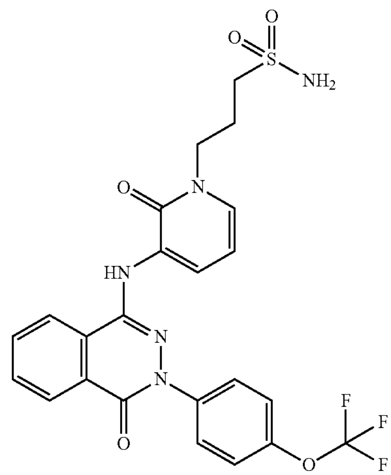 [SMILES: NS(=O)(=O)CCCn1cccc(Nc2nn(-c3ccc(OC(F)(F)F)cc3)c(=O)c3ccccc23)c1=O] | 3-[2-oxo-3-[[4-oxo-3-[4-(trifluoromethoxy)phenyl]phthalazin-1-yl]amino]-1-pyridyl]propane-1-sulfonamide | Intermediate 29 and Intermediate 107 | 536.2 |
| 75 | 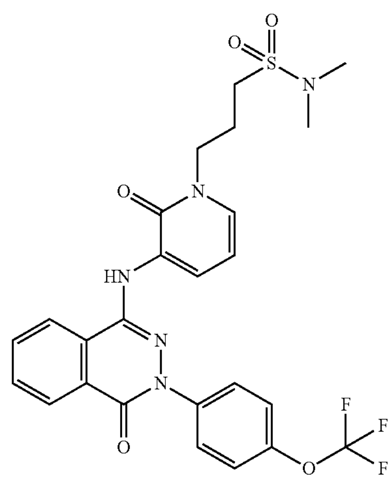 [SMILES: CN(C)S(=O)(=O)CCCn1cccc(Nc2nn(-c3ccc(OC(F)(F)F)cc3)c(=O)c3ccccc23)c1=O] | N,N-dimethyl-3-[2-oxo-3-[[4-oxo-3-[4-(trifluoromethoxy)phenyl]phthalazin-1-yl]amino]-1-pyridyl]propane-1-sulfonamide | Intermediate 29 and Intermediate 108 | 564.2 |
| 76 | 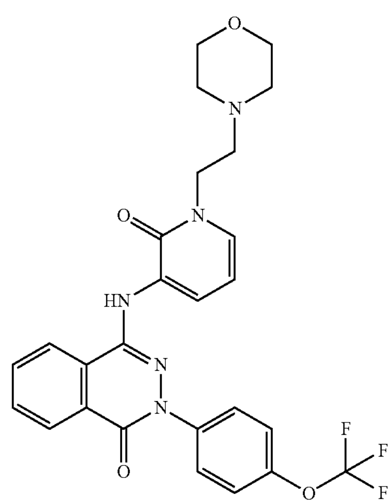 [SMILES: O=c1c(Nc2nn(-c3ccc(OC(F)(F)F)cc3)c(=O)c3ccccc23)cccn1CCN1CCOCC1] | 4-[[1-(2-morpholinoethyl)-2-oxo-3-pyridyl]amino]-2-[4-(trifluoromethoxy)phenyl]phthalazin-1-one | Intermediate 29 and Intermediate 87 | 528.2 |

-continued

| Example No. | Structure | Systematic Name | Starting materials | mass found (M + H)+ |
|---|---|---|---|---|
| 77 | 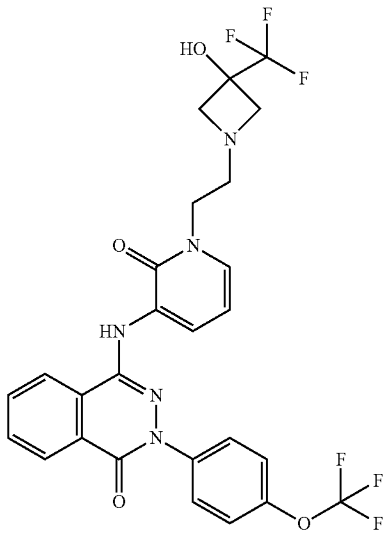 [SMILES: O=c1c(Nc2nn(-c3ccc(OC(F)(F)F)cc3)c(=O)c3ccccc23)cccn1CCN1CC(O)(C(F)(F)F)C1] | 4-[[1-[2-[3-hydroxy-3-(trifluoromethyl)azetidin-1-yl]ethyl]-2-oxo-3-pyridyl]amino]-2-[4-(trifluoromethoxy)phenyl]phthalazin-1-one | Intermediate 29 and Intermediate 88 | 582.2 |
| 78 | 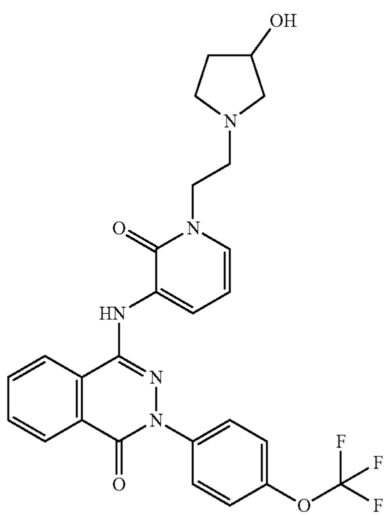 [SMILES: O=c1c(Nc2nn(-c3ccc(OC(F)(F)F)cc3)c(=O)c3ccccc23)cccn1CCN1CCC(O)C1] | 4-[[1-[2-(3-hydroxypyrrolidin-1-yl)ethyl]-2-oxo-3-pyridyl]amino]-2-[4-(trifluoromethoxy)phenyl]phthalazin-1-one | Intermediate 29 and Intermediate 89 | 528.2 |
| 79 | 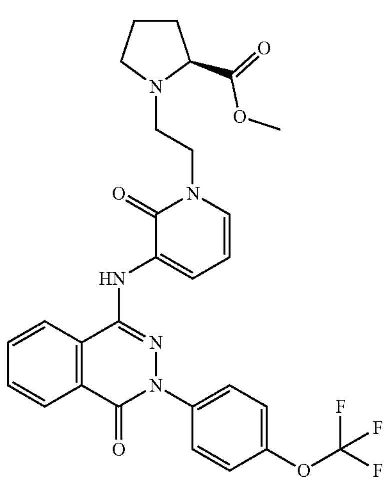 [SMILES: COC(=O)[C@@H]1CCCN1CCn1cccc(Nc2nn(-c3ccc(OC(F)(F)F)cc3)c(=O)c3ccccc23)c1=O] | methyl (2S)-1-[2-[2-oxo-3-[[4-oxo-3-[4-(trifluoromethoxy)phenyl]phthalazin-1-yl]amino]-1-pyridyl]ethyl]pyrrolidine-2-carboxylate | Intermediate 29 and Intermediate 90 | 570.2 |

-continued

| Example No. | Structure | Systematic Name | Starting materials | mass found (M + H)+ |
|---|---|---|---|---|
| 80 | 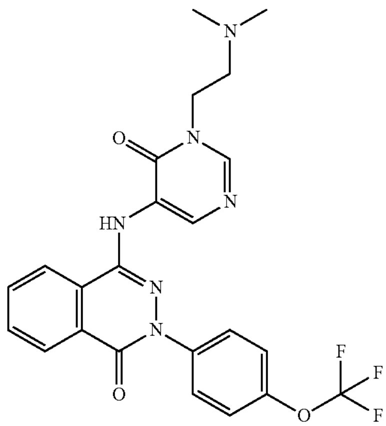 [SMILES: CN(C)CCn1cncc(Nc2nn(-c3ccc(OC(F)(F)F)cc3)c(=O)c3ccccc23)c1=O] | 4-[[1-[2-(dimethylamino)ethyl]-6-oxo-pyrimidin-5-yl]amino]-2-[4-(trifluoromethoxy)phenyl]phthalazin-1-one | Intermediate 29 and Intermediate 95 | 487.2 |
| 81 | 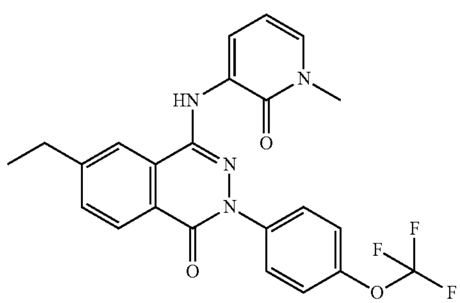 [SMILES: CCc1ccc2c(=O)n(-c3ccc(OC(F)(F)F)cc3)nc(Nc3cccn(C)c3=O)c2c1] | 6-ethyl-4-[(1-methyl-2-oxo-3-pyridyl)amino]-2-[4-(trifluoromethoxy)phenyl]phthalazin-1-one | Intermediate 30 and CAS 33631-01-5 | 457.2 |
| 82 | 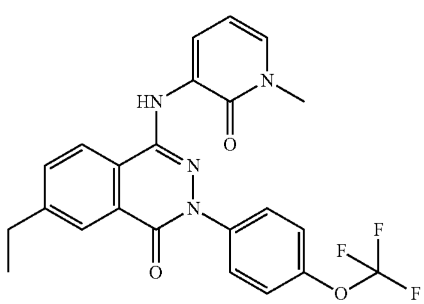 [SMILES: CCc1ccc2c(Nc3cccn(C)c3=O)nn(-c3ccc(OC(F)(F)F)cc3)c(=O)c2c1] | 7-ethyl-4-[(1-methyl-2-oxo-3-pyridyl)amino]-2-[4-(trifluoromethoxy)phenyl]phthalazin-1-one | Intermediate 30 and CAS 33631-01-5 | 457.2 |
| 83 | 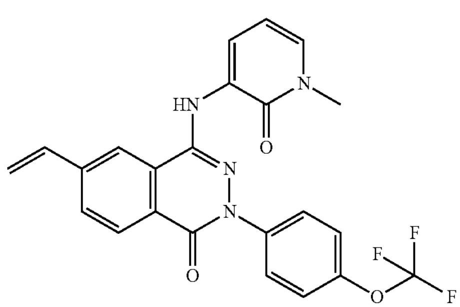 [SMILES: C=Cc1ccc2c(=O)n(-c3ccc(OC(F)(F)F)cc3)nc(Nc3cccn(C)c3=O)c2c1] | 4-[(1-methyl-2-oxo-3-pyridyl)amino]-2-[4-(trifluoromethoxy)phenyl]-6-vinyl-phthalazin-1-one | Intermediate 31 and 33631-01-5 | 455.2 |

| Example No. | Structure | Systematic Name | Starting materials | mass found (M + H)+ |
|---|---|---|---|---|
| 84 | 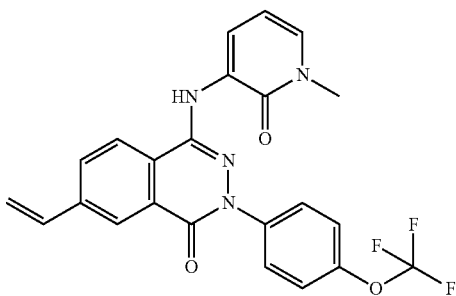 [SMILES: C=Cc1ccc2c(Nc3cccn(C)c3=O)nn(-c3ccc(OC(F)(F)F)cc3)c(=O)c2c1] | 4-[(1-methyl-2-oxo-3-pyridyl)amino]-2-[4-(trifluoromethoxy)phenyl]-7-vinyl-phthalazin-1-one | Intermediate 31 and 33631-01-5 | 455.2 |
| 85 | 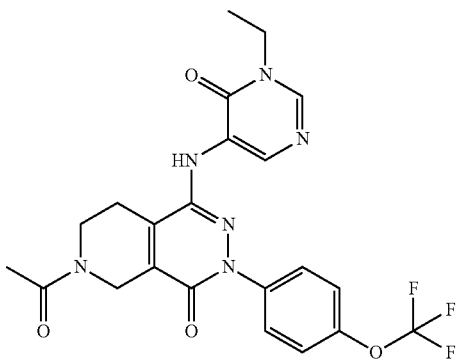 [SMILES: CCn1cncc(Nc2nn(-c3ccc(OC(F)(F)F)cc3)c(=O)c3c2CCN(C(C)=O)C3)c1=O] | 6-acetyl-1-[(1-ethyl-6-oxo-pyrimidin-5-yl)amino]-3-[4-(trifluoromethoxy)phenyl]-7,8-dihydro-5H-pyrido[3,4-d]pyridazin-4-one | Intermediate 36 and Intermediate 99 | 491.2 |
| 86 | 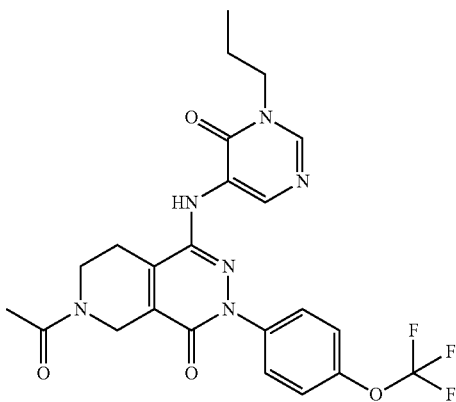 [SMILES: CCCn1cncc(Nc2nn(-c3ccc(OC(F)(F)F)cc3)c(=O)c3c2CCN(C(C)=O)C3)c1=O] | 6-acetyl-1-[(6-oxo-1-propyl-pyrimidin-5-yl)amino]-3-[4-(trifluoromethoxy)phenyl]-7,8-dihydro-5H-pyrido[3,4-d]pyridazin-4-one | Intermediate 36 and Intermediate 100 | 505.2 |

| Example No. | Structure | Systematic Name | Starting materials | mass found (M + H)+ |
|---|---|---|---|---|
| 87 | 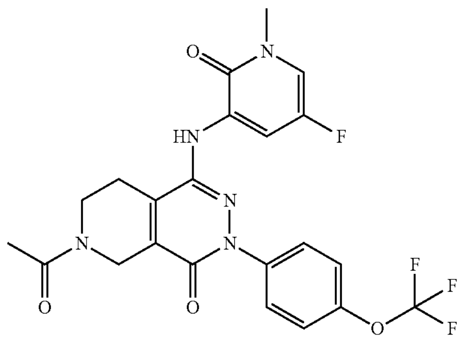 [SMILES: CC(=O)N1CCc2c(Nc3cc(F)cn(C)c3=O)nn(-c3ccc(OC(F)(F)F)cc3)c(=O)c2C1] | 6-acetyl-1-[(5-fluoro-1-methyl-2-oxo-3-pyridyl)amino]-3-[4-(trifluoromethoxy)phenyl]-7,8-dihydro-5H-pyrido[3,4-d]pyridazin-4-one | Intermediate 36 and CAS 1781125-38-9 | 494.2 |

Example 88

4-[[1-(2-Morpholino-2-oxo-ethyl)-2-oxo-3-pyridyl]amino]-2-[4-(trifluoromethoxy)phenyl]phthalazin-1-one

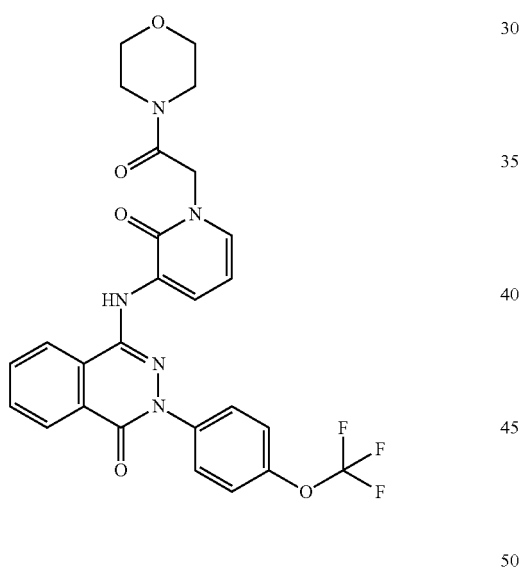

To a solution of 2-[2-oxo-3-[[4-oxo-3-[4-(trifluoromethoxy)phenyl]phthalazin-1-yl]amino]-1-pyridyl]acetic acid (Intermediate 67; 35 mg, 74.1 μmol), morpholine (19.4 mg, 222 mol) and Et3N (37.5 mg, 51.6 μl, 370 μmol) in DMF (3 mL) was added HATU (42.3 mg, 111 μmol) and the mixture was stirred at rt for 4 h. After removal of the solvent, the residue was mixed with 0.5N HCl (10 mL) and ultra-sonicated for 5 min. The solid was collected and washed with water (5 mL twice). The solid was dried to afford Example 88 as a light grey solid (32 mg, yield: 78%). MS (m/e): 542.2 (M+H)+.

In analogy to Example 88 compounds of the following table were prepared using different carboxylic acids and amines as reactants:

| Example No. | Structure | Systematic Name | Starting materials | mass found (M + H)+ |
|---|---|---|---|---|
| 89 | 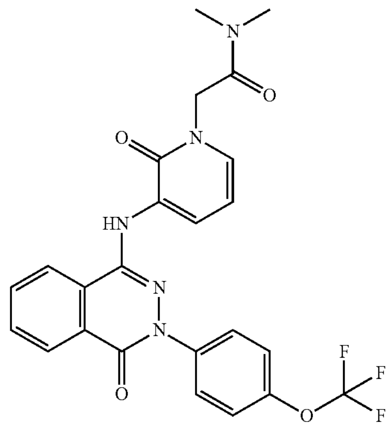 [SMILES: CN(C)C(=O)Cn1cccc(Nc2nn(-c3ccc(OC(F)(F)F)cc3)c(=O)c3ccccc23)c1=O] | N,N-dimethyl-2-[2-oxo-3-[[4-oxo-3-[4-(trifluoromethoxy)phenyl]phthalazin-1-yl]amino]-1-pyridyl]acetamide | Intermediate 67 and CAS 124-40-3 | 500.2 |
| 90 | 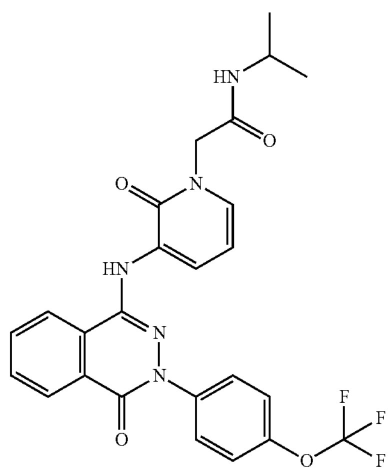 [SMILES: CC(C)NC(=O)Cn1cccc(Nc2nn(-c3ccc(OC(F)(F)F)cc3)c(=O)c3ccccc23)c1=O] | N-isopropyl-2-[2-oxo-3-[[4-oxo-3-[4-(trifluoromethoxy)phenyl]phthalazin-1-yl]amino]-1-pyridyl]acetamide | Intermediate 67 and CAS 75-31-0 | 514.1 |
| 91 | 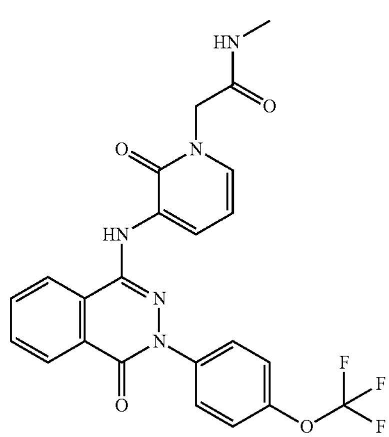 [SMILES: CNC(=O)Cn1cccc(Nc2nn(-c3ccc(OC(F)(F)F)cc3)c(=O)c3ccccc23)c1=O] | N-methyl-2-[2-oxo-3-[[4-oxo-3-[4-(trifluoromethoxy)phenyl]phthalazin-1-yl]amino]-1-pyridyl]acetamide | Intermediate 67 and CAS 74-89-5 | 486.2 |

-continued

| Example No. | Structure | Systematic Name | Starting materials | mass found (M + H)+ |
|---|---|---|---|---|
| 92 | 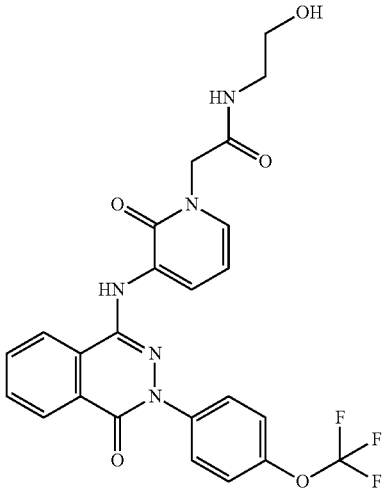 [SMILES: O=C(Cn1cccc(Nc2nn(-c3ccc(OC(F)(F)F)cc3)c(=O)c3ccccc23)c1=O)NCCO] | N-(2-hydroxyethyl)-2-[2-oxo-3-[[4-oxo-3-[4-(trifluoromethoxy)phenyl]phthalazin-1-yl]amino]-1-pyridyl]acetamide | Intermediate 67 and CAS 141-43-5 | 516.2 |
| 93 | 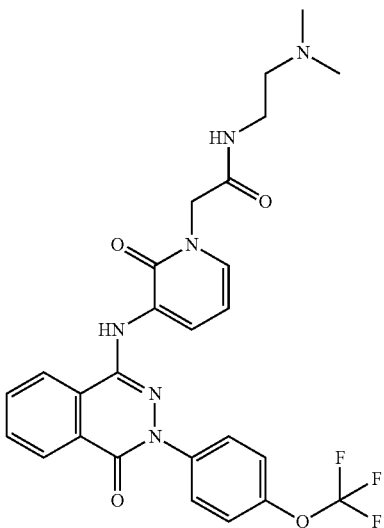 [SMILES: CN(C)CCNC(=O)Cn1cccc(Nc2nn(-c3ccc(OC(F)(F)F)cc3)c(=O)c3ccccc23)c1=O] | N-[2-(dimethylamino)ethyl]-2-[2-oxo-3-[[4-oxo-3-[4-(trifluoromethoxy)phenyl]phthalazin-1-yl]amino]-1-pyridyl]acetamide | Intermediate 67 and CAS 108-00-9 | 543.2 |
| 94 | 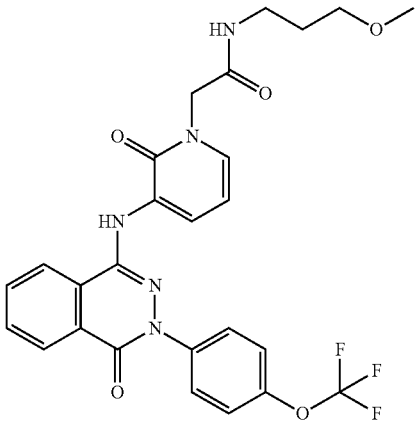 [SMILES: COCCCNC(=O)Cn1cccc(Nc2nn(-c3ccc(OC(F)(F)F)cc3)c(=O)c3ccccc23)c1=O] | N-(3-methoxypropyl)-2-[2-oxo-3-[[4-oxo-3-[4-(trifluoromethoxy)phenyl]phthalazin-1-yl]amino]-1-pyridyl]acetamide | Intermediate 67 and CAS 5332-73-0 | 544.3 |

| Example No. | Structure | Systematic Name | Starting materials | mass found (M + H)+ |
|---|---|---|---|---|
| 95 | 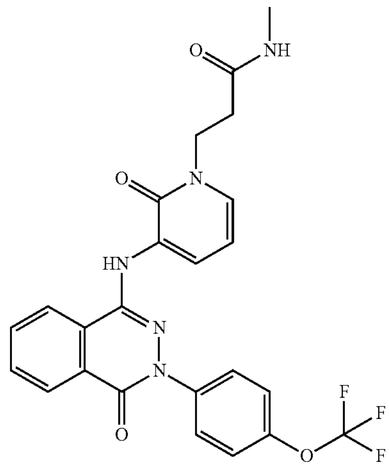 [SMILES: CNC(=O)CCn1cccc(Nc2nn(-c3ccc(OC(F)(F)F)cc3)c(=O)c3ccccc23)c1=O] | N-methyl-3-[2-oxo-3-[[4-oxo-3-[4-(trifluoromethoxy)phenyl]phthalazin-1-yl]amino]-1-pyridyl]propanamide | Example 109 and CAS 74-89-5 | 500.1 |
| 96 | 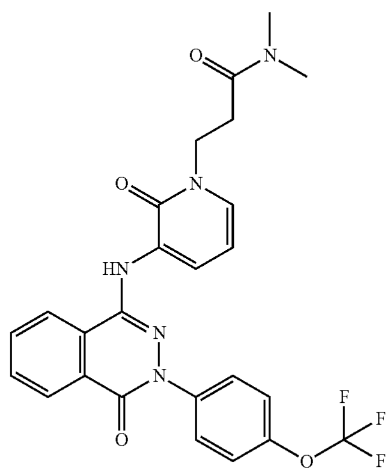 [SMILES: CN(C)C(=O)CCn1cccc(Nc2nn(-c3ccc(OC(F)(F)F)cc3)c(=O)c3ccccc23)c1=O] | N,N-dimethyl-3-[2-oxo-3-[[4-oxo-3-[4-(trifluoromethoxy)phenyl]phthalazin-1-yl]amino]-1-pyridyl]propanamide | Example 109 and CAS 124-40-3 | 514.1 |
| 97 | 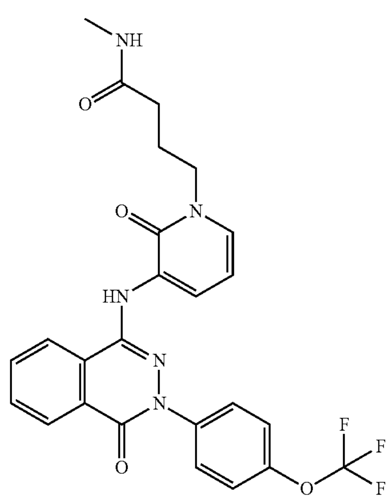 [SMILES: CNC(=O)CCCn1cccc(Nc2nn(-c3ccc(OC(F)(F)F)cc3)c(=O)c3ccccc23)c1=O] | N-methyl-4-[2-oxo-3-[[4-oxo-3-[4-(trifluoromethoxy)phenyl]phthalazin-1-yl]amino]-1-pyridyl]butanamide | Example 110 and CAS 74-89-5 | 514.2 |

| Example No. | Structure | Systematic Name | Starting materials | mass found (M + H)+ |
|---|---|---|---|---|
| 98 | 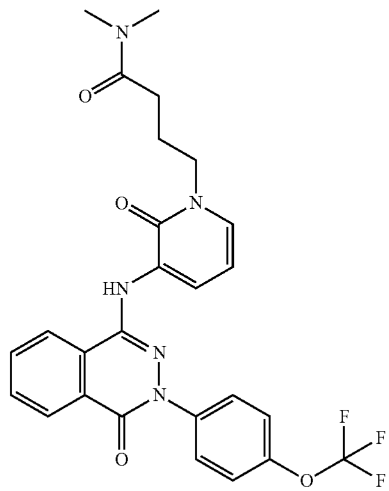 [SMILES: CN(C)C(=O)CCCn1cccc(Nc2nn(-c3ccc(OC(F)(F)F)cc3)c(=O)c3ccccc23)c1=O] | N,N-dimethyl-4-[2-oxo-3-[[4-oxo-3-[4-(trifluoromethoxy)phenyl]phthalazin-1-yl]amino]-1-pyridyl]butanamide | Example 110 and CAS 124-40-3 | 528.2 |
| 99 | 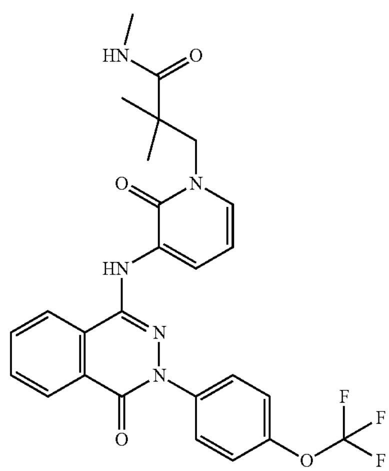 [SMILES: CNC(=O)C(C)(C)Cn1cccc(Nc2nn(-c3ccc(OC(F)(F)F)cc3)c(=O)c3ccccc23)c1=O] | N,2,2-trimethyl-3-[2-oxo-3-[[4-oxo-3-[4-(trifluoromethoxy)phenyl]phthalazin-1-yl]amino]-1-pyridyl]propanamide | Example 111 and CAS 74-89-5 | 528.2 |
| 100 | 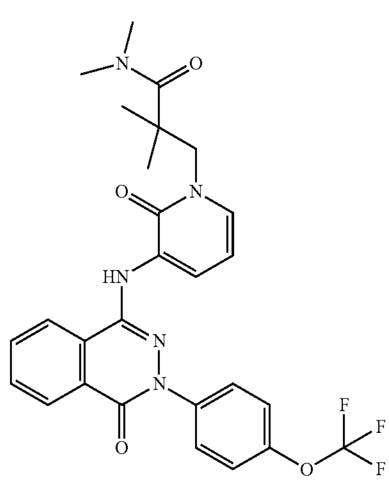 [SMILES: CN(C)C(=O)C(C)(C)Cn1cccc(Nc2nn(-c3ccc(OC(F)(F)F)cc3)c(=O)c3ccccc23)c1=O] | N,N,2,2-tetramethyl-3-[2-oxo-3-[[4-oxo-3-[4-(trifluoromethoxy)phenyl]phthalazin-1-yl]amino]-1-pyridyl]propanamide | Example 111 and CAS 124-40-3 | 542.2 |

-continued

| Example No. | Structure | Systematic Name | Starting materials | mass found (M + H)+ |
|---|---|---|---|---|
| 101 | 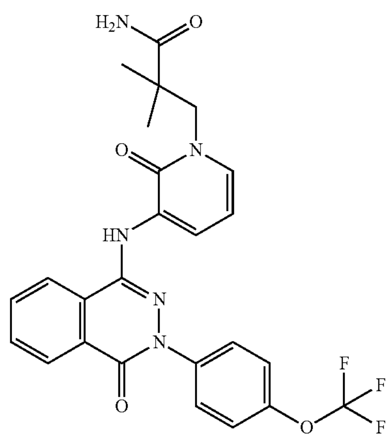 [SMILES: CC(C)(Cn1cccc(Nc2nn(-c3ccc(OC(F)(F)F)cc3)c(=O)c3ccccc23)c1=O)C(N)=O] | 2,2-dimethyl-3-[2-oxo-3-[[4-oxo-3-[4-(trifluoromethoxy)phenyl]phthalazin-1-yl]amino]-1-pyridyl]propanamide | Example 111 and CAS 7664-41-7 | 514.2 |
| 102 | 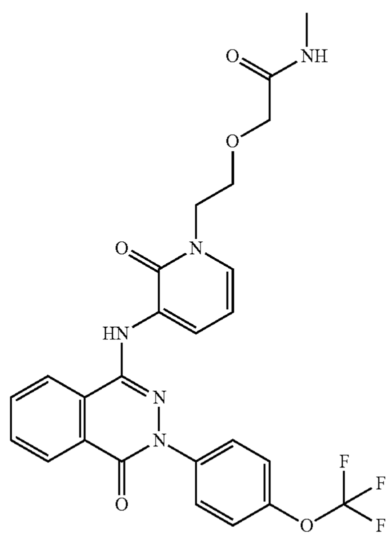 [SMILES: CNC(=O)COCCn1cccc(Nc2nn(-c3ccc(OC(F)(F)F)cc3)c(=O)c3ccccc23)c1=O] | N-methyl-2-[2-[2-oxo-3-[[4-oxo-3-[4-(trifluoromethoxy)phenyl]phthalazin-1-yl]amino]-1-pyridyl]ethoxy]acetamide | Example 112 and CAS 74-89-5 | 530.2 |
| 103 | 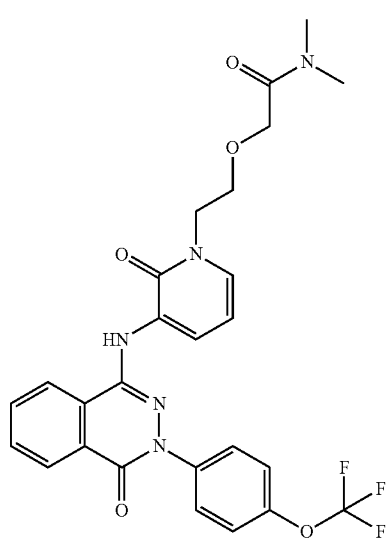 [SMILES: CN(C)C(=O)COCCn1cccc(Nc2nn(-c3ccc(OC(F)(F)F)cc3)c(=O)c3ccccc23)c1=O] | N,N-dimethyl-2-[2-[2-oxo-3-[[4-oxo-3-[4-(trifluoromethoxy)phenyl]phthalazin-1-yl]amino]-1-pyridyl]ethoxy]acetamide | Example 112 and CAS 124-40-3 | 544.2 |

-continued

| Example No. | Structure | Systematic Name | Starting materials | mass found (M + H)+ |
|---|---|---|---|---|
| 104 | 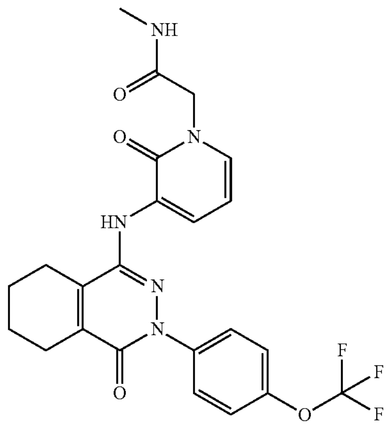 [SMILES: CNC(=O)Cn1cccc(Nc2nn(-c3ccc(OC(F)(F)F)cc3)c(=O)c3c2CCCC3)c1=O] | N-methyl-2-[2-oxo-3-[[4-oxo-3-[4-(trifluoromethoxy)phenyl]-5,6,7,8-tetrahydrophthalazin-1-yl]amino]-1-pyridyl]acetamide | Intermediate 68 and CAS 74-89-5 | 491.2 |
| 105 | 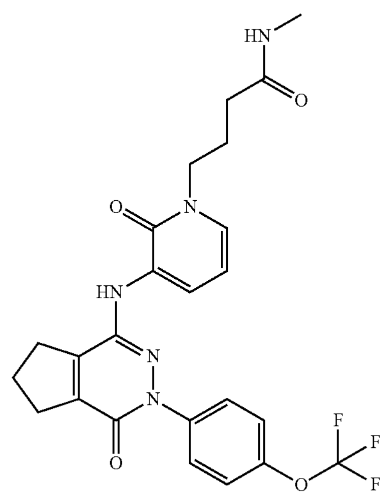 [SMILES: CNC(=O)CCCn1cccc(Nc2nn(-c3ccc(OC(F)(F)F)cc3)c(=O)c3c2CCC3)c1=O] | N-methyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide | Example 118 and CAS 74-89-5 | 504.2 |
| 106 | 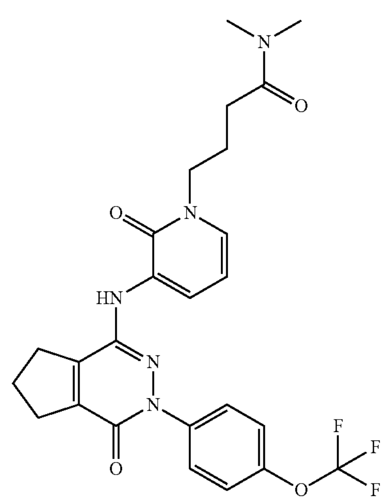 [SMILES: CN(C)C(=O)CCCn1cccc(Nc2nn(-c3ccc(OC(F)(F)F)cc3)c(=O)c3c2CCC3)c1=O] | N,N-dimethyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide | Example 118 and CAS 124-40-3 | 518.3 |

-continued

| Example No. | Structure | Systematic Name | Starting materials | mass found (M + H)+ |
|---|---|---|---|---|
| 107 | 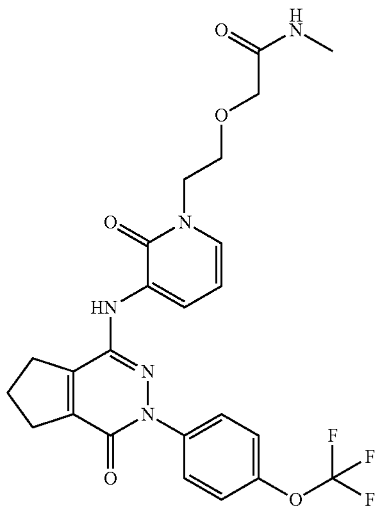 [SMILES: CNC(=O)COCCn1cccc(Nc2nn(-c3ccc(OC(F)(F)F)cc3)c(=O)c3c2CCC3)c1=O] | N-methyl-2-[2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide | Example 119 and CAS 74-89-5 | 520.2 |
| 108 | 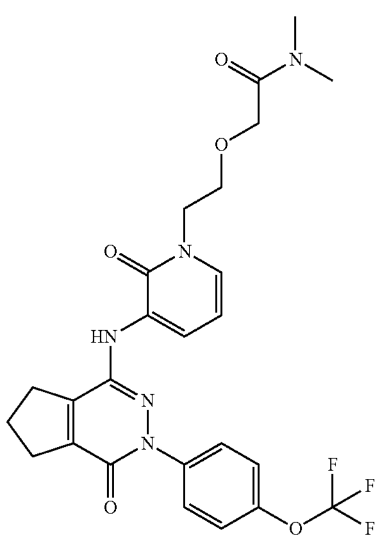 [SMILES: CN(C)C(=O)COCCn1cccc(Nc2nn(-c3ccc(OC(F)(F)F)cc3)c(=O)c3c2CCC3)c1=O] | N,N-dimethyl-2-[2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide | Example 119 and CAS 124-40-3 | 534.3 |

Example 109

3-[2-Oxo-3-[[4-oxo-3-[4-(trifluoromethoxy)phenyl]phthalazin-1-yl]amino]-1-pyridyl]propanoic acid

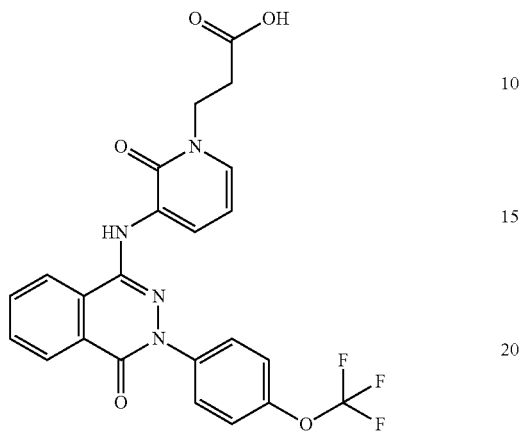

To a solution of methyl 3-[2-oxo-3-[[4-oxo-3-[4-(trifluoromethoxy)phenyl]phthalazin-1-yl]amino]-1-pyridyl]propanoate (Example 69; 116 mg, 0.232 mmol) in THF (5 mL) and water (5 mL) was added lithium hydroxide monohydrate (29.4 mg, 0.7 mmol), and the mixture was stirred for 3 h. After removal of THF, the remained aqueous solution was acidified by HCl to pH 3 and extracted by EtOAc. The organic phase was washed with brine, dried over anhydrous $Na_2SO_4$ and concentrated to afford a light grey solid (112 mg, yield: 94%). MS (m/e): 587.1 (M+H)+.

In analogy to Example 109 compounds of the following table were prepared using different esters and LiOH as reactants:

| Example No. | Structure | Systematic Name | Starting materials | mass found (M + H)+ |
|---|---|---|---|---|
| 110 | 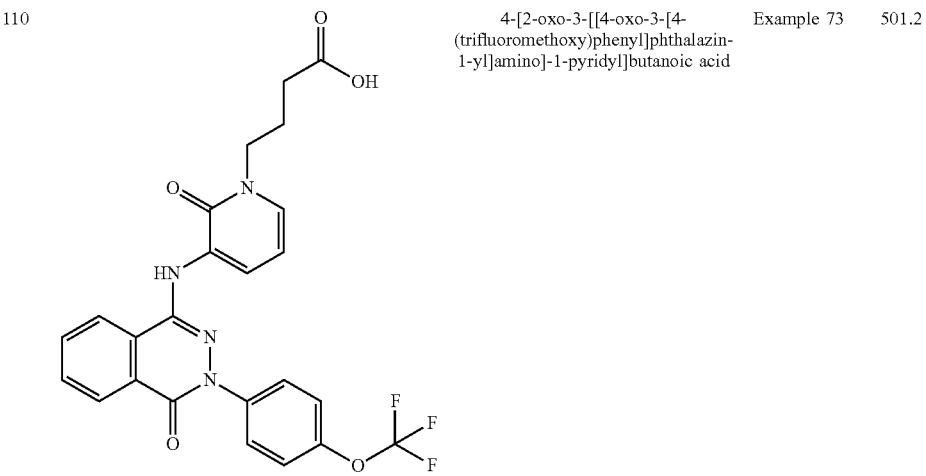 | 4-[2-oxo-3-[[4-oxo-3-[4-(trifluoromethoxy)phenyl]phthalazin-1-yl]amino]-1-pyridyl]butanoic acid | Example 73 | 501.2 |

-continued

| Example No. | Structure | Systematic Name | Starting materials | mass found (M + H)+ |
|---|---|---|---|---|
| 111 | 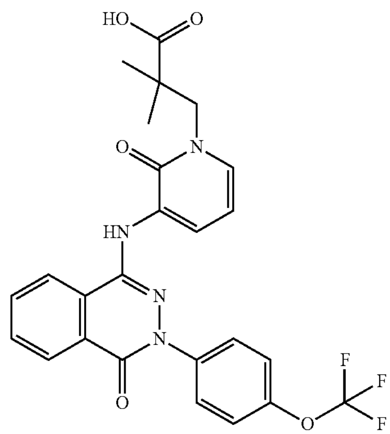 [SMILES: CC(C)(Cn1cccc(Nc2nn(-c3ccc(OC(F)(F)F)cc3)c(=O)c3ccccc23)c1=O)C(=O)O] | 2,2-dimethyl-3-[2-oxo-3-[[4-oxo-3-[4-(trifluoromethoxy)phenyl]phthalazin-1-yl]amino]-1-pyridyl]propanoic acid | Example 4 | 515.2 |
| 112 | 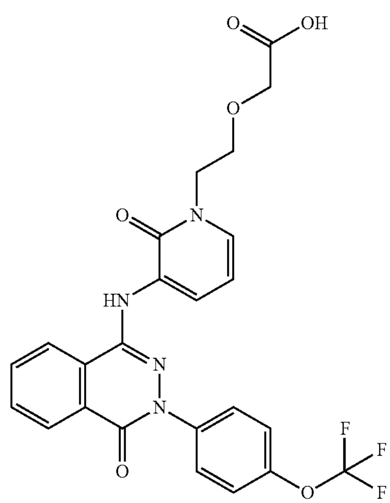 [SMILES: O=C(O)COCCn1cccc(Nc2nn(-c3ccc(OC(F)(F)F)cc3)c(=O)c3ccccc23)c1=O] | 2-[2-[2-oxo-3-[[4-oxo-3-[4-(trifluoromethoxy)phenyl]phthalazin-1-yl]amino]-1-pyridyl]ethoxy]acetic acid | Example 5 | 517.2 |
| 113 | 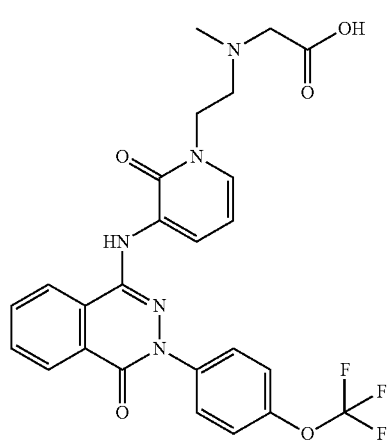 [SMILES: CN(CCn1cccc(Nc2nn(-c3ccc(OC(F)(F)F)cc3)c(=O)c3ccccc23)c1=O)CC(=O)O] | 2-[methyl-[2-[2-oxo-3-[[4-oxo-3-[4-(trifluoromethoxy)phenyl]phthalazin-1-yl]amino]-1-pyridyl]ethyl]amino]acetic acid | Intermediate 39 | 530.2 |

| Example No. | Structure | Systematic Name | Starting materials | mass found (M + H)+ |
|---|---|---|---|---|
| 114 | 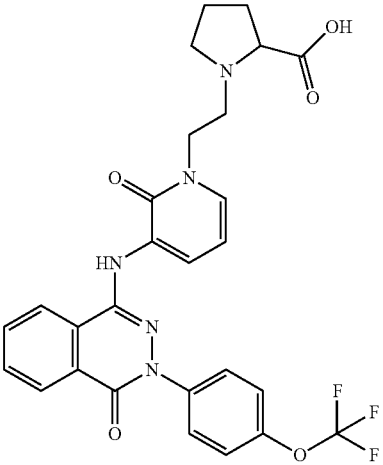 [SMILES: O=C(O)C1CCCN1CCn1cccc(Nc2nn(-c3ccc(OC(F)(F)F)cc3)c(=O)c3ccccc23)c1=O] | 1-[2-[2-oxo-3-[[4-oxo-3-[4-(trifluoromethoxy)phenyl]phthalazin-1-yl]amino]-1-pyridyl]ethyl]pyrrolidine-2-carboxylic acid | Intermediate 40 | 556.2 |
| 115 | 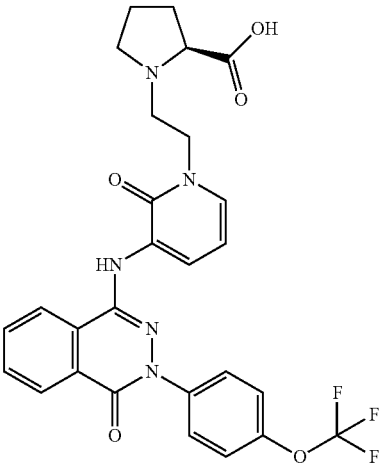 [SMILES: O=C(O)[C@@H]1CCCN1CCn1cccc(Nc2nn(-c3ccc(OC(F)(F)F)cc3)c(=O)c3ccccc23)c1=O] | (2S)-1-[2-[2-oxo-3-[[4-oxo-3-[4-(trifluoromethoxy)phenyl]phthalazin-1-yl]amino]-1-pyridyl]ethyl]pyrrolidine-2-carboxylic acid | Example 79 | 556.2 |
| 116 | 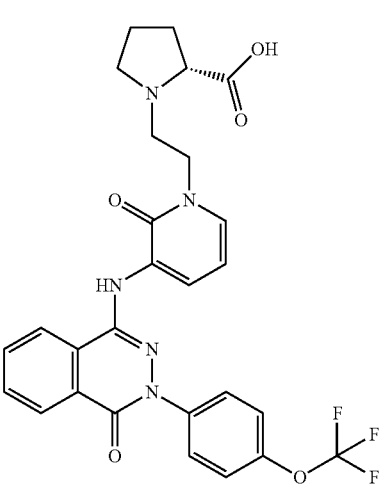 [SMILES: O=C(O)[C@H]1CCCN1CCn1cccc(Nc2nn(-c3ccc(OC(F)(F)F)cc3)c(=O)c3ccccc23)c1=O] | (2R)-1-[2-[2-oxo-3-[[4-oxo-3-[4-(trifluoromethoxy)phenyl]phthalazin-1-yl]amino]-1-pyridyl]ethyl]pyrrolidine-2-carboxylic acid | Example 6 | 556.2 |

| Example No. | Structure | Systematic Name | Starting materials | mass found (M + H)+ |
|---|---|---|---|---|
| 117 | 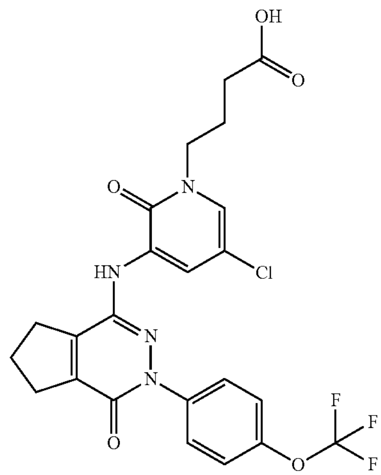 [SMILES: O=C(O)CCCn1cc(Cl)cc(Nc2nn(-c3ccc(OC(F)(F)F)cc3)c(=O)c3c2CCC3)c1=O] | 4-[5-chloro-2-oxo-3-[[4-oxo-3-[4-(trifluoromethoxy)phenyl]-6,7-dihydro-5H-cyclopenta[d]pyridazin-1-yl]amino]-1-pyridyl]butanoic acid | Example 37 | 525.2 |
| 118 | 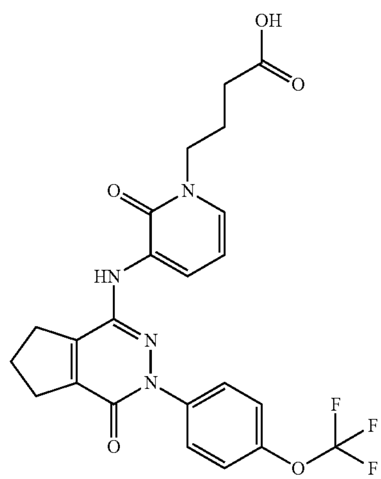 [SMILES: O=C(O)CCCn1cccc(Nc2nn(-c3ccc(OC(F)(F)F)cc3)c(=O)c3c2CCC3)c1=O] | 4-[2-oxo-3-[[4-oxo-3-[4-(trifluoromethoxy)phenyl]-6,7-dihydro-5H-cyclopenta[d]pyridazin-1-yl]amino]-1-pyridyl]butanoic acid | Example 38 | 491.2 |
| 119 | 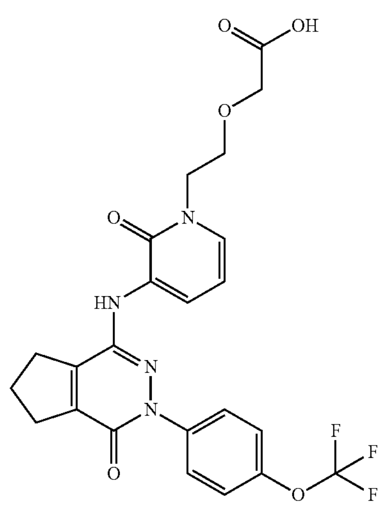 [SMILES: O=C(O)COCCn1cccc(Nc2nn(-c3ccc(OC(F)(F)F)cc3)c(=O)c3c2CCC3)c1=O] | 2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetic acid | Example 39 | 507.2 |

| Example No. | Structure | Systematic Name | Starting materials | mass found (M + H)+ |
|---|---|---|---|---|
| 120 | 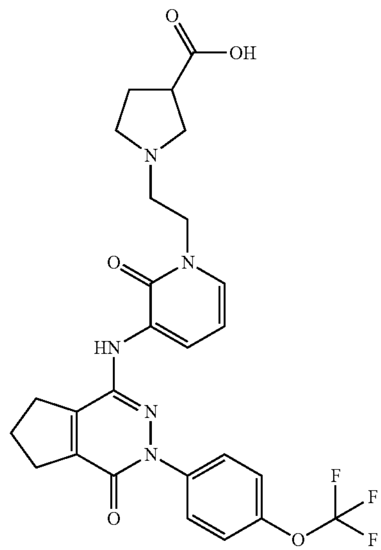 [SMILES: O=C(O)C1CCN(CCn2cccc(Nc3nn(-c4ccc(OC(F)(F)F)cc4)c(=O)c4c3CCC4)c2=O)C1] | 1-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]pyrrolidine-3-carboxylic acid | Intermediate 41 | 546.2 |
| 121 | 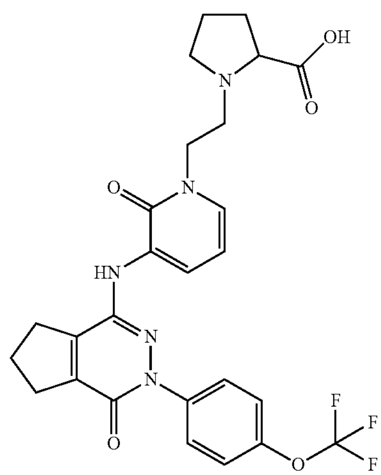 [SMILES: O=C(O)C1CCCN1CCn1cccc(Nc2nn(-c3ccc(OC(F)(F)F)cc3)c(=O)c3c2CCC3)c1=O] | 1-[2-[2-oxo-3-[[4-oxo-3-[4-(trifluoromethoxy)phenyl]-6,7-dihydro-5H-1-yl]amino]-1-pyridyl]ethyl]pyrrolidine-2-carboxylic acid | Intermediate 42 | 546.2 |
| 122 | 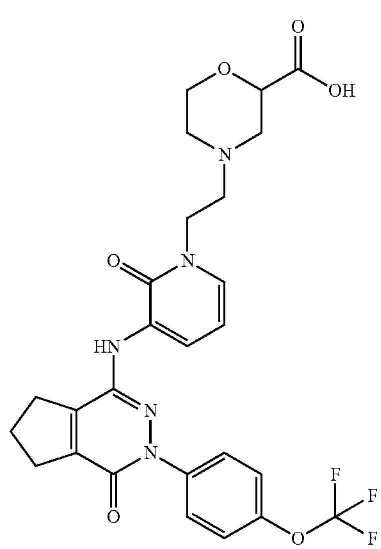 [SMILES: O=C(O)C1CN(CCn2cccc(Nc3nn(-c4ccc(OC(F)(F)F)cc4)c(=O)c4c3CCC4)c2=O)CCO1] | 4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-2-carboxylic acid | Example 41 | 562.2 |

| Example No. | Structure | Systematic Name | Starting materials | mass found (M + H)+ |
|---|---|---|---|---|
| 123 | 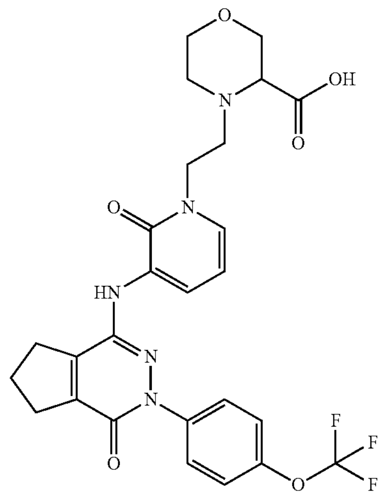 [SMILES: O=C(O)C1COCCN1CCn1cccc(Nc2nn(-c3ccc(OC(F)(F)F)cc3)c(=O)c3c2CCC3)c1=O] | 4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-3-carboxylic acid | Intermediate 43 | 562.2 |
| 124 | 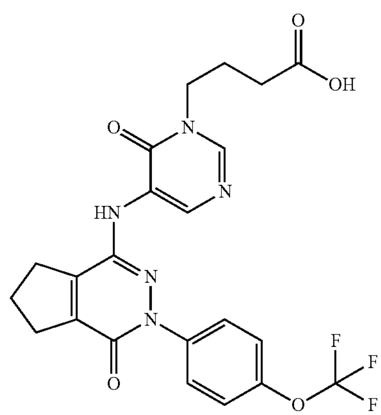 [SMILES: O=C(O)CCCn1cncc(Nc2nn(-c3ccc(OC(F)(F)F)cc3)c(=O)c3c2CCC3)c1=O] | 4-[6-oxo-5-[[4-oxo-3-[4-(trifluoromethoxy)phenyl]-6,7-dihydro-5H-cyclopenta[d]pyridazin-1-yl]amino]pyrimidin-1-yl]butanoic acid | Intermediate 56 | 492.1 |

Example 125

7-Hydroxy-4-[(1-methyl-2-oxo-3-pyridyl)amino]-2-[4-(trifluoromethoxy)phenyl]phthalazin-1-one

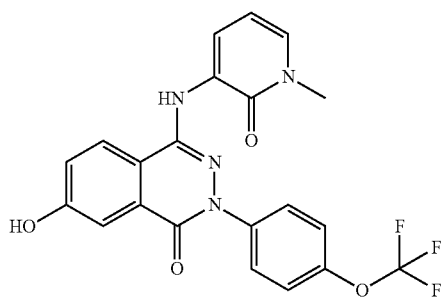 [SMILES: Cn1cccc(Nc2nn(-c3ccc(OC(F)(F)F)cc3)c(=O)c3cc(O)ccc23)c1=O]

To a solution of 7-benzyloxy-4-[(1-methyl-2-oxo-3-pyridyl)amino]-2-[4-(trifluoromethoxy)phenyl]phthalazin-1-one (Intermediate 37; 180.0 mg, 0.34 mmol) in THF (5.0 mL) was added Pd/C (100 mg) at 20° C. Then the mixture was stirred for 3 h at 20° C. under H₂ balloon. Solvent was removed in vacuum to dryness to give crude product which was purified by prep-HPLC (base) to give the title compound (25.5 mg, 16.8% yield) as white solid. MS (m/e): 445.1 (M+H)+.

Example 126

6-Hydroxy-4-[(1-methyl-2-oxo-3-pyridyl)amino]-2-[4-(trifluoromethoxy)phenyl]phthalazin-1-one

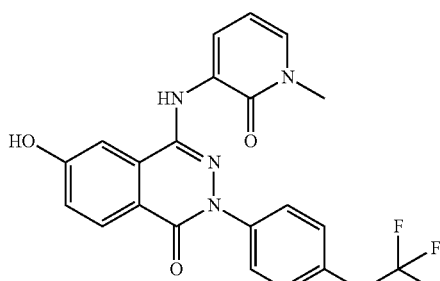

A mixture of compound 6-benzyloxy-4-[(1-methyl-2-oxo-3-pyridyl)amino]-2-[4-(trifluoromethoxy)phenyl]phthalazin-1-one (Intermediate 38; 0.15 g, 0.28 mmol) and Pd/C (30.0 mg) in THF (10 mL) was stirred under $H_2$ (balloon, 15 psi) at 25° C. for 2 h. The reaction mixture was filtered and the filtration was concentrated to give the crude product (0.18 g). The crude product was firstly purified recrystallized from EA (10 mL×2) to give the title product (35.8 mg, 29.8%) as a white solid. MS (m/e): 445.2 $(M+H)^+$.

Example 127

1-[[1-(morpholin-3-ylmethyl)-2-oxo-3-pyridyl]amino]-3-[4-(trifluoromethoxy)phenyl]-6,7-dihydro-5H-cyclopenta[d]pyridazin-4-one

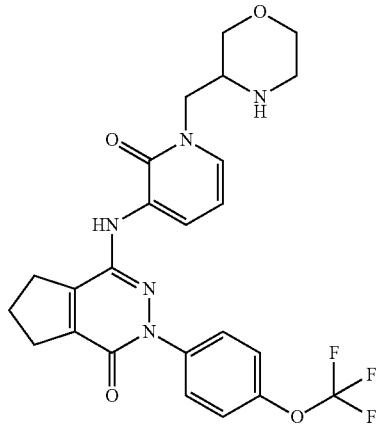 [SMILES: O=c1c(Nc2nn(-c3ccc(OC(F)(F)F)cc3)c(=O)c3c2CCC3)cccn1CC1COCCN1]

To a solution of 1-[[1-[(4-benzylmorpholin-3-yl)methyl]-2-oxo-3-pyridyl]amino]-3-[4-(trifluoromethoxy)phenyl]-6,7-dihydro-5H-cyclopenta[d]pyridazin-4-one (Intermediate 57; 150 mg, 0.162 mmol) and TEA (135 mg, 1.35 mmol) in DCM (5.0 mL) was added 1-chloroethyl carbonochloridate (195 mg, 1.35 mmol) at 0° C. under $N_2$. Then the reaction was stirred at 20° C. for 16 hr. The mixture was concentrated to give a residue which was redissolved in MeOH (5.0 mL) and the mixture was heated to reflux and stirred for another 3 h. The mixture was concentrated, dissolved with DCM (10.0 mL), washed with water (5.0 mL), dried and concentrated to give a residue which was purified by prep-HPLC (formic acid) to give the title compound as its formate salt (47.5 mg, 27% yield) as a yellow solid. MS (m/e): 504.1 $(M+H)^+$.

Example 128

1-[[1-[2-(Methylamino)ethyl]-6-oxo-pyrimidin-5-yl]amino]-3-[4-(trifluoromethoxy)phenyl]-6,7-dihydro-5H-cyclopenta[d]pyridazin-4-one

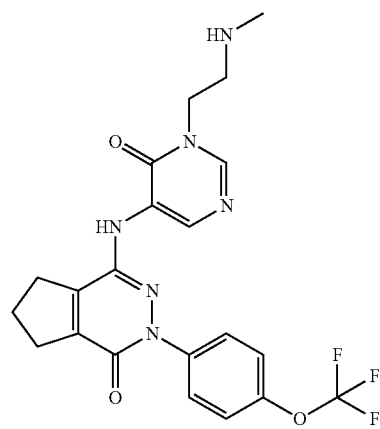 [SMILES: CNCCn1cncc(Nc2nn(-c3ccc(OC(F)(F)F)cc3)c(=O)c3c2CCC3)c1=O]

This was prepared as its formate salt from 1-[[1-[2-[benzyl(methyl)amino]ethyl]-6-oxo-pyrimidin-5-yl]amino]-3-[4-(trifluoromethoxy)phenyl]-6,7-dihydro-5H-cyclopenta[d]pyridazin-4-one (Intermediate 59) using a procedure analogous to that used to prepare example 127. MS (m/e): 463.0 $(M+H)^+$.

Example 129

2-[2-[2-Oxo-3-[[4-oxo-3-[4-(trifluoromethoxy)phenyl]-6,7-dihydro-5H-cyclopenta[d]pyridazin-1-yl]amino]-1-pyridyl]ethylamino]acetic acid

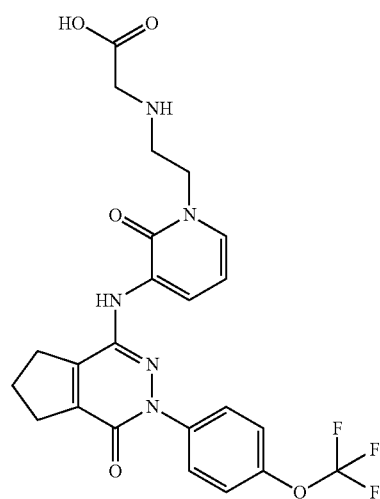 [SMILES: O=C(O)CNCCn1cccc(Nc2nn(-c3ccc(OC(F)(F)F)cc3)c(=O)c3c2CCC3)c1=O]

To a solution of 2-[tert-butoxycarbonyl-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]amino]acetic acid (Example 43; 35 mg, 58.4 µmol, Eq: 1) in DCM (3 mL) was added TFA (740 mg, 0.5 mL, 6.49 mmol), and the mixture was stirred at rt overnight. After removal of DCM and excess TFA, the residue was purified by RP-HPLC to give the title compound as a solid (27 mg, yield of 90%). MS (m/e): 506.2 (M+H)+.

Example 130

1-[[1-(2-Aminoethyl)-2-oxo-3-pyridyl]amino]-3-[4-(trifluoromethoxy)phenyl]-6,7-dihydro-5H-cyclopenta[d]pyridazin-4-one

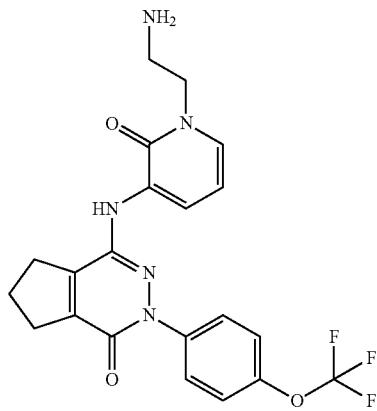 [SMILES: NCCn1cccc(Nc2nn(-c3ccc(OC(F)(F)F)cc3)c(=O)c3c2CCC3)c1=O]

The title compound was prepared from Example 45 using an analogous method to that used to prepare example 129. MS (m/e): 448.2 (M+H)+.

Example 131

1-[[2-Oxo-1-(pyrrolidin-2-ylmethyl)-3-pyridyl]amino]-3-[4-(trifluoromethoxy)phenyl]-6,7-dihydro-5H-cyclopenta[d]pyridazin-4-one

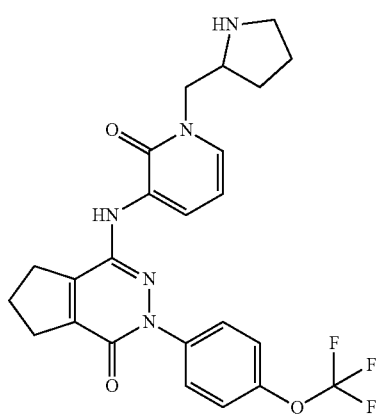 [SMILES: O=c1c(Nc2nn(-c3ccc(OC(F)(F)F)cc3)c(=O)c3c2CCC3)cccn1CC1CCCN1]

A mixture of 1-[[1-[[1-[(4-methoxyphenyl)methyl]pyrrolidin-2-yl]methyl]-2-oxo-3-pyridyl]amino]-3-[4-(trifluoromethoxy)phenyl]-6,7-dihydro-5H-cyclopenta[d]pyridazin-4-one (Intermediate 60; 0.15 g, 0.24 mmol), CF3COOH (1.0 mL) in DCM (10 mL) was stirred under nitrogen at 15° C. for 16 h. The reaction mixture was filtered and the filtrate was concentrated to give the crude product (0.21 g). The crude product was purified by prep-HPLC to give the title compound (33.8 mg, 23.4%) as a white solid. MS (m/e): 488.3 (M+H)+.

Example 132 and Example 133

6-Methyl-1-[(1-methyl-2-oxo-3-pyridyl)amino]-3-[4-(trifluoromethoxy)phenyl]-7,8-dihydro-5H-pyrido[3,4-d]pyridazin-4-one and 6-Methyl-4-[(1-methyl-2-oxo-3-pyridyl)amino]-2-[4-(trifluoromethoxy)phenyl]-7,8-dihydro-5H-pyrido[3,4-d]pyridazin-1-one

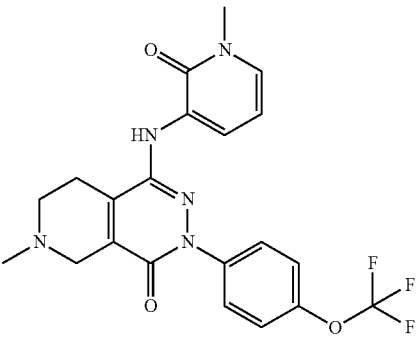

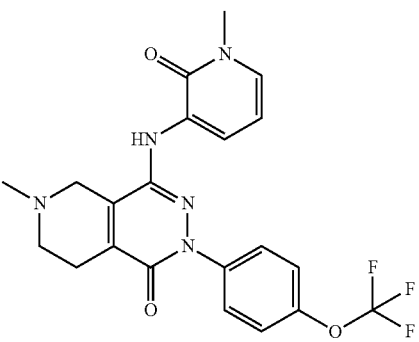

To a solution of a 1:1 mixture of 1-bromo-6-methyl-3-[4-(trifluoromethoxy)phenyl]-7,8-dihydro-5H-pyrido[3,4-d]pyridazin-4-one and 4-bromo-6-methyl-2-[4-(trifluoromethoxy)phenyl]-7,8-dihydro-5H-pyrido[3,4-d]pyridazin-1-one (Intermediate 32; 150.0 mg, 0.37 mmol), K2CO3 (153 mg, 1.11 mmol) and 3-amino-1-methyl-pyridin-2-one hydrochloride (CAS 1523570-95-7, 72.3 mg, 0.45 mmol) in dioxane (20 mL) was added Xantphos (30 mg) and Pd2(dba)3 (20 mg) under N2 atmosphere, and then the mixture was stirred at 110° C. for another 16 h. The solvent was removed by concentration to give the crude product, which was purified by chromatography on silica gel (DCM:MeOH=2:1) to give a mixture of mixture compound (100 mg) as green solid, which was separated by chiral SFC to give 6-methyl-1-[(1-methyl-2-oxo-3-pyridyl)amino]-3-[4-(trifluoromethoxy)phenyl]-7,8-dihydro-5H-pyrido[3,4-d]pyridazin-4-one (61.3 mg) as a green solid and 6-methyl-4-[(1-methyl-2-oxo-3-pyridyl)amino]-2-[4-(trifluoromethoxy)phenyl]-7,8-dihydro-5H-pyrido[3,4-d]pyridazin-1-one (11.6 mg) as a green solid. MS (m/e): 448.1 (M+H)+.

Example 134

1-[(1-Methyl-2-oxo-3-pyridyl)amino]-3-[4-(trifluoromethoxy)phenyl]-5,6,7,8-tetrahydropyrido[3,4-d]pyridazin-4-one

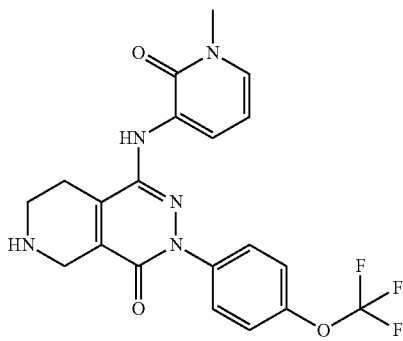 [SMILES: Cn1cccc(Nc2nn(-c3ccc(OC(F)(F)F)cc3)c(=O)c3c2CCNC3)c1=O]

To a solution of 6-[(4-methoxyphenyl)methyl]-1-[(1-methyl-2-oxo-3-pyridyl)amino]-3-[4-(trifluoromethoxy)phenyl]-7,8-dihydro-5H-pyrido[3,4-d]pyridazin-4-one (Intermediate 61; 300 mg, 0.54 mmol) and TEA (0.16 mL, 1.08 mmol) in DCM (20 mL) was added 1-chloroethyl carbonochloridate (154 mg, 1.08 mmol) at 25° C., and the mixture stirred for 2 h. The solvent was removed by concentration and the residue was dissolved in 10 mL MeOH, then the solution was heated to reflux for 2 h. The solvent was removed by concentration to give the crude product (0.4 g, crude) as a brown solid, which was purified by prep-HPLC (TFA) separation to give the title compound as its trifluoroacetate salt (23.8 mg, 10.2% yield). MS (m/e): 434.1 (M+H)$^+$.

Example 135

1-[[1-[[(2S)-Morpholin-2-yl]methyl]-2-oxo-3-pyridyl]amino]-3-[4-(trifluoromethoxy)phenyl]-6,7-dihydro-5H-cyclopenta[d]pyridazin-4-one

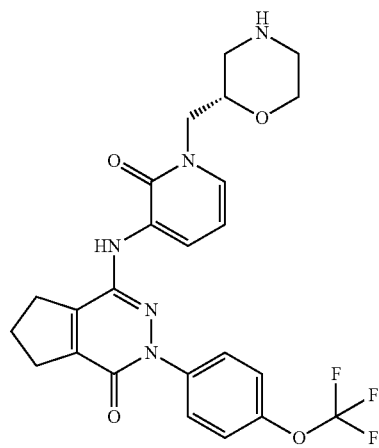 [SMILES: O=c1c(Nc2nn(-c3ccc(OC(F)(F)F)cc3)c(=O)c3c2CCC3)cccn1C[C@@H]1CNCCO1]

The title compound was prepared from 1-[[1-[[(2S)-4-[(4-methoxyphenyl)methyl]morpholin-2-yl]methyl]-2-oxo-3-pyridyl]amino]-3-[4-(trifluoromethoxy)phenyl]-6,7-dihydro-5H-cyclopenta[d]pyridazin-4-one (Intermediate 58) using an analagous method to that used to prepare example 134. MS (m/e): 488.3 (M+H)$^+$.

Example 136

6-(2-Methoxyethoxy)-4-[(1-methyl-2-oxo-3-pyridyl)amino]-2-[4-(trifluoromethoxy)phenyl]phthalazin-1-one

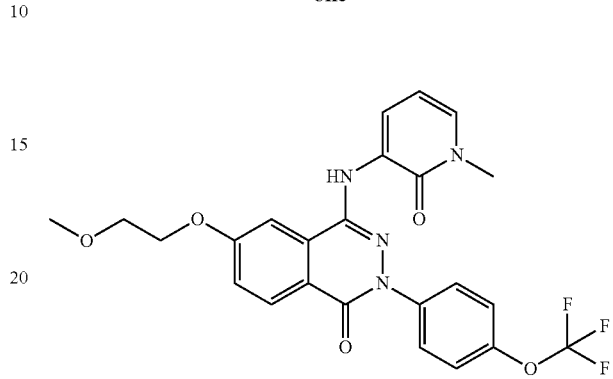

To a solution of tert-butyl N-[7-(2-methoxyethoxy)-4-oxo-3-[4-(trifluoromethoxy)phenyl]phthalazin-1-yl]-N-(1-methyl-2-oxo-3-pyridyl)carbamate (Intermediate 48; 91.0 mg, 0.15 mmol) in DCM (5 mL) was added TFA (1 mL), the reaction was stirred at 25° C. for 2 h. The solvent was evaporated to give a crude product, the crude product was purified by silica chromatography column to give the title compound (75.4 mg, yield: 99.3%) as a green solid. MS (m/e): 503.1 (M+H)$^+$.

Example 137

7-(2-Methoxyethoxy)-4-[(1-methyl-2-oxo-3-pyridyl)amino]-2-[4-(trifluoromethoxy)phenyl]phthalazin-1-one

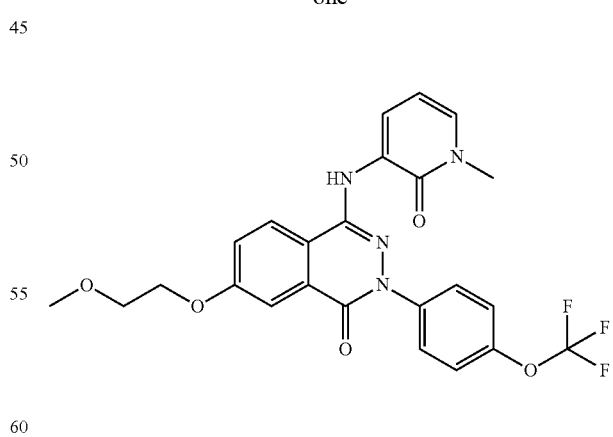

The title compound was prepared from tert-butyl N-[6-(2-methoxyethoxy)-4-oxo-3-[4-(trifluoromethoxy)phenyl]phthalazin-1-yl]-N-(1-methyl-2-oxo-3-pyridyl)carbamate (Intermediate 49) using an analogous method to that used to prepare example 136. MS (m/e): 503.1 (M+H)$^+$.

Example 138

5-(2-Methoxyethoxy)-4-[(1-methyl-2-oxo-3-pyridyl)amino]-2-[4-(trifluoromethoxy)phenyl]phthalazin-1-one

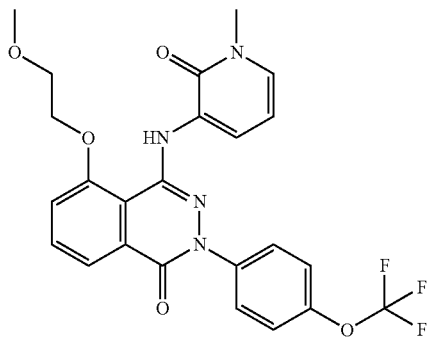 [SMILES: COCCOc1cccc2c(=O)n(-c3ccc(OC(F)(F)F)cc3)nc(Nc3cccn(C)c3=O)c12]

The title compound was prepared from tert-butyl N-[8-(2-methoxyethoxy)-4-oxo-3-[4-(trifluoromethoxy)phenyl]phthalazin-1-yl]-N-(1-methyl-2-oxo-3-pyridyl)carbamate (Intermediate 50) using an analogous method to that used to prepare example 136. MS (m/e): 503.1 (M+H)$^+$.

Example 139

1-[(1-Methyl-2-oxo-3-pyridyl)amino]-4-oxo-3-[4-(trifluoromethoxy)phenyl]phthalazine-6-carboxamide

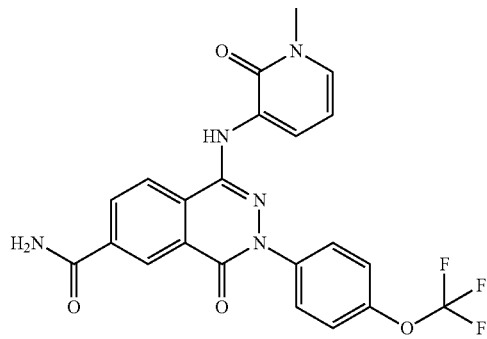 [SMILES: Cn1cccc(Nc2nn(-c3ccc(OC(F)(F)F)cc3)c(=O)c3cc(C(N)=O)ccc23)c1=O]

A mixture of ethyl 1-[(1-methyl-2-oxo-3-pyridyl)amino]-4-oxo-3-[4-(trifluoromethoxy)phenyl]phthalazine-6-carboxylate (Intermediate 51; 0.2 g, 0.4 mmol), NH$_3$ (30 mL of ethanol saturation solution) in THF (30 mL) under autoclave was stirred at 100° C. for 40 h. The mixture was evaporated to dryness. The residue was purified by recrystallized from DCM (10 mL×2) to give the title compound (40.3 mg, 21.4%) as a light white solid. MS (m/e): 501.0 (M+H)$^+$.

Example 140

7-(1-Hydroxyethyl)-4-[(1-methyl-2-oxo-3-pyridyl)amino]-2-[4-(trifluoromethoxy)phenyl]phthalazin-1-one

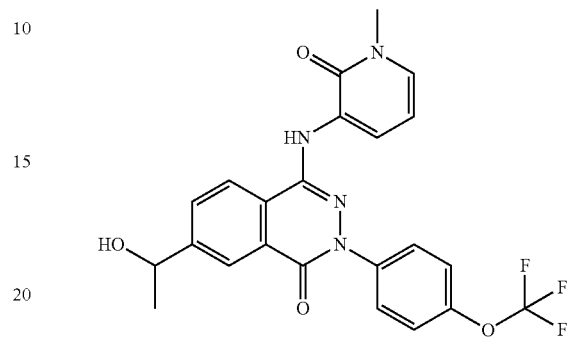

To a solution of 1-[(1-methyl-2-oxo-3-pyridyl)amino]-4-oxo-3-[4-(trifluoromethoxy)phenyl]phthalazine-6-carbaldehyde (Intermediate 52; 0.15 g, 0.33 mmol) in THF (15.0 mL) was added MeMgBr (0.22 mL, 3 M) dropwise over 1 min. After the addition was over, the mixture was stirred at −78° C. for 2 h. The crude product was firstly purified by preparative-TLC and then recrystallized from CH$_3$OH (10 mL×2) to give the title compound (26.5 mg, 17.0%) as a white solid. MS (m/e): 473.1 (M+H)$^+$.

Example 141

7-(Hydroxymethyl)-4-[(1-methyl-2-oxo-3-pyridyl)amino]-2-[4-(trifluoromethoxy)phenyl]phthalazin-1-one

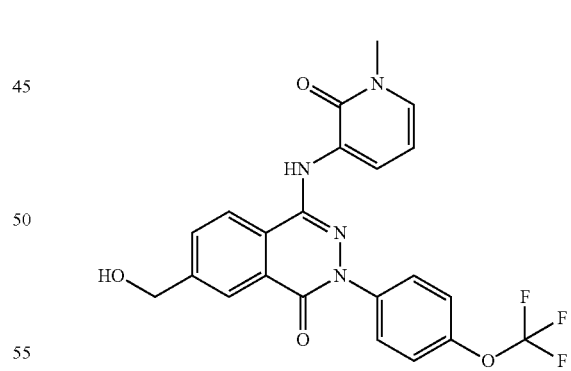

A mixture of ethyl 1-[(1-methyl-2-oxo-3-pyridyl)amino]-4-oxo-3-[4-(trifluoromethoxy)phenyl]phthalazine-6-carboxylate (Intermediate 51; 0.2 g, 0.4 mmol), LiAlH$_4$ (31.0 mg, 0.8 mmol) in THF (20 mL) was stirred at 0° C. for 2 h. The mixture was diluted with EA (20 mL), washed with saturated aqueous sodium bicarbonate and brine, dried with anhydrous Na$_2$SO$_4$, filtered and concentrated in vacuum. The crude product was purified by recrystallized from CH$_3$OH (10 mL×2) to give the title compound (140.0 mg, 76.5%) as a white solid. MS (m/e): 459.0 (M+H)$^+$.

Example 142

7-Amino-4-[(1-methyl-2-oxo-3-pyridyl)amino]-2-[4-(trifluoromethoxy)phenyl]phthalazin-1-one

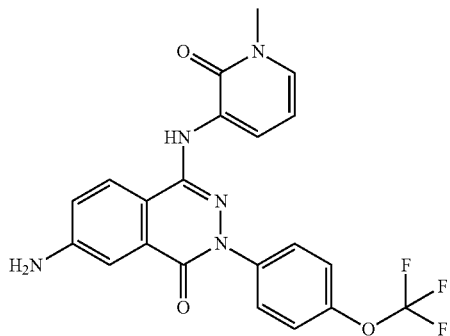 [SMILES: Cn1cccc(Nc2nn(-c3ccc(OC(F)(F)F)cc3)c(=O)c3cc(N)ccc23)c1=O]

To a solution of 4-[(1-methyl-2-oxo-3-pyridyl)amino]-7-nitro-2-[4-(trifluoromethoxy)phenyl]phthalazin-1-one (Intermediate 53; 180.0 mg, 0.38 mmol) in EtOH (20 mL) and H$_2$O (1 mL) was added Na$_2$S$_2$O$_4$ (330.8 mg, 1.9 mmol) at 15° C., and then the solution was stirred at 80° C. for 1 hr. The solvent was removed by concentration to give the crude product, which was purified by prep-HPLC to give the the trifluoroacetate salt of the title compound (14.6 mg, 8.8% yield) as a brown solid. MS (m/e): 444.2 (M+H)$^+$.

Example 143

7-(Aminomethyl)-4-[(1-methyl-2-oxo-3-pyridyl)amino]-2-[4-(trifluoromethoxy)phenyl]phthalazin-1-one

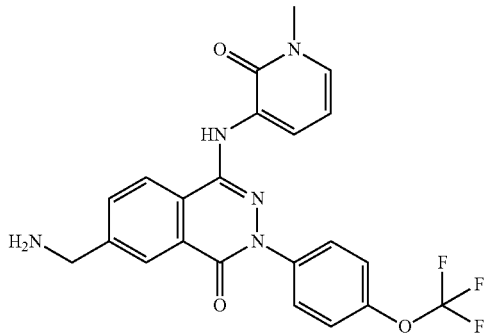 [SMILES: Cn1cccc(Nc2nn(-c3ccc(OC(F)(F)F)cc3)c(=O)c3cc(CN)ccc23)c1=O]

To a solution of 1-[(1-methyl-2-oxo-3-pyridyl)amino]-4-oxo-3-[4-(trifluoromethoxy)phenyl]phthalazine-6-carbaldehyde oxime (Intermediate 54; 75.0 mg, 0.16 mmol) in AcOH (2.0 mL) was added Zn (30.0 mg, 0.48 mmol), the mixture was stirred at 80° C. for 2 h. The reaction mixture was filtered and the filtrate was concentrated to give the crude product (0.1 g). The crude product was purified by prep-HPLC to give the trifluoroacetate salt of the title compound (44.6 mg, 61.0%) as a yellow solid. MS (m/e): 458.2 (M+H)$^+$.

Example 144

7-[(Dimethylamino)methyl]-4-[(1-methyl-2-oxo-3-pyridyl)amino]-2-[4-(trifluoromethoxy)phenyl]phthalazin-1-one

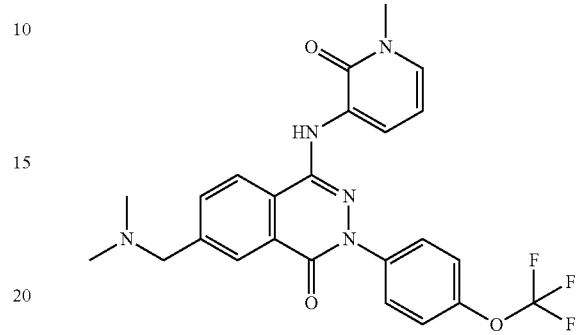

To a solution of 1-[(1-methyl-2-oxo-3-pyridyl)amino]-4-oxo-3-[4-(trifluoromethoxy)phenyl]phthalazine-6-carbaldehyde (Intermediate 52; 0.2 g, 0.44 mmol) in 1:1 THF:CH$_3$OH (8.0 mL) was added dimethylamine (0.44 mL, 0.88 mmol). The mixture was stirred at 25° C. for 1 h. After 1 h, NaBH$_3$CN (81.6 mg, 1.32 mmol) was added to the mixture, then the reaction was stirred at 25° C. for 15 h. The reaction mixture was filtered and the filtrate was concentrated to give the crude product (0.3 g). The crude product was purified by prep-HPLC to give the title compound (62.9 mg, 29.5%) as a yellow solid. MS (m/e): 486.1 (M+H)$^+$.

Example 145

6-(2-Hydroxypropyl)-1-[(1-methyl-2-oxo-3-pyridyl)amino]-3-[4-(trifluoromethoxy)phenyl]-7,8-dihydro-5H-pyrido[3,4-d]pyridazin-4-one

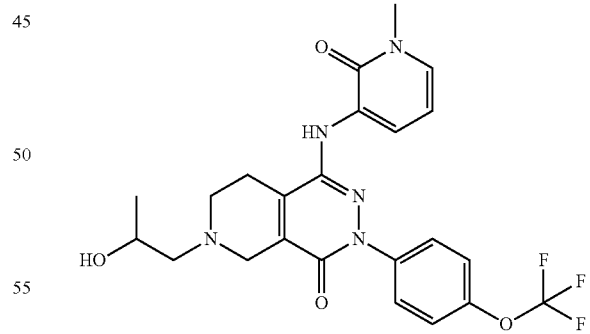

A solution of 1-[(1-methyl-2-oxo-3-pyridyl)amino]-3-[4-(trifluoromethoxy)phenyl]-5,6,7,8-tetrahydropyrido[3,4-d]pyridazin-4-one (example 134; 100 mg, 0.23 mmol) and 2-methyloxirane (CAS 75-56-9; 26.7 mg) in EtOH (10 mL) was then stirred at 80° C. for 16 h. The solvent was removed by concentration to give the crude product, which was purified by prep-HPLC (TFA) separation to give the title compound as its trifluoroacetate salt (41 mg, 36% yield) as a brown oil. MS (m/e): 492.3 (M+H)$^+$.

Example 146

6-(2-Hydroxy-2-methyl-propyl)-1-[(1-methyl-2-oxo-3-pyridyl)amino]-3-[4-(trifluoromethoxy)phenyl]-7,8-dihydro-5H-pyrido[3,4-d]pyridazin-4-one

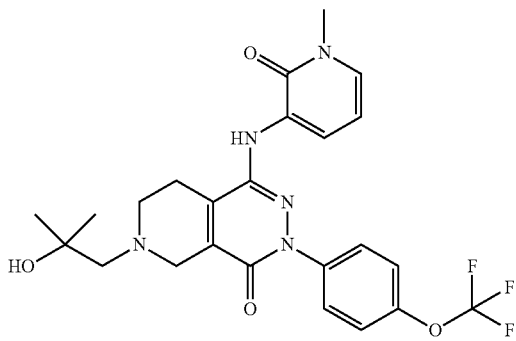 [SMILES: Cn1cccc(Nc2nn(-c3ccc(OC(F)(F)F)cc3)c(=O)c3c2CCN(CC(C)(C)O)C3)c1=O]

This was prepared as its trifluoroacetate salt from 1-[(1-methyl-2-oxo-3-pyridyl)amino]-3-[4-(trifluoromethoxy)phenyl]-5,6,7,8-tetrahydropyrido[3,4-d]pyridazin-4-one (example 134) and 2,2-dimethyloxirane (CAS 558-30-5) using a procedure analogous to that used to prepare example 145. MS (m/e): 506.3 (M+H)$^+$.

Example 147

6-(2-Hydroxyethyl)-1-[(1-methyl-2-oxo-3-pyridyl)amino]-3-[4-(trifluoromethoxy)phenyl]-7,8-dihydro-5H-pyrido[3,4-d]pyridazin-4-one

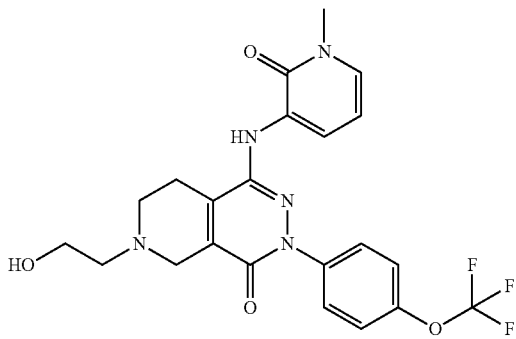 [SMILES: Cn1cccc(Nc2nn(-c3ccc(OC(F)(F)F)cc3)c(=O)c3c2CCN(CCO)C3)c1=O]

A solution of 1-[(1-methyl-2-oxo-3-pyridyl)amino]-3-[4-(trifluoromethoxy)phenyl]-5,6,7,8-tetrahydropyrido[3,4-d]pyridazin-4-one (example 134; 100 mg, 0.23 mmol), 2-bromoethanol (CAS 540-51-2; 57.4 mg, 0.46 mmol) and K$_2$CO$_3$ (63.4 mg, 0.46 mmol) in acetonitrile (10 mL) was stirred at 80° C. for 16 h. The solid was filtered off and the filtrate was concentrated to give the crude product, which was purified by prep-HPLC (TFA) separation to give compound the title compound as its trifluoroacetate salt (46.5 mg, 42% yield) as a brown oil. MS (m/e): 478.1 (M+H)$^+$.

Example 148

6-Acetyl-1-[(1-methyl-2-oxo-3-pyridyl)amino]-3-[4-(trifluoromethoxy)phenyl]-7,8-dihydro-5H-pyrido[3,4-d]pyridazin-4-one

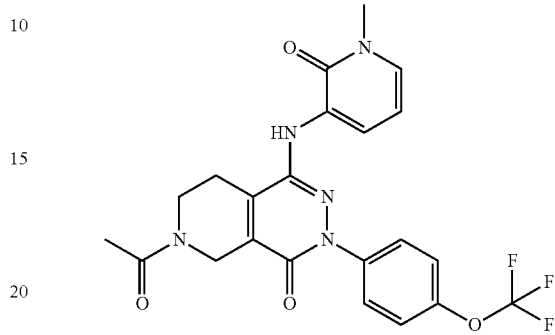

To a solution of 1-[(1-methyl-2-oxo-3-pyridyl)amino]-3-[4-(trifluoromethoxy)phenyl]-5,6,7,8-tetrahydropyrido[3,4-d]pyridazin-4-one (example 134; 30 mg, 0.05 mmol) and TEA (10.1 mg, 0.1 mmol) in DCM (10 mL) was added CH$_3$COCl (7.9 mg, 0.1 mmol) at 25° C., and then the solution was stirred for further 1 h. The solvent was removed by concentration to give the crude product, which was purified by prep-HPLC separation to give the title compound (19 mg, 81.2% yield) as a yellow solid. MS (m/e): 476.2 (M+H)$^+$.

Example 149

6-Acetyl-4-[(1-methyl-2-oxo-3-pyridyl)amino]-2-[4-(trifluoromethoxy)phenyl]-7,8-dihydro-5H-pyrido[3,4-d]pyridazin-1-one

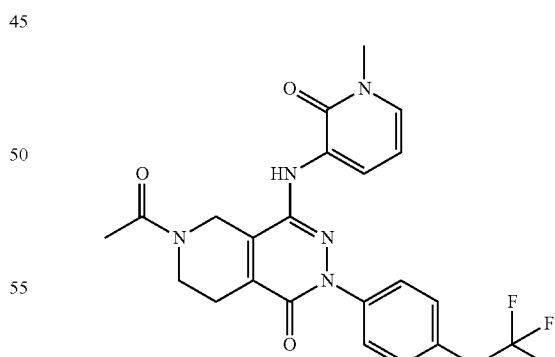

The title compound was prepared from 4-[(1-methyl-2-oxo-3-pyridyl)amino]-2-[4-(trifluoromethoxy)phenyl]-5,6,7,8-tetrahydropyrido[3,4-d]pyridazin-1-one (Intermediate 55) using an analogous method to that used to prepare example 148. MS (m/e): 476.2 (M+H)$^+$.

Example 150

6-Acetyl-1-[(1-methyl-6-oxo-pyrimidin-5-yl)amino]-3-[4-(trifluoromethoxy)phenyl]-7,8-dihydro-5H-pyrido[3,4-d]pyridazin-4-one

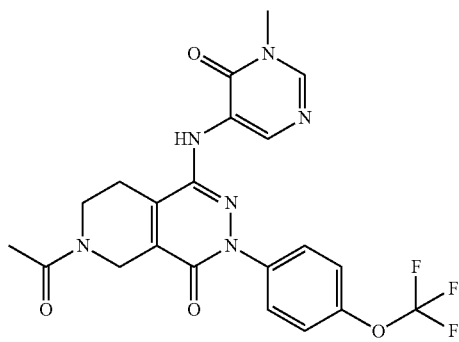 [SMILES: CC(=O)N1CCc2c(Nc3cncn(C)c3=O)nn(-c3ccc(OC(F)(F)F)cc3)c(=O)c2C1]

The title compound was prepared from 1-[(1-methyl-6-oxo-pyrimidin-5-yl)amino]-3-[4-(trifluoromethoxy)phenyl]-5,6,7,8-tetrahydropyrido[3,4-d]pyridazin-4-one (Intermediate 62) using an analogous method to that used to prepare example 148. MS (m/e): 476.2 (M+H)$^+$.

Example 151

6-Acetyl-4-[(1-methyl-6-oxo-pyrimidin-5-yl)amino]-2-[4-(trifluoromethoxy)phenyl]-7,8-dihydro-5H-pyrido[3,4-d]pyridazin-1-one

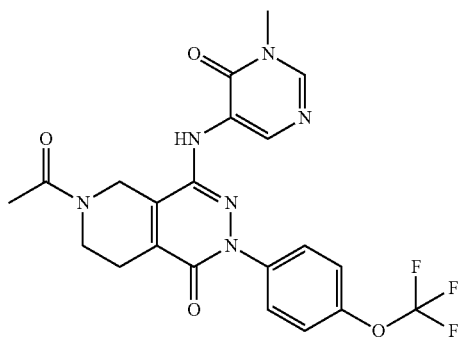 [SMILES: CC(=O)N1CCc2c(c(Nc3cncn(C)c3=O)nn(-c3ccc(OC(F)(F)F)cc3)c2=O)C1]

The title compound was prepared from 4-[(1-methyl-6-oxo-pyrimidin-5-yl)amino]-2-[4-(trifluoromethoxy)phenyl]-5,6,7,8-tetrahydropyrido[3,4-d]pyridazin-1-one (Intermediate 63) using an analogous method to that used to prepare example 148. MS (m/e): 476.2 (M+H)$^+$.

Example 152

Methyl 4-[(1-methyl-2-oxo-3-pyridyl)amino]-1-oxo-2-[4-(trifluoromethoxy)phenyl]-7,8-dihydro-5H-pyrido[3,4-d]pyridazine-6-carboxylate

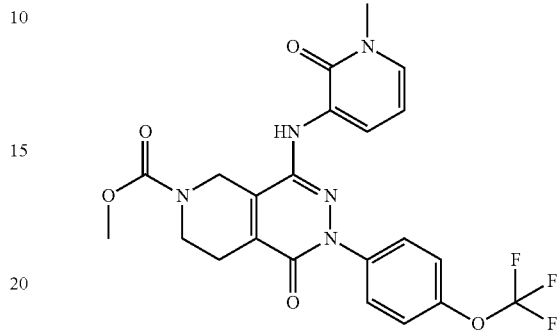

To a solution of 4-[(1-methyl-2-oxo-3-pyridyl)amino]-2-[4-(trifluoromethoxy)phenyl]-5,6,7,8-tetrahydropyrido[3,4-d]pyridazin-1-one (Intermediate 55, step 3; 0.1 g, 0.23 mmol) and triethylamine (46.5 mg, 0.46 mmol) in DCM (10 mL) was added methylchloroformate (26.5 mg, 0.28 mmol) at 0° C., and the solution was stirred for further 2 h. 10 mL MeOH was added and the solvent was removed by concentration to give the crude product, which was purified by prep-HPLC (TFA) separation to give the title compound (16.9 mg, 15% yield) as a yellow solid. MS (m/e): 492.3 (M+H)$^+$.

Example 153

Methyl 1-[(1-methyl-2-oxo-3-pyridyl)amino]-4-oxo-3-[4-(trifluoromethoxy)phenyl]-7,8-dihydro-5H-pyrido[3,4-d]pyridazine-6-carboxylate

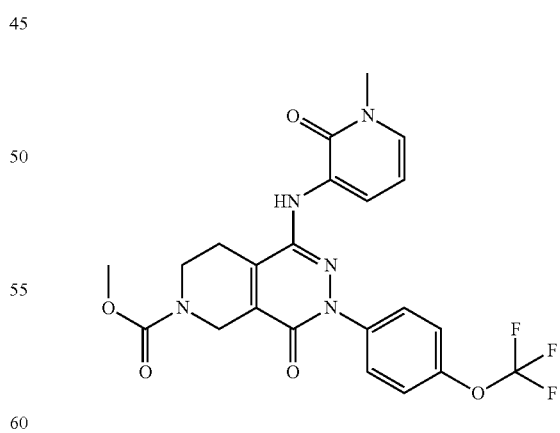

The title compound was prepared from 1-[(1-methyl-2-oxo-3-pyridyl)amino]-3-[4-(trifluoromethoxy)phenyl]-5,6,7,8-tetrahydropyrido[3,4-d]pyridazin-4-one (example 134) using a procedure analogous to that used to prepare example 152. MS (m/e): 492.1 (M+H)$^+$.

Example 154

4-[(1-Methyl-2-oxo-3-pyridyl)amino]-1-oxo-2-[4-(trifluoromethoxy)phenyl]-7,8-dihydro-5H-pyrido[3,4-d]pyridazine-6-carbaldehyde

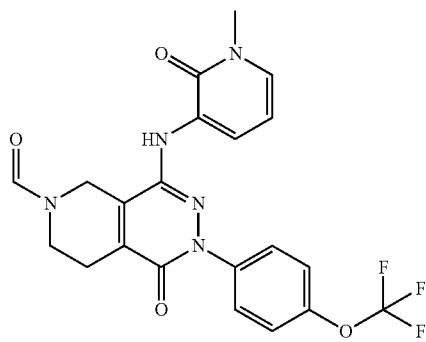 [SMILES: Cn1cccc(Nc2nn(-c3ccc(OC(F)(F)F)cc3)c(=O)c3c2CN(C=O)CC3)c1=O]

A solution of compound 4-[(1-methyl-2-oxo-3-pyridyl)amino]-2-[4-(trifluoromethoxy)phenyl]-5,6,7,8-tetrahydropyrido[3,4-d]pyridazin-1-one (Intermediate 55, step 3; 0.2 g, 0.46 mmol) in HCOOH (10 mL) was stirred at 60° C. for 72 h. The solvent was removed by concentration to give the crude product, which was purified by prep-HPLC (formic acid) separation to give the formate salt of the title compound (30.2 mg, 15% yield) as a white solid. MS (m/e): 462.2 (M+H)$^+$.

Example 155

1-[(1-Methyl-2-oxo-3-pyridyl)amino]-4-oxo-3-[4-(trifluoromethoxy)phenyl]-7,8-dihydro-5H-pyrido[3,4-d]pyridazine-6-carbaldehyde

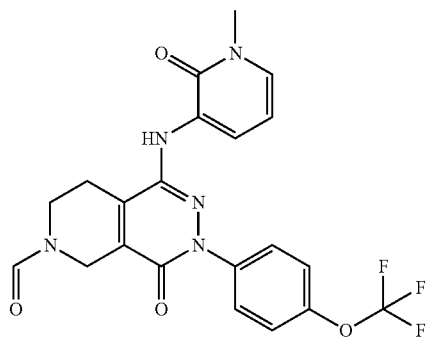 [SMILES: Cn1cccc(Nc2nn(-c3ccc(OC(F)(F)F)cc3)c(=O)c3c2CCN(C=O)C3)c1=O]

The title compound was prepared from 1-[(1-methyl-2-oxo-3-pyridyl)amino]-3-[4-(trifluoromethoxy)phenyl]-5,6,7,8-tetrahydropyrido[3,4-d]pyridazin-4-one (example 134) using a procedure analogous to that used to prepare example 150. MS (m/e): 462.1 (M+H)$^+$.

Example 156

1-[(1-Methyl-2-oxo-3-pyridyl)amino]-6-methylsulfonyl-3-[4-(trifluoromethoxy)phenyl]-7,8-dihydro-5H-pyrido[3,4-d]pyridazin-4-one

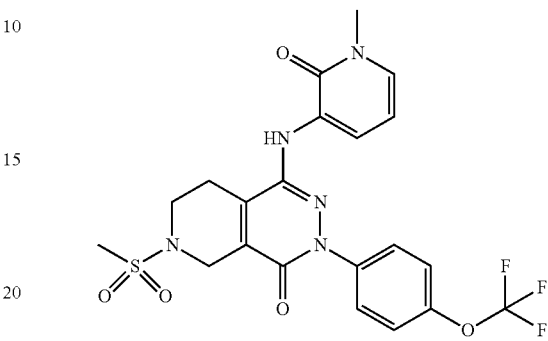

To a solution of 1-[(1-methyl-2-oxo-3-pyridyl)amino]-3-[4-(trifluoromethoxy)phenyl]-5,6,7,8-tetrahydropyrido[3,4-d]pyridazin-4-one (example 134; 100 mg, 0.23 mmol) and TEA (46.5 mg, 0.46 mmol) in DCM (10 mL) was added MsCl (40 mg, 0.35 mmol) at 0° C., and then stirred for further 2 h at 25° C. The solvent was removed by concentration to give the crude product, which purified by prep-HPLC (TFA) separation to give the title compound (22.8 mg, 19% yield) as a yellow solid. MS (m/e): 512.1 (M+H)$^+$.

Example 157

4-[(1-Methyl-2-oxo-3-pyridyl)amino]-6-methylsulfonyl-2-[4-(trifluoromethoxy)phenyl]-7,8-dihydro-5H-pyrido[3,4-d]pyridazin-1-one

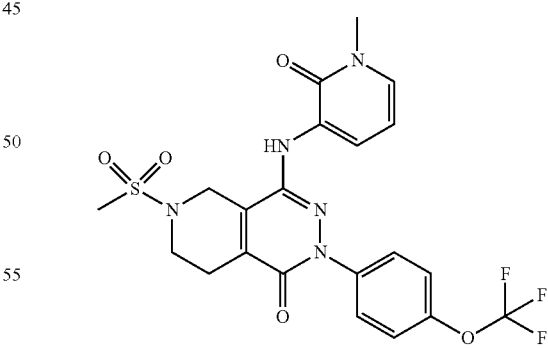

The title compound was prepared from 4-[(1-methyl-2-oxo-3-pyridyl)amino]-2-[4-(trifluoromethoxy)phenyl]-5,6,7,8-tetrahydropyrido[3,4-d]pyridazin-1-one (Intermediate 55, step 3) using a procedure analogous to that used to prepare example 156. MS (m/e): 512.1 (M+H)$^+$.

Example 158

6-Ethyl-1-[(1-methyl-2-oxo-3-pyridyl)amino]-3-[4-(trifluoromethoxy)phenyl]-7,8-dihydro-5H-pyrido[3,4-d]pyridazin-4-one

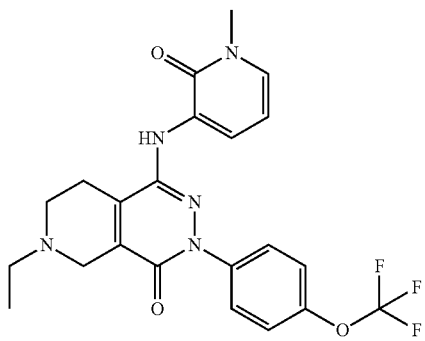 [SMILES: CCN1CCc2c(Nc3cccn(C)c3=O)nn(-c3ccc(OC(F)(F)F)cc3)c(=O)c2C1]

To a solution of 1-[(1-methyl-2-oxo-3-pyridyl)amino]-3-[4-(trifluoromethoxy)phenyl]-5,6,7,8-tetrahydropyrido[3,4-d]pyridazin-4-one (example 134; 100 mg, 0.23 mmol) and CH$_3$CHO (0.46 mL, 0.46 mmol, 1 M in EtOH) in EtOH (10 mL) was added NaBH$_3$CN (28.8 mg, 0.46 mmol) at 25° C., and then stirred for further 2 h. The solvent was removed by concentration to give the crude product, which was purified by prep-HPLC (TFA) separation to give the trifluoroacetate salt of the title compound (16.7 mg, 15.7% yield) as a white solid. MS (m/e): 462.1 (M+H)$^+$.

Example 159

6-Isopropyl-1-[(1-methyl-2-oxo-3-pyridyl)amino]-3-[4-(trifluoromethoxy)phenyl]-7,8-dihydro-5H-pyrido[3,4-d]pyridazin-4-one

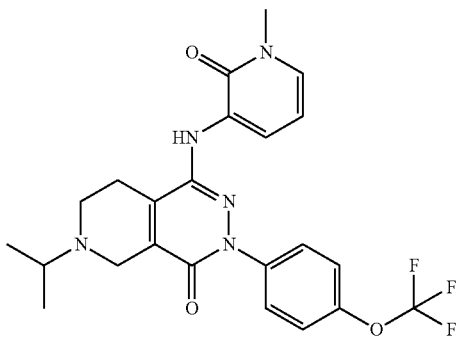 [SMILES: CC(C)N1CCc2c(Nc3cccn(C)c3=O)nn(-c3ccc(OC(F)(F)F)cc3)c(=O)c2C1]

The title compound was prepared as its trifluoroacetate salt from 1-[(1-methyl-2-oxo-3-pyridyl)amino]-3-[4-(trifluoromethoxy)phenyl]-5,6,7,8-tetrahydropyrido[3,4-d]pyridazin-4-one (example 134) and acetone using a procedure analogous to that used to prepare example 158. MS (m/e): 476.1 (M+H)$^+$.

Example 160

N-Methyl-4-[(1-methyl-2-oxo-3-pyridyl)amino]-1-oxo-2-[4-(trifluoromethoxy)phenyl]-7,8-dihydro-5H-pyrido[3,4-d]pyridazine-6-carboxamide

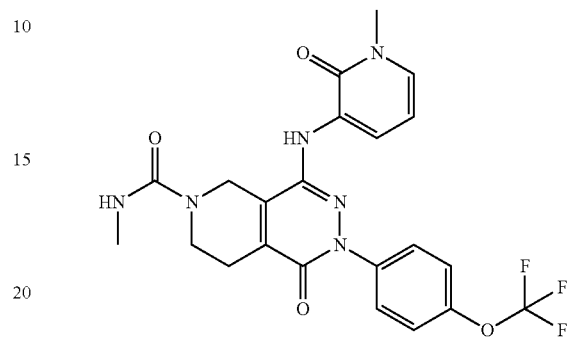

To a solution of 4-[(1-methyl-2-oxo-3-pyridyl)amino]-2-[4-(trifluoromethoxy)phenyl]-5,6,7,8-tetrahydropyrido[3,4-d]pyridazin-1-one (Intermediate 55, step 3; 0.1 g, 0.23 mmol) and triethylamine (46.5 mg, 0.46 mmol) in DCM (10 mL) was added N-methylcarbamoyl chloride (26.5 mg, 0.28 mmol) at 0° C., and the solution was stirred for further 2 h. 10 mL MeOH was added and the solvent was removed by concentration to give the crude product, which was purified by prep-HPLC (TFA) separation to give the title compound (12 mg, 10.6% yield) as a yellow solid. MS (m/e): 491.3 (M+H)$^+$.

Example 161

N-Methyl-1-[(1-methyl-2-oxo-3-pyridyl)amino]-4-oxo-3-[4-(trifluoromethoxy)phenyl]-7,8-dihydro-5H-pyrido[3,4-d]pyridazine-6-carboxamide

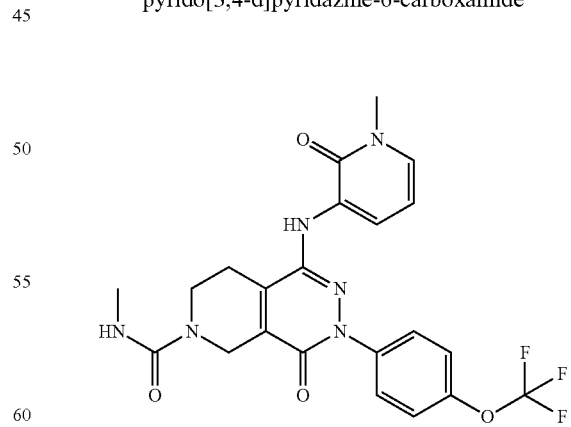

The title compound was prepared from 1-[(1-methyl-2-oxo-3-pyridyl)amino]-3-[4-(trifluoromethoxy)phenyl]-5,6,7,8-tetrahydropyrido[3,4-d]pyridazin-4-one (example 134) using a procedure analogous to that used to prepare example 160. MS (m/e): 491.2 (M+H)$^+$.

Example 162

2-[4-(1-Hydroxy-1-methyl-ethyl)phenyl]-4-[(1-methyl-2-oxo-3-pyridyl)amino]phthalazin-1-one

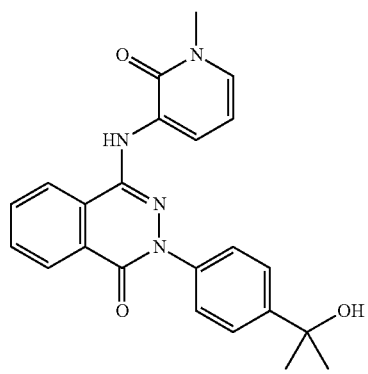 [SMILES: Cn1cccc(Nc2nn(-c3ccc(C(C)(C)O)cc3)c(=O)c3ccccc23)c1=O]

To a mixture of ethyl 4-[4-[(1-methyl-2-oxo-3-pyridyl)amino]-1-oxo-phthalazin-2-yl]benzoate (Intermediate 65; 50 mg, 120 µmol) in 20 mL ethyl ether was added methylmagnesium bromide (600 µl, 600 µmol) and the mixture was stirred for 1 h at rt. The reaction was quenched by adding saturated aqueous $NH_4Cl$ (20 ml), and the mixture was extracted with EtOAc (100 mL). The organic layer was washed with brine (50 mL), and dried over anhydrous $Na_2SO_4$ and concentrated. The residue was purified by RP-HPLC to afford the title compound as a white solid (2 mg). MS (m/e): 403.0 $(M+H)^+$.

Example 163

4-[[1-(2-Hydroxyethyl)-2-oxo-3-pyridyl]amino]-2-[4-(trifluoromethoxy)phenyl]phthalazin-1-one

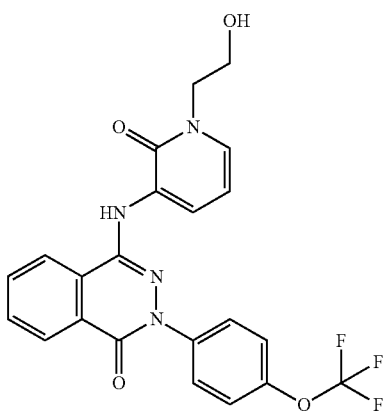 [SMILES: O=c1c(Nc2nn(-c3ccc(OC(F)(F)F)cc3)c(=O)c3ccccc23)cccn1CCO]

To a solution of methyl 2-(2-oxo-3-((4-oxo-3-(4-(trifluoromethoxy)phenyl)-3,4-dihydrophthalazin-1-yl)amino)pyridin-1(2H)-yl)acetate (Example 3; 30 mg, 61.7 µmol) in THF (3 mL) was added $LiAlH_4$ (4.68 mg, 123 µmol) and the mixture was stirred at rt for 10 min. The reaction was quenched by addition of 3 drops of water and the mixture was stirred for 30 min. and dried over anhydrous $Na_2SO_4$. After filtration, the filtrate was concentrated and the residue was purified by flash chromatography to afford the title compound as a light green solid (19 mg, yield: 66%). MS (m/e): 459.1 $(M+H)^+$.

Example 164 and Example 165

7-Hydroxy-4-[(1-methyl-2-oxo-3-pyridyl)amino]-2-[4-(trifluoromethoxy)phenyl]-5,6,7,8-tetrahydrophthalazin-1-one and 6-hydroxy-4-[(1-methyl-2-oxo-3-pyridyl)amino]-2-[4-(trifluoromethoxy)phenyl]-5,6,7,8-tetrahydrophthalazin-1-one

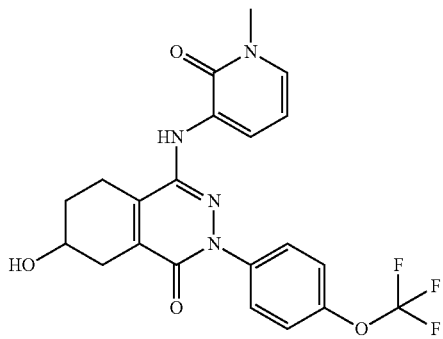

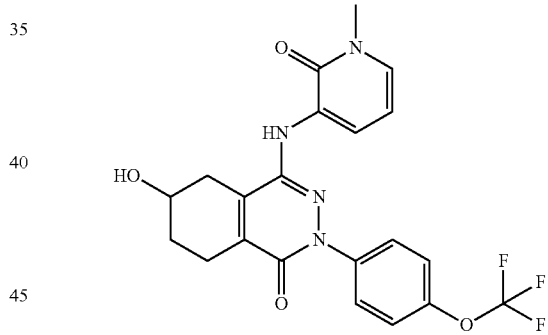

To a solution of 4-[(1-methyl-2-oxo-3-pyridyl)amino]-2-[4-(trifluoromethoxy)phenyl]-5,8-dihydrophthalazin-1-one (Intermediate 66, 120 mg, 279 µmol) in 10 mL of THF was added borane-tetrahydrofuran (1M, 558 µl, 558 µmol), and the resulting mixture was stirred at rt for 3 h. The mixture was quenched with water and a aqueous solution of NaOH (5%, 33.5 mg, 836 mol) and hydrogen peroxide (28.5 µl, 836 µmol) was added. The reaction mixture was stirred at 50° C. for 30 min. before treated with $K_2CO_3$. The crude product was extracted by EtOAc and purified by RP-HPLC to afford 7-Hydroxy-4-[(1-methyl-2-oxo-3-pyridyl)amino]-2-[4-(trifluoromethoxy)phenyl]-5,6,7,8-tetrahydrophthalazin-1-one (14 mg) and 6-hydroxy-4-[(1-methyl-2-oxo-3-pyridyl)amino]-2-[4-(trifluoromethoxy)phenyl]-5,6,7,8-tetrahydrophthalazin-1-one as white solids. MS (m/e): 449.2 $(M+H)^+$.

Example 166

1-[[1-(3-Amino-2-hydroxy-2-methyl-propyl)-2-oxo-3-pyridyl]amino]-3-[4-(trifluoromethoxy)phenyl]-6,7-dihydro-5H-cyclopenta[d]pyridazin-4-one

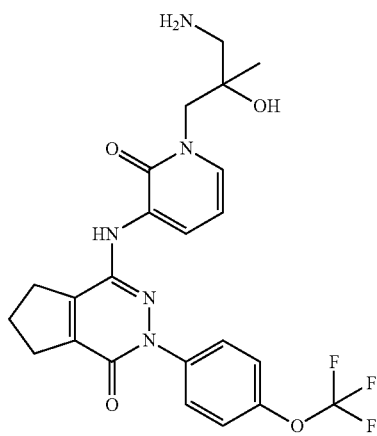 [SMILES: CC(O)(CN)Cn1cccc(Nc2nn(-c3ccc(OC(F)(F)F)cc3)c(=O)c3c2CCC3)c1=O]

A mixture of tert-butyl N-[2-hydroxy-2-methyl-3-[2-oxo-3-[[4-oxo-3-[4-(trifluoromethoxy)phenyl]-6,7-dihydro-5H-cyclopenta[d]pyridazin-1-yl]amino]-1-pyridyl]propyl]carbamate (Intermediate 109; 150.0 mg, 0.253 mmol) and TFA (1.0 mL) in DCM (2.0 mL) was stirred at 20° C. for 3 hr. Solvent was removed in vacuum to dryness to give a residue which was purified by prep-HPLC (TFA) to give the title compound (50 mg, TFA salt) as yellow solid. The solid was dissolved in DCM (10 mL) and sat NaHCO3 solution (10 mL) was added, the organic layer was dried and concentrated to give the title compound (26.2 mg, 21% yield) as a yellow solid. MS (m/e): 492.2 (M+H)$^+$.

Example 167

1-[[2-Oxo-1-(2-oxo-2-piperazin-1-yl-ethyl)-3-pyridyl]amino]-3-[4-(trifluoromethoxy)phenyl]-6,7-dihydro-5H-cyclopenta[d]pyridazin-4-one

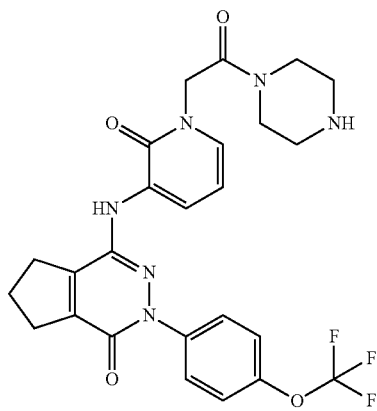 [SMILES: O=C(Cn1cccc(Nc2nn(-c3ccc(OC(F)(F)F)cc3)c(=O)c3c2CCC3)c1=O)N1CCNCC1]

To a solution of tert-butyl 4-[2-[2-oxo-3-[[4-oxo-3-[4-(trifluoromethoxy)phenyl]-6,7-dihydro-5H-cyclopenta[d]pyridazin-1-yl]amino]-1-pyridyl]acetyl]piperazine-1-carboxylate (Intermediate 64; 0.14 g, 0.22 mmol) DCM (1.5 mL) was added TFA (0.5 mL), and the mixture was stirred at 20° C. for 3 h. Solvent was removed in vacuum to dryness to give a residue which was purified by prep-HPLC (formic acid) to give the formate salt of the title compound (16.9 mg, 14.5% yield) as a white solid. MS (m/e): 531.2 (M+H)$^+$.

Example 168

1-[[1-[2-(Oxetan-3-ylamino)ethyl]-2-oxo-3-pyridyl]amino]-3-[4-(trifluoromethoxy)phenyl]-6,7-dihydro-5H-cyclopenta[d]pyridazin-4-one

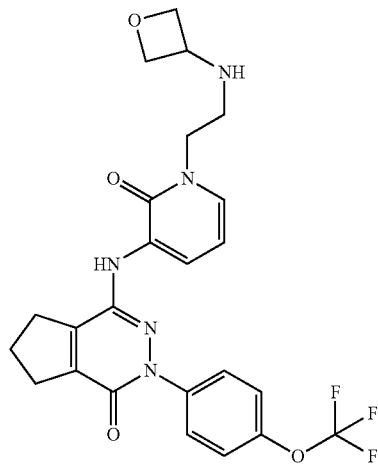 [SMILES: O=c1c(Nc2nn(-c3ccc(OC(F)(F)F)cc3)c(=O)c3c2CCC3)cccn1CCNC1COC1]

To a solution of 1-[[1-(2-hydroxyethyl)-2-oxo-3-pyridyl]amino]-3-[4-(trifluoromethoxy)phenyl]-6,7-dihydro-5H-cyclopenta[d]pyridazin-4-one (Intermediate 46; 200.0 mg, 0.44 mmol) and TEA (53.2 mg, 0.528 mmol) in DCM (5.0 mL) was added MsCl (60.4 mg, 0.528 mmol) at 0° C. under N$_2$, then the mixture was stirred at 20° C. for 1 h. The reaction was quenched by water (10.0 mL), extracted with DCM (10.0 mL), dried and concentrated to give a crude product (220 mg) which was used in next step. To this product in MeCN (5.0 mL) was added K$_2$CO$_3$ (121.6 mg, 0.88 mmol) and NaI (13.2 mg, 0.088 mmol), then oxetan-3-amine (CAS 21635-88-1; 64.4 mg, 0.88 mmol) was added 20° C. under N$_2$. The reaction was heated to 40° C. and stirred for 7 h. Solvent was removed in vacuum to dryness to give a residue which was purified by column chromatography on silica gel (EA to DCM/MeOH=30/1) to give crude product (100 mg). The crude product was purified by prep-HPLC (HCOOH) to give the title compound as its formate salt (37.6 mg, 14.4% yield) as a white solid. MS (m/e): 504.1 (M+H)$^+$.

Example 169

1-[[1-[2-(3-Hydroxyazetidin-1-yl)ethyl]-6-oxo-pyrimidin-5-yl]amino]-3-[4-(trifluoromethoxy)phenyl]-6,7-dihydro-5H-cyclopenta[d]pyridazin-4-one

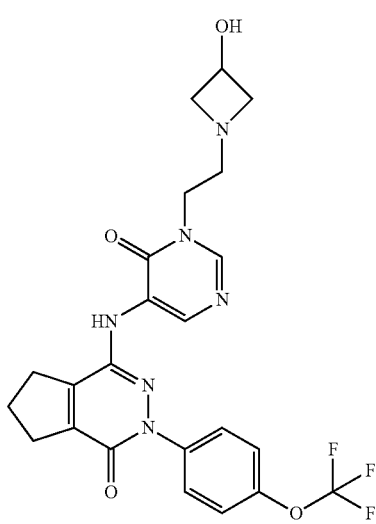 [SMILES: O=c1c(Nc2nn(-c3ccc(OC(F)(F)F)cc3)c(=O)c3c2CCC3)cncn1CCN1CC(O)C1]

The title compound was prepared from 1-[[1-(2-hydroxyethyl)-6-oxo-pyrimidin-5-yl]amino]-3-[4-(trifluoromethoxy)phenyl]-6,7-dihydro-5H-cyclopenta[d]pyridazin-4-one (example 47) and azetidin-3-ol hydrochloride (CAS 18621-18-6) using a method similar to that used to prepare example 168. MS (m/e): 505.2 (M+H)$^+$.

Example 170 trans-1-[[1-[(5-Amino-1,3-dioxan-2-yl)methyl]-2-oxo-3-pyridyl]amino]-3-[4-(trifluoromethoxy)phenyl]-6,7-dihydro-5H-cyclopenta[d]pyridazin-4-one

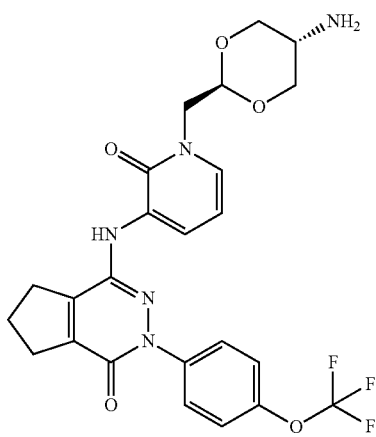 [SMILES: N[C@H]1CO[C@H](Cn2cccc(Nc3nn(-c4ccc(OC(F)(F)F)cc4)c(=O)c4c3CCC4)c2=O)OC1]

To a solution of trans-2-[2-[[2-oxo-3-[[4-oxo-3-[4-(trifluoromethoxy)phenyl]-6,7-dihydro-5H-cyclopenta[d]pyridazin-1-yl]amino]-1-pyridyl]methyl]-1,3-dioxan-5-yl]isoindoline-1,3-dione (Intermediate 69; 180 mg, 0.27 mmol) in EtOH (10 mL) was added NH$_2$NH$_2$.H$_2$O (2 mL). The reaction was heated to 70° C. and stirred for 5 hrs. The solvent was evaporated and the residue was purified by Prep-TLC (PE:EA=1:1) to give the title product (56.1 mg, yield 39.2%) as a white solid. MS (m/e): 520.0 (M+H)$^+$.

Example 171

1-[(1-Methyl-2-oxo-3-pyridyl)amino]-3-[2-methyl-4-(trifluoromethoxy)phenyl]-6,7-dihydro-5H-cyclopenta[d]pyridazin-4-one

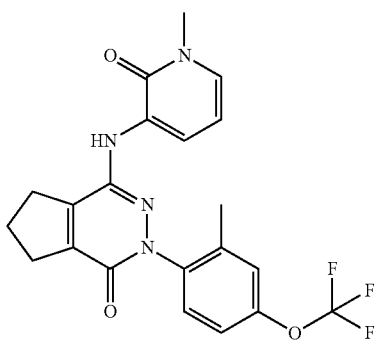 [SMILES: Cc1cc(OC(F)(F)F)ccc1-n1nc(Nc2cccn(C)c2=O)c2c(c1=O)CCC2]

The title compound was prepared from [3-[2-methyl-4-(trifluoromethoxy)phenyl]-4-oxo-6,7-dihydro-5H-cyclopenta[d]pyridazin-1-yl]trifluoromethanesulfonate (Intermediate 113) and 3-amino-1-methyl-pyridin-2-one (CAS 33631-01-5) using a procedure analogous to that used to prepare example 1. MS (m/e): 433.2 (M+H)$^+$.

Example 172

3-(3,4-Dimethoxyphenyl)-1-[(1-methyl-2-oxo-3-pyridyl)amino]-6,7-dihydro-5H-cyclopenta[d]pyridazin-4-one

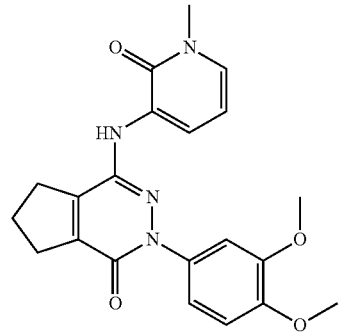 [SMILES: COc1ccc(-n2nc(Nc3cccn(C)c3=O)c3c(c2=O)CCC3)cc1OC]

The title compound was prepared from [3-(3,4-dimethoxyphenyl)-4-oxo-6,7-dihydro-5H-cyclopenta[d]pyridazin-1-yl]trifluoromethanesulfonate (Intermediate 114) and 3-amino-1-methyl-pyridin-2-one (CAS 33631-01-5) using a procedure analogous to that used to prepare example 1. MS (m/e): 395.2 (M+H)$^+$.

Example 173

3-[3-Methoxy-4-(trifluoromethyl)phenyl]-1-[(1-methyl-2-oxo-3-pyridyl)amino]-6,7-dihydro-5H-cyclopenta[d]pyridazin-4-one

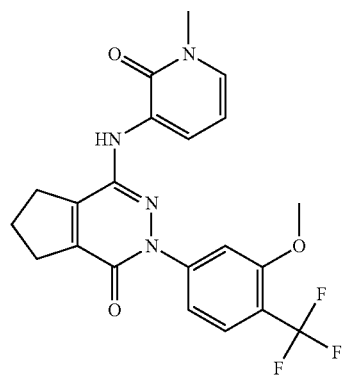 [SMILES: COc1cc(-n2nc(Nc3cccn(C)c3=O)c3c(c2=O)CCC3)ccc1C(F)(F)F]

The title compound was prepared from [3-[3-methoxy-4-(trifluoromethyl)phenyl]-4-oxo-6,7-dihydro-5H-cyclopenta[d]pyridazin-1-yl]trifluoromethanesulfonate (Intermediate 115) and 3-amino-1-methyl-pyridin-2-one (CAS 33631-01-5) using a procedure analogous to that used to prepare example 1. MS (m/e): 459.0 (M+H)$^+$.

Example 174

N,1-Dimethyl-6-oxo-5-[[4-oxo-3-[4-(trifluoromethoxy)phenyl]-5,6,7,8-tetrahydrophthalazin-1-yl]amino]pyridine-3-carboxamide

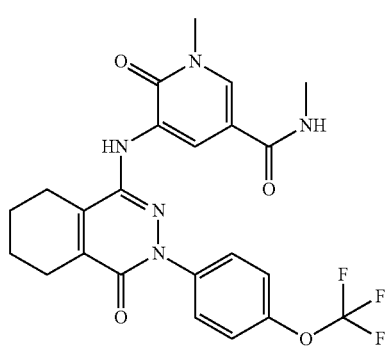 [SMILES: CNC(=O)c1cc(Nc2nn(-c3ccc(OC(F)(F)F)cc3)c(=O)c3c2CCCC3)c(=O)n(C)c1]

A mixture of 1-methyl-6-oxo-5-[[4-oxo-3-[4-(trifluoromethoxy)phenyl]-5,6,7,8-tetrahydrophthalazin-1-yl]amino]pyridine-3-carboxylic acid (Intermediate 116; 25 mg, 52.5 μmol), HATU (29.9 mg, 78.7 μmol), TEA (26.6 mg, 36.6 μl, 262 μmol) and methanamine hydrochloride (10.6 mg, 157 μmol) in acetonitrile (3 mL) and DCM (3 mL) was stirred at room temperature overnight. After evaporation of solvent, to the residue was added EA (5 mL) and water (5 mL), and a white solid was precipitated. The mixture was filtered, the solid residue was washed with a small amount of EA and water. The solid was collected and dried to give the title compound (16 mg, 62% yield). MS (m/e): 490.2 (M+H)$^+$.

Example 175

N,1-Dimethyl-6-oxo-5-[[4-oxo-3-[4-(trifluoromethoxy)phenyl]phthalazin-1-yl]amino]pyridine-3-carboxamide

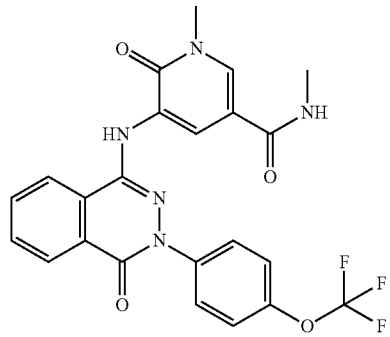 [SMILES: CNC(=O)c1cc(Nc2nn(-c3ccc(OC(F)(F)F)cc3)c(=O)c3ccccc23)c(=O)n(C)c1]

The title compound was prepared from 1-methyl-6-oxo-5-[[4-oxo-3-[4-(trifluoromethoxy)phenyl]phthalazin-1-yl]amino]pyridine-3-carboxylic acid (Intermediate 117) using a procedure analogous to that used to prepare Example 174. MS (m/e): 486.1 (M+H)$^+$.

Example 176

4-[[1-methyl-2-oxo-5-(trifluoromethyl)-3-pyridyl]amino]-2-[4-(trifluoromethoxy)phenyl]phthalazin-1-one

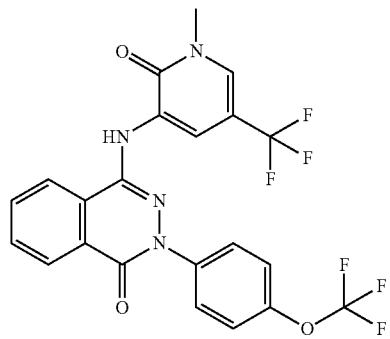 [SMILES: Cn1cc(C(F)(F)F)cc(Nc2nn(-c3ccc(OC(F)(F)F)cc3)c(=O)c3ccccc23)c1=O]

The title compound was prepared from 4-bromo-2-[4-(trifluoromethoxy)phenyl]phthalazin-1-one (Intermediate 29) and 3-amino-1-methyl-5-(trifluoromethyl)pyridin-2-one (CAS 1553950-73-4) using a procedure analogous to that used to prepare Example 1. MS (m/e): 497.2 (M+H)$^+$.

Example 177

Luciferase Reporter Assay ("LRA")

The assay used to determine the antiviral activity of the compounds of present invention is a standard in vitro virus reporter assay. Briefly, the inhibitory effect of the molecules tested is detected by measuring luminescence from the conversion of substrate by Nanoluc gene (NanoLuc® Luciferase by Promega, Madison/US) in the virus (proportional to virus quantity).

The luciferase reporter A/WSN/33 virus was engineered by the Mehle laboratory (Tran V. et al., *J Virol* (2013) 87(24):13321-13329). Despite the insertion of the "extremely bright luciferase variant NanoLuc" at the 3' end of PA (see below for the details of insertion), this system was shown to behave similarly to the Wild type virus and to recapitulate known antiviral treatment. These characteristics made it a valuable tool for our Roche Flu programs and was validated with compounds described as targeting the flu Cap and Endo.

Virus

The reporter Influenza A/WSN/33-Luciferase virus (from Dr Andrew Mehle, Department of Medical Microbiology and Immunology, University of Wisconsin, USA) was produced in MDBK cells, aliquoted and stored at −80° C. Viral stock titers were determined by plaque assay in-house and the quality of the newly produced stock was confirmed by deep-sequencing in-house as well.

The Nano-Luc cassette was inserted at the 3' end of PA with a self-cleaving 2A peptide to generate discrete PA and NLuc proteins. Repeated regions of the PA ORF that contain packaging signal were introduced at the 3'end of NLuc. Silent mutations were introduced at the 3' end of PA to avoid duplication with the packaging signal at the 3' end of NLuc.

Cells

Madin-Darby bovine kidney cells MDBK (from Roche Non-Clinical Biosample Repository (RNCB), Basel/CH, number CL002178) were cultivated in MEM/Glutamax I supplemented with heat-inactivated 10% FBS (Gibco, Thermo Fisher, Waltham/US, batch 1420751) and 1% Pen/Strep.

Human lung cells A549 (from RNCB, number CL000104) were cultured in DMEM High Glucose/Glutamax I supplemented with heat-inactivated 10% FBS (Gibco, batch 1420751) and 1% Pen/Strep ("Growth Medium" or "GM"). Compound treatments and infection were performed in DMEM High Glucose/Glutamax I supplemented with 1% Pen/Strep, 0.3% BSA and 25 mM HEPES ("Infection Medium" or "IM").

Infection and Treatment of A549 Cells

Compound plates with compounds diluted in 100% DMSO were kept at −20° C. till use.

A549 cells 95% confluent were trypsinized, counted, seeded at 5,000 cells/well in TC-treated optical 384-well plates and incubated for 24 h at 37° C. 5% $CO_2$. Cells were then washed with 25 µl PBS 1× and infected with 10 µl of A/WSN/33-Luc virus at an MOI of 0.1 for 1 h. 15 µl of culture media and 2.7 µl of compounds (final concentration of 1% DMSO) were added on top. Three days later, the antiviral activity of compounds was determined by measure of the Luciferase signal using the NanoGlo® Luciferase Assay System (Promega Cat. No 1120). 18 µl of NanoGlo Reagent was added on top of cells, incubated for 10 minutes with shaking and the luciferase signal was measured using a Paradigm instrument using 0.14 second reading time In parallel, a series of uninfected A549 cells were treated similarly with compounds from the same master plate to determine the cytotoxicity of the compounds. No infection was carried out. Cell viability was determined 72 h post treatment using 18 µl of CellTiter-Glo® Luminescent Cell Viability Assay (Promega, Cat. no. G7572).

The table below provides IC50 values for antiviral activity obtained according to the above Luciferase reporter assay for the compounds of the present invention. Particular compounds of the present invention exhibit IC50 values ≤5000 nM, more particular compounds of the present invention exhibit IC50 values ≤500 nM, even more particular compounds of the present invention exhibit IC50 values ≤50 nM, most particular compounds of the present invention exhibit IC50 values ≤20 nM.

| Ex. | IC50 [nM] |
|---|---|
| 1 | 22 |
| 2 | 54 |
| 3 | 38 |
| 4 | 489 |
| 5 | 485 |
| 6 | 52 |
| 7 | 4340 |
| 8 | 73 |
| 9 | 275 |
| 10 | 259 |
| 11 | 2010 |
| 12 | 407 |
| 13 | 1510 |
| 14 | 109 |
| 15 | 132 |
| 16 | 12 |
| 17 | 100 |
| 18 | 122 |
| 19 | 59500 |
| 20 | 4 |
| 21 | 5 |
| 22 | 16 |
| 23 | 712 |
| 24 | 22 |
| 25 | 14 |
| 26 | 25 |
| 27 | 41 |
| 28 | 8 |
| 29 | 22 |
| 30 | 37 |
| 31 | 8 |
| 32 | 12 |
| 33 | 6 |
| 34 | 195 |
| 35 | 68 |
| 36 | 579 |
| 37 | 20 |
| 38 | 23 |
| 39 | 230 |
| 40 | 100 |
| 41 | 60 |
| 42 | 40 |
| 43 | 84 |
| 44 | 28 |
| 45 | 286 |
| 46 | 33 |
| 47 | 71 |
| 48 | 18 |
| 49 | 16 |
| 50 | 28 |
| 51 | 44 |
| 52 | 62 |
| 53 | 24 |
| 54 | 52 |
| 55 | 303 |
| 56 | 278 |
| 57 | 352 |
| 58 | 17 |
| 59 | 137 |
| 60 | 11 |
| 61 | 60 |
| 62 | 186 |
| 63 | 33 |
| 64 | 355 |
| 65 | 405 |
| 66 | 36 |
| 67 | 563 |
| 68 | 1710 |
| 69 | 228 |
| 70 | 19 |
| 71 | 54 |
| 72 | 24 |
| 73 | 49 |

| Ex. | IC50 [nM] |
|---|---|
| 74 | 34 |
| 75 | 25 |
| 76 | 34 |
| 77 | 108 |
| 78 | 31 |
| 79 | 32 |
| 80 | 68 |
| 81 | 465 |
| 82 | 79 |
| 83 | 1490 |
| 84 | 176 |
| 85 | 56 |
| 86 | 34 |
| 87 | 17 |
| 88 | 23 |
| 89 | 38 |
| 90 | 162 |
| 91 | 41 |
| 92 | 178 |
| 93 | 166 |
| 94 | 45 |
| 95 | 102 |
| 96 | 42 |
| 97 | 9 |
| 98 | 10 |
| 99 | 291 |
| 100 | 36 |
| 101 | 109 |
| 102 | 37 |
| 103 | 38 |
| 104 | 39 |
| 105 | 15 |
| 106 | 14 |
| 107 | 49 |
| 108 | 29 |
| 109 | 842 |
| 110 | 482 |
| 111 | 1510 |
| 112 | 2990 |
| 113 | 161 |
| 114 | 110 |
| 115 | 180 |
| 116 | 261 |
| 117 | 114 |
| 118 | 953 |
| 119 | 3760 |
| 120 | 1125 |
| 121 | 156 |
| 122 | 3710 |
| 123 | 485 |
| 124 | 4930 |
| 125 | 88 |
| 126 | 191 |
| 127 | 33 |
| 128 | 92 |
| 129 | 79 |
| 130 | 62 |
| 131 | 30 |
| 132 | 87 |
| 133 | 538 |
| 134 | 521 |
| 135 | 85 |
| 136 | 61 |
| 137 | 136 |
| 138 | 110 |
| 139 | 62 |
| 140 | 32 |
| 141 | 12 |
| 142 | 46 |
| 143 | 271 |
| 144 | 625 |
| 145 | 129 |
| 146 | 167 |
| 147 | 76 |
| 148 | 19 |
| 149 | 71 |
| 150 | 104 |
| 151 | 372 |
| 152 | 32 |
| 153 | 61 |
| 154 | 144 |
| 155 | 86 |
| 156 | 266 |
| 157 | 167 |
| 158 | 105 |
| 159 | 186 |
| 160 | 86 |
| 161 | 112 |
| 162 | 1400 |
| 163 | 62 |
| 164 | 46 |
| 165 | 24 |
| 166 | 107 |
| 167 | 148 |
| 168 | 24 |
| 169 | 307 |
| 170 | 83 |
| 171 | 6830 |
| 172 | 3480 |
| 173 | 74600 |
| 174 | 14600 |
| 175 | 74400 |
| 176 | 80500 |

The invention claimed is:
1. A compound of formula (I)

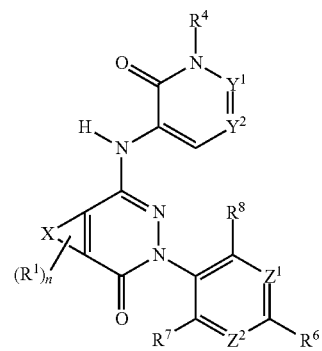

wherein
X is —$CH_2$—$CH_2$—$CH_2$—, —CH=CH—CH=CH—, —$CH_2$—$CH_2$—$CH_2$—$CH_2$—, —$CH_2$—O—$CH_2$—$CH_2$—, $CH_2$—$CH_2$—O—$CH_2$—, —$CH_2$—$NR^2$—$CH_2$—$CH_2$—, or —$CH_2$—$CH_2$—$NR^2$—$CH_2$—;
n is 0, 1 or 2;
each $R^1$ is independently selected from halo, $C_{1-7}$ alkyl, $C_{2-7}$ alkenyl, hydroxy, $C_{1-7}$ alkoxy, $NR^{10}R^{11}$, and $CONR^{10}R^{11}$;
wherein $C_{1-7}$ alkyl and $C_{1-7}$ alkoxy are optionally substituted by one or more $C_{1-7}$ alkyl, hydroxy, $C_{1-7}$ alkoxy, $NR^{10}R^{11}$ or $COR^9$;
$R^2$ is H, $C_{1-7}$ alkyl, hydroxy-$C_{1-7}$ alkyl, $COR^9$, $CONR^{10}R^{11}$, or $SO_2$—$C_{1-7}$ alkyl;
$Y^1$ is N, CH or $CCH_3$,
$Y^2$ is N or $CR^3$;
with the proviso that not both of $Y^1$ and $Y^2$ are N;
$R^3$ is H, halogen, $C_{1-7}$ alkyl, halo-$C_{1-7}$ alkyl, $CONR^{10}R^{11}$ or CO—$C_{1-7}$ alkoxy;

R⁴ is H or C₁₋₇ alkyl, wherein C₁₋₇ alkyl is optionally substituted with one or more R⁵;

each R⁵ is independently selected from hydroxy, C₁₋₇ alkoxy, NR¹²R¹³, COR⁹, CONR¹⁰R¹¹, SO₂—C₁₋₇ alkyl, SO₂—NR¹⁰R¹¹, heterocycloalkyl and heteroaryl;
wherein C₁₋₇ alkoxy is optionally substituted by COR⁹ or CONR¹⁰R¹¹;
wherein heterocycloalkyl and heteroaryl are optionally substituted with one or more substituents selected from halo, C₁₋₇ alkyl, halo-C₁₋₇ alkyl, hydroxy, C₁₋₇ alkoxy, oxo, COR⁹, C₁₋₇ alkyl-COR⁹ or NR¹⁰R¹¹;

Z¹ is N, CH or CO—CH₃;
Z² is N or CH;
R⁶ is C₁₋₇ alkyl, hydroxy-C₁₋₇ alkyl, halo-C₁₋₇ alkyl, C₁₋₇ alkoxy-C₁₋₇ alkyl, C₁₋₇ alkoxy, halo-C₁₋₇ alkoxy, C₁₋₇ alkoxy-C₁₋₇ alkoxy, S-halo-C₁₋₇ alkyl, SF₅, C₃₋₇ cycloalkyl, heterocycloalkyl or heterocycloalkyl substituted by C₁₋₇ alkyl;
R⁷ is H, halogen or C₁₋₇ alkyl;
R⁸ is H, halogen or C₁₋₇ alkyl;
R⁹ is H, C₁₋₇ alkyl, hydroxy, or C₁₋₇ alkoxy;
R¹⁰ is H or C₁₋₇ alkyl;
wherein C₁₋₇ alkyl is optionally substituted with one or more hydroxy, C₁₋₇ alkoxy, COOH, or CO—C₁₋₇ alkoxy;
R¹¹ is H, C₁₋₇ alkyl, CO—C₁₋₇ alkoxy or heterocycloalkyl;
wherein C₁₋₇ alkyl is optionally substituted with one or more hydroxy, C₁₋₇ alkoxy, NH₂, N(C₁₋₇ alkyl)₂, COOH, or CO—C₁₋₇ alkoxy;
or R¹⁰ and R¹¹ together with the interconnecting nitrogen form a heterocycloalkyl which is optionally substituted with one or more halo, C₁₋₇ alkyl, halo-C₁₋₇ alkyl, hydroxy, C₁₋₇ alkoxy, oxo, COOH, CO—C₁₋₇ alkoxy or NH₂;
R¹² is H or C₁₋₇ alkyl;
wherein C₁₋₇ alkyl is optionally substituted with one or more hydroxy, C₁₋₇ alkoxy, COOH, or CO—C₁₋₇ alkoxy;
R¹³ is H, C₁₋₇ alkyl, CO—C₁₋₇ alkoxy or heterocycloalkyl,
wherein C₁₋₇ alkyl is optionally substituted with one or more hydroxy, C₁₋₇ alkoxy, NH₂, N(C₁₋₇ alkyl)₂, COOH, or CO—C₁₋₇ alkoxy;
or a pharmaceutically acceptable salt thereof.

2. The compound of claim 1 having formula (IA)

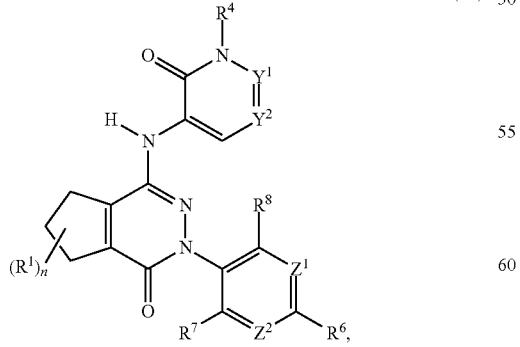

(IA)

wherein Y¹, Y², Z¹, Z², n, R¹, R⁴ and R⁶ to R⁸ are as described in claim 1, or a pharmaceutically acceptable salt thereof.

3. The compound of claim 1 having formula (IB)

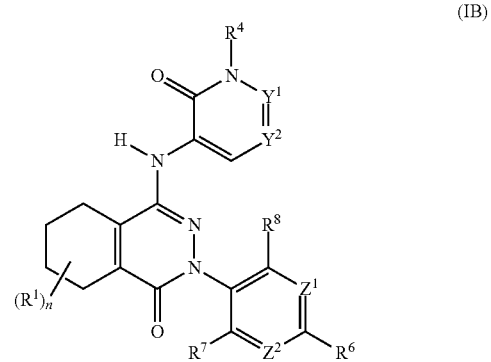

(IB)

wherein Y¹, Y², Z¹, Z², n, R¹, R⁴ and R⁶ to R⁸ are as described in claim 1, or a pharmaceutically acceptable salt thereof.

4. The compound of claim 1 having formula (IC)

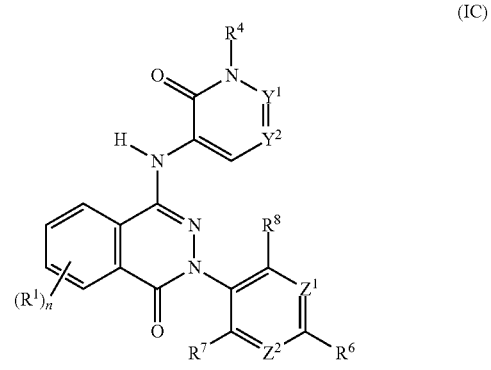

(IC)

wherein Y¹, Y², Z¹, Z², n, R¹, R⁴ and R⁶ to R⁸ are as described in claim 1, or a pharmaceutically acceptable salt thereof.

5. The compound of claim 1 having formula (ID)

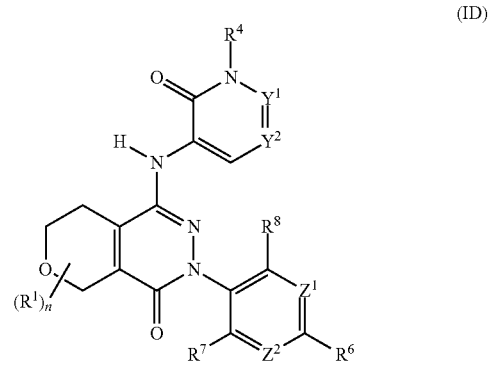

(ID)

wherein Y¹, Y², Z¹, Z², n, R¹, R⁴ and R⁶ to R⁸ are as described herein, or a pharmaceutically acceptable salt thereof.

6. The compound of claim 1 having formula (IE)

(IE)

wherein $Y^1$, $Y^2$, $Z^1$, $Z^2$, n, $R^1$, $R^4$ and $R^6$ to $R^8$ are as described herein, or a pharmaceutically acceptable salt thereof.

7. The compound of claim 1 having formula (IF)

(IF)

wherein $Y^1$, $Y^2$, $Z^1$, $Z^2$, n, $R^1$, $R^2$, $R^4$ and $R^6$ to $R^8$ are as described in claim 1, or a pharmaceutically acceptable salt thereof.

8. The compound of claim 1 having formula (IG)

(IG)

wherein $Y^1$, $Y^2$, $Z^1$, $Z^2$, n, $R^1$, $R^2$, $R^4$ and $R^6$ to $R^8$ are as described in claim 1, or a pharmaceutically acceptable salt thereof.

9. The compound of claim 1, wherein n is 0 or 1.

10. The compound of claim 1, wherein each $R^1$ is independently selected from $C_{1-7}$ alkyl, hydroxy, $C_{1-7}$ alkoxy, and $NR^{10}R^{11}$; wherein $C_{1-7}$ alkyl is optionally substituted by one hydroxy.

11. The compound of claim 1, wherein each $R^1$ is independently selected from fluoro, methyl, ethyl, ethenyl, hydroxy, methoxy, ethoxy, $NH_2$ and $CONH_2$;
wherein methyl, ethyl, methoxy, and ethoxy are optionally substituted by one methyl, hydroxy, methoxy, $NH_2$ or $N(CH_3)_2$.

12. The compound of claim 1, wherein $R^2$ is $COR^9$.

13. The compound of claim 1, wherein $R^2$ is H, methyl, ethyl, isopropyl, propyl, isobutyl, hydroxy-methyl, hydroxy-ethyl, hydroxy-isopropyl, hydroxy-propyl, hydroxy-isobutyl, COH, $COCH_3$, $COOCH_3$, $CONHCH_3$, or $SO_2$—$CH_3$.

14. The compound of claim 1, wherein $Y^1$ is N or CH, with the proviso that not both of $Y^1$ and $Y^2$ are N.

15. The compound of claim 1, wherein $Y^2$ is $CR^3$.

16. The compound of claim 1, wherein $R^3$ is H, halogen, or $C_{1-7}$ alkyl.

17. The compound of claim 1, wherein $R^3$ is H, fluoro, chloro, methyl, ethyl, isopropyl, trifluoromethyl, $CONHCH_3$ or $COOCH_3$.

18. The compound of claim 1, wherein $R^4$ is H or $C_{1-7}$ alkyl, wherein $C_{1-7}$ alkyl is optionally substituted with one $R^5$.

19. The compound of claim 1, wherein $R^4$ is H, methyl, ethyl, propyl or isobutyl, wherein methyl, ethyl, propyl and isobutyl are optionally substituted with one or two $R^5$.

20. The compound of claim 1, wherein each $R^5$ is independently selected from hydroxy, $C_{1-7}$ alkoxy, $NR^{12}R^{13}$, $COR^9$, $CONR^{10}R^{11}$, $SO_2$—$C_{1-7}$ alkyl, $SO_2$—$NR^{10}R^{11}$, heterocycloalkyl and heteroaryl;
wherein $C_{1-7}$ alkoxy is optionally substituted by $COR^9$ or $CONR^{10}R^{11}$;
wherein heterocycloalkyl and heteroaryl are optionally substituted with one or two substituents selected from halo, $C_{1-7}$ alkyl, halo-$C_{1-7}$ alkyl, hydroxy, $C_{1-7}$ alkoxy, oxo, $COR^9$, $C_{1-7}$ alkyl-$COR^9$ and $NR^{10}R^{11}$.

21. The compound of claim 1, wherein each $R^5$ is independently selected from hydroxy, methoxy, $NH_2$, $NHCH_3$, $N(CH_3)$, $N(CH_2CH_3)_2$, $NH(CH_2COOH)$, $NH(COO$-tert-butyl), $N(CH_3)(CH_2COOH)$, $N(CH_2COOH)(COO$-tert-butyl), NH(oxetanyl), COOH, $COOCH_3$, $CONH_2$, $CONH(CH_3)$, $CONH(CH_2CH_2N(CH_3)_2$, $CONH(CH_2CH_2OH)$, $CONH(CH_2CH_2CH_2OCH_3)$, $CONH(CH(CH_3)_2)$, $CON(CH_3)_2$, $SO_2$-methyl, $SO_2$—$NH_2$, azetidinyl, pyrrolidinyl, piperazinyl, morpholinyl and imidazolyl;
wherein methoxy is optionally substituted by COOH, $COOCH_2CH_3$, $CONH(CH_3)$, or $CON(CH_3)_2$;
wherein azetidinyl, pyrrolidinyl, piperazinyl, morpholinyl and imidazolyl are optionally substituted with one or two substituents selected from methyl, trifluoromethyl, hydroxy, methoxy, COOH, $COOCH_3$, and $COOCH_2CH_3$.

22. The compound of claim 1, wherein $Z^1$ is N or CH.

23. The compound of claim 1, wherein $Z^2$ is CH.

24. The compound of claim 1, wherein $R^6$ is $C_{1-7}$ alkyl, halo-$C_{1-7}$ alkyl, or halo-$C_{1-7}$ alkoxy.

25. The compound of claim 1, wherein $R^6$ is tert-butyl, hydroxy-isopropyl, trifluoromethyl, methoxy, ethoxy, methoxy-ethoxy, difluoromethoxy, trifluoromethoxy, cyclopropyl, oxetanyl or methyl-oxetanyl.

26. The compound of claim 1, wherein $R^7$ is H.

27. The compound of claim 1, wherein $R^8$ is H, fluoro or methyl.

28. The compound of claim 1, wherein $R^9$ is H, $C_{1-7}$ alkyl or $C_{1-7}$ alkoxy.

29. The compound of claim 1, wherein $R^9$ is H, methyl, hydroxy, methoxy or ethoxy.

30. The compound of claim 1, wherein $R^{10}$ is H, $C_{1-7}$ alkyl or $C_{1-7}$ alkyl substituted with one COOH.

31. The compound of claim 1, wherein $R^{10}$ is H, methyl, ethyl or $CH_2$—COOH.

32. The compound of claim 1, wherein $R^{11}$ is H, $C_{1-7}$ alkyl, $C_{1-7}$ alkyl substituted with one hydroxy, $C_{1-7}$ alkyl substituted with one $C_{1-7}$ alkoxy, $C_{1-7}$ alkyl substituted with one $N(CH_3)_2$, $C_{1-7}$ alkyl substituted with one COOH, CO—$C_{1-7}$ alkoxy or heterocycloalkyl.

33. The compound of claim 1, wherein $R^{11}$ is H, methyl, ethyl, isopropyl, hydroxy-ethyl, methoxy-propyl, ethyl substituted with one $N(CH_3)_2$, $CH_2$—COOH, CO-tert-butoxy or oxetanyl.

34. The compound of claim 1, wherein $R^{10}$ and $R^{11}$ together with the interconnecting nitrogen form azetidinyl, piperazinyl, morpholinyl, imidazolyl or pyrrolidinyl, each optionally substituted with one or two halo, $C_{1-7}$ alkyl, halo-$C_{1-7}$ alkyl, hydroxy, $C_{1-7}$ alkoxy, oxo, COOH, CO—$C_{1-7}$ alkoxy or $NH_2$.

35. The compound of claim 1, wherein $R^{10}$ and $R^{11}$ together with the interconnecting nitrogen form azetidinyl, piperazinyl, morpholinyl, imidazolyl or pyrrolidinyl, each optionally substituted with one or two methyl, trifluoromethyl, hydroxy, methoxy, COOH, CO-methoxy or CO-ethoxy.

36. The compound of claim 1, wherein $R^{12}$ is H, $C_{1-7}$ alkyl or alkyl substituted by one COOH.

37. The compound of claim 1, wherein $R^{12}$ is H, $C_{1-7}$ alkyl, $C_{1-7}$ alkyl substituted with one COOH, CO—$C_{1-7}$ alkoxy or heterocycloalkyl.

38. The compound of claim 1, selected from the group consisting of:
- 4-[(1-methyl-2-oxo-3-pyridyl)amino]-2-[4-(trifluoromethoxy)phenyl]phthalazin-1-one;
- 4-[(2-oxo-1H-pyridin-3-yl)amino]-2-[4-(trifluoromethoxy)phenyl]phthalazin-1-one; methyl 2-[2-oxo-3-[[4-oxo-3-[4-(trifluoromethoxy)phenyl]phthalazin-1-yl]amino]-1-pyridyl]acetate;
- methyl 2,2-dimethyl-3-[2-oxo-3-[[4-oxo-3-[4-(trifluoromethoxy)phenyl]phthalazin-1-yl]amino]-1-pyridyl]propanoate;
- ethyl 2-[2-[2-oxo-3-[[4-oxo-3-[4-(trifluoromethoxy)phenyl]phthalazin-1-yl]amino]-1-pyridyl]ethoxy]acetate;
- methyl (2R)-1-[2-[2-oxo-3-[[4-oxo-3-[4-(trifluoromethoxy)phenyl]phthalazin-1-yl]amino]-1-pyridyl]ethyl]pyrrolidine-2-carboxylate;
- 4-[(1-methyl-2-oxo-3-pyridyl)amino]-2-[2-methyl-4-(trifluoromethoxy)phenyl]phthalazin-1-one;
- 2-(6-tert-butyl-3-pyridyl)-4-[(1-methyl-2-oxo-3-pyridyl)amino]phthalazin-1-one;
- 2-(2-tert-butylpyrimidin-5-yl)-4-[(1-methyl-2-oxo-3-pyridyl)amino]phthalazin-1-one;
- 2-[4-(3-methyloxetan-3-yl)phenyl]-4-[(1-methyl-2-oxo-3-pyridyl)amino]phthalazin-1-one;
- 4-[(1-methyl-2-oxo-3-pyridyl)amino]-2-[4-(oxetan-3-yl)phenyl]phthalazin-1-one;
- 2-(4-cyclopropylphenyl)-4-[(1-methyl-2-oxo-3-pyridyl)amino]phthalazin-1-one;
- 2-[4-(2-methoxyethyl)phenyl]-4-[(1-methyl-2-oxo-3-pyridyl)amino]phthalazin-1-one;
- 2-(4-tert-butylphenyl)-4-[(1-methyl-2-oxo-3-pyridyl)amino]phthalazin-1-one;
- 2-(4-tert-butylphenyl)-4-[(2-oxo-1H-pyridin-3-yl)amino]phthalazin-1-one;
- 7-methoxy-4-[(1-methyl-2-oxo-3-pyridyl)amino]-2-[4-(trifluoromethoxy)phenyl]phthalazin-1-one;
- 8-fluoro-4-[(1-methyl-2-oxo-3-pyridyl)amino]-2-[4-(trifluoromethoxy)phenyl]phthalazin-1-one;
- 5-fluoro-4-[(1-methyl-2-oxo-3-pyridyl)amino]-2-[4-(trifluoromethoxy)phenyl]phthalazin-1-one;
- 5-methoxy-4-[(1-methyl-2-oxo-3-pyridyl)amino]-2-[4-(trifluoromethoxy)phenyl]phthalazin-1-one;
- 2-(4-tert-butylphenyl)-7-ethyl-4-[(1-methyl-2-oxo-3-pyridyl)amino]phthalazin-1-one;
- 4-[(1-methyl-2-oxo-3-pyridyl)amino]-2-[4-(trifluoromethoxy)phenyl]-5,6,7,8-tetrahydrophthalazin-1-one;
- 4-[(1-methyl-6-oxo-pyrimidin-5-yl)amino]-2-[4-(trifluoromethoxy)phenyl]-5,6,7,8-tetrahydrophthalazin-1-one;
- methyl 1-methyl-6-oxo-5-[[4-oxo-3-[4-(trifluoromethoxy)phenyl]-5,6,7,8-tetrahydrophthalazin-1-yl]amino]pyridine-3-carboxylate;
- methyl 2-[2-oxo-3-[[4-oxo-3-[4-(trifluoromethoxy)phenyl]-5,6,7,8-tetrahydrophthalazin-1-yl]amino]-1-pyridyl]acetate;
- 4-[[1-[2-(dimethylamino)ethyl]-6-oxo-pyrimidin-5-yl]amino]-2-[4-(trifluoromethoxy)phenyl]-5,6,7,8-tetrahydrophthalazin-1-one;
- 2-(6-tert-butyl-3-pyridyl)-4-[(1-methyl-2-oxo-3-pyridyl)amino]-5,6,7,8-tetrahydrophthalazin-1-one;
- 2-[4-(difluoromethoxy)phenyl]-4-[(1-methyl-2-oxo-3-pyridyl)amino]-5,6,7,8-tetrahydrophthalazin-1-one;
- 1-[(1-methyl-2-oxo-3-pyridyl)amino]-3-[4-(trifluoromethoxy)phenyl]-6,7-dihydro-5H-cyclopenta[d]pyridazin-4-one;
- 1-[(2,6-dimethyl-3-oxo-pyridazin-4-yl)amino]-3-[4-(trifluoromethoxy)phenyl]-6,7-dihydro-5H-cyclopenta[d]pyridazin-4-one;
- 1-[(1-methyl-6-oxo-pyrimidin-5-yl)amino]-3-[4-(trifluoromethoxy)phenyl]-6,7-dihydro-5H-cyclopenta[d]pyridazin-4-one;
- 1-[(5-fluoro-1-methyl-2-oxo-3-pyridyl)amino]-3-[4-(trifluoromethoxy)phenyl]-6,7-dihydro-5H-cyclopenta[d]pyridazin-4-one;
- 1-[(1,5-dimethyl-2-oxo-3-pyridyl)amino]-3-[4-(trifluoromethoxy)phenyl]-6,7-dihydro-5H-cyclopenta[d]pyridazin-4-one;
- 1-[(5-chloro-1-methyl-2-oxo-3-pyridyl)amino]-3-[4-(trifluoromethoxy)phenyl]-6,7-dihydro-5H-cyclopenta[d]pyridazin-4-one;
- 1-[[1-methyl-2-oxo-5-(trifluoromethyl)-3-pyridyl]amino]-3-[4-(trifluoromethoxy)phenyl]-6,7-dihydro-5H-cyclopenta[d]pyridazin-4-one;
- 1-[(5-ethyl-1-methyl-2-oxo-3-pyridyl)amino]-3-[4-(trifluoromethoxy)phenyl]-6,7-dihydro-5H-cyclopenta[d]pyridazin-4-one;
- 1-[(5-isopropyl-1-methyl-2-oxo-3-pyridyl)amino]-3-[4-(trifluoromethoxy)phenyl]-6,7-dihydro-5H-cyclopenta[d]pyridazin-4-one;
- methyl 4-[5-chloro-2-oxo-3-[[4-oxo-3-[4-(trifluoromethoxy)phenyl]-6,7-dihydro-5H-cyclopenta[d]pyridazin-1-yl]amino]-1-pyridyl]butanoate;
- methyl 4-[2-oxo-3-[[4-oxo-3-[4-(trifluoromethoxy)phenyl]-6,7-dihydro-5H-cyclopenta[d]pyridazin-1-yl]amino]-1-pyridyl]butanoate;
- ethyl 2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetate;

1-[[1-(2-imidazol-1-ylethyl)-2-oxo-3-pyridyl]amino]-3-[4-(trifluoromethoxy)phenyl]-6,7-dihydro-5H-cyclopenta[d]pyridazin-4-one;
ethyl 4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-2-carboxylate;
1-[[1-[2-(3-methoxypyrrolidin-1-yl)ethyl]-2-oxo-3-pyridyl]amino]-3-[4-(trifluoromethoxy)phenyl]-6,7-dihydro-5H-cyclopenta[d]pyridazin-4-one;
2-[tert-butoxycarbonyl-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]amino]acetic acid;
1-[[1-(3-morpholinopropyl)-2-oxo-3-pyridyl]amino]-3-[4-(trifluoromethoxy)phenyl]-6,7-dihydro-5H-cyclopenta[d]pyridazin-4-one;
tert-butyl N-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]carbamate;
1-[[1-[2-(3-hydroxyazetidin-1-yl)ethyl]-2-oxo-3-pyridyl]amino]-3-[4-(trifluoromethoxy)phenyl]-6,7-dihydro-5H-cyclopenta[d]pyridazin-4-one;
1-[[1-(2-hydroxyethyl)-6-oxo-pyrimidin-5-yl]amino]-3-[4-(trifluoromethoxy)phenyl]-6,7-dihydro-5H-cyclopenta[d]pyridazin-4-one;
1-[[1-[3-(4-methylpiperazin-1-yl)propyl]-2-oxo-3-pyridyl]amino]-3-[4-(trifluoromethoxy)phenyl]-6,7-dihydro-5H-cyclopenta[d]pyridazin-4-one;
1-[[1-(3-hydroxypropyl)-2-oxo-3-pyridyl]amino]-3-[4-(trifluoromethoxy)phenyl]-6,7-dihydro-5H-cyclopenta[d]pyridazin-4-one;
1-[[1-[2-(dimethylamino)ethyl]-6-oxo-pyrimidin-5-yl]amino]-3-[4-(trifluoromethoxy)phenyl]-6,7-dihydro-5H-cyclopenta[d]pyridazin-4-one;
1-[[1-[2-(diethylamino)ethyl]-6-oxo-pyrimidin-5-yl]amino]-3-[4-(trifluoromethoxy)phenyl]-6,7-dihydro-5H-cyclopenta[d]pyridazin-4-one;
1-[[6-oxo-1-(2-pyrrolidin-1-ylethyl)pyrimidin-5-yl]amino]-3-[4-(trifluoromethoxy)phenyl]-6,7-dihydro-5H-cyclopenta[d]pyridazin-4-one;
3-(4-tert-butyl-2-fluoro-phenyl)-1-[(1-methyl-2-oxo-3-pyridyl)amino]-6,7-dihydro-5H-cyclopenta[d]pyridazin-4-one;
3-[2-fluoro-4-(trifluoromethyl)phenyl]-1-[(1-methyl-2-oxo-3-pyridyl)amino]-6,7-dihydro-5H-cyclopenta[d]pyridazin-4-one;
3-(6-ethoxy-3-pyridyl)-1-[(1-methyl-2-oxo-3-pyridyl)amino]-6,7-dihydro-5H-cyclopenta[d]pyridazin-4-one;
3-(6-methoxy-3-pyridyl)-1-[(1-methyl-2-oxo-3-pyridyl)amino]-6,7-dihydro-5H-cyclopenta[d]pyridazin-4-one;
1-[(5-fluoro-1-methyl-2-oxo-3-pyridyl)amino]-3-(6-methoxy-3-pyridyl)-6,7-dihydro-5H-cyclopenta[d]pyridazin-4-one;
3-(6-tert-butyl-3-pyridyl)-1-[(1-methyl-2-oxo-3-pyridyl)amino]-6,7-dihydro-5H-cyclopenta[d]pyridazin-4-one;
3-[4-(difluoromethoxy)phenyl]-1-[(1-methyl-2-oxo-3-pyridyl)amino]-6,7-dihydro-5H-cyclopenta[d]pyridazin-4-one;
1-[(1-methyl-2-oxo-3-pyridyl)amino]-3-[4-(trifluoromethyl)phenyl]-6,7-dihydro-5H-cyclopenta[d]pyridazin-4-one;
6,6-dimethyl-1-[(1-methyl-2-oxo-3-pyridyl)amino]-3-[4-(trifluoromethoxy)phenyl]-5,7-dihydrocyclopenta[d]pyridazin-4-one;
1-[(1-methyl-2-oxo-3-pyridyl)amino]-3-[4-(trifluoromethoxy)phenyl]-7,8-dihydro-5H-pyrano[3,4-d]pyridazin-4-one;
4-[(1-methyl-2-oxo-3-pyridyl)amino]-2-[4-(trifluoromethoxy)phenyl]-7,8-dihydro-5H-pyrano[3,4-d]pyridazin-1-one;
4-[(1,6-dimethyl-2-oxo-3-pyridyl)amino]-2-[4-(trifluoromethoxy)phenyl]phthalazin-1-one;
4-[(2-methyl-6-oxo-1H-pyrimidin-5-yl)amino]-2-[4-(trifluoromethoxy)phenyl]phthalazin-1-one;
4-[(1-methyl-6-oxo-pyrimidin-5-yl)amino]-2-[4-(trifluoromethoxy)phenyl]phthalazin-1-one;
4-[(5-ethyl-1-methyl-2-oxo-3-pyridyl)amino]-2-[4-(trifluoromethoxy)phenyl]phthalazin-1-one;
4-[(6-methyl-2-oxo-1H-pyridin-3-yl)amino]-2-[4-(trifluoromethoxy)phenyl]phthalazin-1-one;
methyl 3-[2-oxo-3-[[4-oxo-3-[4-(trifluoromethoxy)phenyl]phthalazin-1-yl]amino]-1-pyridyl]propanoate;
4-[[1-[2-(dimethylamino)ethyl]-2-oxo-3-pyridyl]amino]-2-[4-(trifluoromethoxy)phenyl]phthalazin-1-one;
4-[[1-(2-methoxyethyl)-2-oxo-3-pyridyl]amino]-2-[4-(trifluoromethoxy)phenyl]phthalazin-1-one;
4-[[1-(2-methylsulfonylethyl)-2-oxo-3-pyridyl]amino]-2-[4-(trifluoromethoxy)phenyl]phthalazin-1-one;
methyl 4-[2-oxo-3-[[4-oxo-3-[4-(trifluoromethoxy)phenyl]phthalazin-1-yl]amino]-1-pyridyl]butanoate;
3-[2-oxo-3-[[4-oxo-3-[4-(trifluoromethoxy)phenyl]phthalazin-1-yl]amino]-1-pyridyl]propane-1-sulfonamide;
N,N-dimethyl-3-[2-oxo-3-[[4-oxo-3-[4-(trifluoromethoxy)phenyl]phthalazin-1-yl]amino]-1-pyridyl]propane-1-sulfonamide;
4-[[1-(2-morpholinoethyl)-2-oxo-3-pyridyl]amino]-2-[4-(trifluoromethoxy)phenyl]phthalazin-1-one;
4-[[1-[2-[3-hydroxy-3-(trifluoromethyl)azetidin-1-yl]ethyl]-2-oxo-3-pyridyl]amino]-2-[4-(trifluoromethoxy)phenyl]phthalazin-1-one;
4-[[1-[2-(3-hydroxypyrrolidin-1-yl)ethyl]-2-oxo-3-pyridyl]amino]-2-[4-(trifluoromethoxy)phenyl]phthalazin-1-one;
methyl (2S)-1-[2-[2-oxo-3-[[4-oxo-3-[4-(trifluoromethoxy)phenyl]phthalazin-1-yl]amino]-1-pyridyl]ethyl]pyrrolidine-2-carboxylate;
4-[[1-[2-(dimethylamino)ethyl]-6-oxo-pyrimidin-5-yl]amino]-2-[4-(trifluoromethoxy)phenyl]phthalazin-1-one;
6-ethyl-4-[(1-methyl-2-oxo-3-pyridyl)amino]-2-[4-(trifluoromethoxy)phenyl]phthalazin-1-one;
7-ethyl-4-[(1-methyl-2-oxo-3-pyridyl)amino]-2-[4-(trifluoromethoxy)phenyl]phthalazin-1-one;
4-[(1-methyl-2-oxo-3-pyridyl)amino]-2-[4-(trifluoromethoxy)phenyl]-6-vinyl-phthalazin-1-one;
4-[(1-methyl-2-oxo-3-pyridyl)amino]-2-[4-(trifluoromethoxy)phenyl]-7-vinyl-phthalazin-1-one;
6-acetyl-1-[[(1-ethyl-6-oxo-pyrimidin-5-yl)amino]-3-[4-(trifluoromethoxy)phenyl]-7,8-dihydro-5H-pyrido[3,4-d]pyridazin-4-one;
6-acetyl-1-[[(6-oxo-1-propyl-pyrimidin-5-yl)amino]-3-[4-(trifluoromethoxy)phenyl]-7,8-dihydro-5H-pyrido[3,4-d]pyridazin-4-one;
6-acetyl-1-[(5-fluoro-1-methyl-2-oxo-3-pyridyl)amino]-3-[4-(trifluoromethoxy)phenyl]-7,8-dihydro-5H-pyrido[3,4-d]pyridazin-4-one;
4-[[1-(2-morpholino-2-oxo-ethyl)-2-oxo-3-pyridyl]amino]-2-[4-(trifluoromethoxy)phenyl]phthalazin-1-one;
N,N-dimethyl-2-[2-oxo-3-[[4-oxo-3-[4-(trifluoromethoxy)phenyl]phthalazin-1-yl]amino]-1-pyridyl]acetamide;

N-isopropyl-2-[2-oxo-3-[[4-oxo-3-[4-(trifluoromethoxy)phenyl]phthalazin-1-yl]amino]-1-pyridyl]acetamide;
N-methyl-2-[2-oxo-3-[[4-oxo-3-[4-(trifluoromethoxy)phenyl]phthalazin-1-yl]amino]-1-pyridyl]acetamide;
N-(2-hydroxyethyl)-2-[2-oxo-3-[[4-oxo-3-[4-(trifluoromethoxy)phenyl]phthalazin-1-yl]amino]-1-pyridyl]acetamide;
N-[2-(dimethylamino)ethyl]-2-[2-oxo-3-[[4-oxo-3-[4-(trifluoromethoxy)phenyl]phthalazin-1-yl]amino]-1-pyridyl]acetamide;
N-(3-methoxypropyl)-2-[2-oxo-3-[[4-oxo-3-[4-(trifluoromethoxy)phenyl]phthalazin-1-yl]amino]-1-pyridyl]acetamide;
N-methyl-3-[2-oxo-3-[[4-oxo-3-[4-(trifluoromethoxy)phenyl]phthalazin-1-yl]amino]-1-pyridyl]propanamide;
N,N-dimethyl-3-[2-oxo-3-[[4-oxo-3-[4-(trifluoromethoxy)phenyl]phthalazin-1-yl]amino]-1-pyridyl]propanamide;
N-methyl-4-[2-oxo-3-[[4-oxo-3-[4-(trifluoromethoxy)phenyl]phthalazin-1-yl]amino]-1-pyridyl]butanamide;
N,N-dimethyl-4-[2-oxo-3-[[4-oxo-3-[4-(trifluoromethoxy)phenyl]phthalazin-1-yl]amino]-1-pyridyl]butanamide;
N,2,2-trimethyl-3-[2-oxo-3-[[4-oxo-3-[4-(trifluoromethoxy)phenyl]phthalazin-1-yl]amino]-1-pyridyl]propanamide;
N,N,2,2-tetramethyl-3-[2-oxo-3-[[4-oxo-3-[4-(trifluoromethoxy)phenyl]phthalazin-1-yl]amino]-1-pyridyl]propanamide;
2,2-dimethyl-3-[2-oxo-3-[[4-oxo-3-[4-(trifluoromethoxy)phenyl]phthalazin-1-yl]amino]-1-pyridyl]propanamide;
N-methyl-2-[2-[2-oxo-3-[[4-oxo-3-[4-(trifluoromethoxy)phenyl]phthalazin-1-yl]amino]-1-pyridyl]ethoxy]acetamide;
N,N-dimethyl-2-[2-[2-oxo-3-[[4-oxo-3-[4-(trifluoromethoxy)phenyl]phthalazin-1-yl]amino]-1-pyridyl]ethoxy]acetamide;
N-methyl-2-[2-oxo-3-[[4-oxo-3-[4-(trifluoromethoxy)phenyl]-5,6,7,8-tetrahydrophthalazin-1-yl]amino]-1-pyridyl]acetamide;
N-methyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;
N,N-dimethyl-4-[2-oxo-3-[[4-oxo-3-[4-(trifluoromethoxy)phenyl]-6,7-dihydro-5H-cyclopenta[d]pyridazin-1-yl]amino]-1-pyridyl]butanamide;
N-methyl-2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide;
N,N-dimethyl-2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetamide;
3-[2-oxo-3-[[4-oxo-3-[4-(trifluoromethoxy)phenyl]phthalazin-1-yl]amino]-1-pyridyl]propanoic acid;
4-[2-oxo-3-[[4-oxo-3-[4-(trifluoromethoxy)phenyl]phthalazin-1-yl]amino]-1-pyridyl]butanoic acid;
2,2-dimethyl-3-[2-oxo-3-[[4-oxo-3-[4-(trifluoromethoxy)phenyl]phthalazin-1-yl]amino]-1-pyridyl]propanoic acid;
2-[2-[2-oxo-3-[[4-oxo-3-[4-(trifluoromethoxy)phenyl]phthalazin-1-yl]amino]-1-pyridyl]ethoxy]acetic acid;
2-[methyl-[2-[2-oxo-3-[[4-oxo-3-[4-(trifluoromethoxy)phenyl]phthalazin-1-yl]amino]-1-pyridyl]ethyl]amino]acetic acid;
1-[2-[2-oxo-3-[[4-oxo-3-[4-(trifluoromethoxy)phenyl]phthalazin-1-yl]amino]-1-pyridyl]ethyl]pyrrolidine-2-carboxylic acid;
(2S)-1-[2-[2-oxo-3-[[4-oxo-3-[4-(trifluoromethoxy)phenyl]phthalazin-1-yl]amino]-1-pyridyl]ethyl]pyrrolidine-2-carboxylic acid;
(2R)-1-[2-[2-oxo-3-[[4-oxo-3-[4-(trifluoromethoxy)phenyl]phthalazin-1-yl]amino]-1-pyridyl]ethyl]pyrrolidine-2-carboxylic acid;
4-[5-chloro-2-oxo-3-[[4-oxo-3-[4-(trifluoromethoxy)phenyl]-6,7-dihydro-5H-cyclopenta[d]pyridazin-1-yl]amino]-1-pyridyl]butanoic acid;
4-[2-oxo-3-[[4-oxo-3-[4-(trifluoromethoxy)phenyl]-6,7-dihydro-5H-cyclopenta[d]pyridazin-1-yl]amino]-1-pyridyl]butanoic acid;
2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethoxy]acetic acid;
1-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]pyrrolidine-3-carboxylic acid;
1-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]pyrrolidine-2-carboxylic acid;
4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-2-carboxylic acid;
4-[2-[2-oxo-3-[[4-oxo-3-[4-(trifluoromethoxy)phenyl]-6,7-dihydro-5H-cyclopenta[d]pyridazin-1-yl]amino]-1-pyridyl]ethyl]morpholine-3-carboxylic acid;
4-[6-oxo-5-[[4-oxo-3-[4-(trifluoromethoxy)phenyl]-6,7-dihydro-5H-cyclopenta[d]pyridazin-1-yl]amino]pyrimidin-1-yl]butanoic acid;
7-hydroxy-4-[(1-methyl-2-oxo-3-pyridyl)amino]-2-[4-(trifluoromethoxy)phenyl]phthalazin-1-one;
6-hydroxy-4-[(1-methyl-2-oxo-3-pyridyl)amino]-2-[4-(trifluoromethoxy)phenyl]phthalazin-1-one;
1-[[1-(morpholin-3-ylmethyl)-6-oxo-pyrimidin-5-yl]amino]-3-[4-(trifluoromethoxy)phenyl]-6,7-dihydro-5H-cyclopenta[d]pyridazin-4-one;
1-[[1-[2-(methylamino)ethyl]-6-oxo-pyrimidin-5-yl]amino]-3-[4-(trifluoromethoxy)phenyl]-6,7-dihydro-5H-cyclopenta[d]pyridazin-4-one;
2-[2-[2-oxo-3-[[4-oxo-3-[4-(trifluoromethoxy)phenyl]-6,7-dihydro-5H-cyclopenta[d]pyridazin-1-yl]amino]-1-pyridyl]ethylamino]acetic acid;
1-[[1-(2-aminoethyl)-2-oxo-3-pyridyl]amino]-3-[4-(trifluoromethoxy)phenyl]-6,7-dihydro-5H-cyclopenta[d]pyridazin-4-one;
1-[[2-oxo-1-(pyrrolidin-2-ylmethyl)-3-pyridyl]amino]-3-[4-(trifluoromethoxy)phenyl]-6,7-dihydro-5H-cyclopenta[d]pyridazin-4-one;
6-methyl-1-[(1-methyl-2-oxo-3-pyridyl)amino]-3-[4-(trifluoromethoxy)phenyl]-7,8-dihydro-5H-pyrido[3,4-d]pyridazin-4-one;
6-methyl-4-[(1-methyl-2-oxo-3-pyridyl)amino]-2-[4-(trifluoromethoxy)phenyl]-7,8-dihydro-5H-pyrido[3,4-d]pyridazin-1-one;
1-[(1-methyl-2-oxo-3-pyridyl)amino]-3-[4-(trifluoromethoxy)phenyl]-5,6,7,8-tetrahydropyrido[3,4-d]pyridazin-4-one;
1-[[1-[[(2S)-Morpholin-2-yl]methyl]-2-oxo-3-pyridyl]amino]-3-[4-(trifluoromethoxy)phenyl]-6,7-dihydro-5H-cyclopenta[d]pyridazin-4-one;
6-(2-methoxyethoxy)-4-[(1-methyl-2-oxo-3-pyridyl)amino]-2-[4-(trifluoromethoxy)phenyl]phthalazin-1-one;

7-(2-methoxyethoxy)-4-[(1-methyl-2-oxo-3-pyridyl)amino]-2-[4-(trifluoromethoxy)phenyl]phthalazin-1-one;
5-(2-methoxyethoxy)-4-[(1-methyl-2-oxo-3-pyridyl)amino]-2-[4-(trifluoromethoxy)phenyl]phthalazin-1-one;
1-[(1-methyl-2-oxo-3-pyridyl)amino]-4-oxo-3-[4-(trifluoromethoxy)phenyl]phthalazine-6-carboxamide;
7-(1-hydroxyethyl)-4-[(1-methyl-2-oxo-3-pyridyl)amino]-2-[4-(trifluoromethoxy)phenyl]phthalazin-1-one;
7-(hydroxymethyl)-4-[(1-methyl-2-oxo-3-pyridyl)amino]-2-[4-(trifluoromethoxy)phenyl]phthalazin-1-one;
7-amino-4-[(1-methyl-2-oxo-3-pyridyl)amino]-2-[4-(trifluoromethoxy)phenyl]phthalazin-1-one;
7-(aminomethyl)-4-[(1-methyl-2-oxo-3-pyridyl)amino]-2-[4-(trifluoromethoxy)phenyl]phthalazin-1-one;
7-[(dimethylamino)methyl]-4-[(1-methyl-2-oxo-3-pyridyl)amino]-2-[4-(trifluoromethoxy)phenyl]phthalazin-1-one;
6-(2-hydroxypropyl)-1-[(1-methyl-2-oxo-3-pyridyl)amino]-3-[4-(trifluoromethoxy)phenyl]-7,8-dihydro-5H-pyrido[3,4-d]pyridazin-4-one;
6-(2-hydroxy-2-methyl-propyl)-1-[(1-methyl-2-oxo-3-pyridyl)amino]-3-[4-(trifluoromethoxy)phenyl]-7,8-dihydro-5H-pyrido[3,4-d]pyridazin-4-one;
6-(2-hydroxyethyl)-1-[(1-methyl-2-oxo-3-pyridyl)amino]-3-[4-(trifluoromethoxy)phenyl]-7,8-dihydro-5H-pyrido[3,4-d]pyridazin-4-one;
6-acetyl-1-[(1-methyl-2-oxo-3-pyridyl)amino]-3-[4-(trifluoromethoxy)phenyl]-7,8-dihydro-5H-pyrido[3,4-d]pyridazin-4-one;
6-acetyl-4-[(1-methyl-2-oxo-3-pyridyl)amino]-2-[4-(trifluoromethoxy)phenyl]-7,8-dihydro-5H-pyrido[3,4-d]pyridazin-1-one;
6-acetyl-1-[(1-methyl-6-oxo-pyrimidin-5-yl)amino]-3-[4-(trifluoromethoxy)phenyl]-7,8-dihydro-5H-pyrido[3,4-d]pyridazin-4-one;
6-acetyl-4-[(1-methyl-6-oxo-pyrimidin-5-yl)amino]-2-[4-(trifluoromethoxy)phenyl]-7,8-dihydro-5H-pyrido[3,4-d]pyridazin-1-one;
methyl 4-[(1-methyl-2-oxo-3-pyridyl)amino]-1-oxo-2-[4-(trifluoromethoxy)phenyl]-7,8-dihydro-5H-pyrido[3,4-d]pyridazine-6-carboxylate;
methyl 1-[(1-methyl-2-oxo-3-pyridyl)amino]-4-oxo-3-[4-(trifluoromethoxy)phenyl]-7,8-dihydro-5H-pyrido[3,4-d]pyridazine-6-carboxylate;
4-[(1-methyl-2-oxo-3-pyridyl)amino]-1-oxo-2-[4-(trifluoromethoxy)phenyl]-7,8-dihydro-5H-pyrido[3,4-d]pyridazine-6-carbaldehyde;
1-[(1-methyl-2-oxo-3-pyridyl)amino]-4-oxo-3-[4-(trifluoromethoxy)phenyl]-7,8-dihydro-5H-pyrido[3,4-d]pyridazine-6-carbaldehyde;
1-[(1-methyl-2-oxo-3-pyridyl)amino]-6-methylsulfonyl-3-[4-(trifluoromethoxy)phenyl]-7,8-dihydro-5H-pyrido[3,4-d]pyridazin-4-one;
4-[(1-methyl-2-oxo-3-pyridyl)amino]-6-methylsulfonyl-2-[4-(trifluoromethoxy)phenyl]-7,8-dihydro-5H-pyrido[3,4-d]pyridazin-1-one;
6-ethyl-1-[(1-methyl-2-oxo-3-pyridyl)amino]-3-[4-(trifluoromethoxy)phenyl]-7,8-dihydro-5H-pyrido[3,4-d]pyridazin-4-one;
6-isopropyl-1-[(1-methyl-2-oxo-3-pyridyl)amino]-3-[4-(trifluoromethoxy)phenyl]-7,8-dihydro-5H-pyrido[3,4-d]pyridazin-4-one;
N-methyl-4-[(1-methyl-2-oxo-3-pyridyl)amino]-1-oxo-2-[4-(trifluoromethoxy)phenyl]-7,8-dihydro-5H-pyrido[3,4-d]pyridazine-6-carboxamide;
N-methyl-1-[(1-methyl-2-oxo-3-pyridyl)amino]-4-oxo-3-[4-(trifluoromethoxy)phenyl]-7,8-dihydro-5H-pyrido[3,4-d]pyridazine-6-carboxamide;
2-[4-(1-hydroxy-1-methyl-ethyl)phenyl]-4-[(1-methyl-2-oxo-3-pyridyl)amino]phthalazin-1-one;
4-[[1-(2-hydroxyethyl)-2-oxo-3-pyridyl]amino]-2-[4-(trifluoromethoxy)phenyl]phthalazin-1-one;
7-hydroxy-4-[(1-methyl-2-oxo-3-pyridyl)amino]-2-[4-(trifluoromethoxy)phenyl]-5,6,7,8-tetrahydrophthalazin-1-one;
6-hydroxy-4-[(1-methyl-2-oxo-3-pyridyl)amino]-2-[4-(trifluoromethoxy)phenyl]-5,6,7,8-tetrahydrophthalazin-1-one;
1-[[1-(3-amino-2-hydroxy-2-methyl-propyl)-2-oxo-3-pyridyl]amino]-3-[4-(trifluoromethoxy)phenyl]-6,7-dihydro-5H-cyclopenta[d]pyridazin-4-one;
1-[[2-Oxo-1-(2-oxo-2-piperazin-1-yl-ethyl)-3-pyridyl]amino]-3-[4-(trifluoromethoxy)phenyl]-6,7-dihydro-5H-cyclopenta[d]pyridazin-4-one;
1-[[1-[2-(Oxetan-3-ylamino)ethyl]-2-oxo-3-pyridyl]amino]-3-[4-(trifluoromethoxy)phenyl]-6,7-dihydro-5H-cyclopenta[d]pyridazin-4-one;
1-[[1-[2-(3-Hydroxyazetidin-1-yl)ethyl]-6-oxo-pyrimidin-5-yl]amino]-3-[4-(trifluoromethoxy)phenyl]-6,7-dihydro-5H-cyclopenta[d]pyridazin-4-one;
trans-1-[[1-[(5-Amino-1,3-dioxan-2-yl)methyl]-2-oxo-3-pyridyl]amino]-3-[4-(trifluoromethoxy)phenyl]-6,7-dihydro-5H-cyclopenta[d]pyridazin-4-one;
1-[(1-Methyl-2-oxo-3-pyridyl)amino]-3-[2-methyl-4-(trifluoromethoxy)phenyl]-6,7-dihydro-5H-cyclopenta[d]pyridazin-4-one;
3-(3,4-Dimethoxyphenyl)-1-[(1-methyl-2-oxo-3-pyridyl)amino]-6,7-dihydro-5H-cyclopenta[d]pyridazin-4-one;
3-[3-Methoxy-4-(trifluoromethyl)phenyl]-1-[(1-methyl-2-oxo-3-pyridyl)amino]-6,7-dihydro-5H-cyclopenta[d]pyridazin-4-one;
N, 1-Dimethyl-6-oxo-5-[[4-oxo-3-[4-(trifluoromethoxy)phenyl]-5,6,7,8-tetrahydrophthalazin-1-yl]amino]pyridine-3-carboxamide;
N, 1-Dimethyl-6-oxo-5-[[4-oxo-3-[4-(trifluoromethoxy)phenyl]phthalazin-1-yl]amino]pyridine-3-carboxamide;
4-[[1-methyl-2-oxo-5-(trifluoromethyl)-3-pyridyl]amino]-2-[4-(trifluoromethoxy)phenyl]phthalazin-1-one;
and pharmaceutically acceptable salts thereof.

39. A process for the preparation of compounds of formula (I) and pharmaceutically acceptable salts thereof according to claim 1, comprising a palladium-mediated amination reaction of a compound of formula (IV)

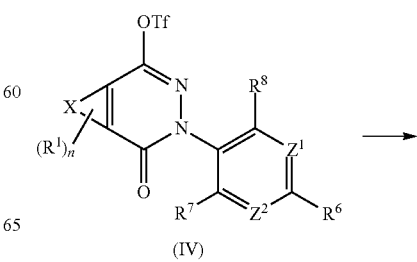

(IV)

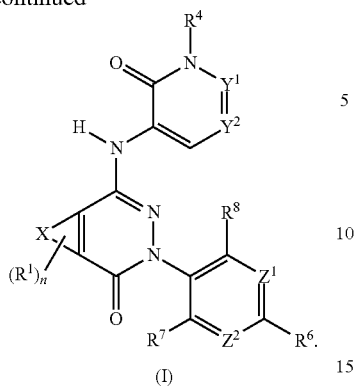

(I)

40. A process for the preparation of compounds of formula (I) and pharmaceutically acceptable salts thereof according to claim 1, comprising a palladium-mediated amination reaction of a compound of formula (VII)

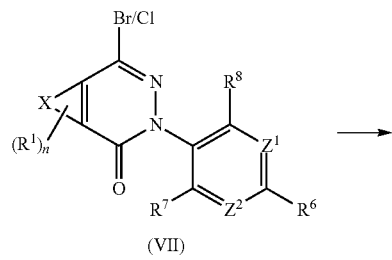

(VII)

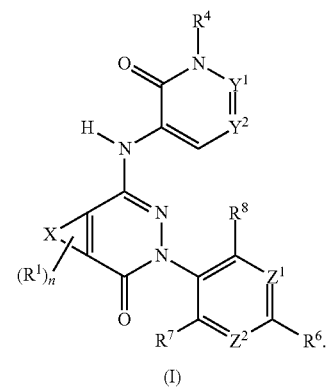

(I)

41. A pharmaceutical composition comprising a compound of claim 1, or a pharmaceutically acceptable salt thereof, and at least one pharmaceutically acceptable excipient.

42. A method for the treatment of influenza A, which method comprises administering a compound of claim 1, or a pharmaceutically salt thereof, to a human being or animal.

* * * * *